United States Patent
Li et al.

(10) Patent No.: US 12,268,674 B2
(45) Date of Patent: Apr. 8, 2025

(54) Mi-2β INHIBITOR AS AN IMMUNOTHERAPY AGENT

(71) Applicant: BioVentures, LLC, Little Rock, AR (US)

(72) Inventors: Hong-yu Li, Little Rock, AR (US); Zhengyu Wang, Little Rock, AR (US); Jingwei Shao, Little Rock, AR (US); Rutao Cui, Hangzhou (CN)

(73) Assignee: BioVentures, LLC, Little Rock, AR (US)

( * ) Notice: Subject to any disclaimer, the term of this patent is extended or adjusted under 35 U.S.C. 154(b) by 0 days.

(21) Appl. No.: 17/696,610

(22) Filed: Mar. 16, 2022

(65) Prior Publication Data
US 2022/0304990 A1   Sep. 29, 2022

Related U.S. Application Data

(60) Provisional application No. 63/161,651, filed on Mar. 16, 2021.

(51) Int. Cl.
| | | |
|---|---|---|
| A61K 31/437 | (2006.01) | |
| A61K 31/4725 | (2006.01) | |
| A61K 31/497 | (2006.01) | |
| A61K 45/06 | (2006.01) | |
| C07D 471/04 | (2006.01) | |
| C07D 519/00 | (2006.01) | |

(52) U.S. Cl.
CPC ........ *A61K 31/437* (2013.01); *A61K 31/4725* (2013.01); *A61K 31/497* (2013.01); *A61K 45/06* (2013.01); *C07D 471/04* (2013.01); *C07D 519/00* (2013.01)

(58) Field of Classification Search
CPC .......... A61K 31/437; A61K 31/444; A61K 31/4725; A61K 31/497; A61K 31/498; A61K 45/06; C07D 471/04; C07D 519/00; A61P 35/00; A61P 37/02
See application file for complete search history.

(56) References Cited

FOREIGN PATENT DOCUMENTS

WO    WO-2018200889 A1 * 11/2018

OTHER PUBLICATIONS

Zhu et al., Mi-2β-targeted inhibition induces immunotherapy response in melanoma, Research Square, posted Dec. 16, 2020 ( Year: 2020).*
Abou El Hassan, M. et al. Cancer Cells Hijack PRC2 to Modify Multiple Cytokine Pathways. PLoS One 10, e0126466 (2015).
Abril-Rodriguez, G. et al. PAK4 inhibition improves PD-1 blockade immunotherapy. Nature Cancer 1, 46-58 (2020).
Amin, A. et al. Phase II study of vemurafenib followed by ipilimumab in patients with previously untreated BRAF-mutated metastatic melanoma. J Immunother Cancer 4, 44 (2016).
(Continued)

*Primary Examiner* — Sarah Pihonak
*Assistant Examiner* — Padmaja S Rao
(74) *Attorney, Agent, or Firm* — Quarles & Brady, LLP

(57) ABSTRACT

Mi-2β inhibitors and methods of using the same are disclosed. The methods comprise administering an effective amount of a Mi-2β inhibitor to the subject or contacting a cancer cell or a tumor with an effective amount of a Mi-2β inhibitor.

18 Claims, 26 Drawing Sheets
Specification includes a Sequence Listing.

(56) References Cited

OTHER PUBLICATIONS

Benci, J.L. et al Tumor Interferon Signaling Regulates a Multigenic Resistance Program to Immune Checkpoint Blockade. Cell 167, 1540-1554 e1512 (2016).
Blackledge, N.P. et al. Targeting Polycomb systems to regulate gene expression: modifications to a complex story. Nat Rev Mol Cell Biol 16, 643-649 (2015).
Bornelöv, S. et al. The Nucleosome Remodeling and Deacetylation Complex Modulates Chromatin Structure at Sites of Active Transcription to Fine-Tune Gene Expression. Mol Cell 71, 56-72 e54 (2018).
Bronte, V. et al. Boosting antitumor responses of T lymphocytes infiltrating human prostate cancers. J Exp Med 201, 1257-1268 (2005).
Chan, T.A. et al. Genetic Basis for Clinical Response to CTLA-4 Blockade in Melanoma. N Engl J Med 373, 1984 (2015).
Chen, S. et al. Combination of 4-1BB agonist and PD-1 antagonist promotes antitumor effector/memory CD8 T cells in a poorly immunogenic tumor model. Cancer Immunol Res 3, 149-160 (2015).
Dankort, D. et al. Braf(V600E) cooperates with Pten loss to induce metastatic melanoma. Nat Genet 41, 544-552 (2009).
Flaherty, K.T. et al. Combined BRAF and MEK inhibition in melanoma with Braf V600 mutations. N Engl J Med 367, 1694-1703 (2012).
Frederick, D.T. et al. BRAF inhibition is associated with enhanced melanoma antigen expression and a more favorable tumor microenvironment in patients with metastatic melanoma. Clin Cancer Res 19, 1225-1231 (2013).
Gao, H. et al Opposing effects of SWI/SNF and Mi-2/NuRD chromatin remodeling complexes on epigenetic reprogramming by EBF and Pax5. Proc Natl Acad Sci U S A 106, 11258-11263 (2009).
Gao, J. et al. Loss of IFN-γ Pathway Genes in Tumor Cells as a Mechanism of Resistance to Anti-CTLA-4 Therapy. Cell 167, 397-404 e399 (2016).
Ghorani, E. & Quezada, S.A. Chromatin regulation and immune escape. Science 359, 745-746 (2018).
Gómez-Del Arco, P. et al The Chromatin Remodeling Complex Chd4/NuRD Controls Striated Muscle Identity and Metabolic Homeostasis. Cell Metab 23, 881-892 (2016).
Groom, J.R. & Luster, A.D. CXCR3 ligands: redundant, collaborative and antagonistic functions. Immunol Cell Biol 89, 207-215 (2011).
Gubin, M.M. et al., Checkpoint blockade cancer immunotherapy targets tumour-specific mutant antigens. Nature 515, 577-581 (2014).
Heidorn, S.J. et al. Kinase-dead BRAF and oncogenic RAS cooperate to drive tumor progression through CRAF. Cell 140, 209-221 (2010).
Hodis, E. et al. A landscape of driver mutations in melanoma. Cell 150, 251-263 (2012).
Hugo, W. et al. Genomic and Transcriptomic Features of Response to Anti-PD-1 Therapy in Metastatic Melanoma. Cell 165, 35-44 (2016).
Hu-Lieskovan, S. et al. Improved antitumor activity of immunotherapy with BRAF and MEK inhibitors in BRAF (V600E) melanoma. Sci Transl Med 7, 279ra241 (2015).
Jacobson, M.P. et al. On the role of the crystal environment in determining protein side-chain conformations. J Mol Biol 320, 597-608 (2002).
Kashiwagi, M. et al. Direct control of regulatory T cells by keratinocytes. Nat Immunol 18, 334-343 (2017).
Kim, J. Ikaros DNA-binding proteins direct formation of chromatin remodeling complexes in lymphocytes. Immunity 10, 345-355 (1999).
Knight, D.A. et al. Host immunity contributes to the anti-melanoma activity of BRAF inhibitors. J Clin Invest 123, 1371-1381 (2013).
Koya, R.C. et al. BRAF inhibitor vemurafenib improves the antitumor activity of adoptive cell immunotherapy. Cancer Res 72, 3928-3937 (2012).
Lai, A.Y. & Wade, P.A. Cancer biology and NuRD: a multifaceted chromatin remodelling complex. Nat Rev Cancer 11, 588-596 (2011).
Larkin, J. et al. Combined Nivolumab and Ipilimumab or Monotherapy in Untreated Melanoma. N Engl J Med 373, 23-34 (2015).
Li, B. et al. Comprehensive analyses of tumor immunity: implications for cancer immunotherapy. Genome Biol 17, 174 (2016).
Li, J. et al. Epigenetic driver mutations in ARID1A shape cancer immune phenotype and immunotherapy. J Clin Invest, (2020).
Liu, L. et al. The BRAF and MEK Inhibitors Dabrafenib and Trametinib: Effects on Immune Function and in Combination with Immunomodulatory Antibodies Targeting PD-1, PD-L1, and CTLA-4. Clin Cancer Res 21, 1639-1651 (2015).
Low, J.K.K. et al. CHD4 Is a Peripheral Component of the Nucleosome Remodeling and Deacetylase Complex. J Biol Chem 291, 15853-15866 (2016).
Miao, D. et al. Genomic correlates of response to immune checkpoint therapies in clear cell renal cell carcinoma. Science 359, 801-806 (2018).
Minor, D.R. et al. Severe gastrointestinal toxicity with administration of trametinib in combination with dabrafenib and ipilimumab. Pigment Cell Melanoma Res 28, 611-612 (2015).
Naito, T. et al. Antagonistic interactions between Ikaros and the chromatin remodeler Mi-2beta determine silencer activity and Cd4 gene expression. Immunity 27, 723-734 (2007).
Ni, Z. et al. Apical role for BRG1 in cytokine-induced promoter assembly. Proc Natl Acad Sci U S A 102, 14611-14616 (2005).
Nordin, B.E. et al. ATP Acyl Phosphate Reactivity Reveals Native Conformations of Hsp90 Paralogs and Inhibitor Target Engagement. Biochemistry 54, 3024-3036 (2015).
O'Donnell, J.S. et al. Cancer immunoediting and resistance to T cell-based immunotherapy. Nat Rev Clin Oncol 16, 151-167 (2019).
Overwijk, W.W. et al. Tumor regression and autoimmunity after reversal of a functionally tolerant state of self-reactive CD8+ T cells. J Exp Med 198, 569-580 (2003).
Pan, D. et al. A major chromatin regulator determines resistance of tumor cells to T cell-mediated killing. Science 359, 770-775 (2018).
Pencil, S.D. et al. Candidate metastasis-associated genes of the rat 13762NF mammary adenocarcinoma. Breast Cancer Res Treat 25, 165-174 (1993).
Peng, W. et al. Loss of PTEN Promotes Resistance to T Cell-Mediated Immunotherapy. Cancer Discov 6, 202-216 (2016).
Pitt, J.M. et al. Targeting the tumor microenvironment: removing obstruction to anticancer immune responses and immunotherapy. Ann Oncol 27, 1482-1492 (2016).
Postow, M.A. et al. Nivolumab and ipilimumab versus ipilimumab in untreated melanoma. N Engl J Med 372, 2006-2017 (2015).
Poulikakos, P.I. et al. RAF inhibitors transactivate RAF dimers and ERK signalling in cells with wild-type BRAF. Nature 464, 427-430 (2010).
Ramirez, J. et al. Hagman, MBD2 and multiple domains of CHD4 are required for transcriptional repression by Mi-2/NuRD complexes. Mol Cell Biol 32, 5078-5088 (2012).
Ribas, A. & Wolchok, J.D. Cancer immunotherapy using checkpoint blockade. Science 359, 1350-1355 (2018).
Ribas, A. et al. Association of Pembrolizumab With Tumor Response and Survival Among Patients With Advanced Melanoma. JAMA 315, 1600-1609 (2016).
Ribas, A. et al. Hepatotoxicity with combination of vemurafenib and ipilimumab. N Engl J Med 368, 1365-1366 (2013).
Schadendorf, D. et al. Pooled Analysis of Long-Term Survival Data From Phase II and Phase III Trials of Ipilimumab in Unresectable or Metastatic Melanoma. J Clin Oncol 33, 1889-1894 (2015).
Sharma, P. et al. Primary, Adaptive, and Acquired Resistance to Cancer Immunotherapy. Cell 168, 707-723 (2017).
Skoulidis, F. et al. STK11/LKB1 Mutations and PD-1 Inhibitor Resistance in KRAS-Mutant Lung Adenocarcinoma. Cancer Discov 8, 822-835 (2018).
Smith, M.P. et al. The immune microenvironment confers resistance to MAPK pathway inhibitors through macrophage-derived TNFalpha. Cancer Discov 4, 1214-1229 (2014).
Sosman, J.A. et al. Survival in BRAF V600-mutant advanced melanoma treated with vemurafenib. N Engl J Med 366, 707-714 (2012).

(56) References Cited

OTHER PUBLICATIONS

Steinberg, S.M. et al. BRAF inhibition alleviates immune suppression in murine autochthonous melanoma. Cancer Immunol Res 2, 1044-1050 (2014).

Tokunaga, R. et al. CXCL9, CXCL10, CXCL11/CXCR3 axis for immune activation—A target for novel cancer therapy. Cancer Treat Rev 63, 40-47 (2018).

UniProt, UniProt: a worldwide hub of protein knowledge. Nucleic Acids Res 47, D506-D515 (2019).

Van Elsas, A. et al. Combination immunotherapy of B16 melanoma using anti-cytotoxic T lymphocyte-associated antigen 4 (CTLA-4) and granulocyte/macrophage colony-stimulating factor (GM-CSF)-producing vaccines induces rejection of subcutaneous and metastatic tumors accompanied by autoimmune depigmentation. J Exp Med 190, 355-366 (1999).

Williams, C.J. et al. The chromatin remodeler Mi-2beta is required for CD4 expression and T cell development. Immunity 20, 719-733 (2004).

Woodage, T. et al. Characterization of the CHD family of proteins. Proc Natl Acad Sci U S A 94, 11472-11477 (1997).

Xia, L. et al. CHD4 Has Oncogenic Functions in Initiating and Maintaining Epigenetic Suppression of Multiple Tumor Suppressor Genes. Cancer Cell 31, 653-668 e657 (2017).

Yang, J.G. et al. The chromatin-remodeling enzyme ACF is an ATP-dependent DNA length sensor that regulates nucleosome spacing. Nat Struct Mol Biol 13, 1078-1083 (2006).

Yu, C. et al. Combination of Immunotherapy With Targeted Therapy: Theory and Practice in Metastatic Melanoma. Front Immunol 10, 990 (2019).

Zaretsky, J.M. et al. Mutations Associated with Acquired Resistance to PD-1 Blockade in Melanoma. N Engl J Med 375, 819-829 (2016).

Zhu, B. et al. TBX2 blocks myogenesis and promotes proliferation in rhabdomyosarcoma cells. Int J Cancer 135, 785-797 (2014).

Zhu, B. et al. The protective role of DOT1L in UV-induced melanomagenesis. Nat Commun 9, 259 (2018).

Zingg, D. et al. The Histone Methyltransferase Ezh2 Controls Mechanisms of Adaptive Resistance to Tumor Immunotherapy. Cell Rep 20, 854-867 (2017).

Franklin, C. et al. Immunotherapy in melanoma: Recent advances and future directions. Eur J Surg Oncol 43, 604-611 (2017).

Marincola, F.M. et al. Escape of human solid tumors from T-cell recognition: molecular mechanisms and functional significance. Adv Immunol 74, 181-273 (2000).

O'Donnell, J.S. et al. Resistance to PD1/PDL1 checkpoint inhibition. Cancer Treat Rev 52, 71-81 (2017).

Galon, J. & Bruni, D. Approaches to treat immune hot, altered and cold tumours with combination immunotherapies. Nat Rev Drug Discov 18, 197-218 (2019).

Mueller-Planitz, F. et al. Nucleosome sliding mechanisms: new twists in a looped history. Nat Struct Mol Biol 20, 1026-1032 (2013).

Golstein, P. & Griffiths, G.M. An early history of T cell-mediated cytotoxicity. Nat Rev Immunol 18, 527-535 (2018).

Jacobson, M.A. et al. A hierarchical approach to all-atom protein loop prediction. Proteins 55, 351-367 (2004).

Lowary, P.T. & Widom, J. New DNA sequence rules for high affinity binding to histone octamer and sequence-directed nucleosome positioning. J Mol Biol 276, 19-42 (1998).

Long, G.V. et al. Dabrafenib and trametinib versus dabrafenib and placebo for Val600 BRAF-mutant melanoma: a multicentre, double-blind, phase 3 randomised controlled trial. Lancet 386, 444-451 (2015).

\* cited by examiner

| Gene | In CD8 High melanoma Hazard ratio | p value | In CD8 Low melanoma Hazard ratio | p value |
|---|---|---|---|---|
| EP400 | 3.077725074 | 0.000006 | 1.354535889 | 0.10299 |
| MLL2 | 3.041722964 | 0.000007 | 0.841018861 | 0.305518 |
| PRDM4 | 2.861124705 | 0.000013 | 1.210863739 | 0.418542 |
| USP7 | 2.661960403 | 0.000028 | 0.987004702 | 0.952706 |
| MORF4 | 2.434532166 | 0.000791 | 1.404333478 | 0.098879 |
| EPAA1 | 2.409049909 | 0.022833 | 1.103441114 | 0.57291 |
| SMARCD1 | 2.377989208 | 0.000434 | 1.206210407 | 0.285884 |
| NCOA6 | 2.332410346 | 0.014943 | 1.237860466 | 0.440208 |
| CARM1 | 2.238990202 | 0.034001 | 1.502047388 | 0.102004 |
| SSRP1 | 2.103640978 | 0.000065 | 0.950184208 | 0.69994 |
| NOP2 | 2.080974836 | 0.000177 | 1.306469103 | 0.18777 |
| RCOR1 | 1.990097206 | 0.049709 | 0.840841053 | 0.48609 |
| HDGF | 1.921083098 | 0.000302 | 1.164462880 | 0.48070 |
| RAD1 | 1.855520053 | 0.000278 | 1.083024700 | 0.723256 |
| FBL | 1.821066898 | 0.013822 | 1.188731629 | 0.404807 |
| HDAC4 | 1.834004007 | 0.015848 | 1.018084897 | 0.918887 |
| PARP1 | 1.503980264 | 0.040266 | 1.478467809 | 0.069788 |
| RPS6KA4 | 1.742076808 | 0.042251 | 1.347419803 | 0.007817 |
| KHDRBSP2 | 1.511286340 | 0.026387 | 1.069187784 | 0.855256 |
| CKD7 | 1.502499164 | 0.020769 | 1.019165861 | 0.651018 |
| SKA1 | 1.463062042 | 0.031181 | 1.124396805 | 0.345862 |
| TBLIX | 1.422168622 | 0.021107 | 0.998391308 | 0.48005 |
| HMGA1 | 1.390088515 | 0.000087 | 0.991273431 | 0.950655 |
| SP140 | 0.799734903 | 0.020810 | 0.871050089 | 0.110466 |
| ATM | 0.792597818 | 0.048307 | 0.789397470 | 0.08981 |

| Gene | In CD8 High melanoma Hazard ratio | p value | In CD8 Low melanoma Hazard ratio | p value |
|---|---|---|---|---|
| HIST4H4 | 0.732471944 | 0.024892 | 1.212789354 | 0.063891 |
| SMARCA1 | 0.731147038 | 0.028807 | 1.004283811 | 0.983812 |
| SAP30 | 0.689107547 | 0.044097 | 0.797228467 | 0.070709 |
| CENPQ | 0.684417749 | 0.030499 | 0.811853859 | 0.070862 |
| BAZ2B | 0.682722832 | 0.02704 | 0.834731284 | 0.127386 |
| PARP10 | 0.671937122 | 0.008003 | 0.970810507 | 0.811989 |
| CBX7 | 0.669175702 | 0.008027 | 0.836588235 | 0.082802 |
| ZCWPW1 | 0.664555481 | 0.01047 | 0.907483414 | 0.338018 |
| SP140L | 0.642056347 | 0.003639 | 0.884322465 | 0.115257 |
| NBN | 0.62962183 | 0.024395 | 0.784977803 | 0.135232 |
| DDX60L | 0.624298879 | 0.001189 | 0.831138542 | 0.052775 |
| MTF2 | 0.628240004 | 0.018587 | 0.816130829 | 0.163029 |
| KAT2B | 0.619503511 | 0.008862 | 0.907803199 | 0.308433 |
| DTX3L | 0.609078015 | 0.008684 | 0.810841019 | 0.083021 |
| PARP14 | 0.579181221 | 0.002481 | 0.786902129 | 0.060219 |
| DHX58 | 0.578105591 | 0.008605 | 1.117977278 | 0.304337 |
| DZIP3 | 0.557090151 | 0.0014 | 0.837524823 | 0.211229 |
| SP110 | 0.549807372 | 0.00818 | 0.944204758 | 0.70924 |
| ZMYM8 | 0.548485177 | 0.011895 | 0.724898848 | 0.054387 |
| AEBP2 | 0.527322578 | 0.00838 | 0.857521908 | 0.420235 |
| BRD7 | 0.517959178 | 0.023703 | 0.819168882 | 0.297583 |
| ING4 | 0.516180263 | 0.028097 | 0.745467502 | 0.131765 |
| PARP9 | 0.510245158 | 0.000195 | 0.858791564 | 0.160766 |
| SP100 | 0.508549491 | 0.000869 | 0.841099807 | 0.187389 |
| PHF1 | 0.497779549 | 0.018615 | 0.950183057 | 0.78682 |
| H2AFV | 0.484234238 | 0.030851 | 1.106401561 | 0.872329 |
| CBX3 | 0.470388599 | 0.001441 | 0.910160189 | 0.811973 |
| DPY30 | 0.430340846 | 0.031193 | 0.813181181 | 0.397192 |
| PHF12 | 0.417486293 | 0.042871 | 0.928863009 | 0.783979 |
| HP1BP3 | 0.412182147 | 0.018378 | 1.029822899 | 0.722581 |

B

C

D

A

C

A

Mi-2β INHIBITOR AS AN IMMUNOTHERAPY AGENT

CROSS-REFERENCE TO RELATED APPLICATIONS

The present application claims priority to U.S. Provisional Patent Application No. 63/161,651 that was filed Mar. 16, 2021, the entire contents of which are hereby incorporated by reference.

REFERENCE TO A SEQUENCE LISTING

This application is being filed electronically via EFS-Web and includes an electronically submitted Sequence Listing in .txt format. The .txt file contains a sequence listing entitled "169852_00100_ST25.txt" created on Mar. 15, 2022 and is 64,027 bytes in size. The Sequence Listing contained in this .txt file is part of the specification and is hereby incorporated by reference herein in its entirety.

FIELD OF THE INVENTION

The disclosed technology is generally directed to immunotherapies. More particularly the technology is directed to Mi-2β inhibitors for treating cancer.

BACKGROUND OF THE INVENTION

Immunotherapies, especially immune checkpoint inhibitors, have been successfully used in treating melanoma. The FDA and EMA have approved four immunotherapies for advanced melanoma, including the anti-CTLA-4 antibody ipilimumab (Yervoy), the anti-PD-1 antibodies nivolumab (Opdivo) and pembrolizumab (Keytruda), and the oncolytic virus talimogene laherparepvec (TVEC, Imlygic) (1). Clinical data shows that 20% of melanoma patients respond to ipilimumab (anti-CTLA-4) (2), 33% respond to pembrolizumab (anti-PD-1) (3) and 58% respond to a dual immune checkpoint blockade (anti-PD-1+anti-CTLA-4), but with significant toxicity (4, 5). Even though the most responsive cancer patients maintain long-lasting disease control, one third of those still relapse (6, 7).

Failure of immunotherapy is normally induced by: 1) poor pre-existing antitumor T cell immunity (8, 9), 2) inadequate function of tumor-specific T cells (10, 11), and 3) the impaired formation of T-cell memory (12, 13). Most studies have focused on identifying and overcoming T cell inhibitory mechanisms. However, the critical role of tumor-intrinsic modulation in regulating adaptive resistance to immune checkpoint blockades are attracting increasing attention (14). Tumor-intrinsic interferon signaling has been demonstrated to control tumor sensitivity to T cell rejection and subsequently regulates adaptive resistance to immune checkpoint blockades (15, 16). Furthermore, inhibition of p21-activated kinase 4 (PAK4) increased T cell infiltration and reversed resistance to PD-1 blockade through modulating WNT signaling (17). STK11 LKB1 alterations are the prevalent genomic driver for primary resistance to PD-1 inhibitors in KRAS-mutant lung adenocarcinoma (18). In addition, the loss of PTEN decreases T-cell infiltration in tumors to enhance immune resistance and reduce T cell-mediated cell death (19). Given the significance of chromatin in modulating gene expression and maintaining genome stability, some chromatin regulatory factors and enzymes are involved in the development of resistance to immunotherapies (14). For example, chromatin remodeling PBAF contributes to cancer cell immune resistance (20, 21) whereas BRG1, a chromatin-remodeling enzyme, has also been implicated in enhancing IFN-stimulated gene transcription (22). The overexpression of PRC2, a multiprotein enzyme complex (EZH2, SUz12, EED) regulating the trimethylation of lysine 27 on histone H3 (H3K27me3) (23) is detected in cancer cells and mediates the repression of IFN-γ-stimulated genes. Moreover, EZH2 inhibition enhances T cell-targeting immunotherapies in mouse models of melanoma (24, 25). Interestingly, ARID1A, a member of the SWI/SNF family can interact with EZH2 to inhibit IFN-responsive gene expression in cancer cells whose mutations can shape the cancer immune phenotype and immunotherapy (26). Understanding and targeting the underlying mechanism to convert resistant melanomas to immunotherapy sensitivity, especially the critical role of tumor-intrinsic modulation in regulating adaptive resistance will provide a significant improvement in patient outcome.

BRIEF SUMMARY OF THE INVENTION

Disclosed herein are compounds for use as immunotherapy agents. One aspect of the invention provides for a method for treating cancer, such as melanoma, in a subject comprising administering an effective amount of a Mi-2β inhibitor to the subject. In some embodiments, the Mi-2β inhibitor is co-administered with an immunotherapy, such as a checkpoint inhibitor. In some embodiments, the cancer is resistant to the immunotherapy in the absence of the effective amount of the Mi-2β inhibitor. In some embodiments, the Mi-2β inhibitor binds an ATP binding pocket of the Mi-2β.

In some embodiments, the Mi-2β inhibitor is a compound of formula

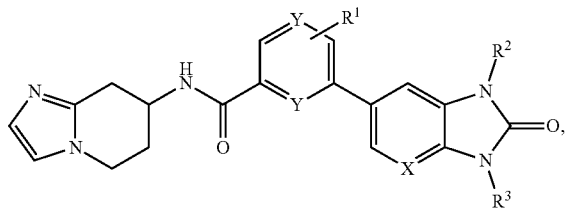

where each X and Y are independently selected from is N or CH; $R^1$ is hydrogen, a halo, or an unsubstituted or substituted, unbranched or branched, saturated or unsaturated C1-C6 alkyl; and $R^2$ and $R^3$ are independently selected from hydrogen, an unsubstituted or substituted, unbranched or branched, saturated or unsaturated $C_1$-$C_6$ alkyl, an unsubstituted or substituted, unbranched or branched, saturated or unsaturated $C_1$-$C_6$ alkylaryl, or an aryl. In some embodiments, the Mi-2β inhibitor is

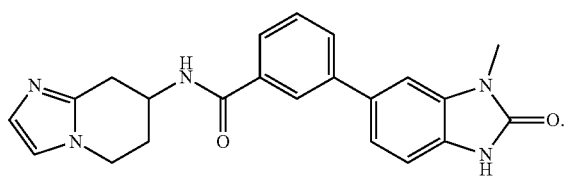 [SMILES: Cn1c(=O)[nH]c2ccc(-c3cccc(C(=O)NC4CCn5ccnc5C4)c3)cc21]

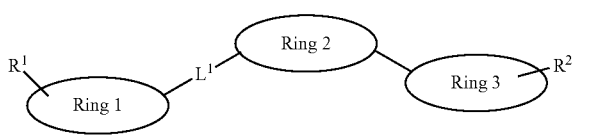

where Ring 1, Ring 2, and Ring 3 are independently selected from unsubstituted or substituted cyclic and heterocyclic rings which containing 3-14 carbon atoms and optionally 1 or more non-carbon atoms selected from N, O, or S; $R^1$ and $R^2$ are independently selected from hydrogen, an unsubstituted or substituted, unbranched or branched, saturated or unsaturated $C_1$-$C_6$ alkyl, an unsubstituted or substituted, unbranched or branched, saturated or unsaturated $C_1$-$C_6$ alkylaryl, an aryl, or -$L^2$-A; $L^1$ and $L^2$ are independently selected from the group consisting of alkylenyl, heteroalkylenyl, and —(($CH_2$)$_m$—W—($CH_2$)$_n$)$_p$—; W is selected from the group consisting of —O—, —N($R^2$)—, —C(=O) N($R^2$)—, —N($R^2$)C(=O)—, —C=C—, and —C≡C— or W is absent; m is 0, 1, 2, 3, 4, 5, 6, 7, or 8; n is 0, 1, 2, 3, 4, 5, 6, 7, or 8; p is 0, 1, 2, or 3; A is selected from the group consisting of:

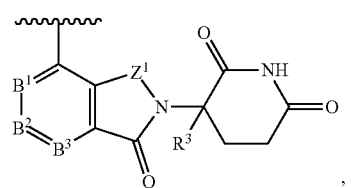

$A^{1a}$

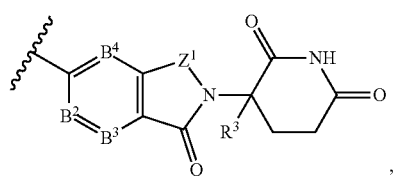

$A^{1b}$

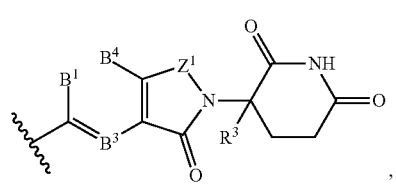

$A^{1c}$

-continued

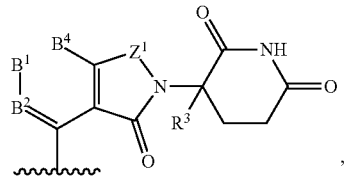

$A^{1d}$

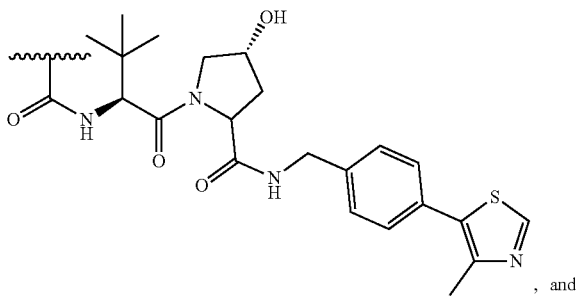

$A^{2a}$

, and

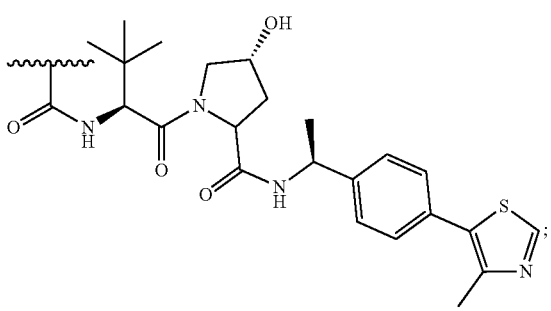

$A^{2b}$ $B^1$, $B^2$, $B^3$, and $B^4$ are independently selected from the group consisting of C($R^3$) and N; $R^3$ is selected from the group consisting of hydrogen, deuterium, methyl, and fluoro; and $Z^1$ is selected from the group consisting of —$CH_2$—, —C(=O)—, and —N=C($CH_3$)— wherein the nitrogen atom of —N=C($CH_3$)— is attached to the hexatomic ring. In some embodiments, the Mi-2β inhibitor comprises a member selected from the group consisting of

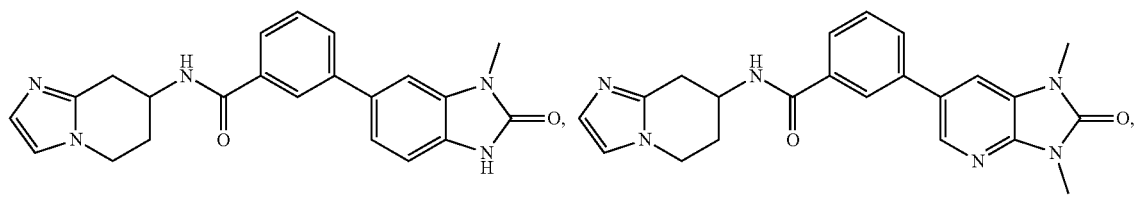

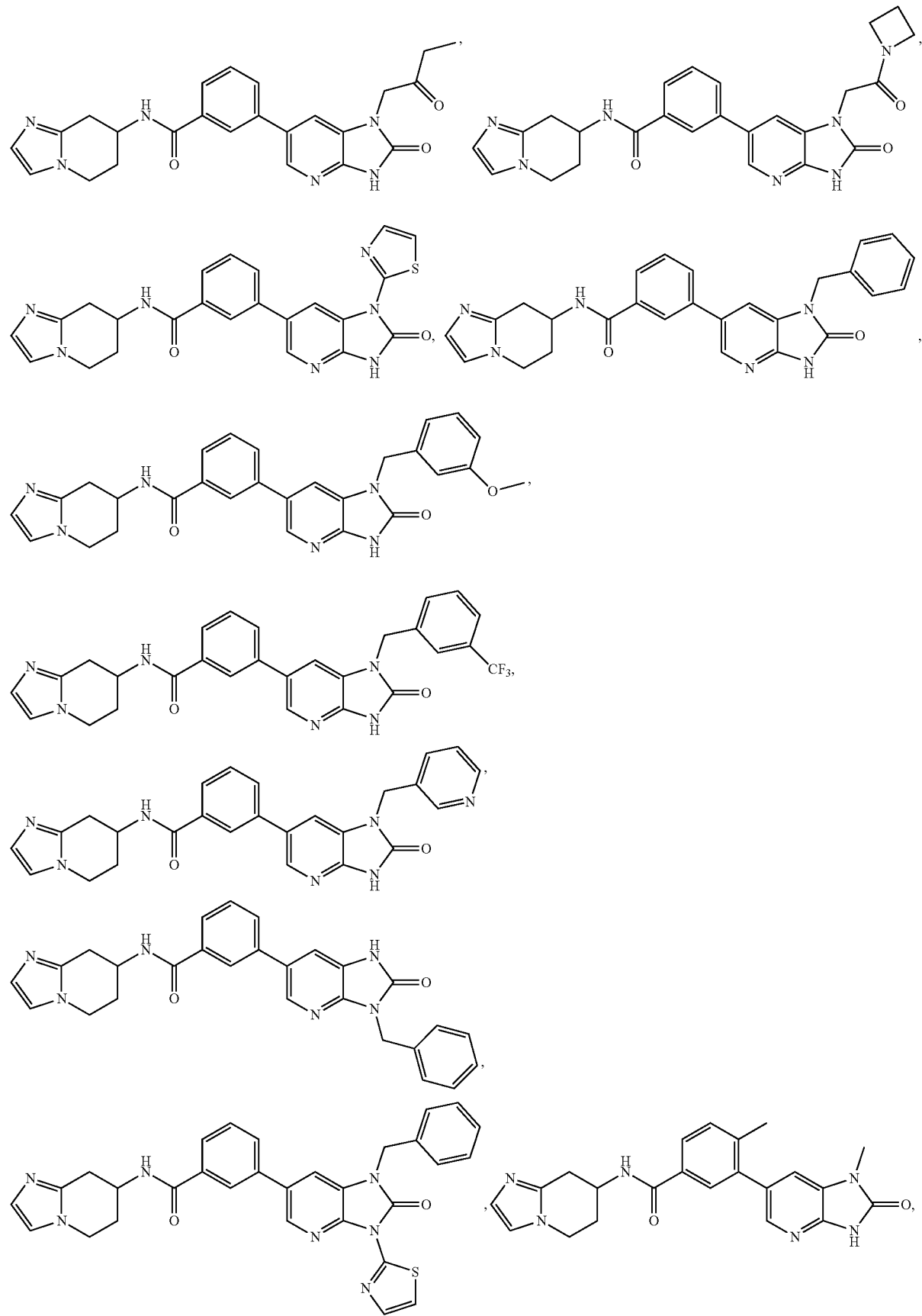

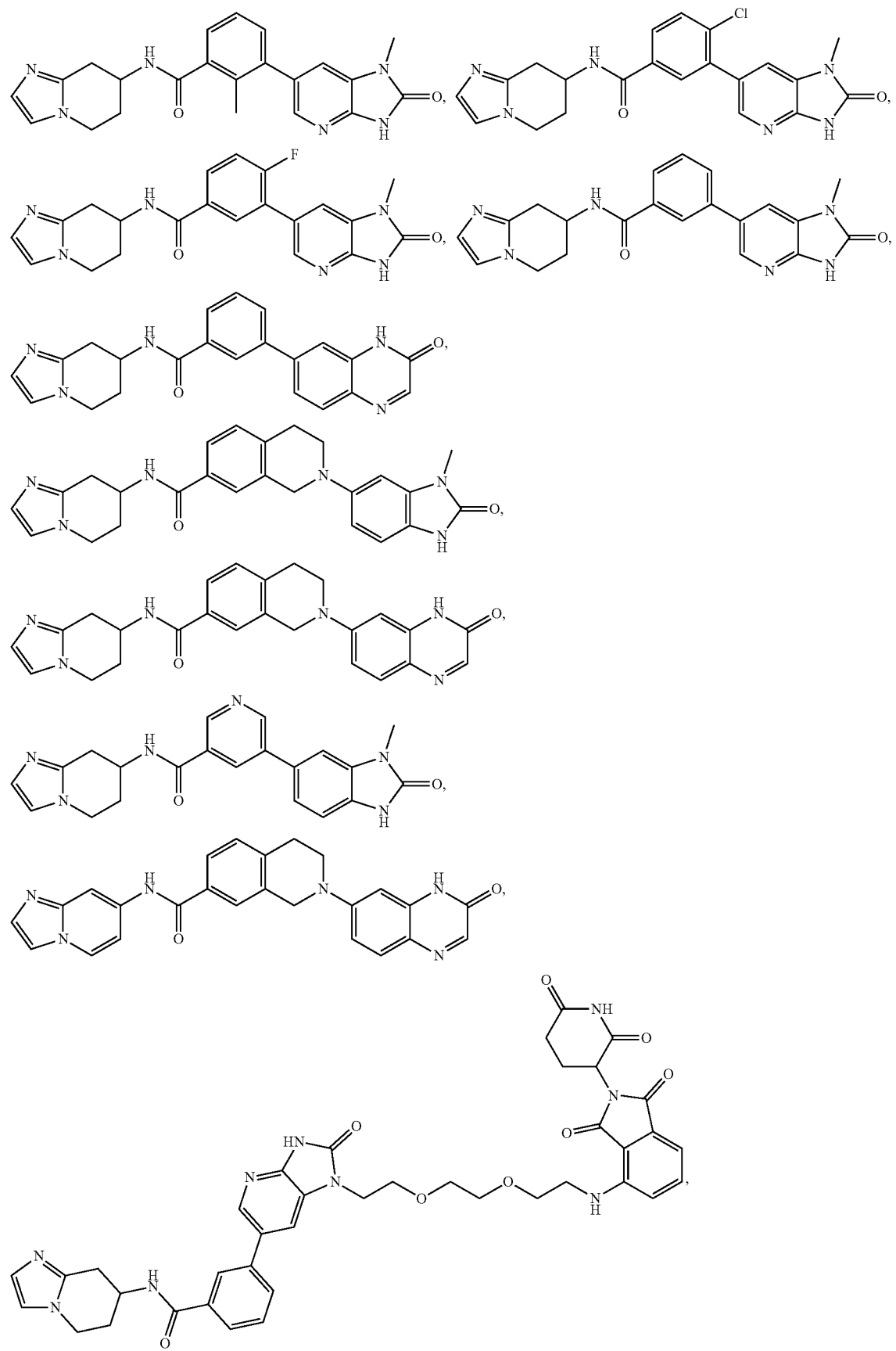

-continued

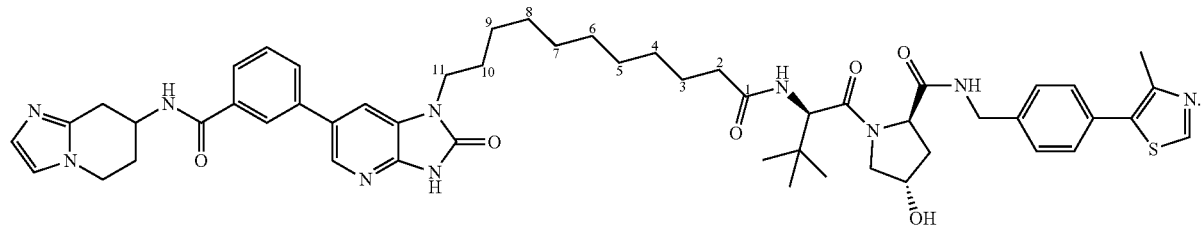

In some embodiments, the Mi-2β inhibitor inhibits expression of Mi-2β. In some embodiments, the Mi-2β inhibitor is a shRNA.

Another aspect of the invention provides for Mi-2β inhibitors and pharmaceutical compositions comprising the same.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention.

DETAILED DESCRIPTION OF THE INVENTION

Figure 1:
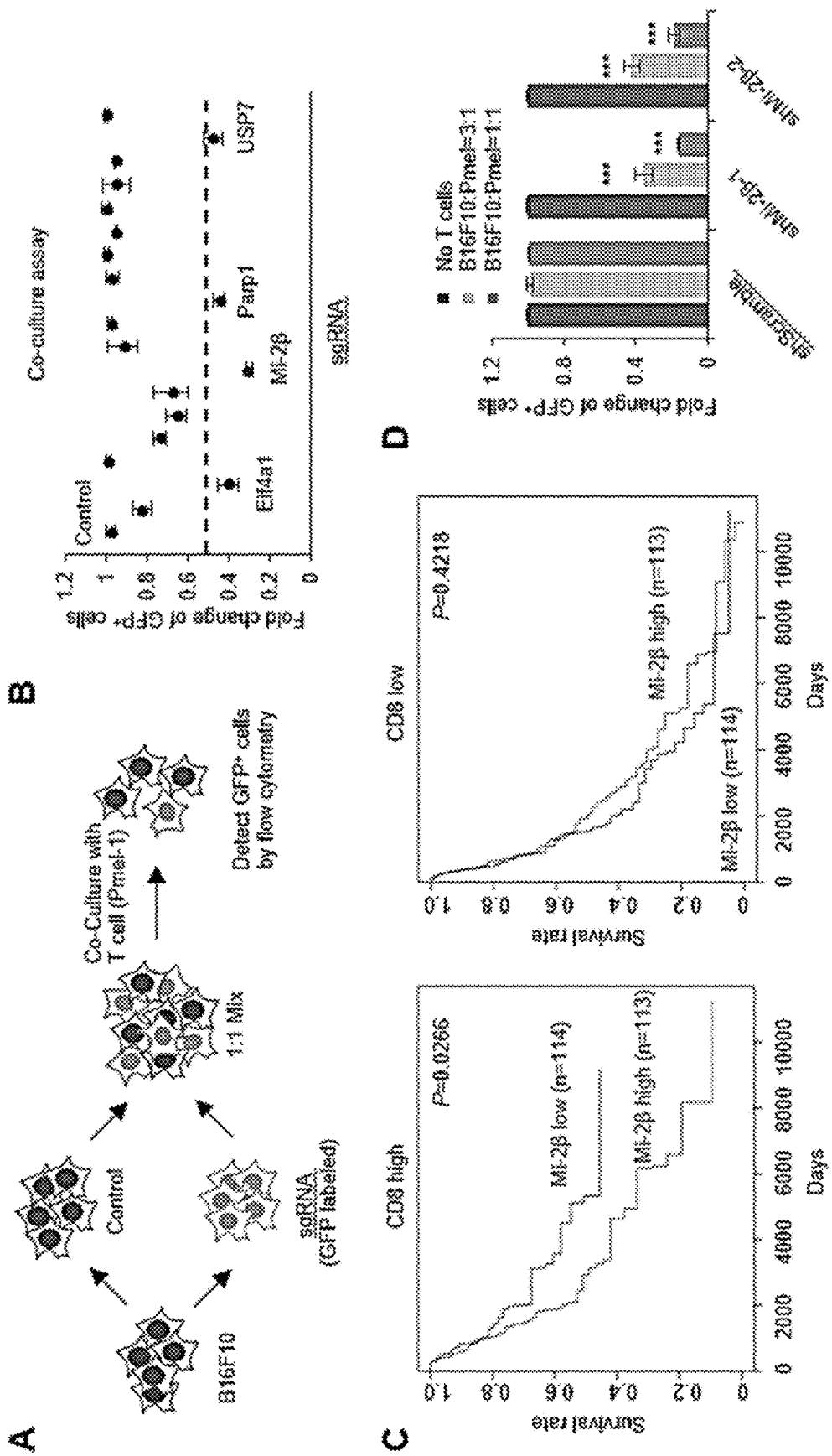
FIG. 1 illustrates identification of Mi-2β regulating melanoma cell resistance to anti-PD-1 response. A, A schematic for co-culture assay. GFP-labelled B16F10 cells with target gene knockout were mixed with non-labelled control cells at a 1:1 ratio, which were then co-cultured with activated Pmel-1 T cells (at a ratio of 1:1) for 3 days. Survival GFP positive tumor cells were assayed with flow cytometry. B, Targeted genes for overcoming resistance to Pmel-1 T cell killing. Targeted genes were plotted based on the survival change of knockout tumor cells compared with control cells. The dash line represents survival ratio changes for 0.5 fold. C, The survival curve of melanoma patients with different Mi-2β mRNA level. All patients in TCGA melanoma were divided into CD8 high or CD8 low groups based on the median expression. The available patients were further split into high- or low-expressing groups according to the median of Mi-2β mRNA level expression. Kaplan-Meier survival curves were shown, with the difference was examined using a log-rank test. D, GFP-labelled Mi-2β knockdown or shScramble B16F10 cells mixed with non-labelled B16F10 parental cells, and then were co-cultured with activated Pmel-1 T cells as indicated ratio for three days. The fold changes of the survival GFP-positive tumor cell were assayed with flow cytometry. Values represent mean±SD. The three bars from left to right: No T cells, B16F10: Pmel=3:1, and B16F10:Pmel=3:1. E-F, Mice bearing Mi-2β knockdown or shScramble B16F10 cells were treated with i.p. injection of control IgG (10 mg/kg) or anti-PD-1 (10 mg/kg) antibodies at day 6, 9, 12, 15 and 18 after tumor cell inoculation (at the end of the study, curves from top to bottom: shScramble+IgG, shMi-2β+IgG, shScramble+anti-PD-1, and shMi-2β+anti-PD-1), tumor volume (E) and tumor weight (F) were measured. Each group n=5. G-I, Tumor-infiltrating lymph cells in graft tumor were measured by flow cytometry. The population of $CD4^+$ T cells (g) and CD8+(H) were gated within $CD45^+$ T cells. I, Granzyme B expression in $CD8^+$ T was measured and quantified with flow cytometry. Values represent mean±SEM. *p<0.05, p<0.01* p<0.001.
Figure 1:
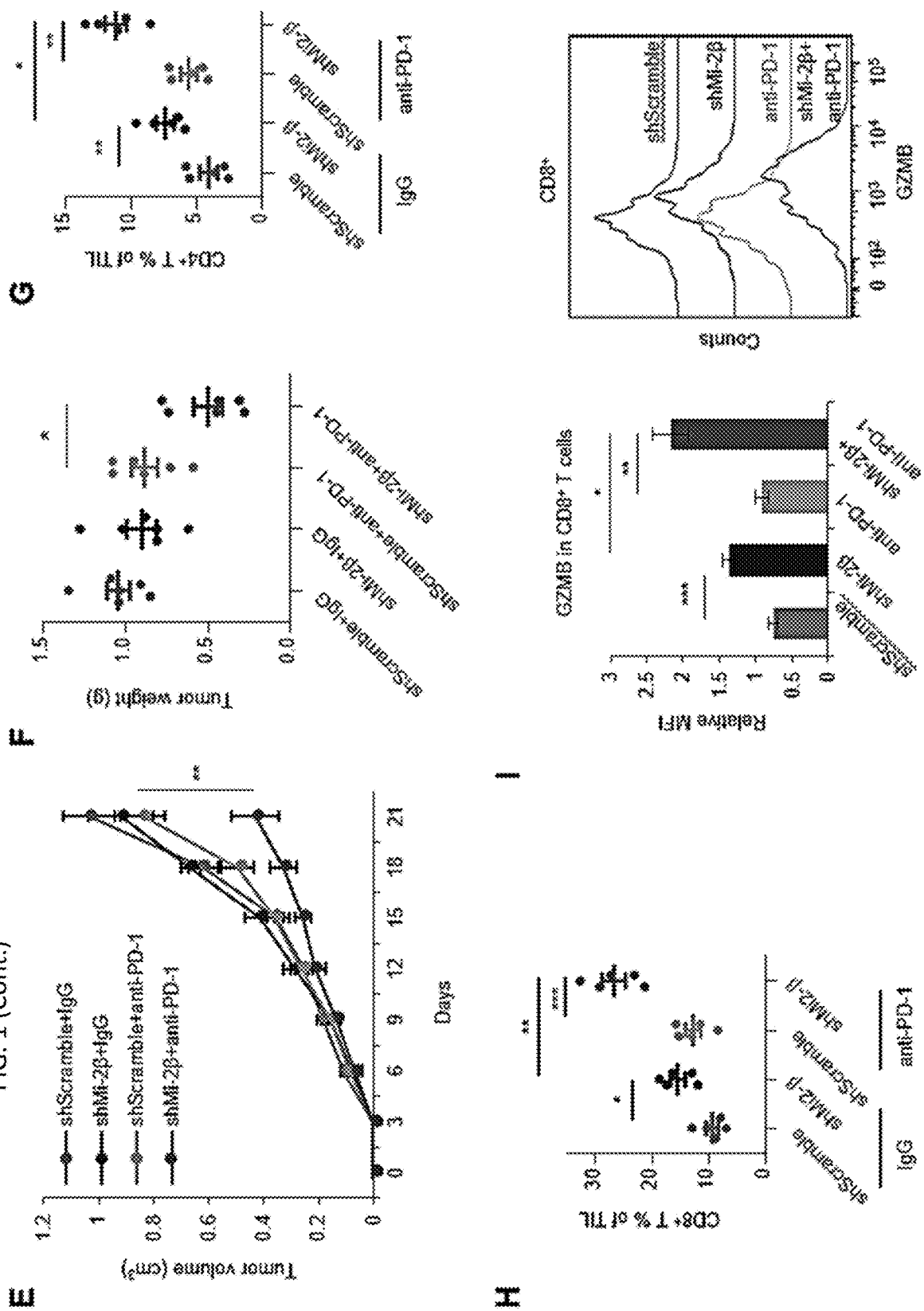

Disclosed herein are immunotherapy agents and methods of using the same. As demonstrated by the Examples, Mi-2β is identified as an effector regulating the adaptive anti-tumor immune response to cancers such as melanoma. Genetically engineered melanoma studies indicated that loss of Mi-2β rescued the immune response to immunotherapy in vivo. Targeting Mi-2β induced the adaptive immune response to immunotherapy by enhancing expression of a set of IFN-γ-responsive genes including CXCL9, CXCL10 and IRF1 implicated in T cell chemoattraction, antigen presentation, and T cell targeting and activation in cold melanoma in vivo. Moreover, Mi-2β inhibitors specifically and effectively induced a response to immunotherapy in otherwise resistant melanomas in vitro and in vivo. The Examples provide a new insight into the epigenetic regulation in adaptive immune responses and a strategy to improve cancer treatment and immunotherapies.

Mi-2β, also named as CHD4 (chromodomain helicase DNA-binding protein 4), is a member of the SNF2/RAD54 helicase family and a CHD family remodeling enzyme in the nucleosome remodeling and deacetylase (NuRD) complex, which includes the histone deacetylases 1 and 2 (HDAC1 and HDAC2), RBBP4/RBBP7, MBD2/MBD3, MTA-1/MTA-2/MTA-3 and GATAD2A/B (32), and plays important roles in chromatin assembly, genomic stability and gene repression (33). The genomic Mi-2β localization is highly enriched at transcription start sites where it plays an important role in transcriptional repression (48). Chromatin remodeling enzymes dynamically modulate gene accessibility by using ATP-derived energy to change nucleosome occupancy, position and composition. They contain a highly conserved ATPase motor domain of helicase family, which are classified as SWR1, ISWI, IN080 and CHD according to sequence homology (34). The most well-studied function of Mi-2/NuRD is its indispensable role in cardiac muscle cell identity (35) and haematopoietic development, including T and B lymphocytes (36-38). The conditional knockout of Mi-2β in mouse keratinocytes induces pro-inflammatory gene expression (31), and in cancer cells, Mi-2/NuRD promotes tumor development and metastasis (39, 40). Given the role of Mi-2β in regulating the immune response, targeting Mi-2β allows for a therapeutic strategy in cancer immunotherapy, such as in combination with checkpoint inhibitors such as anti-PD-1 antibodies.

Methods for treating cancer in a subject with a Mi-2β inhibitor are provided. Suitably the method for treating a subject comprises administering to the subject an effective amount of a Mi-2β inhibitor or a pharmaceutical composition comprising the effective amount of the Mi-2β inhibitor. A Mi-2β inhibitor is a compound or composition capable of inhibiting Mi-2β, degrading Mi-2β, or inhibiting expression of Mi-2β. Mi-2β inhibitors capable of inhibiting Mi-2β include those compounds that can bind to Mi-2β and thereby diminishing its function. Mi-2β inhibitors capable of degrading Mi-2β include those compounds that can bind to Mi-2β recruit one or more additional proteins, such as E3 ubiquitin ligase, thereby enhancing proteolysis of Mi-2β. Mi-2β inhibitors capable of inhibiting expression of Mi-2β include those compounds that interfere with transcription or translation, thereby limiting the amount of Mi-2β present.

As used herein, a "subject" may be interchangeable with "patient" or "individual" and means an animal, which may be a human or non-human animal, in need of treatment. A "subject in need of treatment" may include a subject having a disease, disorder, or condition that is responsive to therapy with a Mi-2β inhibitor. In some embodiments, the subject is responsive to therapy with a Mi-2β inhibitor in combination with an immunotherapy. For example, a "subject in need of treatment" may include a subject in need of treatment for cancer, such as melanoma. In some embodiments, the cancer is resistant to immunotherapy in the absence of the effective amount of the Mi-2β inhibitor. As used herein, the terms "treating" or "to treat" each mean to alleviate symptoms, eliminate the causation of resultant symptoms either on a temporary or permanent basis, and/or to prevent or slow the appearance or to reverse the progression or severity of resultant symptoms of the named disease or disorder. As such, the methods disclosed herein encompass both therapeutic and prophylactic administration.

Methods of increasing T cell cytotoxicity are also provided. The method for increasing T cell cytotoxicity may comprise contacting a cancer cell or tumor with an effective amount of a Mi-23 inhibitor. As demonstrated in the Examples, the use of the Mi-2β inhibitor confers a more favorable microenvironment to cytotoxic T cells that may be used to overcome resistance of a cancer to an immunotherapy. In some embodiments, the Mi-2β inhibitor confers a more favorable microenvironment to cytotoxic T cells that may be used to overcome resistance of a melanoma to an immunotherapy, suitably an anti-PD-1 immunotherapy.

Methods of increasing T cell infiltration of a tumor are also provided. Tumor-infiltrating lymphocytes (TILs) are cells that have migrated towards a tumor and include T cells. TILs may be found in the stroma of a tumor or within the tumor itself. TILs are implicated in killing tumor cells, and the presence in tumors are often associated with better clinical outcomes following surgical, chemotherapeutic, or immunotherapeutic intervention. In some embodiments, administration of a Mi-2β inhibitor to a subject or contacting a cancer cell or tumor with the Mi-2β inhibitor provides for increased T cell infiltration, such as CD8+ T and/or CD4+ T cell infiltration. In some embodiments, administration of a Mi-2β inhibitor to a subject or contacting a cancer cell or tumor with the Mi-2β inhibitor in combination with an immunotherapy provides for increased T cell infiltration, such as CD8+ T and/or CD4+ T cell infiltration.

Methods of upregulating T cell activation markers are also provided. In some embodiments, T cell activation markers such as GZMB, CD69, IFN-γ, CD25, CD107, or combinations thereof are upregulated. In particular embodiments, each of GZMB, CD69, IFN-γ, CD25, and CD107 are upregulated. In some embodiments, administration of a Mi-2β inhibitor to a subject or contacting a cancer cell or tumor with the Mi-2β inhibitor provides for upregulated T cell activation markers. In some embodiments, administration of a Mi-2β inhibitor to a subject or contacting a cancer cell or tumor with the Mi-2β inhibitor in combination with an immunotherapy provides for upregulated T cell activation markers.

Methods of upregulating expression of an IFN-γ-responsive gene are also provided. Many of Mi-2β-controlled IFN-γ-responsive genes function in T cell chemoattraction, antigen presentation, and T cell targeting and activation. In some embodiments, expression of Cxcl9, Cxcl10, Cxcl11, Ccl5, Tap1, CD74, Irf1, Icam1, CD40, Fas, PD-L1 or any combination thereof is upregulated. In particular embodiments, each of Cxcl9, Cxcl10, Cxcl11, Ccl5, Tap1, CD74, Irf1, Icam1, CD40, Fas and PD-L1 are upregulated. In some embodiments, administration of a Mi-2β inhibitor to a subject or contacting a cancer cell or tumor with the Mi-2β inhibitor provides for upregulated IFN-γ-responsive gene expression. In some embodiments, administration of a Mi-2β inhibitor to a subject or contacting a cancer cell or tumor with the Mi-2β inhibitor in combination with an immunotherapy provides for upregulated IFN-γ-responsive gene expression.

Methods of upregulating expression of a cytokine are also provided. Cytokines play a role in inducing and recruiting effector T cells expressing the CXCR3 chemokine receptor into tumor microenvironment to induce anti-tumor immunity. In some embodiments, Cxcl9, Cxcl10, Cxcl11, Ccl5, or any combination thereof is upregulated. In particular embodiments, Cxcl9, Cxcl10, Cxcl11, and Ccl5 are upregulated. In some embodiments, administration of a Mi-2β inhibitor to a subject or contacting a cancer cell or tumor with the Mi-2β inhibitor provides for upregulated cytokine expression. In some embodiments, administration of a Mi-2β inhibitor to a subject or contacting a cancer cell or tumor with the Mi-2β inhibitor in combination with an immunotherapy provides for upregulated cytokine expression.

Methods of upregulating expression of an antigen presenting gene are also provided. In some embodiments, Tap1 or CD74 is upregulated. In particular embodiments, Tap1 and CD74 are upregulated. In some embodiments, administration of a Mi-2β inhibitor to a subject or contacting a cancer cell or tumor with the Mi-2β inhibitor provides for upregulated antigen presenting gene expression. In some embodiments, administration of a Mi-2β inhibitor to a subject or contacting a cancer cell or tumor with the Mi-2β inhibitor in combination with an immunotherapy provides for upregulated antigen presenting gene expression.

Methods of upregulating expression of a regulator of tumor cell immunogenicity are also provided. In some embodiments, Irf1, Icam1, CD40, or any combination thereof is upregulated. In particular embodiments, Irf1, Icam1, and CD40 are upregulated. In some embodiments, administration of a Mi-2β inhibitor to a subject or contacting a cancer cell or tumor with the Mi-2β inhibitor provides for upregulated expression of regulator of tumor cell immunogenicity. In some embodiments, administration of a Mi-2β inhibitor to a subject or contacting a cancer cell or tumor with the Mi-2β inhibitor in combination with an immunotherapy provides for upregulated expression of regulator of tumor cell immunogenicity.

In some embodiments, the methods described herein are practiced in vivo. In other embodiments, the methods described herein are practiced in vitro or ex vivo.

As used herein the term "effective amount" refers to the amount or dose of the Mi-2β inhibitor, upon single or multiple dose administration to the subject, which provides the desired effect. In some embodiments, the effective amount is the amount or dose of the Mi-2β inhibitor, upon single or multiple dose administration to the subject, which provides the desired effect in the subject under diagnosis or treatment. Suitably the desired effect may be increasing the response to an co-administered therapy, overcoming resistance to a co-administered therapy, reducing tumor volume, reducing tumor weight, prolonging survival, increasing T cell cytotoxicity, increasing T cell infiltration of a tumor, upregulating T cell activation markers, upregulating expression of a IFN-γ-responsive gene, upregulating expression of a cytokine, upregulating expression of an antigen presenting gene, upregulating expression of a regulator of tumor cell immunogenicity, or any combination thereof.

An effective amount can be readily determined by those of skill in the art, including an attending diagnostician, by the use of known techniques and by observing results obtained under analogous circumstances. In determining the effective amount or dose of compound administered, a number of factors can be considered by the attending diagnostician, such as: the species of the subject; its size, age, and general health; the degree of involvement or the severity of the disease or disorder involved; the response of the individual subject; the particular compound administered; the mode of administration; the bioavailability characteristics of the preparation administered; the dose regimen selected; the use of concomitant medication; and other relevant circumstances.

In some embodiments, the Mi-2β inhibitor inhibits expression of Mi-2β. In particular embodiments, the Mi-2β inhibitor is an RNA interference (RNAi) agent, such as shRNA, siRNA, miRNA, vectors for expressing shRNA, siRNA, miRNA, and the like. RNAi is a process for inhibiting gene expression. RNA or other nucleic acids that are complementary to endogenous mRNA may be introduced to bind to the target mRNA. The binding functionally inactivates the mRNA. The RNAi may be a small hairpin RNA (shRNA) that includes a region of internal hybridization that creates a hairpin structure. In other embodiments, the RNAi agent is a small interfering RNA (siRNA). When the RNAi agent is transfected into a cell or expressed within a cell, the RNAi agent will knockdown the target mRNA and limit expression/production of the protein encoded by the mRNA.

In other embodiments, the Mi-2β inhibitor is a gene editing agent. The gene editing agent may be suitable for use with a genetic engineering technique, such as a CRISPR gene editing where a nuclease, such as Cas9, and a guide RNA can be introduced into a cell to cut the cell's genome at a desired location. Accordingly, gene editing agents may be used to remove existing genes and/or add new ones that are capable of inhibiting expression of Mi-2β.

In some embodiments, the Mi-2β inhibitor inhibits Mi-2β. The Mi-2β inhibitor may bind to Mi-2β, thereby causing inhibitory activity. In the presence of ATP, Mi-2β induces the histone octamer to translocate along the DNA. The Mi-2β inhibitor may dock into the ATP binding pocket of Mi-2β, thereby inhibiting Mi-2β activity by competitively binding with ATP. Suitably, the Mi-2β inhibitor is selective and specific to Mi-2β ATPase. A Mi-2β inhibitor is selective and specific to Mi-2β ATPase if the Mi-2β inhibitor does not inhibit any of the ATPases in Table 2 by more than 50%. In some embodiments, a selective and specific Mi-2β inhibitor does not inhibit any of the ATPases in Table 2 by more than 45%, 40%, or 35%.

In some embodiments, the Mi-2β inhibitor is a proteolysis targeting chimera (PROTAC). PROTACs are heterobifunctional molecule composed of two active domains and a linker, capable of degrading unwanted proteins. A PROTAC works by inducing selective intracellular proteolysis. PROT-ACs consist of two covalently linked protein-binding molecules: one capable of engaging an E3 ubiquitin ligase, and another that binds to a target protein meant for degradation. Recruitment of the E3 ligase to the target protein results in ubiquitination and subsequent degradation of the target protein via the proteasome.

In some embodiments, the Mi-2β inhibitor is a compound of formula

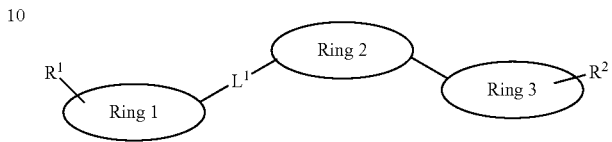

where Ring 1, Ring 2, and Ring 3 are independently selected from unsubstituted or substituted cyclic and heterocyclic rings which containing 3-14 carbon atoms and optionally 1 or more non-carbon atoms selected from N, O, or S; $R^1$ and $R^2$ are independently selected from hydrogen, an unsubstituted or substituted, unbranched or branched, saturated or unsaturated $C_1$-$C_6$ alkyl, an unsubstituted or substituted, unbranched or branched, saturated or unsaturated $C_1$-$C_6$ alkylaryl, an aryl, or -$L^2$-A; $L^1$ and $L^2$ are independently selected from the group consisting of alkylenyl, heteroalkylenyl, and —(($CH_2)_m$—W—($CH_2)_n)_p$—; W is selected from the group consisting of —O—, —N($R^2$)—, —C(=O) N($R^2$)—, —N($R^2$)C(=O)—, —C=C—, and —C≡C—, or W is absent; m is 0, 1, 2, 3, 4, 5, 6, 7, or 8; n is 0, 1, 2, 3, 4, 5, 6, 7, or 8; p is 0, 1, 2, or 3; A is selected from the group consisting of:

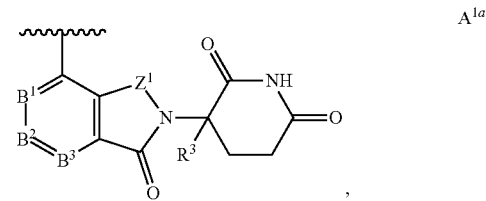

$A^{1a}$

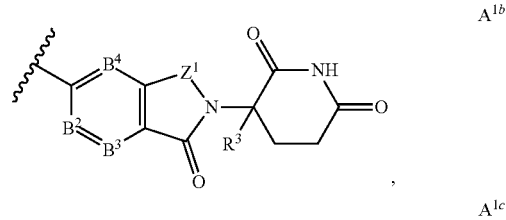

$A^{1b}$

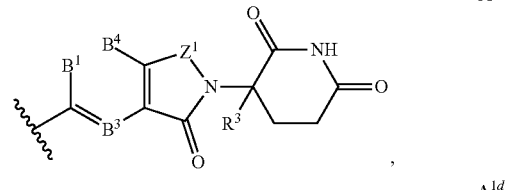

$A^{1c}$

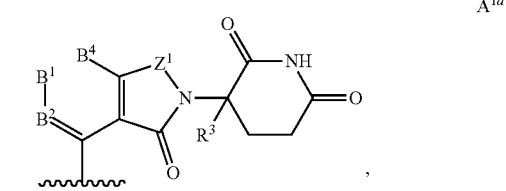

$A^{1d}$

-continued $A^{2a}$

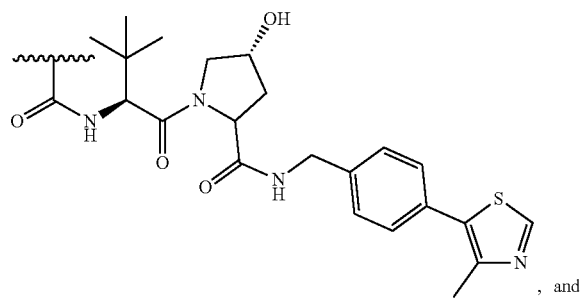

, and $A^{2b}$

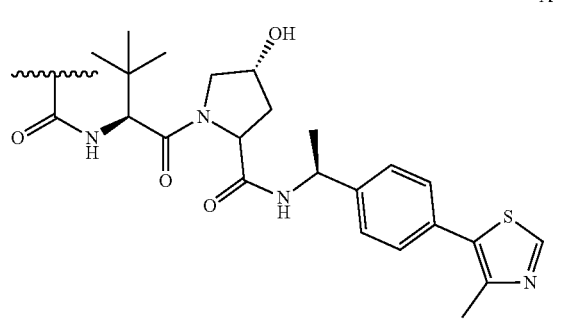

$B^1$, $B^2$, $B^3$, and $B^4$ are independently selected from the group consisting of $C(R^3)$ and N; $R^3$ is selected from the group consisting of hydrogen, deuterium, methyl, and fluoro; $Z^1$ is selected from the group consisting of —$CH_2$—, —$C(=O)$—, and —$N=C(CH_3)$—; wherein the nitrogen atom of —$N=C(CH_3)$— is attached to the hexatomic ring.

In some embodiments, Ring 1 comprises a heterocycle having a protonatable N capable of forming a hydrogen bond with an Asp 873. In some embodiments, Ring 1 is

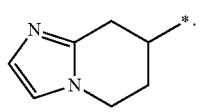

In some embodiments, $L^1$ comprises a carbonyl capable of forming a hydrogen bond with an Gly756. In some embodiments, $L^1$ comprises —NHC(=O)—.

In some embodiments, Ring 2 comprises an aryl or heteroaryl of formula

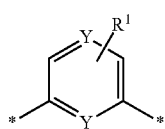

where each Y are independently selected from CH or N and $R^1$ is hydrogen, a halo, or an unsubstituted or substituted, unbranched or branched, saturated or unsaturated $C_1$-$C_6$ alkyl. In other embodiments, Ring 2 is

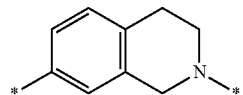 [SMILES: *c1ccc2c(c1)CN(*)CC2]

In some embodiments, Ring 3 comprises a carbonyl capable of forming a hydrogen bond with His727. In some embodiments, Ring 3 is

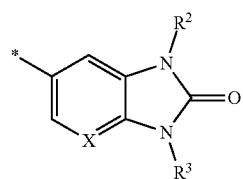

where X is N or CH and $R^2$ and $R^3$ are independently selected from hydrogen, an unsubstituted or substituted, unbranched or branched, saturated or unsaturated $C_1$-$C_6$ alkyl, an unsubstituted or substituted, unbranched or branched, saturated or unsaturated $C_1$-$C_6$ alkylaryl, or an aryl. In other embodiments, Ring 3 is

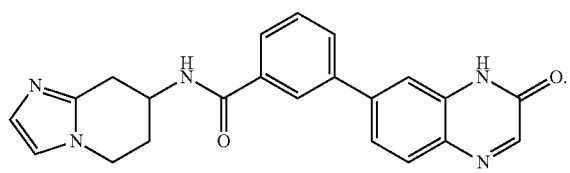

Molecular Weight: 385.4270

In some embodiments, the compound is bifunctional having a structure represented by formula (I):

| Targeting Moiety | Linker | E3 ligase ligand | wherein the targeting moiety represents a Mi-2β inhibitor moiety comprising Rings 1, 2, and 3 that can bind to Mi-2β, the E3 ligase ligand represents a ligand that binds an E3 ubiquitin ligase, and the linker represents a moiety, such as $L^2$, that connects the targeting moiety and the E3 ligase ligand. Exemplary E3 ligase ligands include, without limitation, $A^{1a}$, $A^{1b}$, $A^{1c}$, $A^{2a}$, and $A^{2b}$.

In some embodiments, the Mi-2β inhibitor is a compound of formula (Formula I)

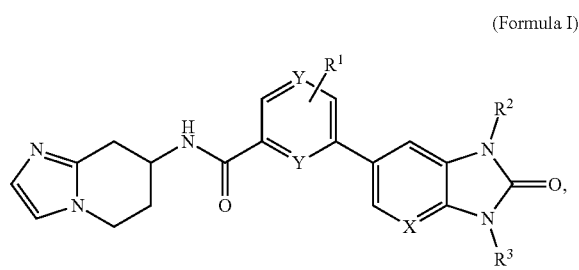

where each X and Y is independently selected from N or CH; $R^1$ is hydrogen, a halo, or an unsubstituted or substituted, unbranched or branched, saturated or unsaturated $C_1$-$C_6$ alkyl; and $R^2$ and $R^3$ are independently selected from hydrogen, an unsubstituted or substituted, unbranched or branched, saturated or unsaturated $C_1$-$C_6$ alkyl, an unsubstituted or substituted, unbranched or branched, saturated or unsaturated $C_1$-$C_6$ alkylaryl, an aryl, or -$L^2$-A.

In some embodiments, each X and Y is CH. In other embodiments, at least one X or Y is N.

In some embodiments, $R^1$ is hydrogen. In other embodiments, $R^1$ is a halo, such as Cl or F. In yet other embodiments, $R^1$ is an unsubstituted or substituted, unbranched or branched, saturated or unsaturated $C_1$-$C_6$ alkyl. Suitably, $R^1$ may be an unsubstituted or substituted methyl, such as —$CH_3$.

In some embodiments, at least one of $R^2$ and $R^3$ is not a hydrogen. In other embodiments, neither $R^2$ nor $R^3$ is a hydrogen.

In some embodiments, at least one of $R^2$ and $R^3$ is an unsubstituted or substituted, unbranched or branched, saturated or unsaturated $C_1$-$C_6$ alkyl. In some embodiments, the alkyl is oxo and/or amine substituted. In particular embodiments, the unsubstituted or substituted, unbranched or branched, saturated or unsaturated $C_1$-$C_6$ alkyl is methyl.

In some embodiments, one of $R^2$ and $R^3$ is an unsubstituted or substituted, unbranched or branched, saturated or unsaturated $C_1$-$C_6$ alkyl and the other is hydrogen. In a particular embodiment, one of $R^2$ and $R^3$ is methyl and the other is hydrogen. Suitably, $R^2$ may be hydrogen and $R^3$ methyl or $R^3$ may be methyl and $R^3$ hydrogen.

In some embodiments, at least one of $R^2$ and $R^3$ is an unsubstituted or substituted, unbranched or branched, saturated or unsaturated $C_1$-$C_6$ alkylaryl. In particular embodiments, the unsubstituted or substituted, unbranched or branched, saturated or unsaturated $C_1$-$C_6$ alkylaryl may be an unsubstituted or substituted methylphenyl or methylpryinidyl.

In some embodiments, at least one of $R^2$ and $R^3$ is an unsubstituted or substituted, unbranched or branched, saturated or unsaturated $C_1$-$C_6$ alkylaryl and the other is hydrogen. In particular embodiments, the unsubstituted or substituted, unbranched or branched, saturated or unsaturated $C_1$-$C_6$ alkylaryl may be an unsubstituted or substituted methylphenyl or methylpryinidyl.

In some embodiments, at least one of $R^2$ and $R^3$ is an aryl. In particular embodiments, the aryl is thiazolyl.

In some embodiments, one of $R^2$ and $R^3$ is an aryl and the other is hydrogen. In particular embodiments, the aryl is thiazolyl.

In some embodiments, one of $R^2$ and $R^3$ is an aryl and the other is an unsubstituted or substituted, unbranched or branched, saturated or unsaturated $C_1$-$C_6$ alkylaryl.

Exemplary compounds are provided in Table 1. In a particular embodiment, the Mi-2β inhibitor is

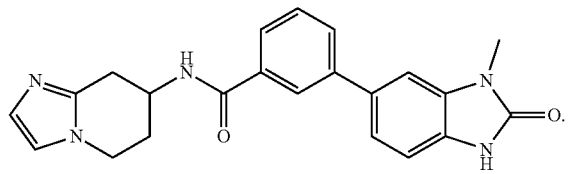 [SMILES: Cn1c(=O)[nH]c2ccc(-c3cccc(C(=O)NC4CCn5ccnc5C4)c3)cc21]

(Z36-MP5)

Mi-2β inhibitors of Formula I may be prepared from the exemplary schemes shown in the Examples. A scheme specific for synthesis of 3-(3-methyl-2-oxo-2,3-dihydro-1H-benzo[d]imidazol-5-yl)-N-(5,6,7,8-tetrahydroimidazo[1,2-a]pyridin-7-yl)benzamide, (Z36-MP5) is also presented. Those of ordinary skill in the art may modify the schemes to prepare any of the Mi-2β inhibitors of Formula I described herein.

As used herein, an asterick "*" or a plus sign "+" may be used to designate the point of attachment for any radical group or substituent group.

The term "alkyl" as contemplated herein includes a straight-chain or branched alkyl radical in all of its isomeric forms, such as a straight or branched group of 1-12, 1-10, or 1-6 carbon atoms, referred to herein as $C_1$-$C_{12}$ alkyl, $C_1$-$C_{10}$-alkyl, and $C_1$-$C_6$-alkyl, respectively.

The term "alkylene" refers to a diradical of an alkyl group. An exemplary alkylene group is —$CH_2CH_2$—.

The term "haloalkyl" refers to an alkyl group that is substituted with at least one halogen. For example, —$CH_2F$, —$CHF_2$, —$CF_3$, —$CH_2CF_3$, —$CF_2CF_3$, and the like The term "heteroalkyl" as used herein refers to an "alkyl" group in which at least one carbon atom has been replaced with a heteroatom (e.g., an O, N, or S atom). One type of heteroalkyl group is an "alkoxyl" group The term "alkenyl" as used herein refers to an unsaturated straight or branched hydrocarbon having at least one carbon-carbon double bond, such as a straight or branched group of 2-12, 2-10, or 2-6 carbon atoms, referred to herein as $C_2$-$C_{12}$-alkenyl, $C_2$-$C_{10}$-alkenyl, and $C_2$-$C_6$-alkenyl, respectively The term "alkynyl" as used herein refers to an unsaturated straight or branched hydrocarbon having at least one carbon-carbon triple bond, such as a straight or branched group of 2-12, 2-10, or 2-6 carbon atoms, referred to herein as C2-C12-alkynyl, C2-C10-alkynyl, and C2-C6-alkynyl, respectively The term "cycloalkyl" refers to a monovalent saturated cyclic, bicyclic, or bridged cyclic (e.g., adamantyl) hydrocarbon group of 3-12, 3-8, 4-8, or 4-6 carbons, referred to herein, e.g., as "$C_{4-8}$-cycloalkyl," derived from a cycloalkane. Unless specified otherwise, cycloalkyl groups are optionally substituted at one or more ring positions with, for example, alkanoyl, alkoxy, alkyl, haloalkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the cycloalkyl group is not substituted, i.e., it is unsubstituted.

The term "cycloalkylene" refers to a diradical of an cycloalkyl group.

The term "partially unsaturated carbocyclyl" refers to a monovalent cyclic hydrocarbon that contains at least one double bond between ring atoms where at least one ring of the carbocyclyl is not aromatic. The partially unsaturated carbocyclyl may be characterized according to the number oring carbon atoms. For example, the partially unsaturated carbocyclyl may contain 5-14, 5-12, 5-8, or 5-6 ring carbon atoms, and accordingly be referred to as a $C_5$-$C_{14}$, $C_5$-$C_{12}$, $C_5$-$C_8$, or $C_5$-$C_6$ membered partially unsaturated carbocyclyl, respectively. The partially unsaturated carbocyclyl may be in the form of a monocyclic carbocycle, bicyclic carbocycle, tricyclic carbocycle, bridged carbocycle, spirocyclic carbocycle, or other carbocyclic ring system. Exemplary partially unsaturated carbocyclyl groups include cycloalkenyl groups and bicyclic carbocyclyl groups that are partially unsaturated. Unless specified otherwise, partially unsaturated carbocyclyl groups are optionally substituted at one or more ring positions with, for example, alkanoyl, alkoxy, alkyl, haloalkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the partially unsaturated carbocyclyl is not substituted, i.e., it is unsubstituted.

The term "aryl" is art-recognized and refers to a carbocyclic or heterocyclyl aromatic group. Representative aryl groups include phenyl, naphthyl, anthracenyl, thiazolyl, and the like. The term "aryl" includes polycyclic ring systems having two or more carbocyclic rings in which two or more carbons are common to two adjoining rings (the rings are "fused rings") wherein at least one of the rings is aromatic and, e.g., the other ring(s) may be cycloalkyls, cycloalkenyls, cycloalkynyls, and/or aryls. Unless specified otherwise, the aromatic ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl or heteroaryl moieties, —CF$_3$, —CN, or the like. In certain embodiments, the aromatic ring is substituted at one or more ring positions with halogen, alkyl, hydroxyl, or alkoxyl. In certain other embodiments, the aromatic ring is not substituted, i.e., it is unsubstituted. In certain embodiments, the aryl group is a 6-10 membered ring structure.

The terms "heterocyclyl" and "heterocyclic group" are art-recognized and refer to saturated, partially unsaturated, or aromatic 3- to 10-membered ring structures, alternatively 3- to 7-membered rings, whose ring structures include one to four heteroatoms, such as nitrogen, oxygen, and sulfur. The number of ring atoms in the heterocyclyl group can be specified using Cx-Cx nomenclature where x is an integer specifying the number of ring atoms. For example, a $C_3$-$C_7$ heterocyclyl group refers to a saturated or partially unsaturated 3- to 7-membered ring structure containing one to four heteroatoms, such as nitrogen, oxygen, and sulfur. The designation "$C_3$-$C_7$" indicates that the heterocyclic ring contains a total of from 3 to 7 ring atoms, inclusive of any heteroatoms that occupy a ring atom position.

The terms "amine" and "amino" are art-recognized and refer to both unsubstituted and substituted amines, wherein substituents may include, for example, alkyl, cycloalkyl, heterocyclyl, alkenyl, and aryl.

The terms "alkoxyl" or "alkoxy" are art-recognized and refer to an alkyl group, as defined above, having an oxygen radical attached thereto. Representative alkoxyl groups include methoxy, ethoxy, tert-butoxy and the like.

An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, and the like.

An "epoxide" is a cyclic ether with a three-atom ring typically include two carbon atoms and whose shape approximates an isosceles triangle. Epoxides can be formed by oxidation of a double bound where the carbon atoms of the double bond form an epoxide with an oxygen atom.

The term "carbonyl" as used herein refers to the radical —C(O)—.

The term "carboxamido" as used herein refers to the radical —C(O)NRR', where R and R' may be the same or different. R and R' may be independently alkyl, aryl, arylalkyl, cycloalkyl, formyl, haloalkyl, heteroaryl, or heterocyclyl.

The term "carboxy" as used herein refers to the radical —COOH or its corresponding salts, e.g. —COONa, etc.

The term "amide" or "amido" as used herein refers to a radical of the form —R$^1$C(O)N(R$^2$)—, —R$^1$C(O)N(R$^2$)R$^3$—, —C(O)NR$^2$R$^3$, or —C(O)NH$_2$, wherein R$^1$, R$^2$ and R$^3$ are independently alkoxy, alkyl, alkenyl, alkynyl, amide, amino, aryl, arylalkyl, carbamate, cycloalkyl, ester, ether, formyl, halogen, haloalkyl, heteroaryl, heterocyclyl, hydrogen, hydroxyl, ketone, or nitro.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," depending on the configuration of substituents around the stereogenic carbon atom. The present invention encompasses various stereo isomers of these compounds and mixtures thereof. Stereoisomers include enantiomers and diastereomers. Mixtures of enantiomers or diastereomers may be designated "(±)" in nomenclature, but the skilled artisan will recognize that a structure may denote a chiral center implicitly. It is understood that graphical depictions of chemical structures, e.g., generic chemical structures, encompass all stereoisomeric forms of the specified compounds, unless indicated otherwise. Compositions comprising substantially purified stereoisomers, epimers, or enantiomers, or analogs or derivatives thereof are contemplated herein (e.g., a composition comprising at least about 90%, 95%, or 99% pure stereoisomer, epimer, or enantiomer.)

The Mi-2β inhibitor utilized in the methods disclosed herein may be formulated as pharmaceutical compositions that include: (a) an effective amount of one or more Mi-2β inhibitors; and (b) one or more pharmaceutically acceptable carriers, excipients, or diluents. The pharmaceutical composition may include the compound in a range of about 0.1 to 2000 mg (preferably about 0.5 to 500 mg, and more preferably about 1 to 100 mg). The pharmaceutical composition may be administered to provide the compound at a daily dose of about 0.1 to 100 mg/kg body weight (preferably about 0.5 to 20 mg/kg body weight, more preferably about 0.1 to 10 mg/kg body weight). In some embodiments, after the pharmaceutical composition is administered to a patient (e.g., after about 1, 2, 3, 4, 5, or 6 hours post-administration), the concentration of the compound at the site of action is about 2 to 10 μM.

The compounds utilized in the methods disclosed herein may be formulated as a pharmaceutical composition in solid dosage form, although any pharmaceutically acceptable dosage form can be utilized. Exemplary solid dosage forms include, but are not limited to, tablets, capsules, sachets, lozenges, powders, pills, or granules, and the solid dosage form can be, for example, a fast melt dosage form, controlled release dosage form, lyophilized dosage form, delayed release dosage form, extended release dosage form, pulsatile release dosage form, mixed immediate release and controlled release dosage form, or a combination thereof.

The compounds utilized in the methods disclosed herein may be formulated as a pharmaceutical composition that includes a carrier. For example, the carrier may be selected from the group consisting of proteins, carbohydrates, sugar, talc, magnesium stearate, cellulose, calcium carbonate, and starch-gelatin paste.

The compounds utilized in the methods disclosed herein may be formulated as a pharmaceutical composition that includes one or more binding agents, filling agents, lubricating agents, suspending agents, sweeteners, flavoring agents, preservatives, buffers, wetting agents, disintegrants, and effervescent agents.

Suitable diluents may include pharmaceutically acceptable inert fillers.

The compounds utilized in the methods disclosed herein may be formulated as a pharmaceutical composition for delivery via any suitable route. For example, the pharmaceutical composition may be administered via oral, intravenous, intramuscular, subcutaneous, topical, and pulmonary route. Examples of pharmaceutical compositions for oral administration include capsules, syrups, concentrates, powders and granules.

The compounds utilized in the methods disclosed herein may be administered in conventional dosage forms prepared by combining the active ingredient with standard pharmaceutical carriers or diluents according to conventional procedures well known in the art. These procedures may involve mixing, granulating and compressing or dissolving the ingredients as appropriate to the desired preparation.

Pharmaceutical compositions comprising the compounds may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

The compounds employed in the compositions and methods disclosed herein may be administered as pharmaceutical compositions and, therefore, pharmaceutical compositions incorporating the compounds are considered to be embodiments of the compositions disclosed herein. Such compositions may take any physical form, which is pharmaceutically acceptable; illustratively, they can be orally administered pharmaceutical compositions. Such pharmaceutical compositions contain an effective amount of a disclosed compound, which effective amount is related to the daily dose of the compound to be administered. Each dosage unit may contain the daily dose of a given compound or each dosage unit may contain a fraction of the daily dose, such as one-half or one-third of the dose. The amount of each compound to be contained in each dosage unit can depend, in part, on the identity of the particular compound chosen for the therapy and other factors, such as the indication for which it is given. The pharmaceutical compositions disclosed herein may be formulated so as to provide quick, sustained, or delayed release of the active ingredient after administration to the patient by employing well known procedures. The compounds for use according to the methods of disclosed herein may be administered as a single compound or a combination of compounds.

As indicated above, pharmaceutically acceptable salts of the compounds are contemplated and also may be utilized in the disclosed methods. The term "pharmaceutically acceptable salt" as used herein, refers to salts of the compounds which are substantially non-toxic to living organisms. Typical pharmaceutically acceptable salts include those salts prepared by reaction of the compounds as disclosed herein with a pharmaceutically acceptable mineral or organic acid or an organic or inorganic base. Such salts are known as acid addition and base addition salts. It will be appreciated by the skilled reader that most or all of the compounds as disclosed herein are capable of forming salts and that the salt forms of pharmaceuticals are commonly used, often because they are more readily crystallized and purified than are the free acids or bases.

Pharmaceutically acceptable esters and amides of the compounds can also be employed in the compositions and methods disclosed herein.

In addition, the methods disclosed herein may be practiced using solvate forms of the compounds or salts, esters, and/or amides, thereof. Solvate forms may include ethanol solvates, hydrates, and the like.

The Mi-2β inhibitors described herein may be used in combination with one or more additional therapeutic modalities or therapeutic agents. In some embodiments, the additional therapeutic modality or therapeutic agent takes advantages of one or more resultant properties that are a consequence of administration or use of the Mi-2β inhibitor described herein, including increasing T cell cytotoxicity, increasing T cell infiltration of a tumor, upregulating T cell activation markers, upregulating expression of a IFN-γ-responsive gene, upregulating expression of a cytokine, upregulating expression of an antigen presenting gene, upregulating expression of a regulator of tumor cell immunogenicity, or any combination thereof. As a result, combination therapies including the administration of the Mi-2β inhibitors described herein with one or more immunotherapies or immunotherapeutic agents, such as checkpoint inhibitor therapy, antibody therapy, CAR T cell therapy, T cell transfer therapy, immune system modulator therapy, cytokine therapy, cancer vaccine therapy, oncolytic virus therapy as well as other therapies may be employed. The therapeutic modality or therapeutic agent used in combination with the Mi-2β inhibitor may be contemporaneously administered with the Mi-2β inhibitor. In other embodiments, the co-administered therapeutic modality may be administered before or after the administration of the compounds described herein. In some embodiments, use of the Mi-2β inhibitor overcomes resistance to the additional therapeutic modality or therapeutic agent.

In some embodiments, Mi-2β inhibitors as described herein are used in combination with a checkpoint inhibitor such as a PD-1, PD-L1, or CTLA-4 checkpoint inhibitor. PD-1 and PD-L1 inhibitors act to inhibit the association of the programmed death-ligand 1 (PD-L1) with its receptor, programmed cell death protein 1 (PD-1). The interaction of PD-L1 on the tumor cells with PD-1 on a T-cell reduces T-cell function signals to prevent the immune system from attacking tumor cells. In some embodiments, inhibitors targeting checkpoints PD-1 (e.g., Pembrolizumab, Nivolumab, and Cemiplimab), PD-L1 (e.g., Atezolizumab, Avelumab, and Durvalumab), and CTLA-4 (e.g., Ipilimumab).

Chromatin regulatory factors may be necessary for regulating resistance to anti-PD-1 antibody treatment in melanoma, (14), such as EZH2 (25) and ARID1A (26). EZH2 inhibition enhances T cell-targeting immunotherapies in vivo (24, 25) whereas ARID1A interacts with EZH2 to inhibit IFN-response gene expression in cancer cells (26). In addition, the PBAF form of the SWI/SNF chromatin remodeling complex, especially the Pbrm1, Arid2, and Brd7 components, regulate tumor cell resistance to T cell-mediated killing through control of interferon-stimulated gene (ISG) expression. The expression of PBRM1 and ARID2 inhibits the expression of T cell cytotoxicity genes and subsequent repression of infiltrated cytotoxic T cells (20, 21). Mutations in other PBAF complex members, such as ARID2 and BRD7, occur in melanoma and overcome resistance of tumor cells to T cell-mediated cytotoxicity (21, 58). The Examples demonstrate that Mi-2β, a chromatin remodeling enzyme, regulates resistance to T cell-mediated cytotoxicity and immunotherapy.

A successful anti-tumor immune response following PD-1/PD-L1 blockade is believed to require reactivation and proliferation of clones of antigen-experienced T cells in the tumor microenvironment (13, 59). Inadequate anti-tumor T-cell effector function may preclude proper T cell function to limit the efficacy of immune checkpoint inhibitors (13, 60). Those important factors include high levels of immune suppressive cytokines or chemokines, and recruitment of immune suppressive cells, such as myeloid-derived suppressor cells (MDSCs) and regulatory T cells (Tregs) (59). The Examples show that depletion or inhibition of a cancer cell-intrinsic epigenetic modulator, Mi-2β, changes the tumor microenvironment to fuel CD8 T cell-mediated anti-tumor immunity, at least in part because Mi-2β is involved in suppression of genes downstream from IFN-γ, and IFN-α signaling.

Targeted therapies have significantly improved clinical outcomes in patients with various cancers including BRAF and MEK/ERK inhibitors in metastatic melanoma (61-63). Targeted therapies have been tested widely in combination with anti-PD-1 therapies, and substantially contribute to anti-tumor immunity with immunotherapy (13, 64, 65), including by increasing tumor antigen expression (66, 67), enhancing the function of effector T cells (68, 69), and overcoming the immune suppressive microenvironment of tumor (70, 71). A variety of clinical trials using a combination of MAPK pathway targeted therapy and immunotherapy in advanced metastatic melanoma have been performed and evaluated (72). However, unexpected toxic side effects are reported in combinational clinical trials (73-75). In addition, the immune microenvironment is a source of resistance to MAPK pathway-targeted therapy which is reinforced during combinational treatment, while on the other hand, the increased TNF-α signaling and tumor-associated macrophages following MAPK blockade may be involved in developing an immunosuppressive tumor microenvironment (76). Here, the effective inhibitors, such as Z36-MP5, can target Mi-2β ATPase activity. Using both syngeneic and transgenic mouse models, the Mi-2β inhibitor induced a response of otherwise anti-PD-1-resistant melanoma to immunotherapy through rescue of interferon-stimulated gene (ISG) expression. The ability to target Mi-2β and recover ISG and inflammatory signals by Z36-MP5 or other Mi-2β inhibits provides for combinational immunotherapy in patients with melanoma and other immune resistant cancers.

MISCELLANEOUS

Unless otherwise specified or indicated by context, the terms "a", "an", and "the" mean "one or more." For example, "a molecule" should be interpreted to mean "one or more molecules."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion additional components other than the components recited in the claims. The term "consisting essentially of" should be interpreted to be partially closed and allowing the inclusion only of additional components that do not fundamentally alter the nature of the claimed subject matter.

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

All references, including publications, patent applications, and patents, cited herein are hereby incorporated by reference to the same extent as if each reference were individually and specifically indicated to be incorporated by reference and were set forth in its entirety herein.

Preferred aspects of this invention are described herein, including the best mode known to the inventors for carrying out the invention. Variations of those preferred aspects may become apparent to those of ordinary skill in the art upon reading the foregoing description. The inventors expect a person having ordinary skill in the art to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Examples

Scheme. Synthesis of Z36-MP5

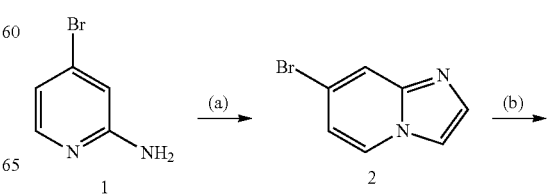

-continued

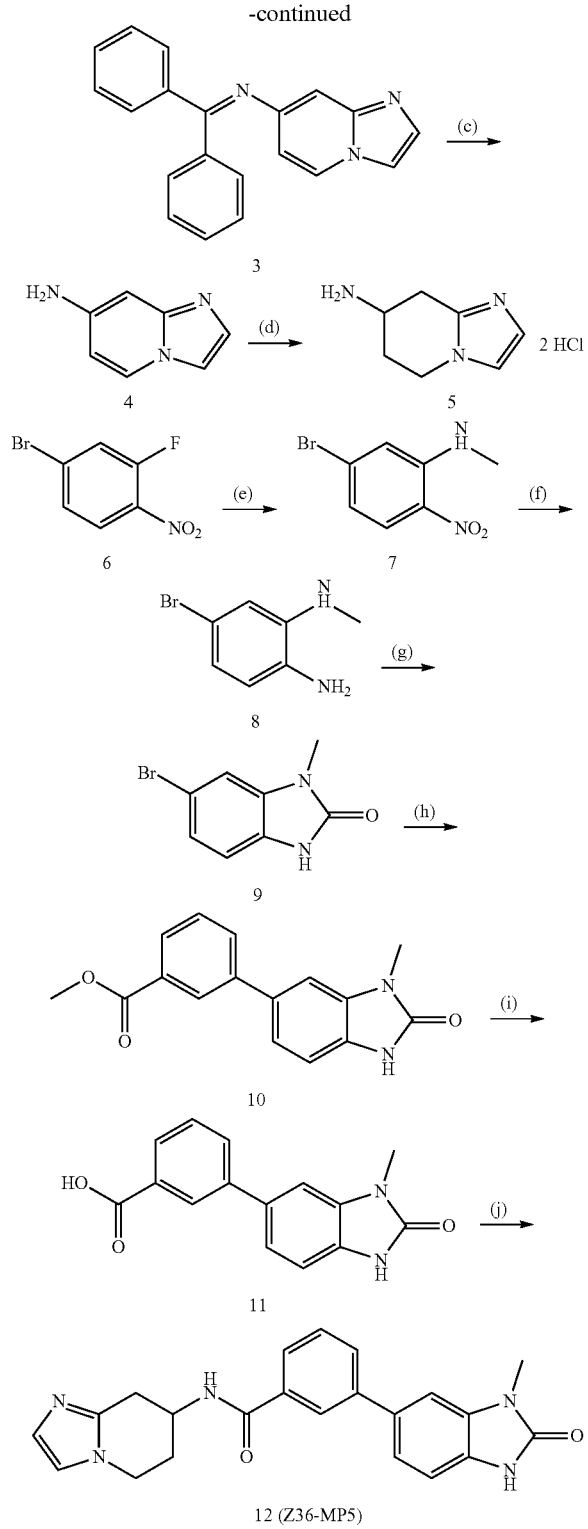

12 (Z36-MP5)

Compound Synthesis

Flash chromatography was performed using silica gel (200-300 mesh). All reactions were monitored by thin-layer chromatography (TLC) on silica gel plates. 1H-NMR spectral data were recorded on Varian Mercury 400 NMR spectrometer, and 13C-NMR was recorded on Varian Mercury 126 NMR spectrometer at ambient temperature. Chemicals shifts (δ) were reported in ppm, coupling constants (J) were in hertz, and the splitting patterns were described as follows: s for singlet; d for doublet; t for triplet; q for quartet; and m for multiplet. Mass spectrometry was conducted using a Thermo Fisher LCQ-DECA spectrometer (ESI-MS mode). All tested compounds were purified to ≥95% purity as determined by high performance liquid chromatography (HPLC).

Reagents and conditions: (a) 50% chloroacetaldehyde in $H_2O$, EtOH, 80° C., 2 h; (b) benzophenone imine, $Pd_2(dba)_3$, BINAP, t-BuONa, toluene, 85° C., overnight; (c) 4 M HCl in 1,4-dioxane, room temperature, 24 h; (d) 4 M HCl in 1,4-dioxane, Pd/C, MeOH, 50° C., 24 h; (e) 2 M methylamine solution in MeOH, EtOH, room temperature, overnight; (f) zinc powder, $NH_4Cl$, $H_2O$, MeOH, room temperature, 1 h; (g) carbonyldiimidazole, ACN, reflux, overnight; (h) 3-methoxycarbonylphenylboronic acid, 2.5 M $Na_2CO_3$, $Pd(PPh_3)_2Cl_2$, LiCl, EtOH, toluene, sealed tube, 95° C., overnight; (i) LiOH·$H_2O$, THF, MeOH, $H_2O$, rt, overnight; (j) 5, HATU, DIPEA, DMF, rt, overnight.

Step a: synthesis of 7-bromoimidazo[1,2-a]pyridine, 2

A mixture of 4-bromopyridin-2-amine (1, 10.4 g, 60.0 mmol) and 50% chloroacetaldehyde in $H_2O$ (18.8 g, 120.0 mmol) in EtOH (150.0 mL) was stirred at 75° C. for 2 hours. After the complete conversion detected by TCL analysis (DCM:MeOH=10:1), the reaction mixture was concentrated under vacuum to afford a yellow thick oil. EA (50.0 mL) was added to the thick oil and the resulting suspension was stirred at room temperature for 30 minutes to generate a yellow suspension. Then the suspension was filtered to afford a light yellow solid which was washed with EA (20.0 mL) and hexanes (20.0 mL) to afford an off-white solid as 7-bromoimidazo[1,2-a]pyridine (2, 11.1 g, 93.7% yields). LC-MS: 197.12 [M]+.

Step b: synthesis of N-(imidazo[1,2-a]pyridin-7-yl)-1,1-diphenylmethanimine, 3

A mixture of 7-bromoimidazo[1,2-a]pyridine (2, 0.4 g, 2.0 mmol), benzophenone imine (0.7 g, 4.0 mmol), t-BuONa (0.4 g, 4.0 mmol), $Pd_2(dba)_3$ (92.0 mg, 0.1 mmol), and BINAP (93.0 mg, 0.15 mmol) in toluene (10.0 mL) was degassed with N2 for 15 minutes. Then the reaction mixture was allowed to stir at 85° C. overnight. After cooling to room temperature, the resulting mixture was diluted with water (50.0 mL) and extracted with EA (50.0 mL*3). The combined organic layers were washed with brine (50.0 mL), dried over anhydrous $Na_2SO_4$, filtered, concentrated under vacuum, absorbed onto silica gel, and purified via flash chromatography (DCM:MeOH=30:1) to afford a yellow oil as N-(imidazo[1,2-a]pyridin-7-yl)-1,1-diphenylmethanimine (3, 0.4 g, 69% yields). LC-MS: 297.40 [M]+.

Step c: synthesis of imidazo[1,2-a]pyridin-7-amine, 4

A solution of N-(imidazo[1,2-a]pyridin-7-yl)-1,1-diphenylmethanimine (3, 0.4 g, 1.4 mmol) in 4 M hydrogen chloride solution in 1,4-dioxane was stirred at room temperature for 24 hours to afford a dark brown suspension. After the complete conversion detected by LC-MS analysis, the resulting mixture was filtered to obtain a brown solid which was washed with DCM (5.0 mL) to afford a dark yellow solid. The dark yellow solid was dissolved in MeOH (10.0 mL), absorbed onto celite, and purified via C18 reversed-phase flash column chromatography (H₂O:MeOH=9:1) to afford a brown solid as imidazo[1,2-a]pyridin-7-amine (4, 0.15 g, 56% yields). LC-MS: 133.41 [M]⁺.

Step d: synthesis of 5,6,7,8-tetrahydroimidazo[1,2-a]pyridin-7-amine dihydrochloride, 5

A mixture of imidazo[1,2-a]pyridin-7-amine (4, 0.1 g, 0.78 mmol), Pd/C (20.0 mg, 20% wt), and 4 M hydrogen chloride solution in 1,4-dioxane (0.2 mL) in MeOH (5.0 mL) was stirred at 50° C. for 24 hours. After the complete conversion detected by TLC (DCM:MeOH=10:1) and LC-MS analysis, the resulting mixture was concentrated under vacuum to afford a yellow solid. DCM (5.0 mL) was added to the yellow solid and the resulting suspension was stirred at room temperature for 15 minutes to generate a light yellow suspension. Then the suspension was filtered to afford a light yellow solid which was washed with a combined solution of DCM and MeOH (DCM:MeOH=10:1, 5 mL) to afford an beige solid as 5,6,7,8-tetrahydroimidazo[1,2-a]pyridin-7-amine dihydrochloride (5, 0.1 g, 61% yields). LC-MS: 137.10 [M]⁺.

Step e: synthesis of 5-bromo-N-methyl-2-nitroaniline, 7

To a solution of 4-bromo-2-fluoro-1-nitrobenzene (6, 4.4 g, 20.0 mmol) in EtOH (50.0 mL) was added 2 M methylamine solution in MeOH (12.0 mL, 240.0 mmol). The reaction mixture was stirred at room temperature overnight. After the complete conversion detected LC-MS analysis, the resulting mixture was concentrated under vacuum, and the residual orange solid was partitioned between water (200.0 mL) and EA (200.0 mL*3). The combined organic phases were washed with brine, dried over anhydrous Na₂SO₄, filtered, concentrated under vacuum to afford a bright orange solid as 5-bromo-N-methyl-2-nitroaniline (7, 4.4 g, 97% yields). LC-MS: 232.30 [M+H]⁺.

Step f: synthesis of 5-bromo-N¹-methylbenzene-1,2-diamine, 8

To a suspension of 5-bromo-N-methyl-2-nitroaniline (7, 3.0 g, 13.0 mmol) and ammonium chloride (7.0 g, 130.0 mmol) in MeOH (17.0 mL) and water (35.0 mL) was added zinc powder (4.2 g, 65.0 mmol) at 0° C. The reaction mixture was allowed to stir at room temperature for 1 hour. After the complete conversion detected LC-MS analysis, the resulting mixture was filtered and the filtered liquid was concentrated under vacuum to remove the MeOH. Then the residual solution was neutralized by the addition of saturated NaHCO₃ aqueous solution to PH 7-8 and extracted with EA (100.0 mL*3). The combined organic phases were washed with brine, dried over anhydrous Na₂SO₄, filtered, concentrated under vacuum, absorbed onto aluminum oxide, and purified via flash column chromatography (EA:hexanes=1:99 to 1:1) to afford a black solid as 5-bromo-N¹-methylbenzene-1,2-diamine (8, 1.8 g, 71% yields). LC-MS: 201.01 [M]⁺.

Step g: synthesis of 6-bromo-1-methyl-1,3-dihydro-2H-benzo[d]imidazol-2-one, 9

To a solution of 5-bromo-N¹-methylbenzene-1,2-diamine (8, 1.0 g, 5.0 mmol) in acetonitrile (20.0 mL) was added carbonyldiimidazole (4.0 g, 24.9 mmol). The reaction mixture was refluxed at 85° C. overnight. After cooling, the resulting mixture was concentrated under vacuum to afford a dark brown residue. The residue was partitioned between water (50.0 mL) and EA (50.0 mL*3). The combined organic layers were washed with brine, dried over anhydrous Na₂SO₄, filtered, concentrated under vacuum, absorbed onto silica gel, and purified via flash column chromatography (DCM:MeOH=99:1 to 95:5) to afford a brown-orange solid as 6-bromo-1-methyl-1,3-dihydro-2H-benzo[d]imidazol-2-one (9, 0.5 g, 41% yields). LC-MS: 227.01 [M]⁺.

Step h: synthesis of methyl 3-(3-methyl-2-oxo-2,3-dihydro-1H-benzo[d]imidazol-5-yl)benzoate, 10

A mixture of 6-bromo-1-methyl-1,3-dihydro-2H-benzo[d]imidazol-2-one (9, 70.0 mg, 0.3 mmol), 3-methoxycarbonylphenylboronic acid (80.1 mg, 0.45 mmol), LiCl (38.2 mg, 0.9 mmol), freshly prepared 2.5 M Na₂CO₃ aqueous solution (0.30 mL, 0.75 mmol), and bis(triphenylphosphine)palladium(II) dichloride (10.6 mg, 0.16 mmol) in toluene (4.0 mL) and EtOH (4.0 mL) was degassed with N2 for 15 minutes. The reaction mixture was sealed in a 20.0 mL vial and stirred at 95° C. overnight. After the complete conversion detected LC-MS analysis, the resulting mixture was concentrated under vacuum, absorbed onto silica gel, and purified via flash column chromatography (DCM:MeOH=99:1 to 10:1) to afford a white solid as methyl 3-(3-methyl-2-oxo-2,3-dihydro-1H-benzo[d]imidazol-5-yl)benzoate (10, 40.0 mg, 47% yields). LC-MS: 283.15 [M]⁺.

Step i: synthesis of 3-(3-methyl-2-oxo-2,3-dihydro-1H-benzo[d]imidazol-5-yl)benzoic acid, 11

To a solution of methyl 3-(3-methyl-2-oxo-2,3-dihydro-1H-benzo[d]imidazol-5-yl)benzoate (10, 40.0 mg, 0.14 mmol) in MeOH (2.1 mL) and tetrahydrofuran (2.1 mL) was added a solution of LiOH·H₂O (8.9 mg, 0.21 mol) in water (0.7 mL). The reaction mixture was stirred at room temperature overnight. After the complete conversion detected LC-MS analysis, the resulting mixture was concentrated under vacuum to remove the organic solvents and diluted with water (2.0 mL). The aqueous solution was acidified via the addition of 2 M HCl solution in water to PH 4 to obtain a white suspension. After filtration, the off-white solid collected was washed with Et₂O (0.5 mL) to afford a white solid as 3-(3-methyl-2-oxo-2,3-dihydro-1H-benzo[d]imidazol-5-yl)benzoic acid (11, 30.0 mg, 80% yields). LC-MS: 269.39 [M]⁺.

Step j: synthesis of 3-(3-methyl-2-oxo-2,3-dihydro-1H-benzo[d]imidazol-5-yl)-N-(5,6,7,8-tetrahydroimidazo[1,2-a]pyridin-7-yl)benzamide, (Z36-MP5)

A mixture of 3-(3-methyl-2-oxo-2,3-dihydro-1H-benzo[d]imidazol-5-yl)benzoic acid (11, 30.0 mg, 0.11 mmol), 5,6,7,8-tetrahydroimidazo[1,2-a]pyridin-7-amine dihydrochloride (5, 19.4 mg, 0.11 mmol), and N,N-diisopropylethylamine (0.12 mL, 0.66 mmol) in anhydrous DMF was stirred at 0° C. for 5 minutes. The HATU (50.2 mg, 0.13 mmol) was added in one portion. The reaction mixture was stirred at room temperature overnight. After the complete conversion detected LC-MS analysis, the resulting mixture was diluted with water (20.0 mL) and extracted with EA (20.0 mL*3). The combined organic layers were washed with brine, dried over anhydrous Na₂SO₄, filtered, concentrated under vacuum, absorbed onto silica gel, and purified via flash column chromatography (DCM:MeOH=99:1 to 10:1) to afford a white solid as 3-(3-methyl-2-oxo-2,3-dihydro-1H-benzo[d]imidazol-5-yl)-N-(5,6,7,8-tetrahydroimidazo[1,2-a]pyridin-7-yl)benzamide (12, 10.2 mg, 23.9% yields). LC-MS: 388.09 [M+H]⁺.

Exemplary Compounds

TABLE 1

Exemplary Mi-2β inhibitors.

| Name | Structure |
|---|---|
| ZW-7-015 (Z36-MP5) | Molecular Weight: 387.44 |
| ZW-7-023 | Molecular Weight: 402.46 |
| ZW-7-060 | Molecular Weight: 444.50 |
| ZW-7-061 | Molecular Weight: 471.52 |
| ZW-7-062 | Molecular Weight: 457.51 |

TABLE 1-continued
Exemplary Mi-2β inhibitors.
| Name | Structure |
|---|---|
| ZW-6-194 | 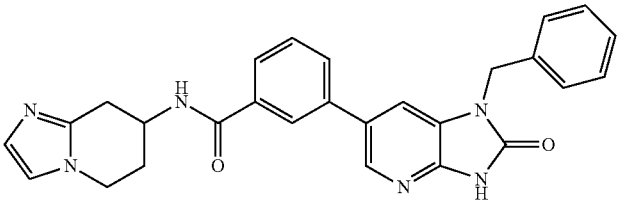 [SMILES: O=C(NC1CCn2ccnc2C1)c1cccc(-c2cnc3[nH]c(=O)n(Cc4ccccc4)c3c2)c1]<br>Molecular Weight: 464.53 |
| ZW-7-053 | 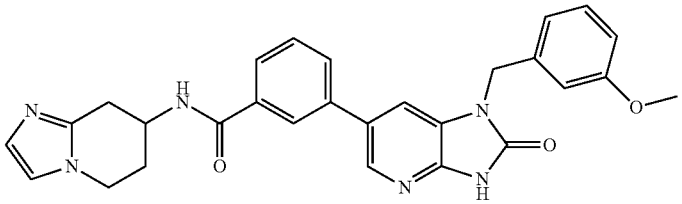 [SMILES: COc1cccc(Cn2c(=O)[nH]c3ncc(-c4cccc(C(=O)NC5CCn6ccnc6C5)c4)cc32)c1]<br>Molecular Weight: 494.56 |
| ZW-7-059 | 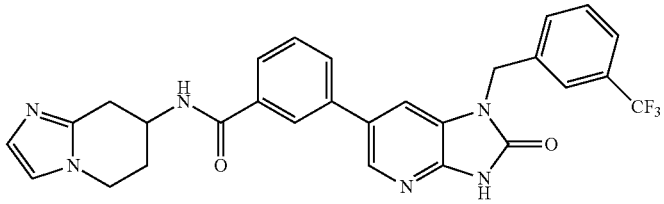 [SMILES: O=C(NC1CCn2ccnc2C1)c1cccc(-c2cnc3[nH]c(=O)n(Cc4cccc(C(F)(F)F)c4)c3c2)c1]<br>Molecular Weight: 532.53 |
| ZW-7-052 | 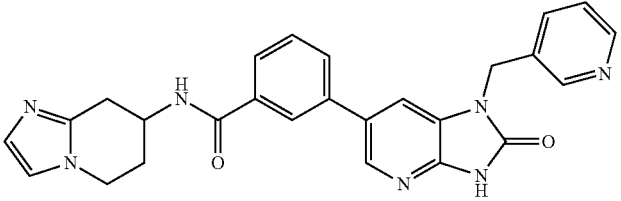 [SMILES: O=C(NC1CCn2ccnc2C1)c1cccc(-c2cnc3[nH]c(=O)n(Cc4cccnc4)c3c2)c1]<br>Molecular Weight: 465.52 |
| ZW-7-008 | 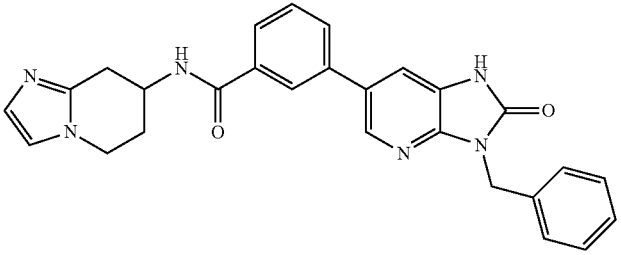 [SMILES: O=C(NC1CCn2ccnc2C1)c1cccc(-c2cnc3c(c2)[nH]c(=O)n3Cc2ccccc2)c1]<br>Molecular Weight: 464.53 |

TABLE 1-continued
Exemplary Mi-2β inhibitors.
| Name | Structure |
|---|---|
| ZW-7-005 | 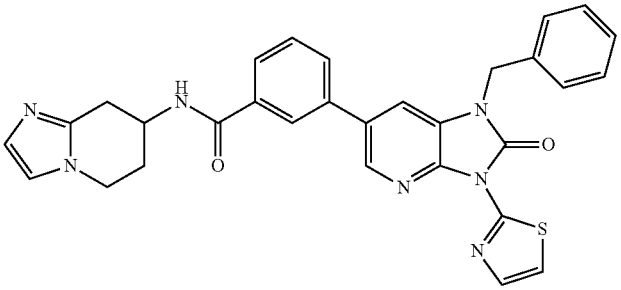 [SMILES: O=C(NC1CCn2ccnc2C1)c1cccc(-c2cnc3c(c2)n(Cc2ccccc2)c(=O)n3-c2nccs2)c1]<br>Molecular Weight: 547.64 |
| SJW-5-200 | 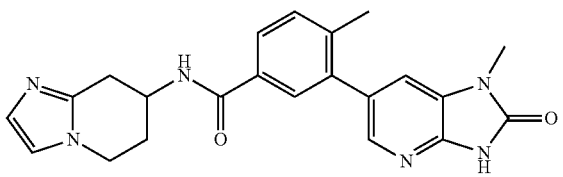 [SMILES: Cc1ccc(C(=O)NC2CCn3ccnc3C2)cc1-c1cnc2[nH]c(=O)n(C)c2c1]<br>Molecular Weight: 402.46 |
| SJW-6-004 | 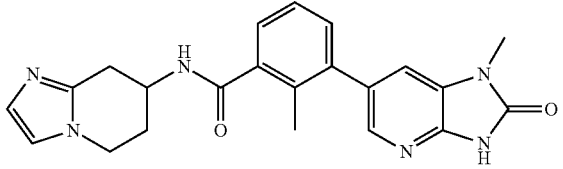<br>Molecular Weight: 402.46 |
| SJW-6-006 | 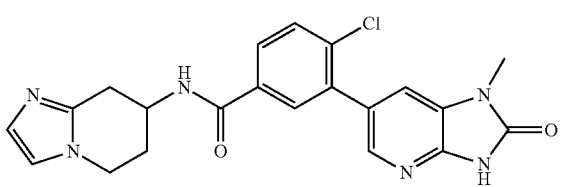 [SMILES: Cn1c(=O)[nH]c2ncc(-c3cc(C(=O)NC4CCn5ccnc5C4)ccc3Cl)cc21]<br>Molecular Weight: 422.87 |
| SJW-6-015 | 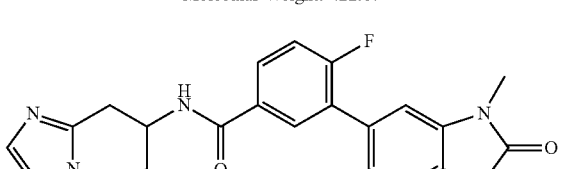<br>Molecular Weight: 406.42 |
| SJW-6-018 (Z36) | 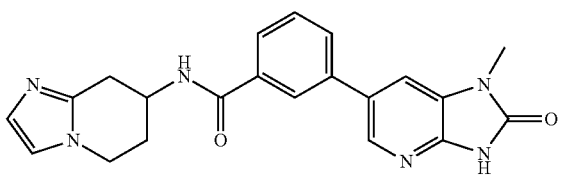<br>Molecular Weight: 388.43 |

TABLE 1-continued
Exemplary Mi-2β inhibitors.
| Name | Structure |
| --- | --- |
| SJW-6-022 | 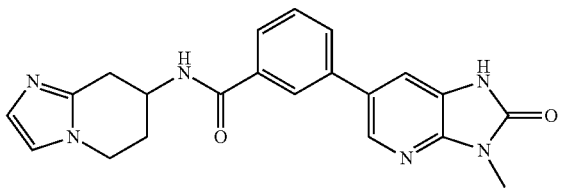 [SMILES: Cn1c(=O)[nH]c2cc(-c3cccc(C(=O)NC4CCn5ccnc5C4)c3)cnc21]
Molecular Weight: 388.43 |
| HT-MI2B-001 | 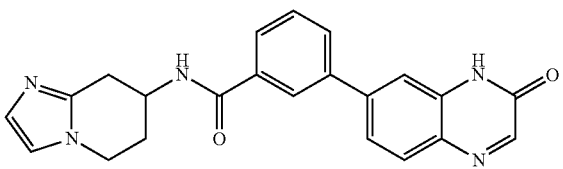 [SMILES: O=C(NC1CCn2ccnc2C1)c1cccc(-c2ccc3ncc(=O)[nH]c3c2)c1]
Molecular Weight: 385.4270 |
| HT-MI2B-002 | 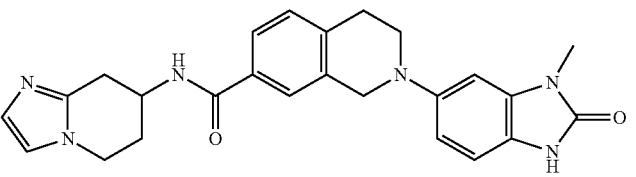 [SMILES: Cn1c(=O)[nH]c2ccc(N3CCc4ccc(C(=O)NC5CCn6ccnc6C5)cc4C3)cc21]
Molecular Weight: 442.5230 |
| HT-MI2B-003 | 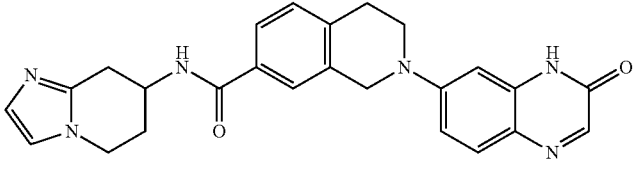 [SMILES: O=C(NC1CCn2ccnc2C1)c1ccc2c(c1)CN(c1ccc3ncc(=O)[nH]c3c1)CC2]
Molecular Weight: 440.5070 |
| HT-MI2B-004 | 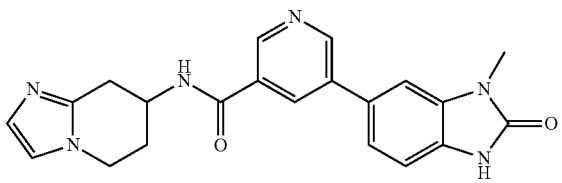 [SMILES: Cn1c(=O)[nH]c2ccc(-c3cncc(C(=O)NC4CCn5ccnc5C4)c3)cc21]
Molecular Weight: 388.4310 |
| HT-MI2B-005 | 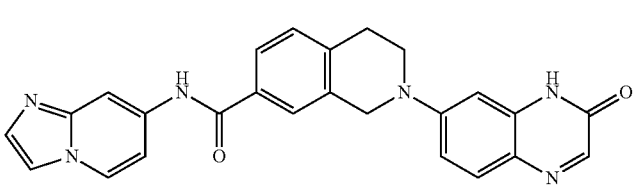 [SMILES: O=C(Nc1ccn2ccnc2c1)c1ccc2c(c1)CN(c1ccc3ncc(=O)[nH]c3c1)CC2]
Molecular Weight: 436.4750 |

TABLE 1-continued
Exemplary Mi-2β inhibitors.
| Name | Structure |
|---|---|
| ZW-7-108 | 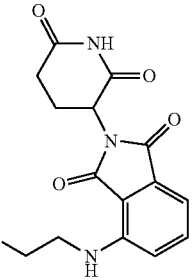 |
| ZW-7-110 | 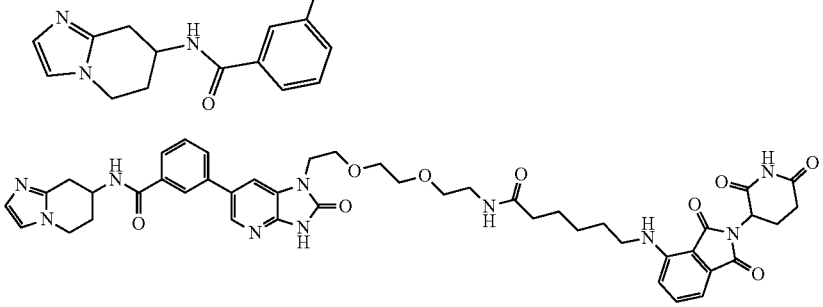 |
| ZW-7-109 | 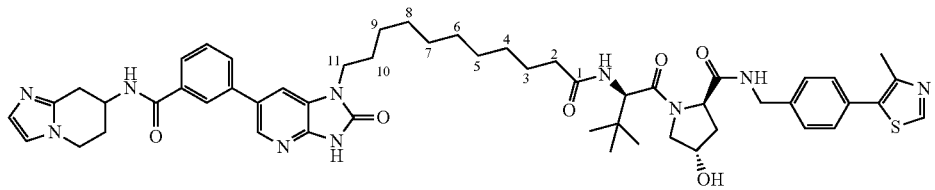 [SMILES: Cc1ncsc1-c1ccc(CNC(=O)[C@H]2C[C@H](O)CN2C(=O)[C@H](NC(=O)CCCCCCCCCCn2c(=O)[nH]c3ncc(-c4cccc(C(=O)NC5CCn6ccnc6C5)c4)cc32)C(C)(C)C)cc1] |
General Synthesis of Compounds
The disclosed compounds of the present disclosure can be prepared by the synthetic schemes outlined below.
General Scheme 1
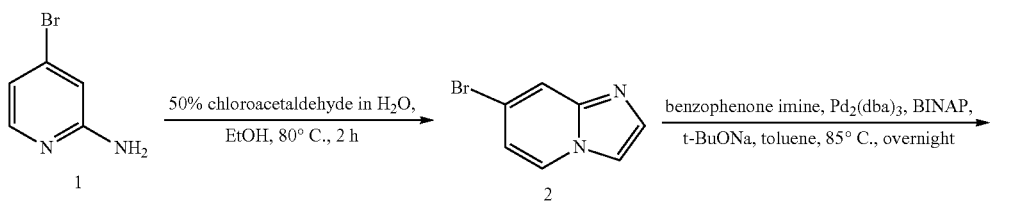
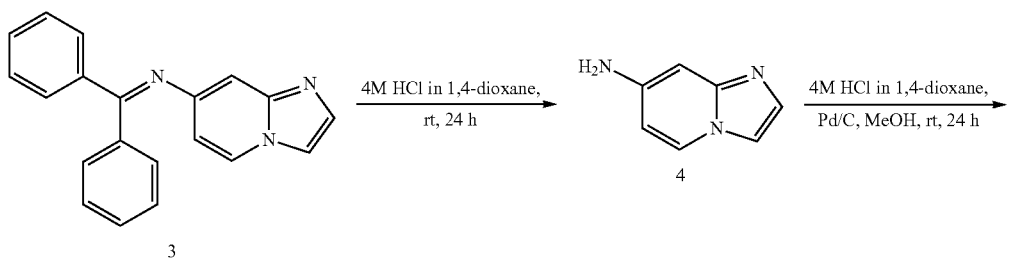

-continued
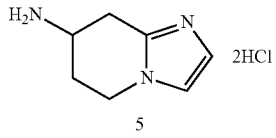
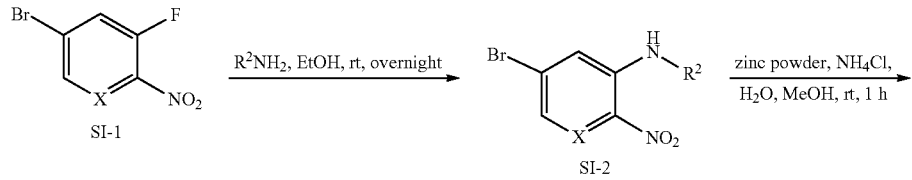
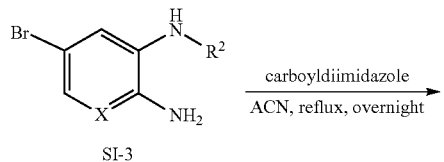
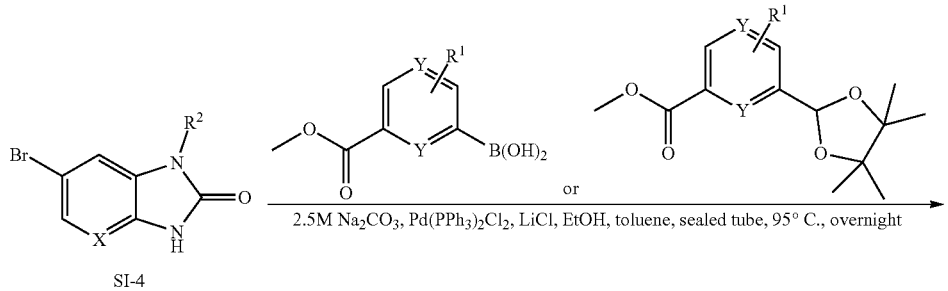
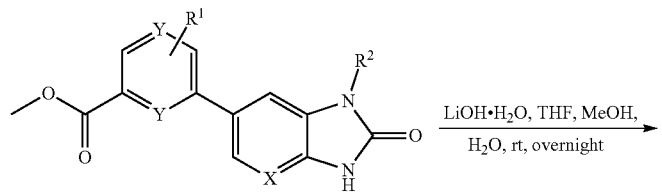
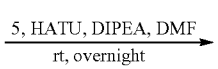
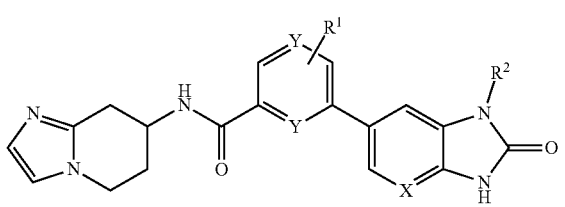
Formula I-1

General Scheme 2
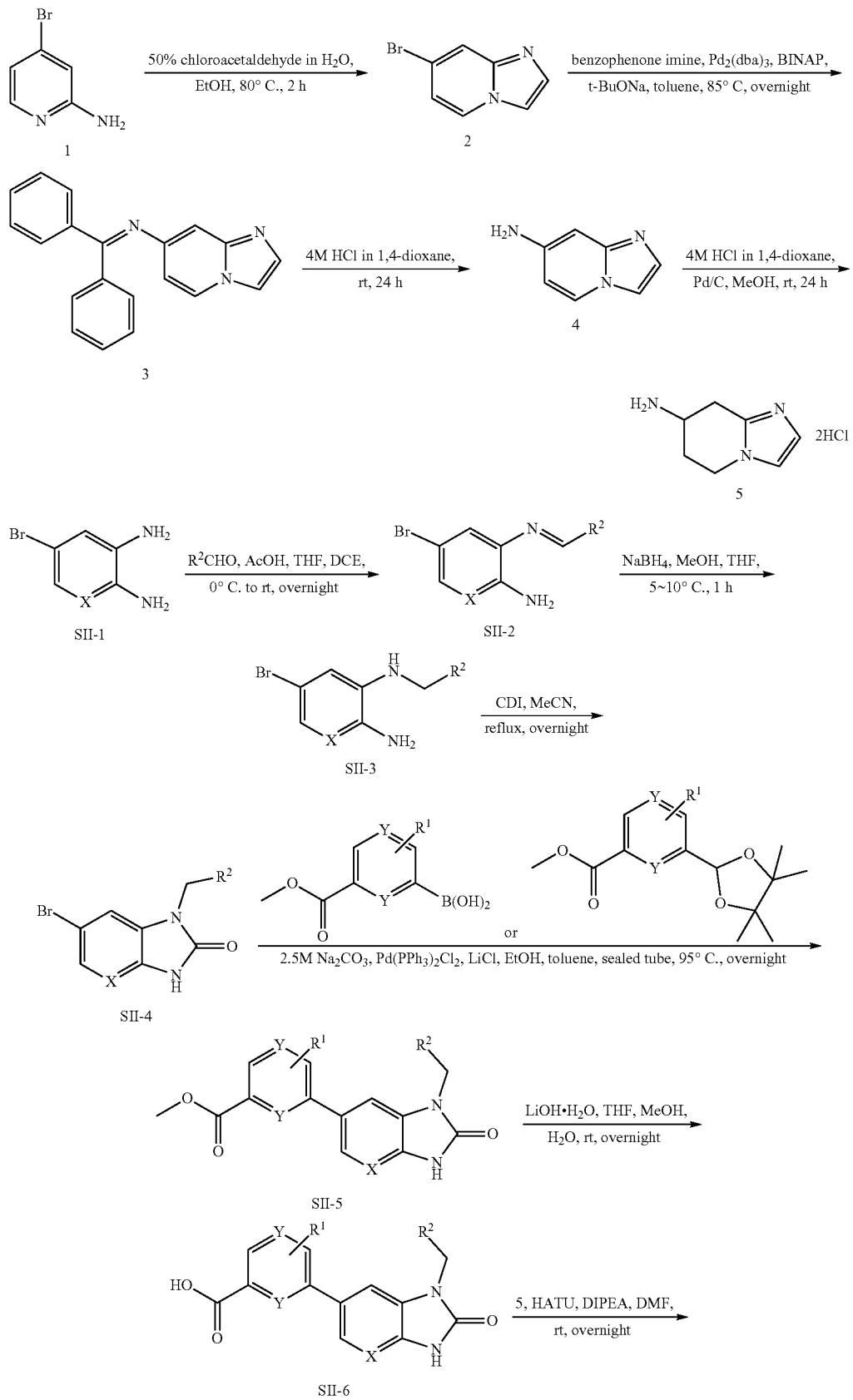

-continued
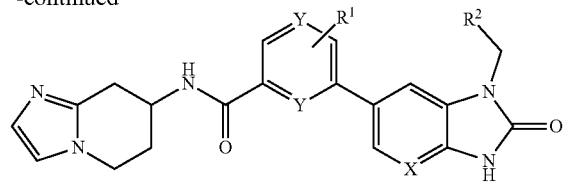
Formula I-2
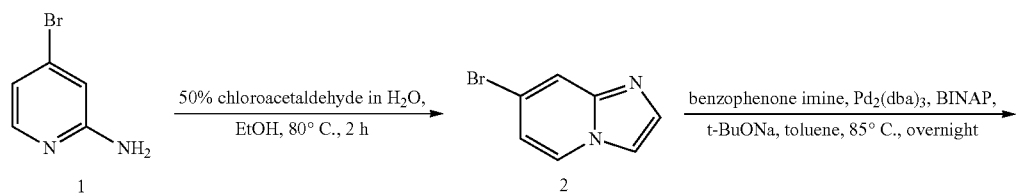
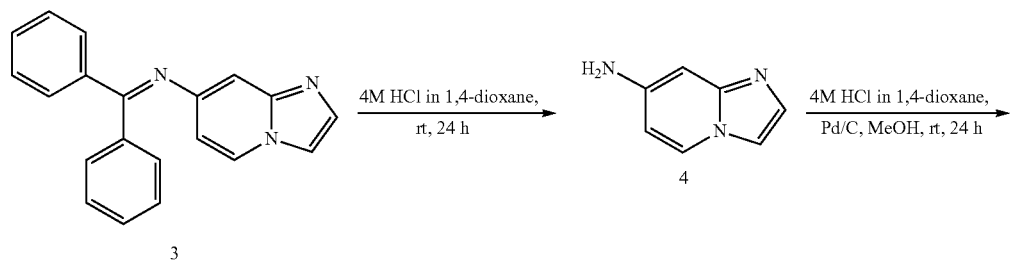
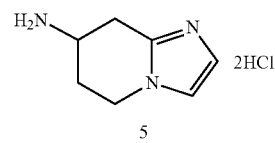
5
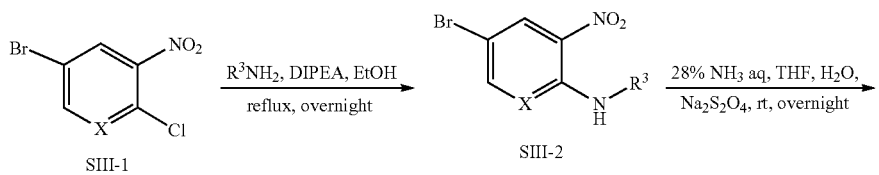
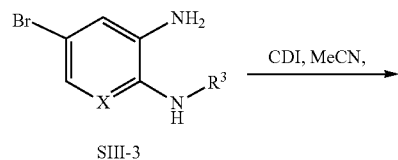
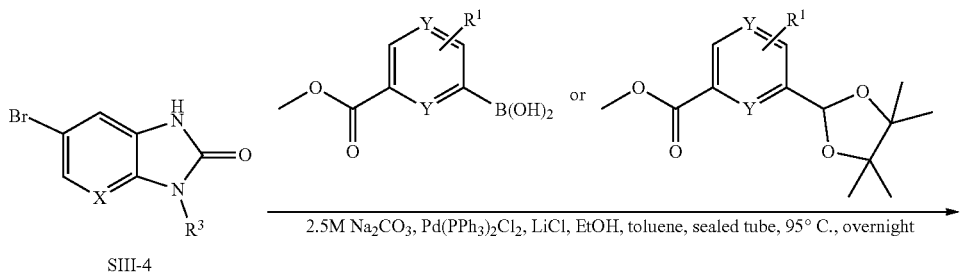

-continued
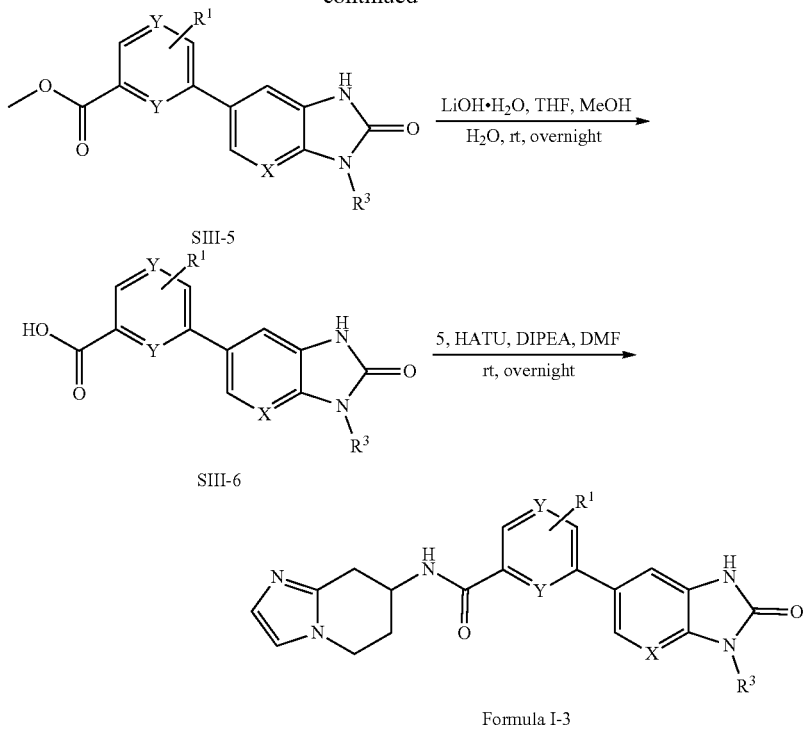
SIII-5
SIII-6
Formula I-3
General Scheme 4
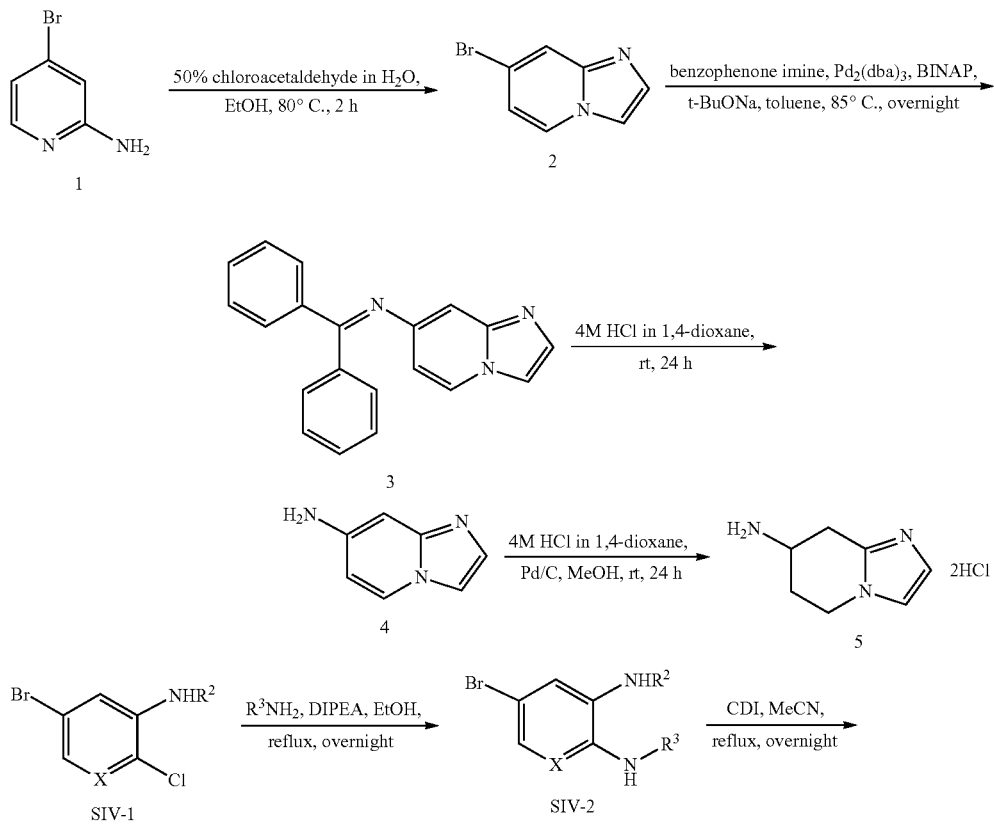

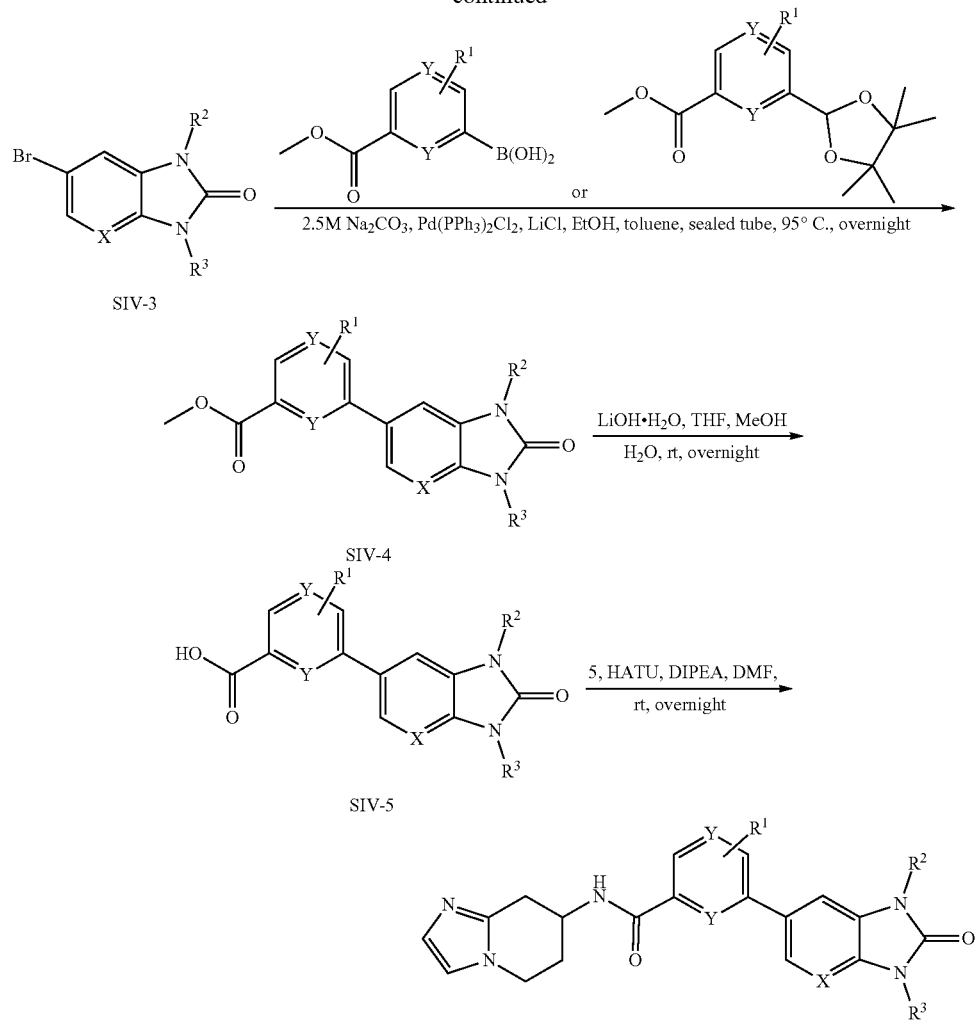
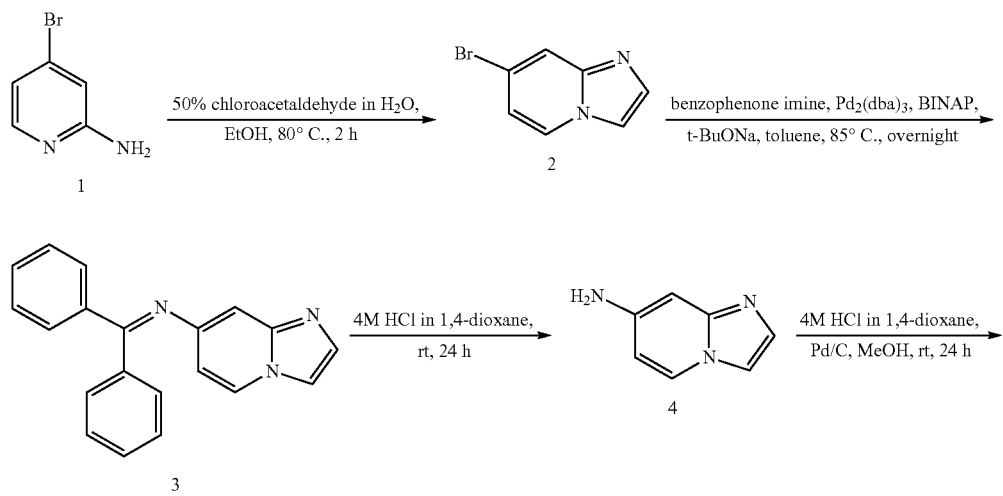
General Scheme 5

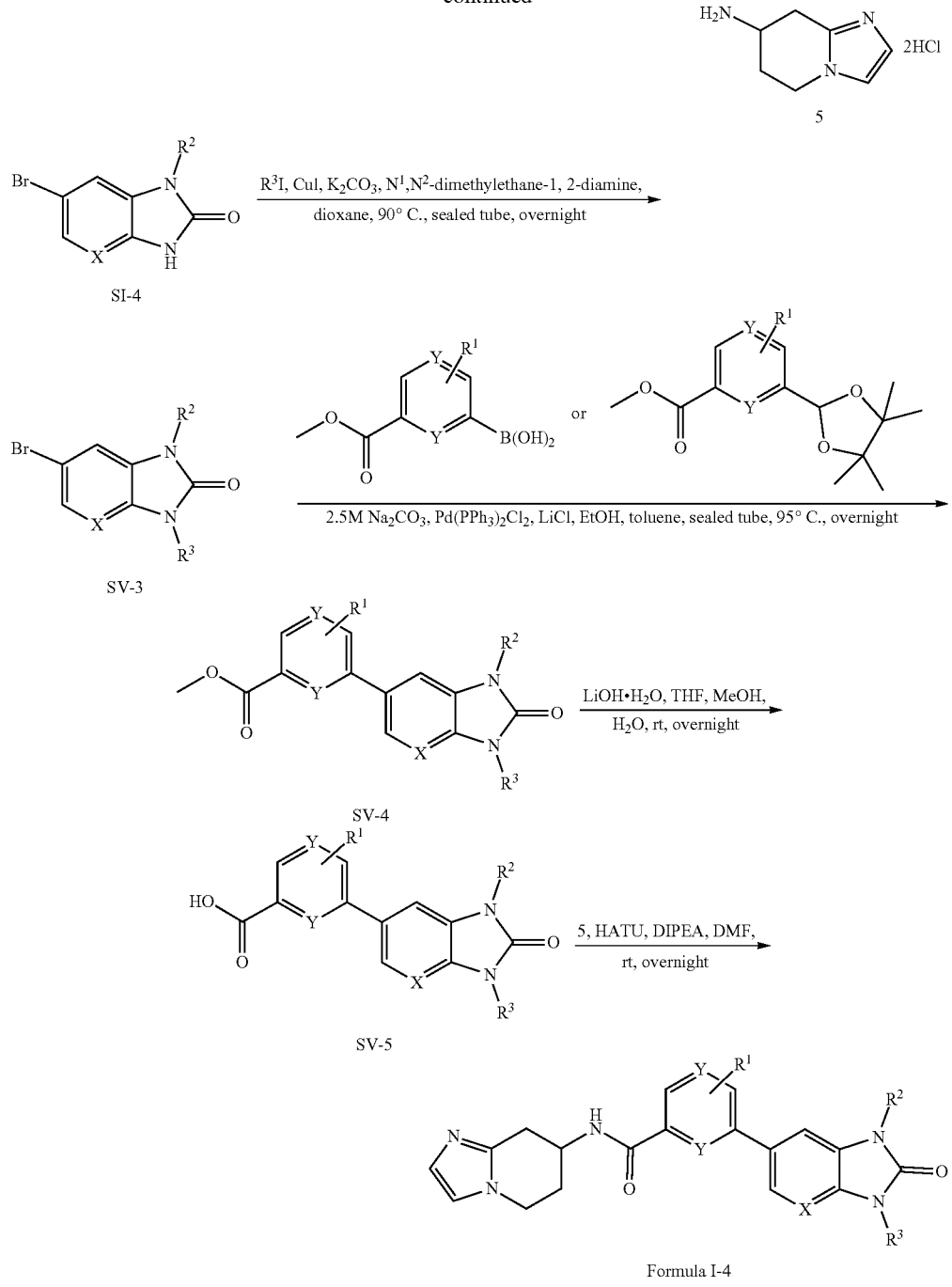
General Scheme 6
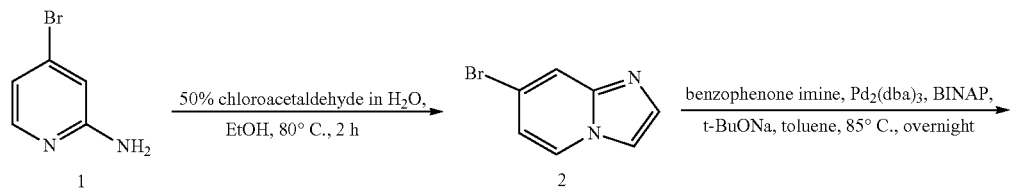

-continued
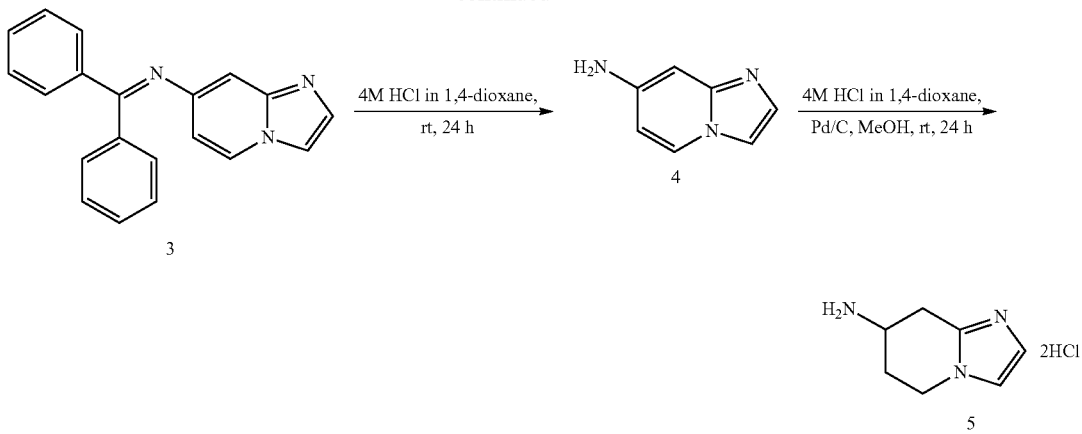
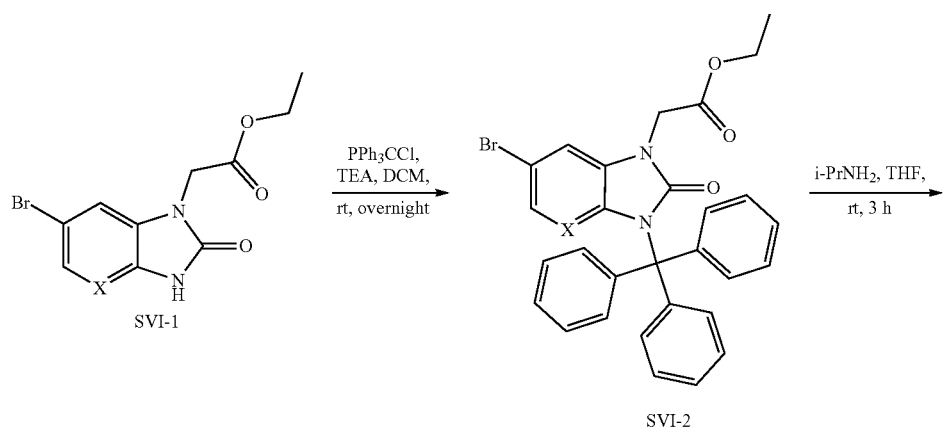
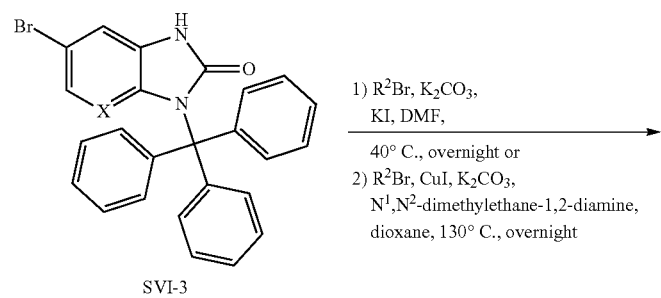
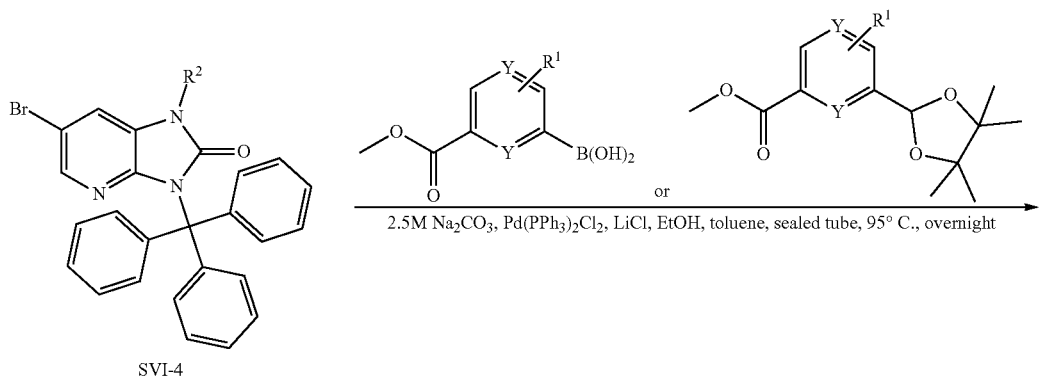

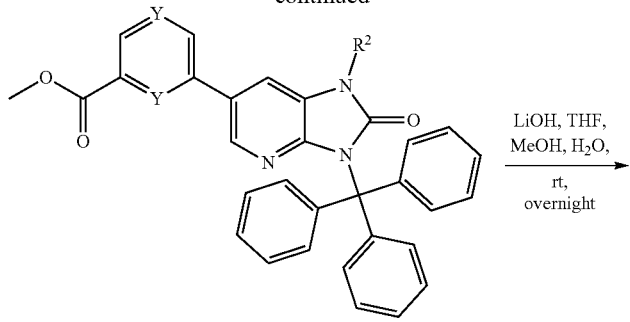
SVI-5
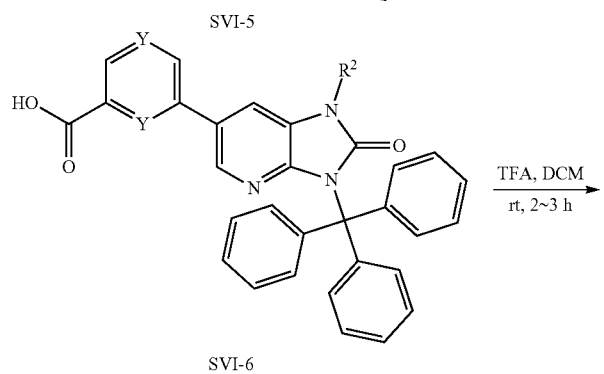
SVI-6
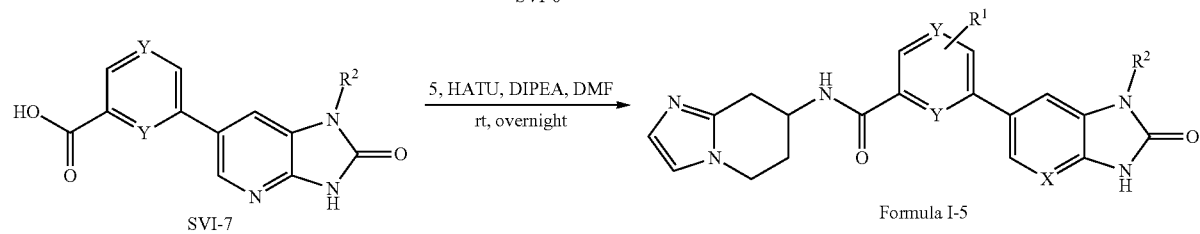
SVI-7 → Formula I-5
General Scheme 7
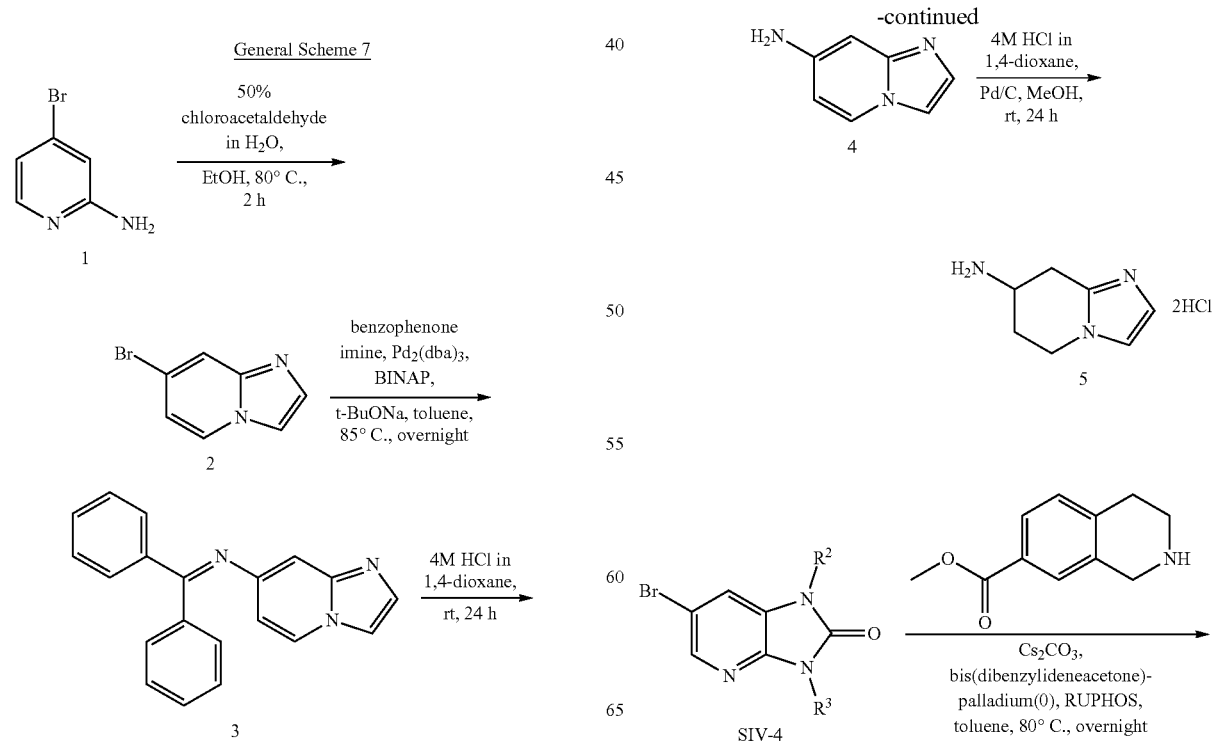

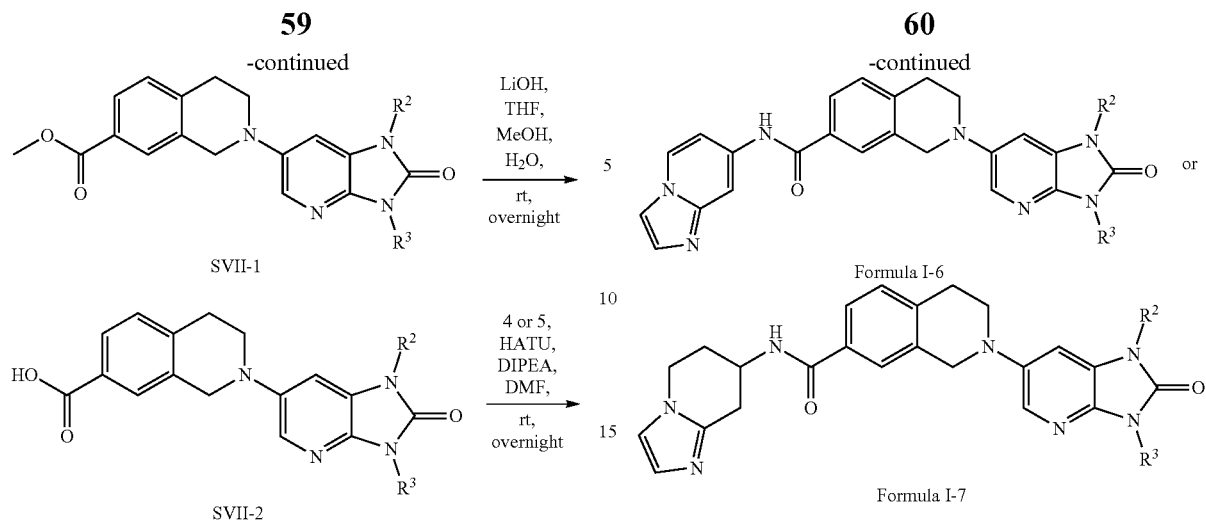
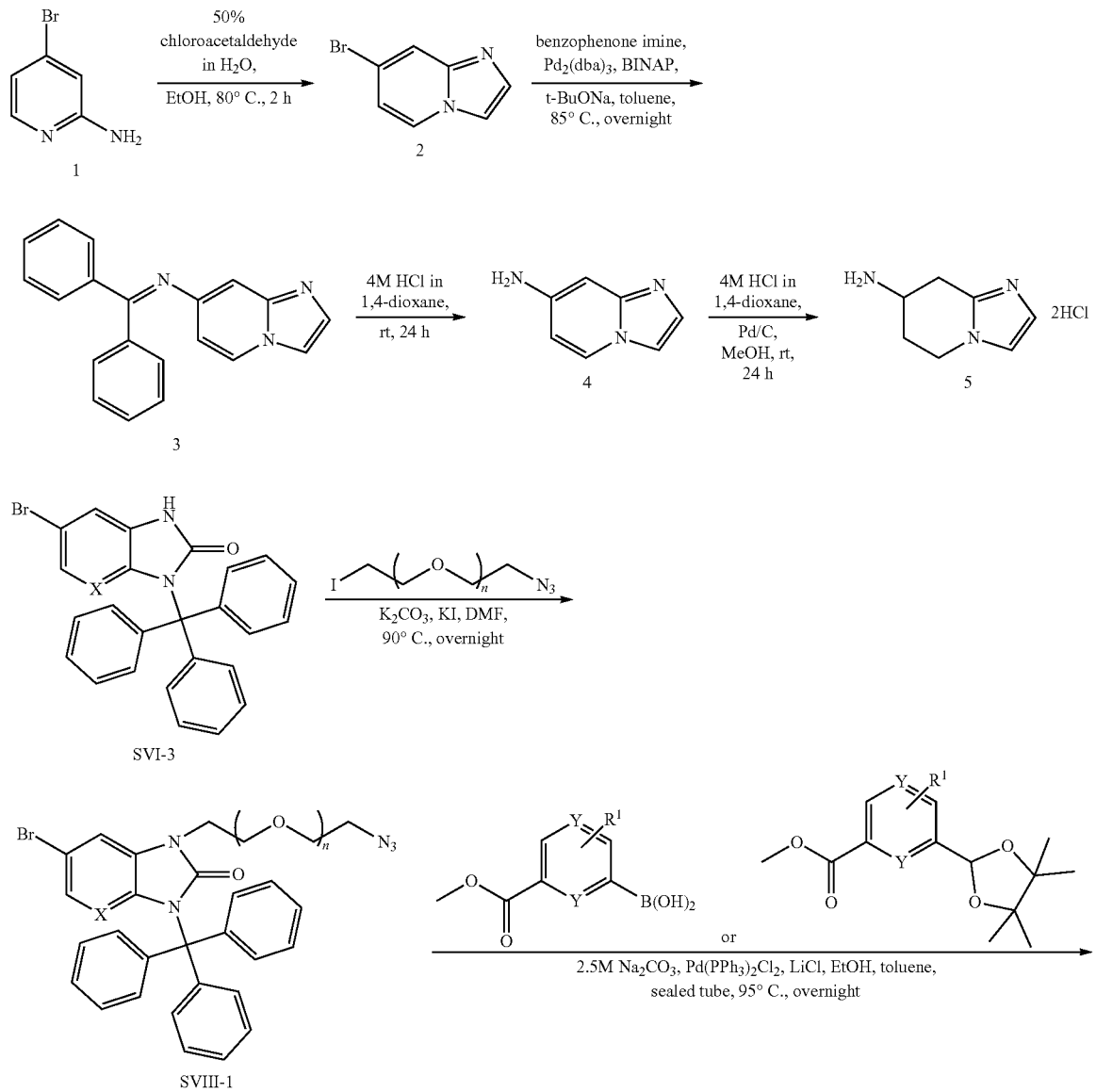
General Scheme 8

-continued
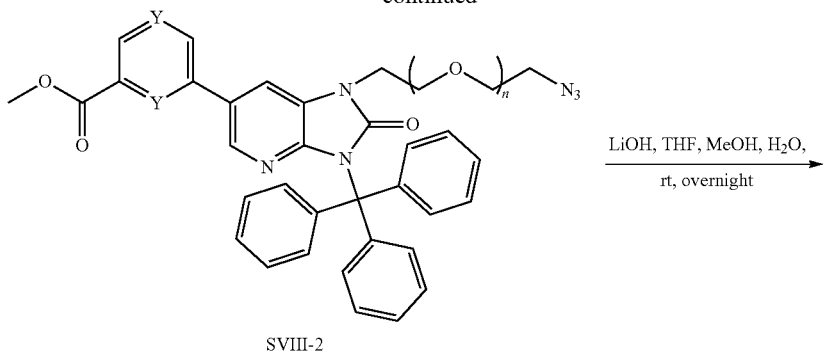
SVIII-2
LiOH, THF, MeOH, H₂O,
rt, overnight
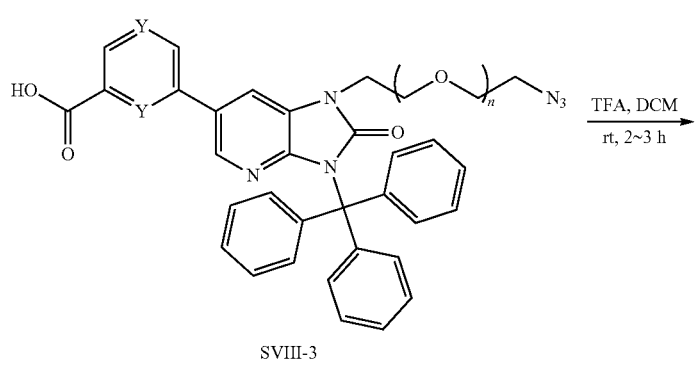
SVIII-3
TFA, DCM
rt, 2~3 h
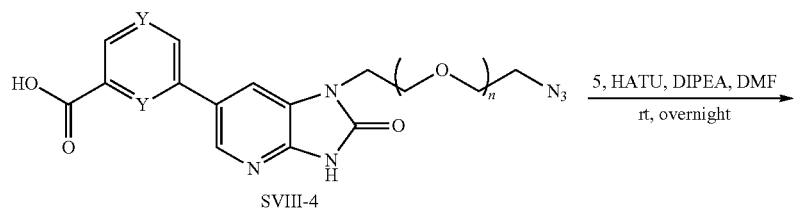
SVIII-4
5, HATU, DIPEA, DMF
rt, overnight
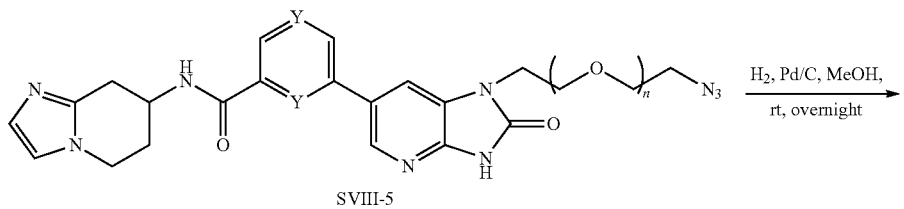
SVIII-5
H₂, Pd/C, MeOH,
rt, overnight
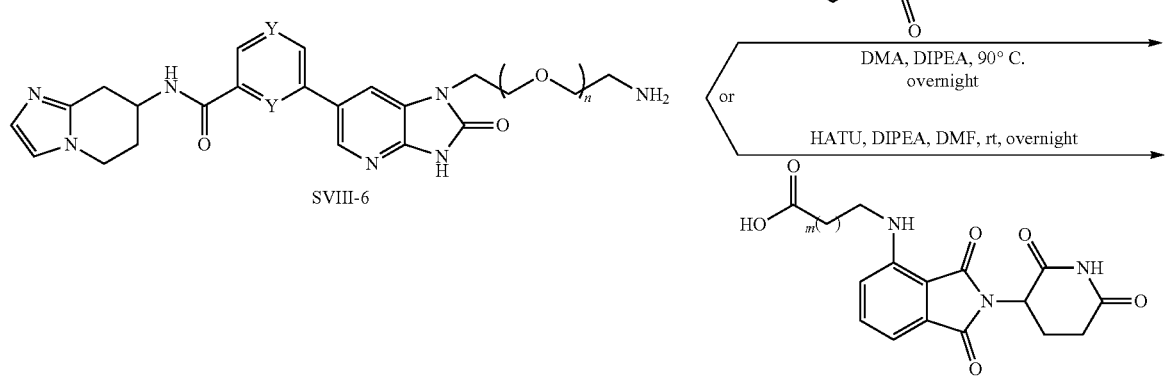
SVIII-6
DMA, DIPEA, 90° C.
overnight
or
HATU, DIPEA, DMF, rt, overnight -continued
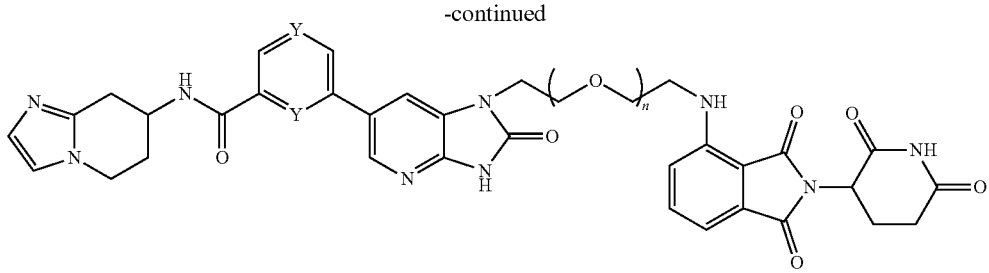
Formula I-8
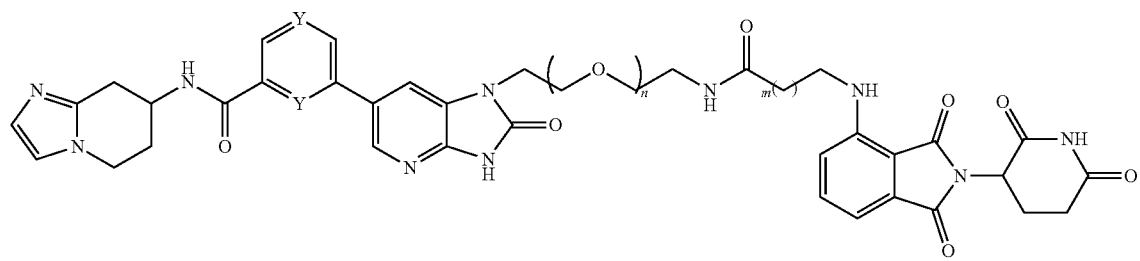
Formula I-9
m, n = 1-10
General Scheme 9
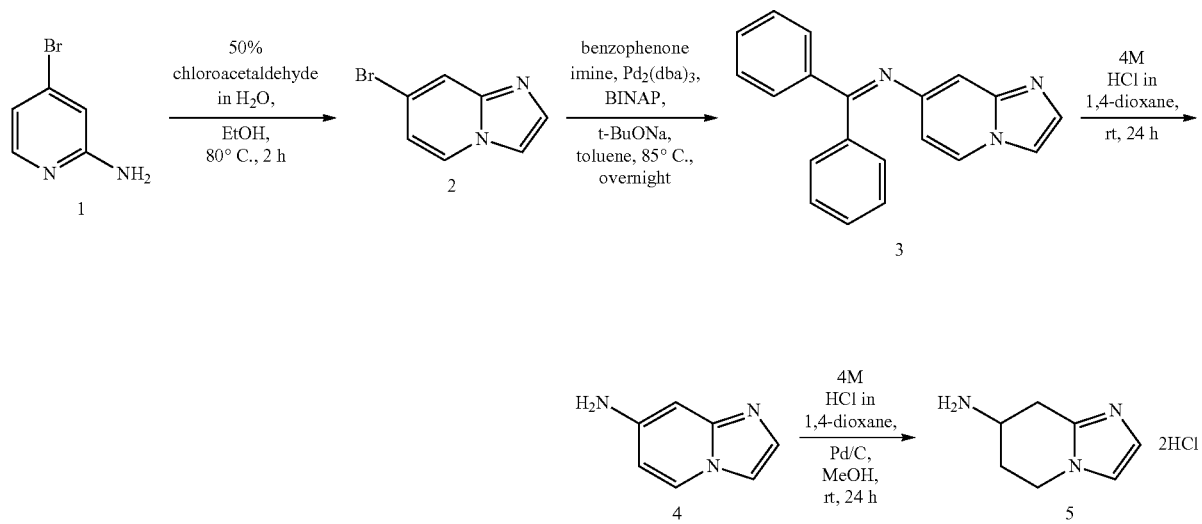
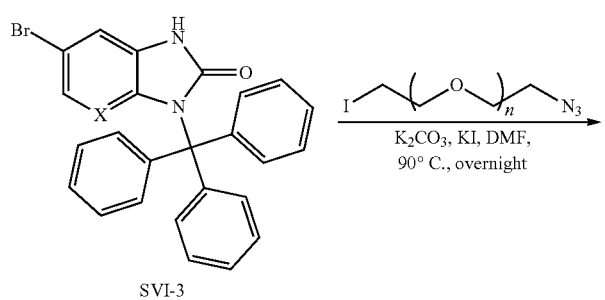

-continued
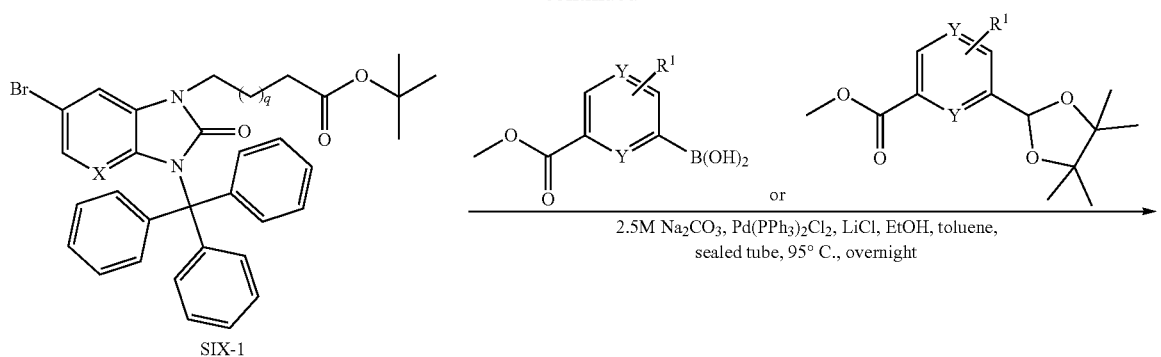
SIX-1
2.5M Na$_2$CO$_3$, Pd(PPh$_3$)$_2$Cl$_2$, LiCl, EtOH, toluene, sealed tube, 95° C., overnight
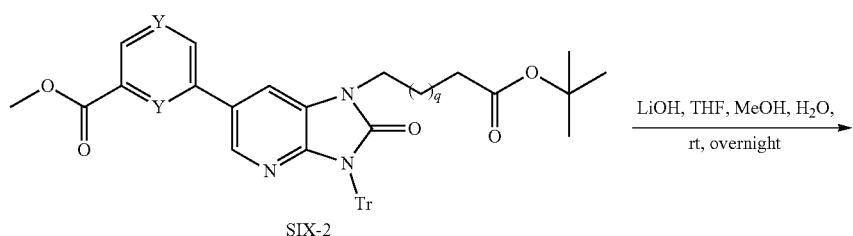
SIX-2
LiOH, THF, MeOH, H$_2$O, rt, overnight
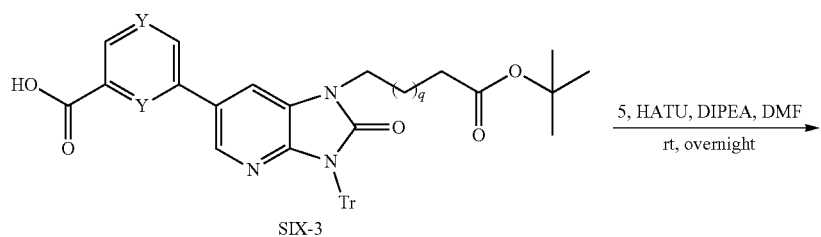
SIX-3
5, HATU, DIPEA, DMF
rt, overnight
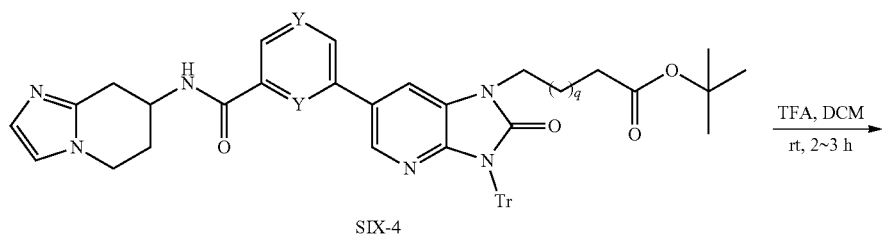
SIX-4
TFA, DCM
rt, 2~3 h
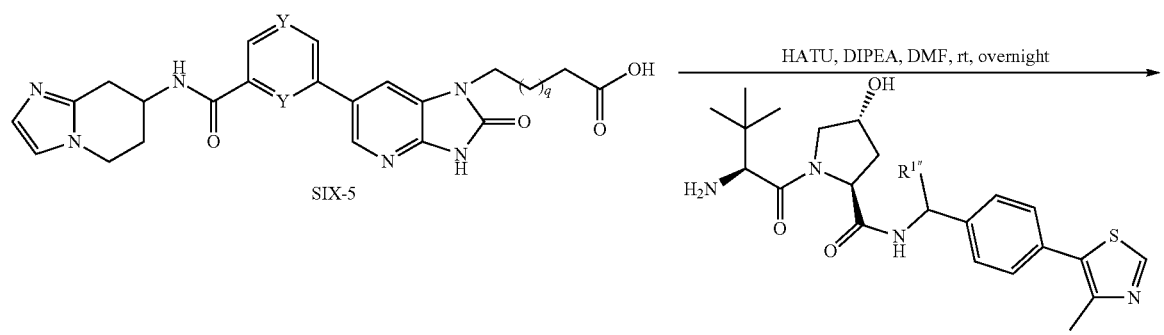
SIX-5
HATU, DIPEA, DMF, rt, overnight

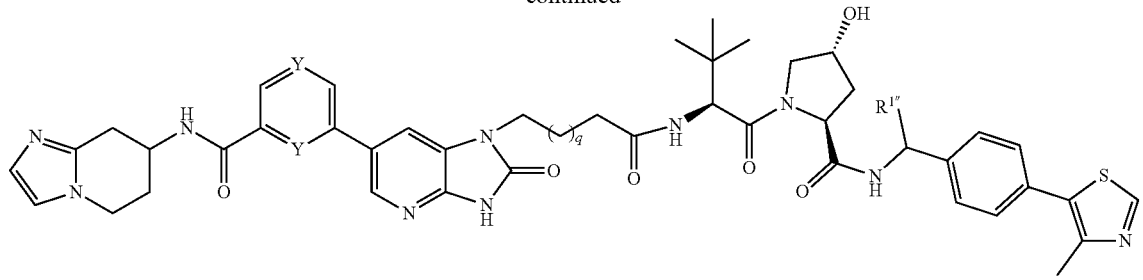

Formula I-10 q = 1-15;
R$^{1''}$ = H or CH$_3$

Results

Figure 2:
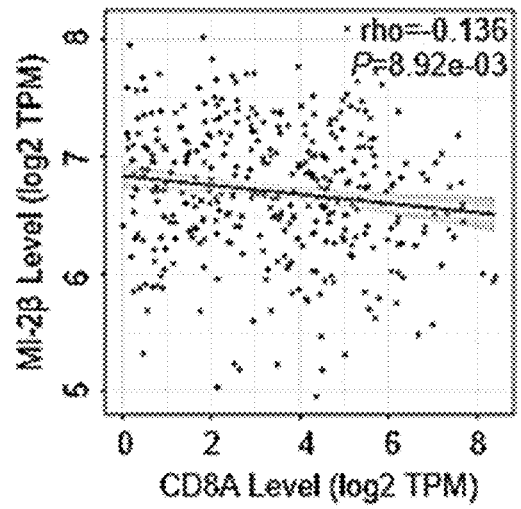
FIG. 2 illustrates hazard ratio of epigenetic factors dependent on CD8 T cell infiltration. A, Hazard ratio of epigenetic factor in melanoma patients depending on level of CD8 T infiltration. All patients in TCGA melanoma were divided into CD8 high or CD8 low groups based on CD8A median expression. The hazard ratio and P values were calculated. The genes (n=55), whose mRNA expression levels significantly correlated with hazard ratio in patients with high CD8 T cell infiltration only, but not in patients with low CD8 T cell infiltration, were shown. B, Analysis of correlation between Mi-2β mRNA level and CD8A or CD8B as T cell infiltration markers in TCGA SKCM-Metastasis (n=368). Plots show the Spearman's correlation. C, Analysis of correlation between Mi-2β mRNA level and GZMB or PRF1 level as cytotoxicity markers. Analysis was performed as indicated in C. D, Western blot assay showing the efficiency of shMi-23 knockdown in B16F10 cells.
Figure 2:
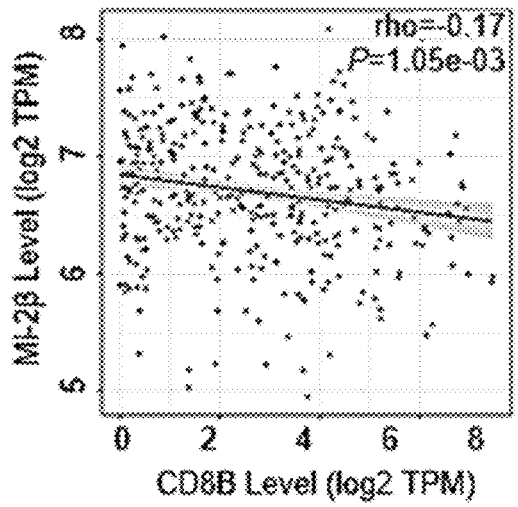
Figure 2:
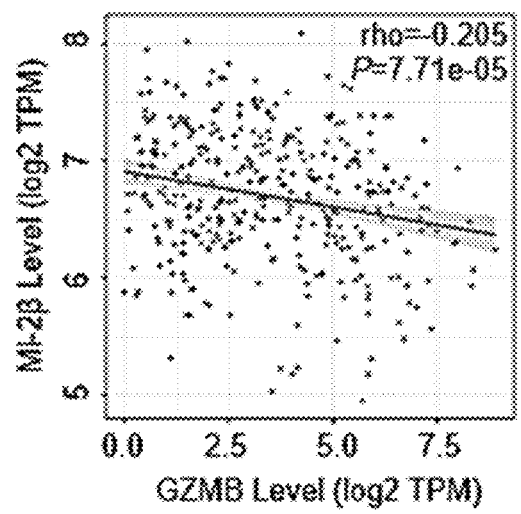
Figure 2:
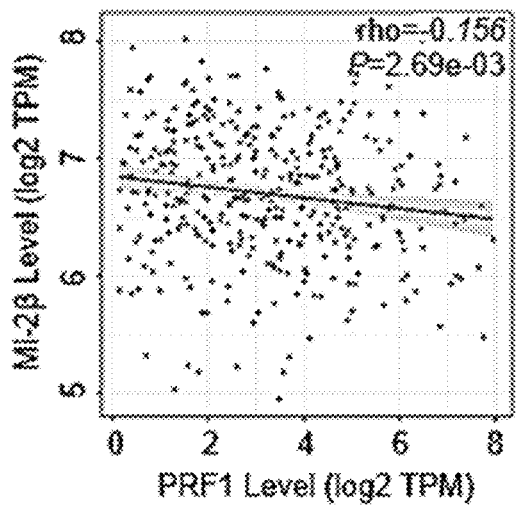
Figure 2:
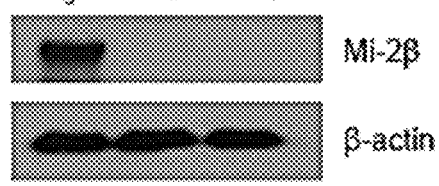

To identify key epigenetic factors that regulate cell sensitivity and resistance to T cell-mediated attack in melanoma, we analyzed the hazard ratio of the different epigenetic factors in melanoma with different levels of T cell infiltrations. Tumor-intrinsic CD8 levels served as a marker to indicate T cell infiltration (27). Epigenetic factors were preliminarily recognized as a potential regulator of immune response if its expression level was significantly correlated with hazard ratio in patients with high CD8 T cell infiltration only, but not in patients with low CD8 T cell infiltration. Fifty-five epigenetic factors were identified (FIG. 2a). The melanoma and T cell co-culture system was used to further identify the role of the most correlated genes (n=18) identified in the hazard ratio analysis in regulating T cell mediated cytotoxicity. In this co-culture system, B16F10 melanoma cells and activated Pmel-1 T cells were co-cultured. Pmel-1 T cells carry a rearranged T cell receptor transgene specific for the mouse homologue of the human pre-melanosome protein of gp100 (28), and B16F10 cells are resistant to immunotherapies, including checkpoint blockade antibodies against PD-1 (29, 30). Each candidate gene was silenced by specific gRNA and in B16F10 cells labeled by GFP. The resulted B16F10 cells were mixed with no labeled parent control B16F10 cells (1:1) and then co-cultured with the activated Pmel-1 cells. The number of GFP$^+$ cells was detected by flow cytometry to determine the B16F10 cell response to cytotoxic T cells (FIG. 1a). Mi-2β, Eif4a1, USP7 or Parp1 silencing significantly induced the response to T cell attack in melanoma cells, and led to more than half the melanoma cells to be eliminated by Pmel-1 T cell-mediated killing (FIG. 1b). Mi-2β was picked for further analysis due to the epidermal inflammation phenotypes in conditional keratinocyte-specific Mi-2β knockout mouse (31).

To validate the significance of Mi-2β in regulating immune microenvironment in human melanoma, the correlations between Mi-2β mRNA level and CD8A and CD8B mRNA levels were first analyzed in melanoma patients collected in The Cancer Genome Atlas (TCGA). Mi-2β mRNA level was negatively correlated with both CD8A and CD8B mRNA levels (p<0.01) (FIG. 2b). These results indicate that lower Mi-2β expression correlates with enrichment of CD8 T cell infiltration in melanoma. Next, to identify the role of Mi-2β in the immune response in melanoma, the correlations between Mi-2β and GZMB or PRF1 were analyzed. GZMB and PRF1 are crucial for the rapid induction of target cell apoptosis by cytotoxic T lymphocytes (CTL) in cell-mediated immune response (41). Mi-2β mRNA level was also negatively correlated with both GZMB and PRF1 mRNA level (p<0.01) in melanoma (FIG. 2c). These results suggest that expression levels of Mi-2β are associated with T cell-mediated killing in melanoma. Consistently, the repression of Mi-2β expression were found to correlate with a substantial survival benefits only in melanoma patients with higher CD8 T cell infiltration (p<0.05), but not in melanoma with low CD8 T cell infiltration (FIG. 1c). To further validate the role of Mi-2β in modulating sensitivity to T cell-mediated killing in melanoma, the melanoma-T cell co-culture system (B16F10/Pmel-1) was used. Mi-2β silencing (FIG. 2d) induced T cell-mediated cytotoxicity in vitro (FIG. 1d). Collectively, these results suggest a critical role for Mi-2β in regulating melanoma resistance to T cell-meditated cytotoxicity with tumor intrinsic Mi-2β levels regulating melanoma sensitivity to T cell-mediated anti-tumor immunotherapy.

Figure 3:
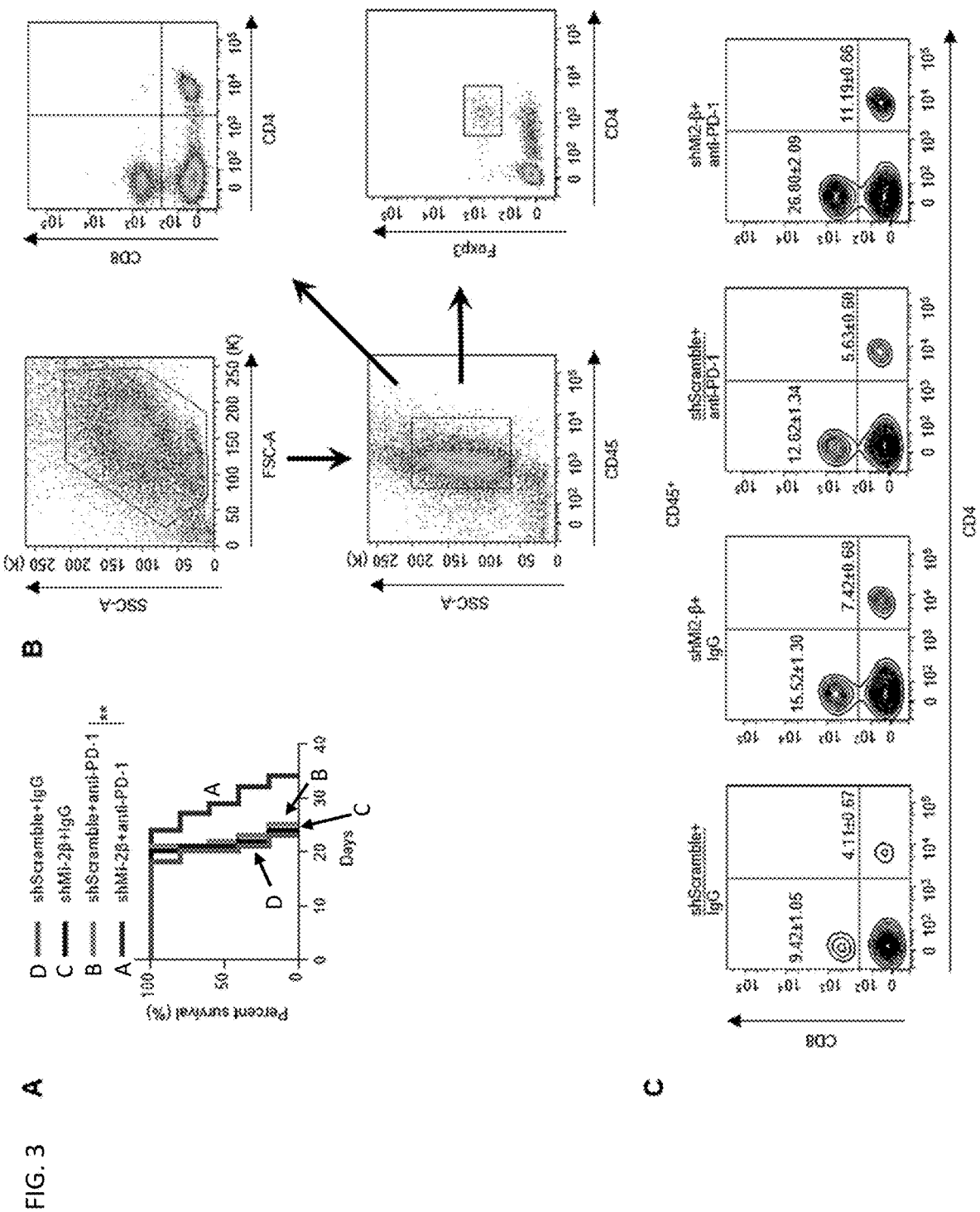
FIG. 3 illustrates Mi-2β silencing melanoma graft with anti-PD-1 treatment. Mice bearing graft of Mi-2β knockdown or shScramble B16F10 cells were treated with i.p. injection of control IgG (10 mg/kg) or anti-PD-1 antibodies (10 mg/kg) at day 6, 9, 12, 15 and 18 after tumor cell inoculation. Each group n=5. A, mouse survival was detected. Log-rank test was used to determine statistical significance of P value. As survival rate drops to 0%, curves from left to right: shScramble+IgG, shMi-2β+IgG, shScramble+anti-PD-1, and shMi-2β+anti-PD-1. B, Tumor-infiltrating lymph cells were assayed by flow cytometry. C, The representative cell populations of $CD4^+$ and $CD8^+$ were shown. Values represent mean±SEM. **p<0.01.
Figure 4:
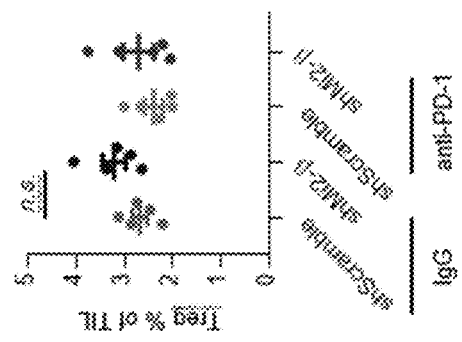
FIG. 4 illustrates treg population in Mi-2β silencing melanoma graft with anti-PD-1. Mice bearing graft of Mi-2β knockdown or shScramble B16F10 cells were treated with control IgG or anti-PD-1. A, The population of Treg cells were quantified within CD45$^+$ T cells. B, The representative images were shown. C, Expression of activation markers of CD8$^+$ T cells were measured by flow cytometry assay. MFI represents mean fluorescence intensity. Values represent mean±SEM. The four bars from left to right: shScramble, shMi-2β, anti-PD-1, and shMi-2β$^+$ anti-PD-1. *p<0.05, p<0.01, *p<0.001. n.s. represents no significance.
Figure 4:
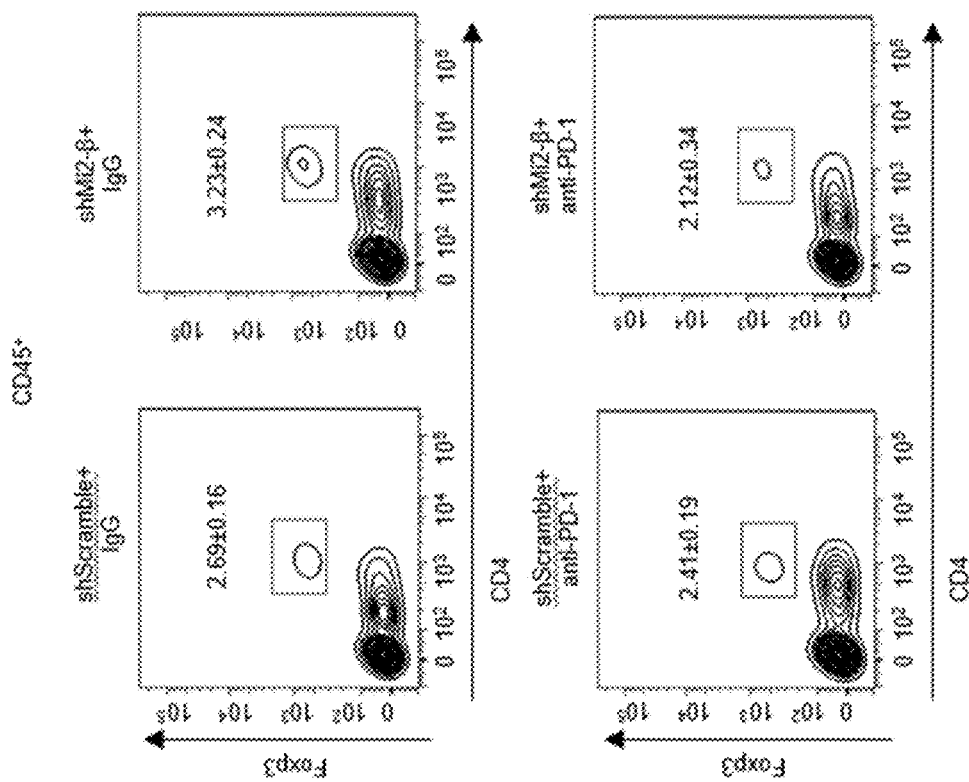
Figure 4:
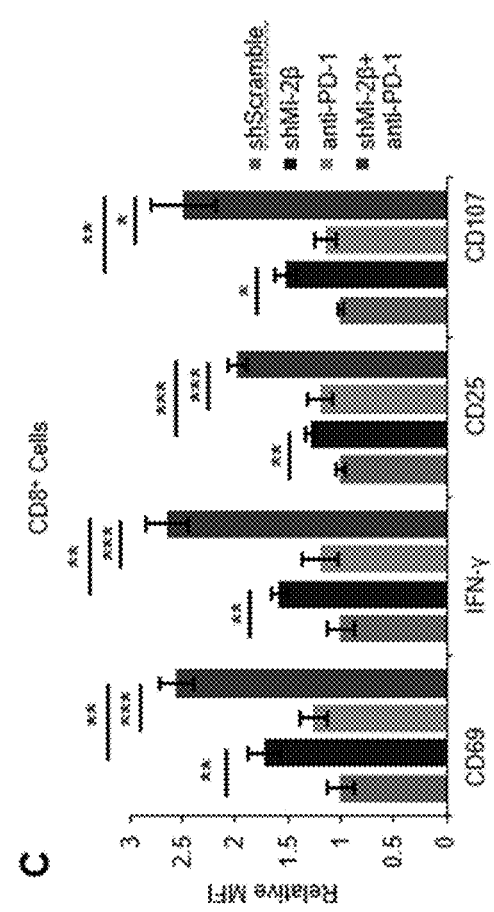

To identify whether Mi-2β depletion induced an immune response in B16F10 melanoma cells, mouse graft melanomas with shMi-2β virus-infected B16F10 cells were treated using anti-PD-1 antibodies (10 mg/kg) at day 6, 9, 12, 15 and 18 after tumor cell inoculation in immunocompetent C57BL/6 mice. Consistent with previous reports (17, 30), mice injected with control B16F10 cells with shScramble were not sensitive to anti-PD-1 treatment. However, Mi-2β silencing combined with anti-PD-1 treatment conferred a substantial inhibition on tumor growth in B16F10 melanoma cells (FIG. 1e-f), and subsequently extended the survival of the treated mice (FIG. 3a). Analysis of the graft tumor microenvironment by flow cytometry (FIG. 3b) showed an increase in CD8$^+$ and CD4$^+$ T cell infiltration was detected in the B16F10 tumor graft after Mi-2β silencing, which was strongly augmented by the anti-PD-1 treatment (FIG. 1g-h and FIG. 3c). At the same time, a minor, but non-significant, increase in tumor-infiltrating Treg cells was also detected in the B16F10 tumor graft following Mi-2β silencing, which was not inhibited by anti-PD-1 treatment and/or Mi-2β silencing (FIG. 4a-b). Moreover, a minor to medium increase of GZMB expression and upregulation of activation of CD69, IFN-γ, CD25 and CD107 were detected in tumor-infiltrating CD8$^+$ T cells from the B16F10 tumor graft after silencing Mi-2β, which were strongly augmented by anti-PD-1 treatment (FIG. 1i and FIG. 4c). These data indicate that Mi-2β silencing sensitizes tumor cells and confers a more favorable tumor microenvironment to induce an adaptive immune response to anti-PD-1 treatment in melanoma.

Figure 5:
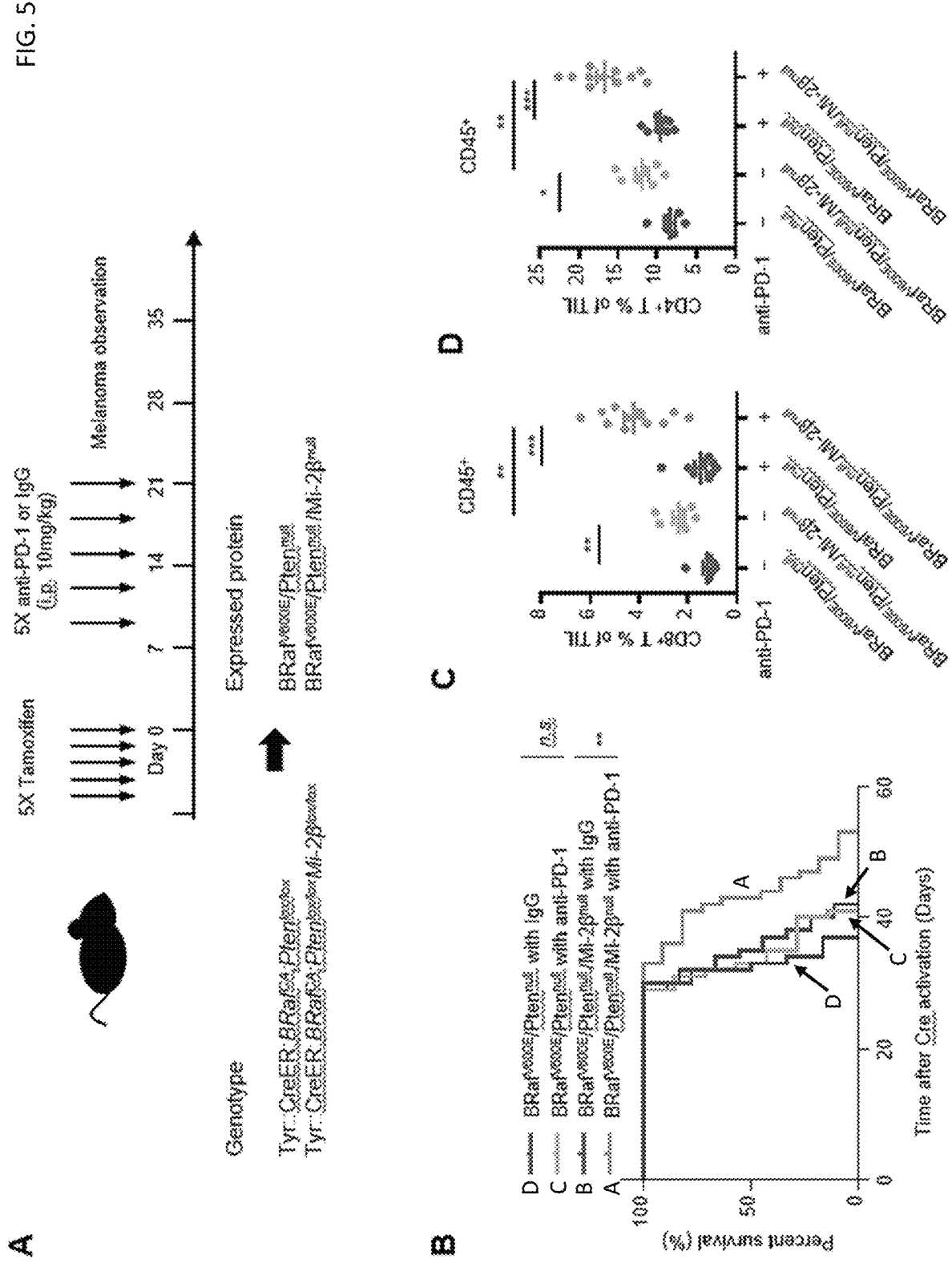
FIG. 5 illustrates Mi-2β deficiency induces responses to anti-PD-1 treatment for melanoma. A, A schematic for experimental strategy with anti-PD-1 treatment on genetically engineered melanoma mouse model. Mice carrying conditional alleles of Tyr::CreER;BRaf$^{CA}$;Pten$^{lox/lox}$ or Tyr::CreER;BRaf$^{CA}$;Pten$^{lox/lox}$ Mi-2β$^{lox/lox}$ were administered with tamoxifen for constant 5 days to activate CreER to cause melanocyte-specific conversion of Braf$^{CA}$ to Braf$^{V600E}$, and the conversion of the Pten$^{lox/lox}$ and Mi-2β$^{lox/lox}$ alleles to null alleles, which expressed proteins of BRaf$^{V600E}$/Pten$^{null}$ or BRaf$^{V600E}$/Pte$^{null}$/Mi-2β$^{lox/lox}$, respectively. Mice with measurable tumors were randomly treated with either control IgG (10 mg/kg) or anti-PD-1 (10 mg/kg) antibodies by i.p. administration at day 9, 12, 15, 18 and 21 after Cre activation. B, Mouse survival of BRaf$^{V600E}$/Pte$^{null}$ mice treated with IgG (n=6) or anti-PD-1 (n=7), and of BRaf$^{V600E}$/Pten$^{null}$/Mi-2β$^{null}$ mice treated with IgG (n=9) or anti-PD-1 (n=11). As survival rate drops to 0%, curves from left to right: BRaf$^{V600E}$/Pten$^{null}$ with IgG, BRaf$^{V600E}$/Pten$^{null}$ with anti-PD-1, BRaf$^{V600E}$/Pten$^{null}$/Mi-2β$^{null}$ with IgG, and BRaf$^{V600E}$/Pten$^{null}$/Mi-2β$^{null}$ with anti-PD-1. Log-rank test was used for P value calculation. TILs were assayed with flow cytometry assay for the population of CD8$^+$ cells (C) and CD4$^+$ T cells (D) gated within CD45$^+$ T cells. E, Granzyme B expression in CD8$^+$ T was determined and quantified with flow cytometry. F, Expression of activation markers on CD8$^+$ T cells were determined with flow cytometry assay. MFI represents mean fluorescence intensity. Values represent mean±SEM. The four bars from left to right: control, Mi-2β KO, anti-PD-1, Mi-2β KO+anti-PD-1. *p<0.05, p<0.01, * p<0.001.
Figure 5:
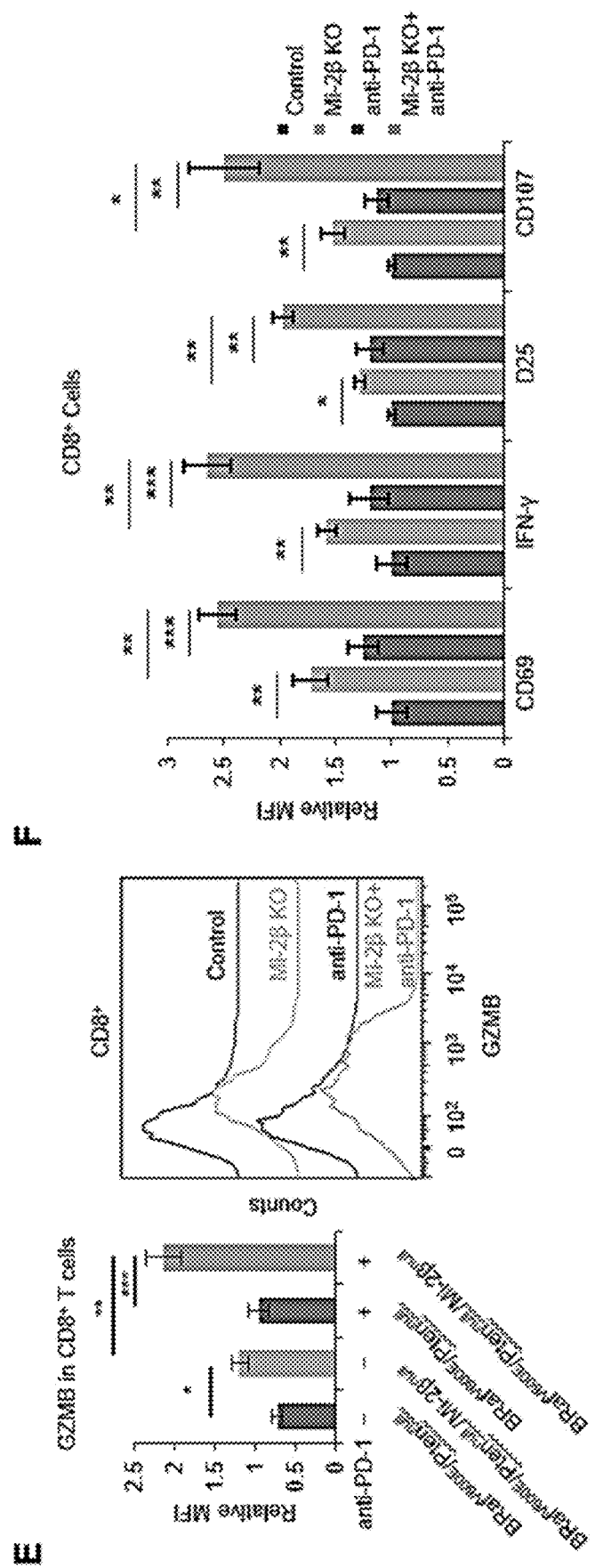
Figure 6:
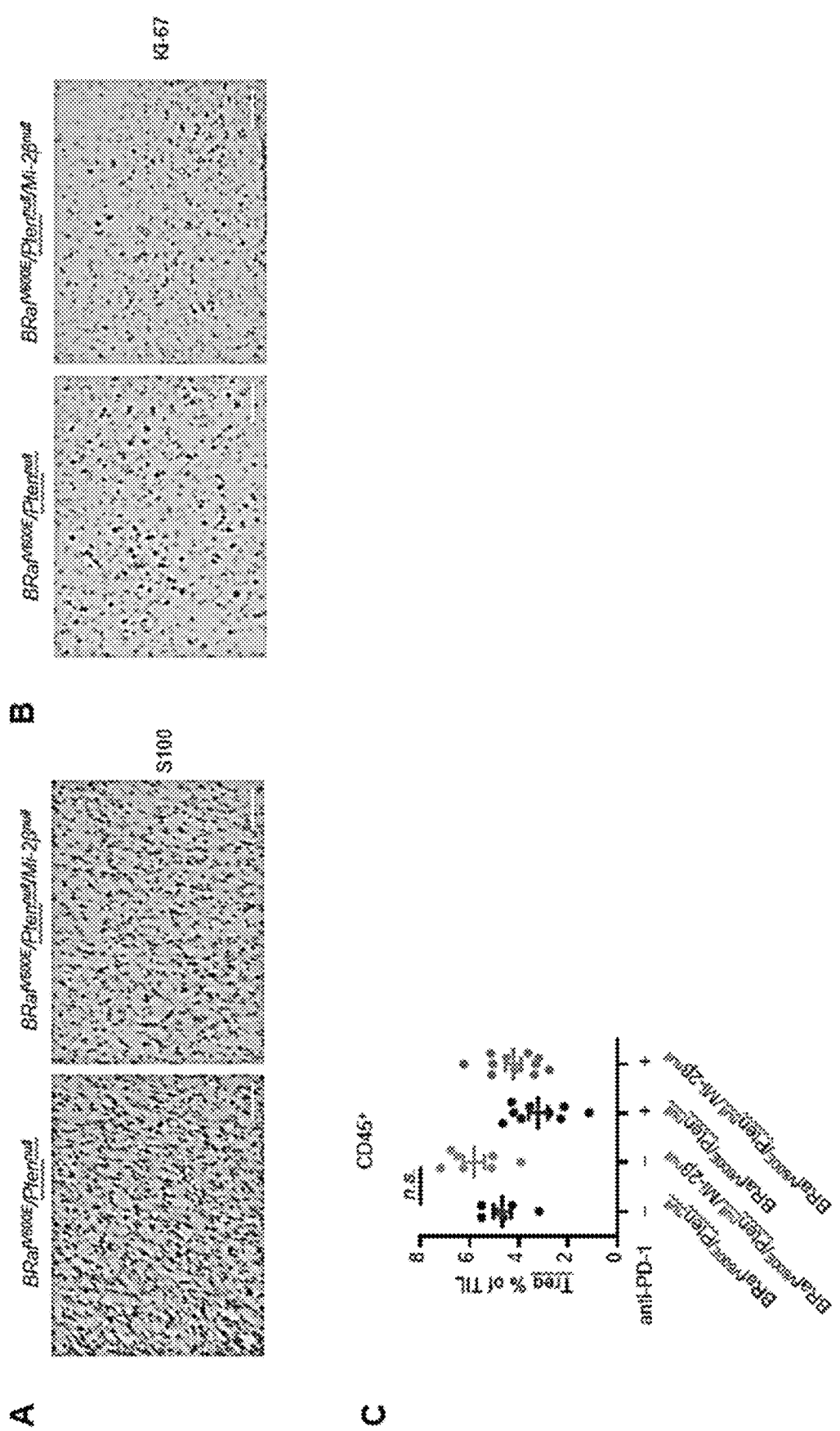
FIG. 6 illustrates analysis of Mi-2β deficient melanoma. The melanomas from BRaf$^{V600E}$/Pten$^{null}$ mice and BRaf$^{V600E}$/Pten$^{null}$/Mi-2β$^{null}$ mice were prepared and processed for immunohistochemistry staining to detect the expression of melanoma marker of S100 (A) and tumor proliferation marker of Ki-67 (B). C, The population of Treg cells within CD45$^+$ T cells in TILs were assayed and quantified by flow cytometry assay. Values represent mean±SEM. Scale bar=200 μm. n.s. represents no significance.

To further examine whether Mi-2β depletion induced an adaptive immune response in melanoma in vivo, Tyr::CreER;BRaf$^{CA}$;Pten$^{lox/lox}$ mice were used for the anti-PD-1 antibody treatment. In this mouse strain, induction of Cre-mediated recombination leads to Braf$^{V600E}$ expression and Pten inactivation (BRaf$^{V600E}$/Pten$^{null}$) in cutaneous melanocytes, resulting in rapid melanoma initiation and progression (42). Mi-2β$^{lox/lox}$ mice (31) were crossed with Tyr::CreER; BRaf$^{CA}$;Pten$^{lox/lox}$ mice to deplete Mi-2β in the BRaf$^{V600E}$/Pten$_{null}$ melanoma background after tamoxifen injection. Mice with visible melanomas were randomly treated with either control IgG antibodies (10 mg/kg) or anti-PD-1 (10 mg/kg) starting at day 9, 12, 15, 18 and 21 after Cre activation (FIG. 5a) and mouse survival analyzed. Consistent with previous reports (19), BRaf$^{V600E}$/Pten$^{null}$ melanoma is a "cold" tumor, lacking substantial immune infiltration, and was insensitive to anti-PD-1 antibody treatment (FIG. 5b). There was no significant difference of mouse survival observed in BRaf$^{V600E}$/Pten$^{null}$ melanoma with different Mi-2β status (FIG. 5b). IHC staining for the melanoma marker S100 and proliferation marker Ki-67 showed no difference between BRaf$^{V600E}$/Pten$^{null}$ melanomas with different Mi-2β status (FIG. 6a-b). Intriguingly, treatment of anti-PD-1 significantly extended mouse survival with BRaf$^{V600E}$/Pten$^{null}$/Mi-2β$^{null}$ melanoma compared with that of BRaf$^{V600E}$/Pten$^{null}$ melanoma (FIG. 2b). To further identify whether the Mi-2β knockout-induced anti-PD-1 response correlates with T cell activation, tumor-infiltrating lymphocytes (TILs) were measured in BRaf$^{V600E}$/Pten$^{null}$ melanomas with different Mi-2β status by flow cytometry. The populations of infiltrating CD8$^+$ and CD4$^+$ T cells were increased to a small extent in the TILs of BRaf$_{V600E}$/Pten$^{null}$/Mi-2β$^{null}$ melanoma. This increase was significantly augmented by the anti-PD-1 treatment (FIG. 5c-d). At the same time, a minor, but non-significant, increase in the Treg population was also detected in BRaf$^{V600E}$/Pten$^{null}$ melanoma after Mi-2β knockout. However, the anti-PD-1 treatment did not change Treg cell population in BRaf$^{V600E}$/Pten$^{null}$ melanomas after Mi-2β knockout (FIG. 6c). Moreover, an increase of GZMB expression and upregulation of CD8$^+$ T cell activation markers, such as CD69, IFN-γ, CD25 and CD107, were detected in BRaf$^{V600E}$/Pten$^{null}$/Mi-2β$^{null}$ melanomas after Mi-2β knockout. These increases were all further strongly augmented by anti-PD-1 treatment (FIG. 5e-f). Taken together, these results indicate that loss of Mi-2β in melanocytes activates CTLs to induce an anti-PD-1 treatment response in "cold" melanomas in vivo.

Figure 7:
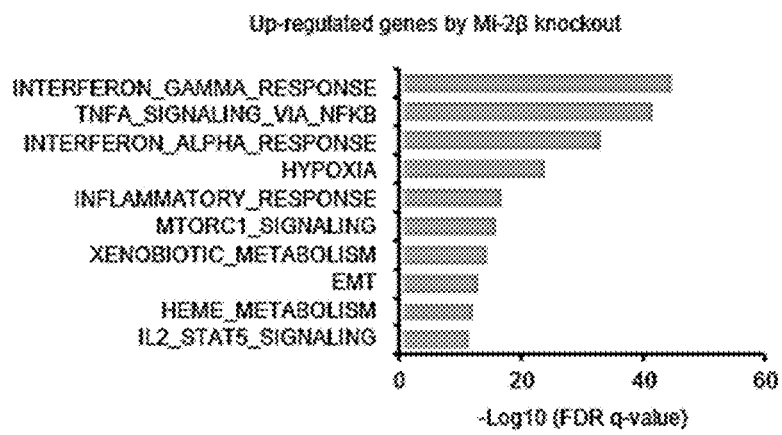
FIG. 7 illustrates the enhanced IFN-γ signaling by Mi-2β knockout in melanoma. A, Microarray data analyzed for hallmark gene sets enriched for upregulated or downregulated mRNA in Mi-2β knockout and control B16F10 cells treated with IFN-γ for 24 hours. B, Heat map showing expression value (z-score expression) of IFN-γ signaling genes in control and Mi-2β knockout B16F10 cells in microarray data. C, The expressions of Mi-2β-regulated IFN-γ signaling genes were measured in IFN-γ-stimulated B16F10 cells with Mi-2β silencing by RT-qPCR assay. Values represent mean±SD. D-E, The amount of secret Cxcl9 (D) or Cxcl10 (E) were measured in IFN-γ (0, 1, or 10 ng/mL, for 24 hours)-stimulated B16F10 cells with Mi-2β silencing by ELISA assay. Values represent mean±SEM. The three bars from left to right at each concentration: shScramble, shMi-2β-1, and shMi-2β-2. F-G, The graft melanomas were isolated to be cultured in PBS with the same amount cells for 4 hours (for each group n=5), and then the secreted amount of the chemokines Cxcl9 and Cxcl10 in the culture medium were measured by ELISA assays. Values represent mean±SEM. *p<0.05, p<0.01, * p<0.001.
Figure 7:
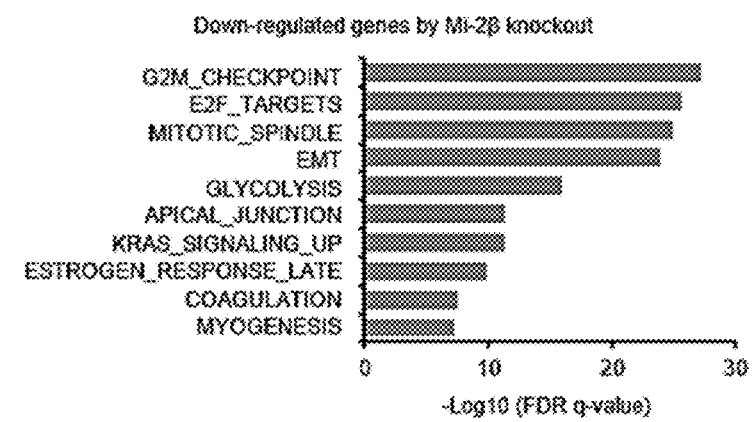
Figure 7:
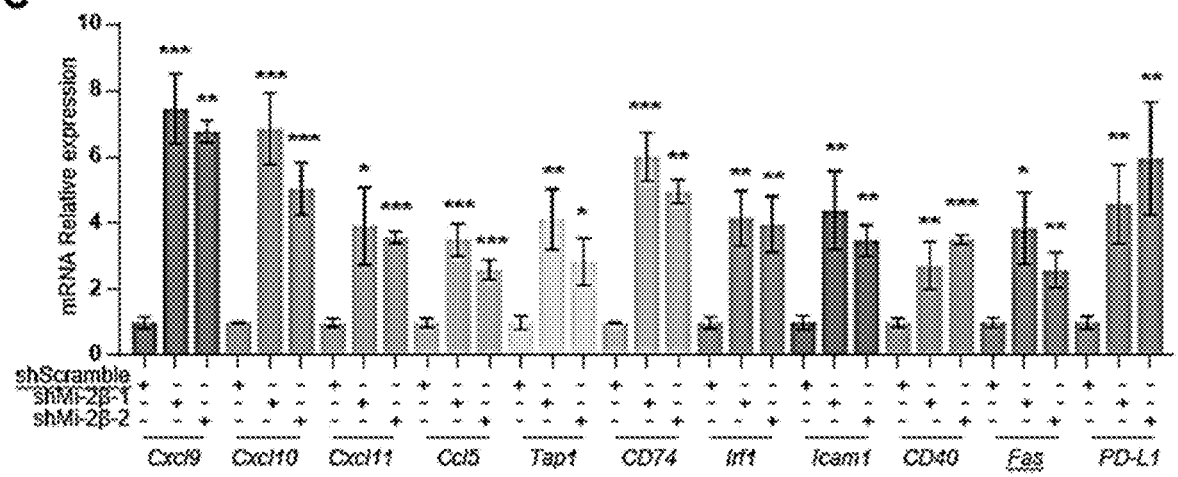
Figure 7:
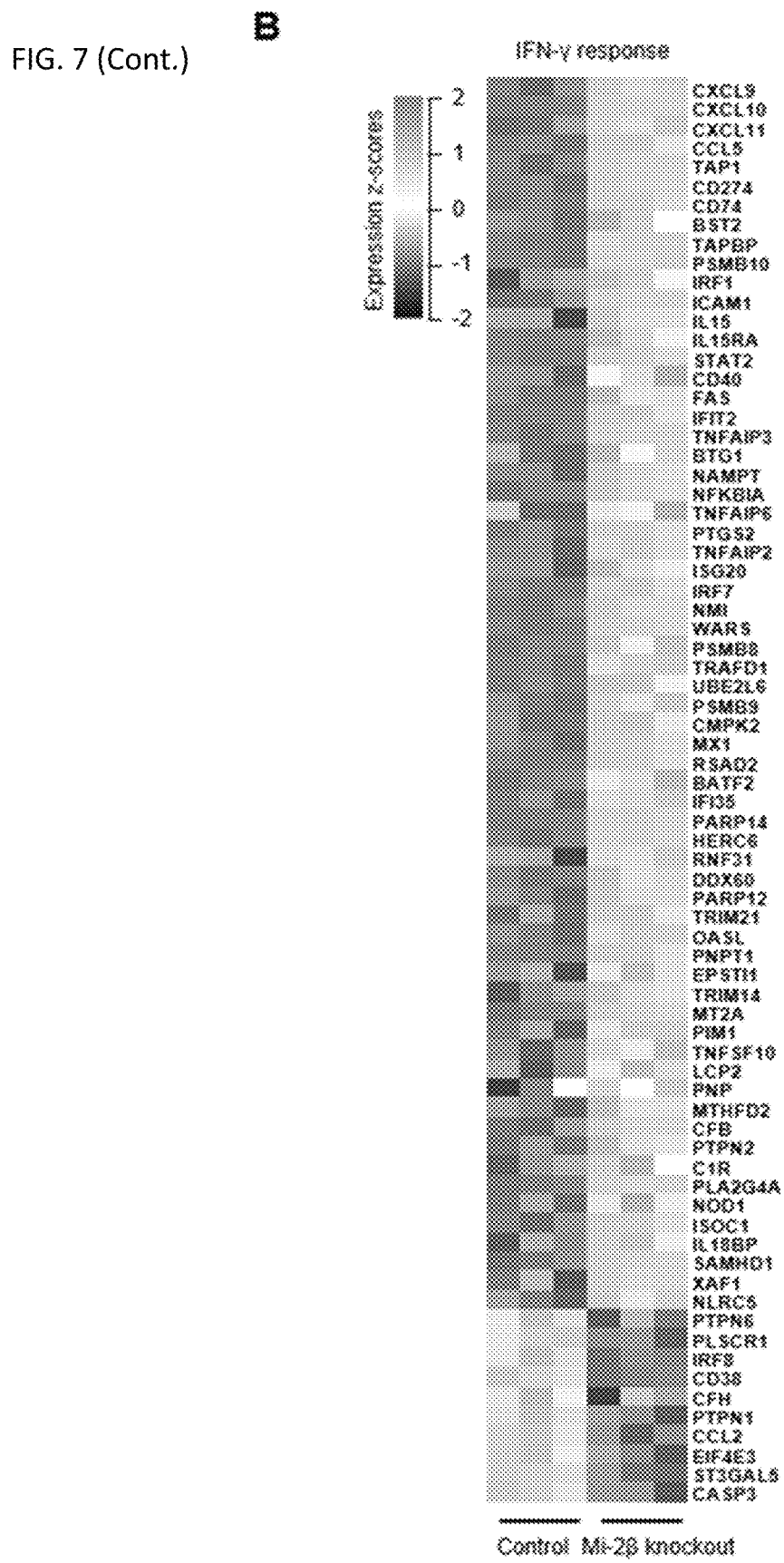
Figure 7:
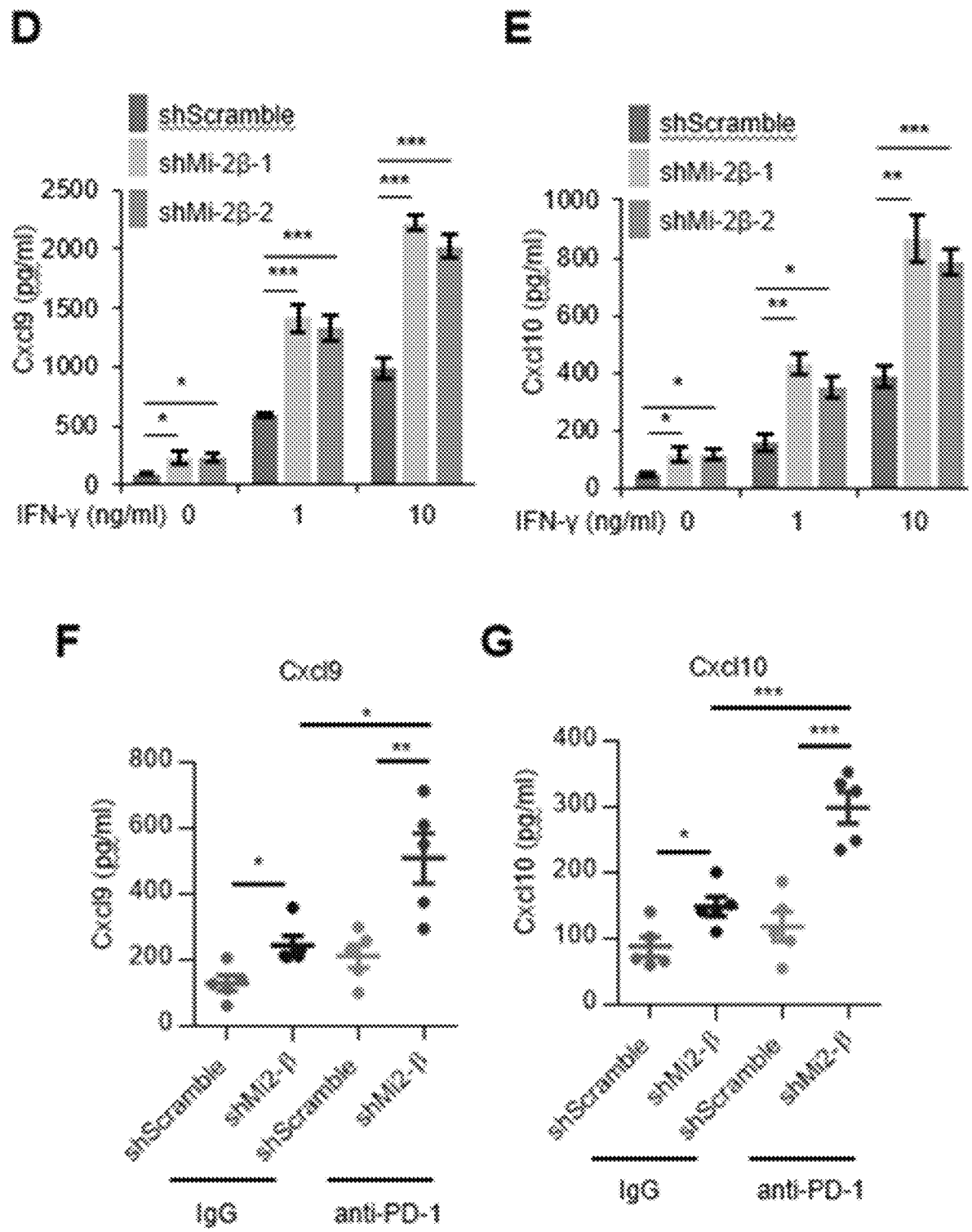

To determine how Mi-2β shapes the immune response in melanoma, Mi-2β-CRISPR/Cas9-knocked and IFN-γ-treated B16F10 cells (43) were used to perform microarray assay. The expression of 1209 genes were significantly repressed (>1.5 fold, p<0.05), and 1283 genes were significantly up-regulated (>1.5 fold, p<0.05) after Mi-2β silencing (Tables 4-5). The deregulated genes identified were further analyzed by Gene Set Enrichment Analysis (GSEA) to identify Mi-20-regulated gene sets and pathways. Interestingly, IFN-γ signaling was activated after Mi-2β knockout (FIG. 7a). IFN-γ production plays a key role in the response to immunotherapy, especially in patients with melanoma (44, 45). Many of Mi-2β-controlled IFN-γ-responsive genes, such as Cxc9, Cxcl10, CD74, Irf1, and CD40, function in T cell chemoattraction, antigen presentation, and T cell targeting and activation (FIG. 7b). Specifically, expression of cytokines such as Cxc9, Cxcl10, Cxcl11 and Ccl5 were upregulated after Mi-2β silencing (FIG. 7b). These cytokines play a key role in inducing and recruiting effector T cells expressing the CXCR3 chemokine receptor into tumor microenvironment to induce anti-tumor immunity (44-46). Several antigen presentation genes, such as Tap1 and CD74 and some regulators involved in tumor cell immunogenicity, such as Irf1, Icam1 and CD40 were also upregulated by Mi-2β knockout in vitro (FIG. 7b).

Figure 8:
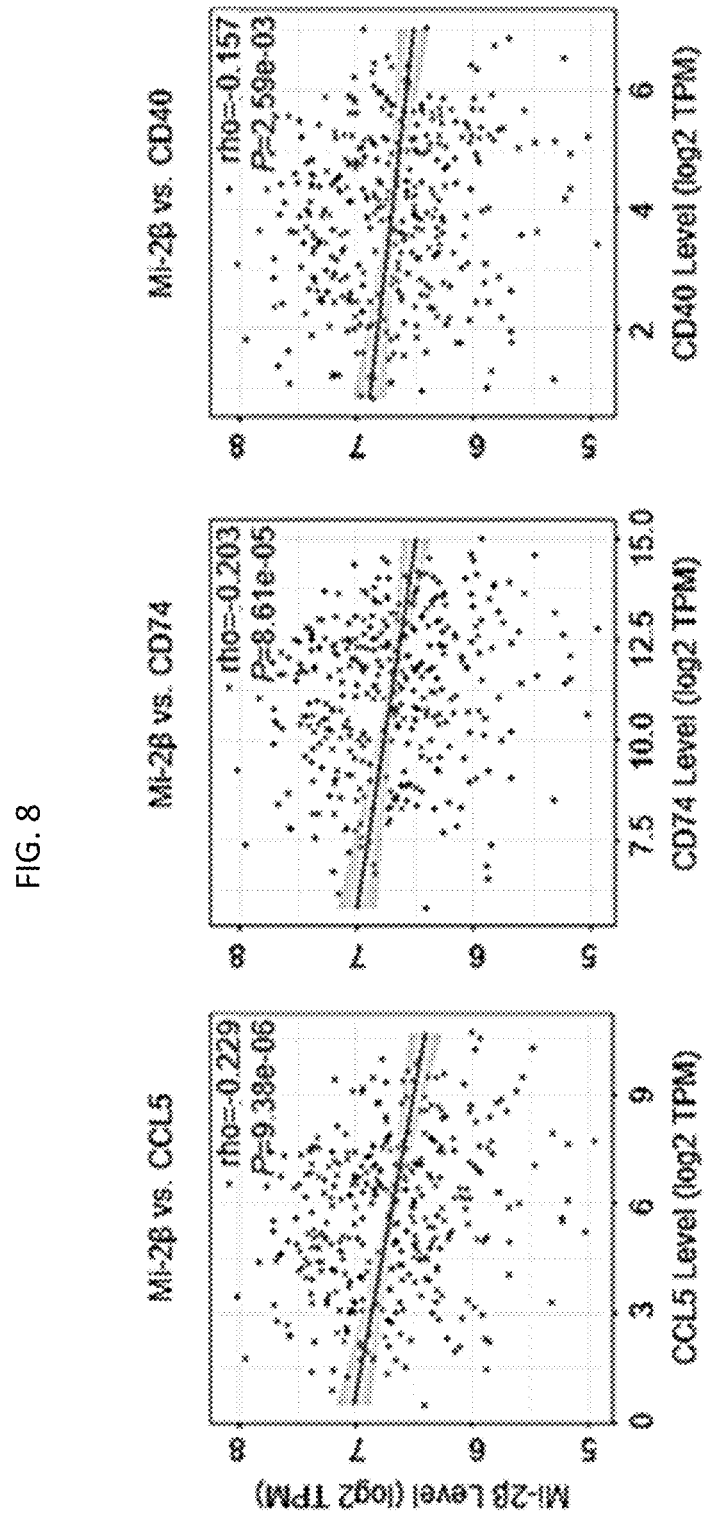
FIG. 8 illustrates Mi-2β directly regulates inflammatory genes. A, Plots showed the Spearman's correlation between Mi-2β mRNA level and CCL5, CD74 or CD40 mRNA expression level in RNA-seq data in TCGA SKCM-Metastasis (n=368). B, The Mi-2β-regulated downstream target genes in IFN-γ signaling were measured in BRaf$^{V600E}$/Pten$^{null}$ and BRaf$^{V600E}$/Pten$^{null}$/Mi-2β$^{null}$ melanoma in mice treated with IgG control or anti-PD-1 with RT-qPCR assay. Values represent mean±SEM. C-E, ChIP assays were performed to detect Mi-2β binding on the promoter of Cxcl9, Cxcl10 and Irf1 genes in both shScramble and Mi-2β knockdown B16F10 cells, with IP by anti-Stat1 was used as the positive binding control. The three bars from left to right: shScramble, shMi-2β-1, and shMi-2β-2. Values represent mean±SD. *p<0.05, p<0.01, *p<0.001.
Figure 8:
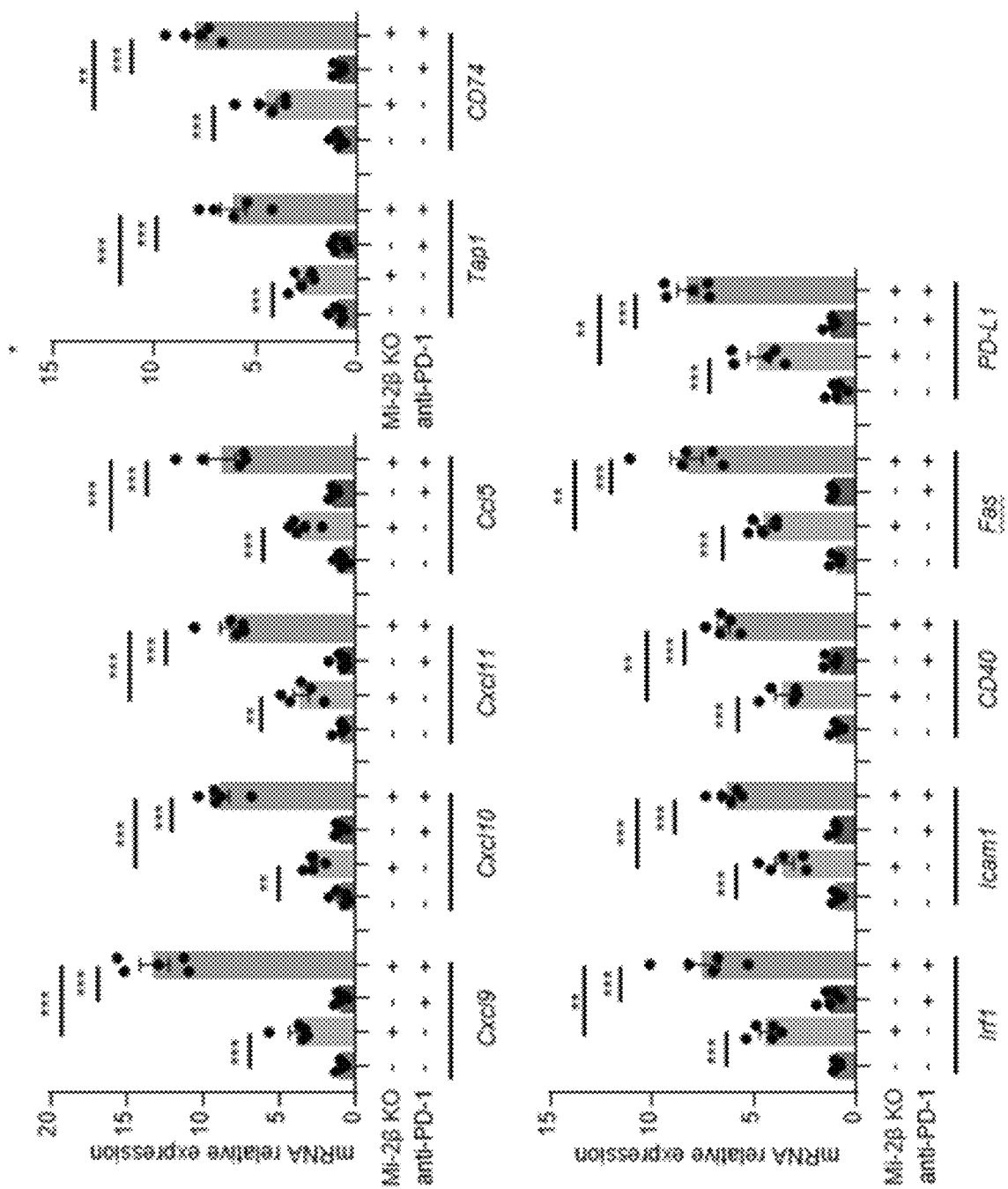
Figure 8:
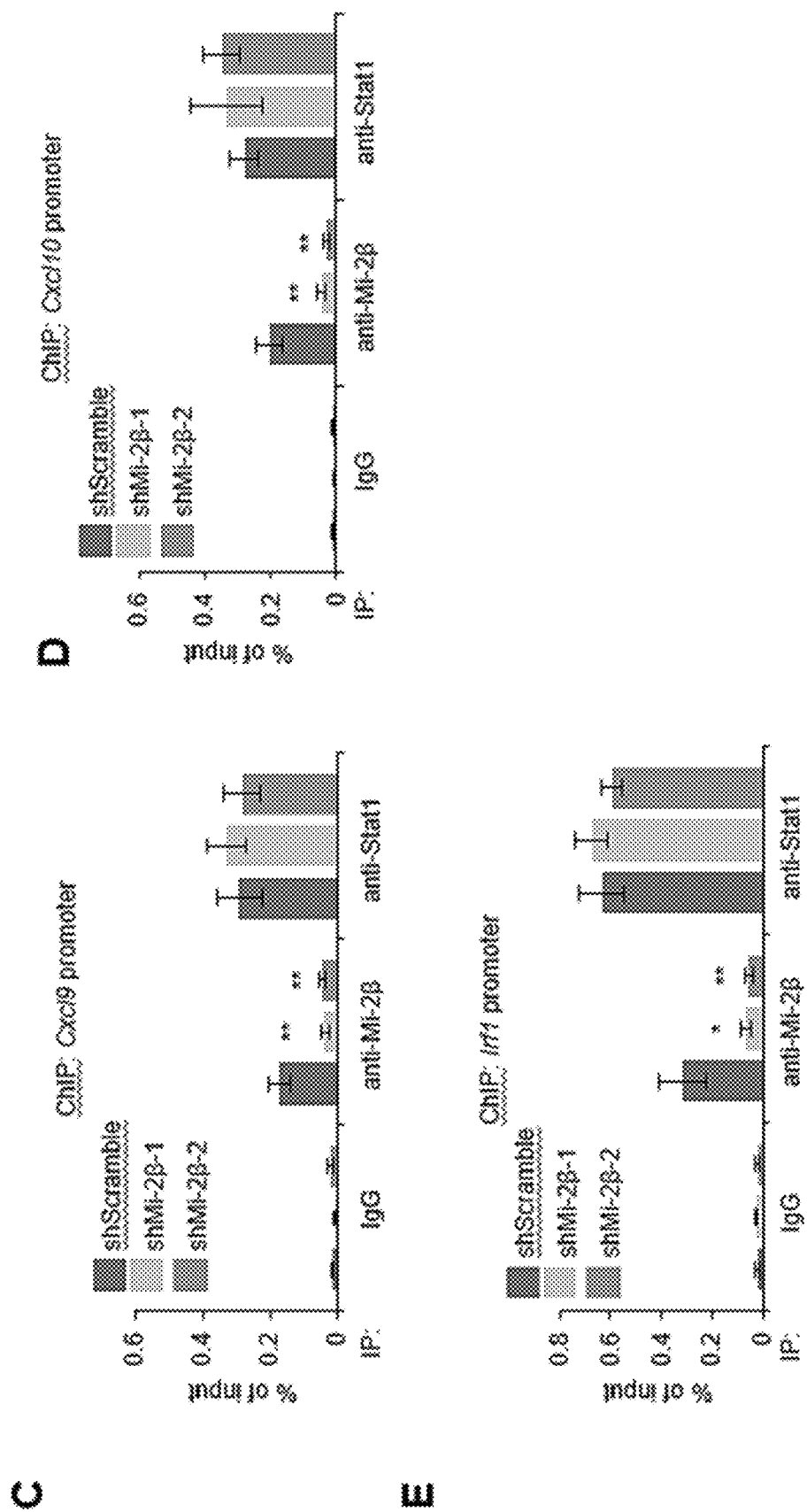

To confirm the regulation of Mi-2β on the downstream targets from IFN-γ signaling, the expression of interferon stimulated genes (ISGs) in the IFN-γ pathway were measured in Mi-2β-depleted B16F10 cells. Mi-2β silencing significantly upregulated the mRNA expression of Cxc9, Cxcl10, Cxcl11, Ccl5, Tap1, CD74, Irf1, Icam1, CD40, Fas and PD-L1 (FIG. 7c) and enhanced the paracrine secretion of Cxcl9 and Cxcl10 both before or after addition of IFN-γ (FIG. 7d-e). In vivo, TIMER analysis (47) indicated that Mi-2β mRNA levels negatively correlated with CXCL9, CCL5, CD74 and CD40 mRNA level in patients in the TCGA melanoma cohort (p<0.01) (FIG. 8a). These data indicate that the Mi-2β-regulated immune response is mediated, at least in part, by IFN-γ signaling pathways in melanoma. To identify how Mi-2β impacts the responses to anti-PD-1 treatment, the expression levels of Cxc19 and Cxcl10 were measured by ELISA in melanomas collected in FIG. 7D-7E. Upregulation of Cxcl9 and Cxcl10 were detected after Mi-2β silencing and anti-PD-1 treatment in melanomas (FIG. 7f-g). In addition, we also measured these factors in the BRaf$^{V600E}$/Pten$^{null}$ melanoma collected in FIG. 7B. Upregulation of Cxc9, Cxcl10, Cxcl11, Ccl5, Tap1, CD74, Irf1, Icam1, CD40, Fas and PD-L1 were detected after Mi-2β silencing and the anti-PD-1 treatment in BRaf$^{V600E}$/Pten$^{null}$ melanomas (FIG. 8b).

To investigate the molecular mechanisms underlying Mi-2β-mediated repression of IFN-γ signaling, chromatin immunoprecipitation (ChIP) assays were performed to identify whether Mi-2β protein binds the promoters of the Cxc9, Cxcl10 and Irf1 genes. We found Mi-2β bound to the promoters of Cxc9, Cxcl10 and Irf1, with anti-Stat1 serving as a positive control (FIG. 8c-e). These data indicate that Mi-2β is directly involved in regulating transcription of Irf1, Cxc19 and Cxcl10.

Figure 9:
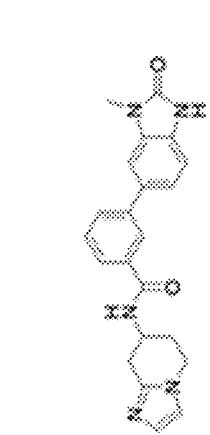
FIG. 9 illustrates Mi-2β inhibitor Z36-MP5 induced immune response to anti-PD-1 therapy in resistant melanoma. A, The chemical structure of Z36-MP5. B, Orientations of Z36-MP5 to homologized Mi-2β. Z36-MP5 was docked into the ATP binding pocket of homologized Mi-2β. The methyl group of Z36-MP5 extended to a solvent-exposed channel lined with the side chains of Tyr729, Leu755, Met966, and Ile1163, with generating H-bonds via the O atom of keto group with His727, O atom of amide group with Gly756, and protonated N atom of imidazole group with Asp873. The atoms of Z36-MP5 were colored as follows: carbon pink, oxygen red, nitrogen blue, and hydrogen white. The H-bonds between Z36-MP5 and homologized Mi-2β were shown as light-yellow dash lines. C, The inhibitory activity of Z36-MP5 for Mi-2β chromatin modulatory activity, measured as fold changes of Mi-2β activity treated with control vehicle. Values presents as means±SD. D, Mice bearing B16F10 cell graft were treated with control IgG or anti-PD-1 antibody, and vehicle control or Z36-MP5, as indicated, and the growth of tumor grafts was shown. For each group n=5. At 18-21 days, the curves from top to bottom: vehicle+IgG, vehicle+anti-PD-1, Z36-MP5+IgG, and Z36-MP5+anti-PD-1. E, Tumor-infiltrating lymph cells were measured by flow cytometry for the population of CD8$^+$ was gated within CD45$^+$ cells. F, Granzyme B expression in CD8$^+$ T was determined and quantified with flow cytometry. G, Mice carrying conditional alleles of Tyr::CreER;BRaf$^{CA}$;Pten$^{lox/lox}$ or Tyr::CreER;BRaf$^{CA}$;Pten$^{lox/lox}$ Mi-2β$^{lox/lox}$ were administered with tamoxifen for constant 5 days to activate CreER to cause melanocyte-specific conversion of Braf$^{CA}$ to Braf$^{V600E}$, and the conversion of the Pten$^{lox/lox}$ and Mi-2β$^{lox/lox}$ alleles to null alleles, which express proteins of BRaf$^{V600E}$/Pten$^{null}$ or BRaf$^{V600E}$/Pten$^{null}$/Mi-2β$^{null}$, respectively. Mice with measurable tumors were randomly treated with either control IgG (10 mg/kg) or anti-PD-1 antibodies (10 mg/kg) and Z36-MP5 (30 mg/kg/day) by i.p. administration as indicated. For each group n=5. Mouse survival was shown with log-rank test for P value. As survival rate drops to 0%, curves from left to right: BRaf$^{V600E}$/Pten$^{null}$ with control, BRaf$^{V600E}$/Pten$^{null}$ with anti-PD-1, BRaf$^{V600E}$/Pten$^{null}$ with Z36-MP5, and BRaf$^{V600E}$/Pten$^{null}$ with Z36-MP5+anti-PD-1. H, TILs were assayed by flow cytometry to detect the population of CD8$^+$ T cells gated within CD45$^+$ T cells. I, The expression of Granzyme B in CD8$^+$ T was determined and quantified with flow cytometry assay. MFI, mean fluorescence intensity. Values represent mean±SEM. *p<0.05, p<0.01, * p<0.001.
Figure 9:
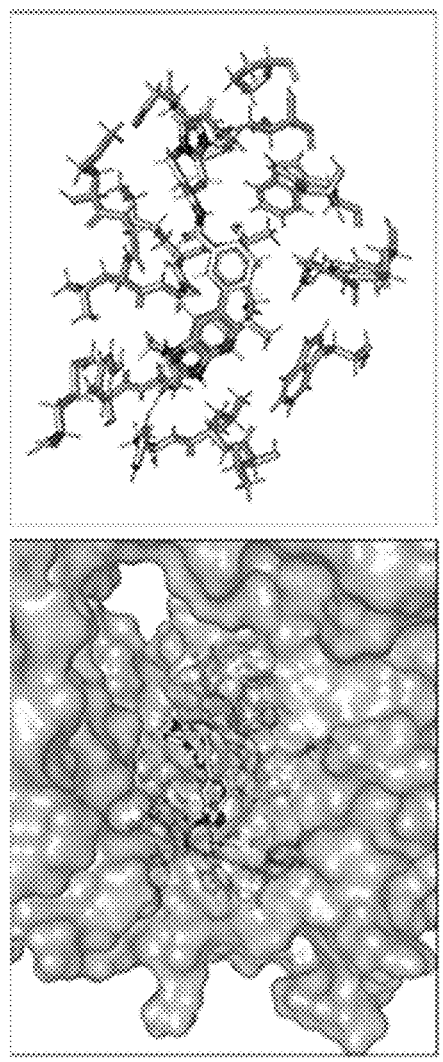
Figure 9:
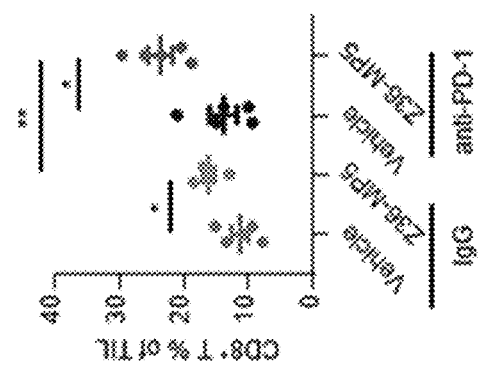
Figure 9:
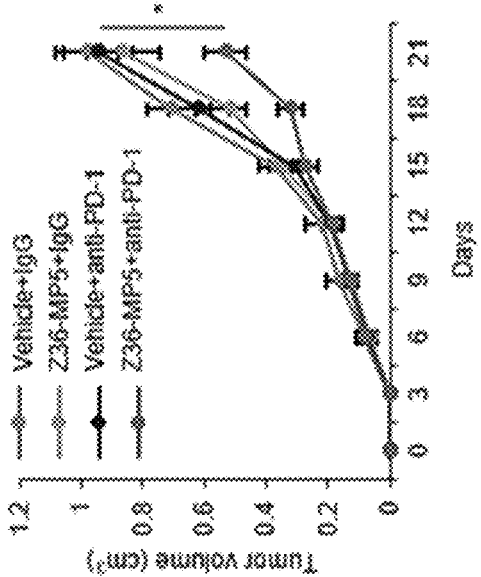
Figure 9:
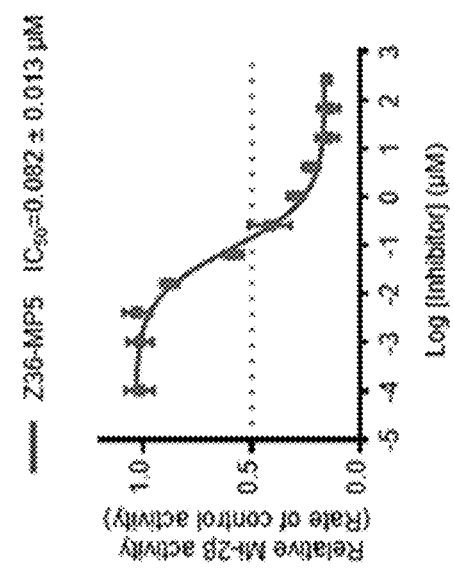
Figure 9:
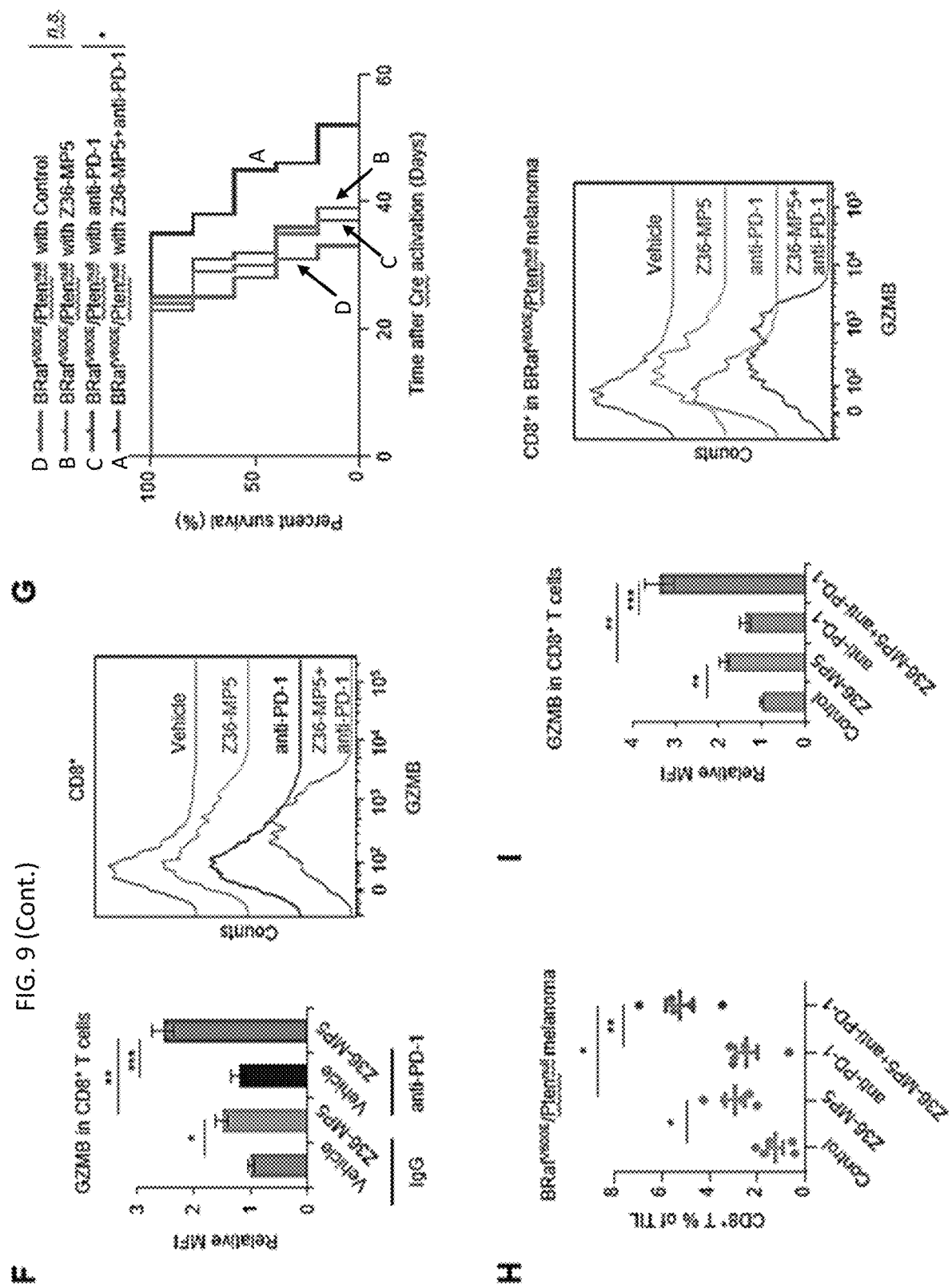
Figure 10:
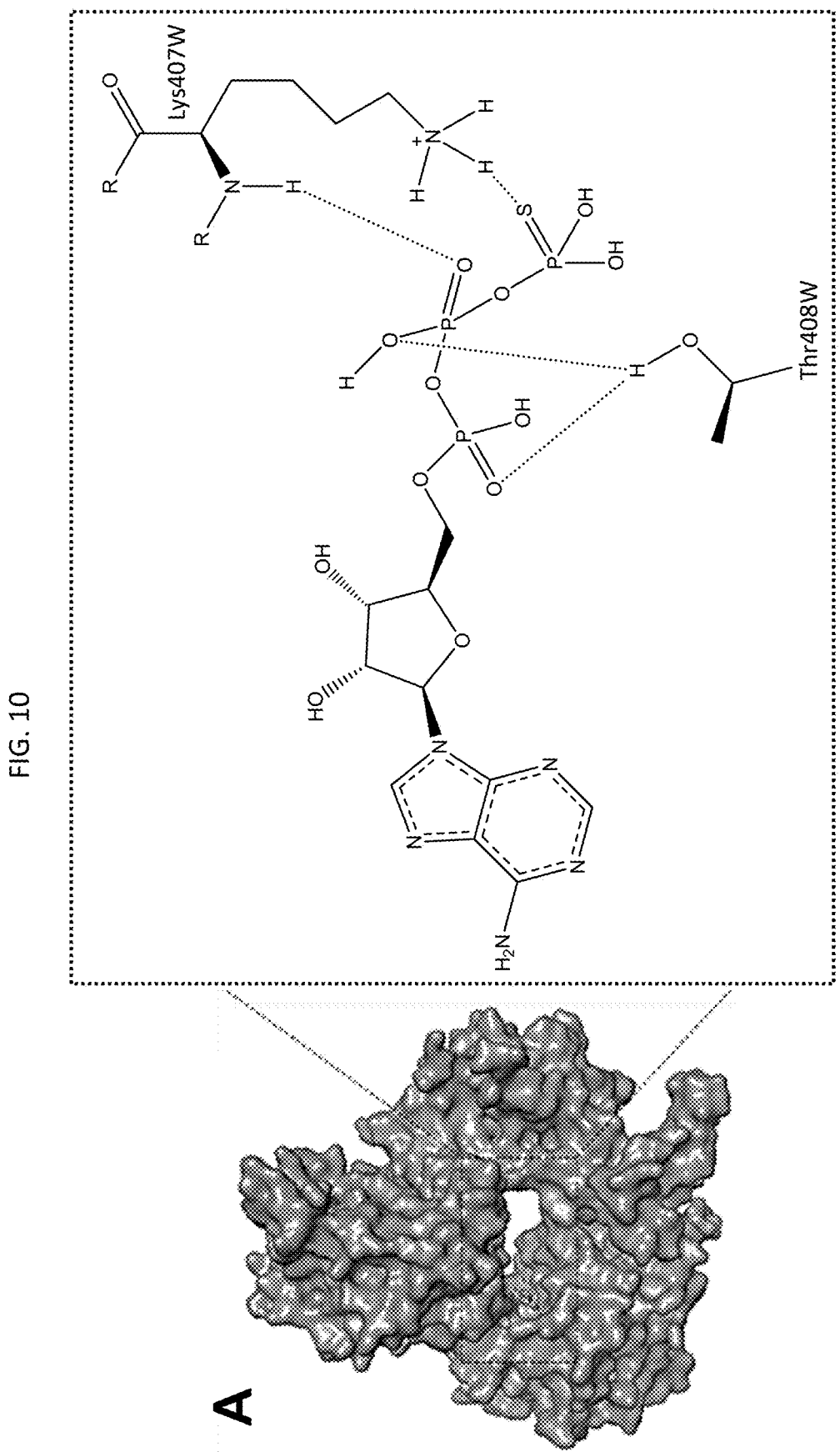
FIG. 10 illustrates In vitro nucleosome remodeling reactions. A, The candidate protein structure for homology modelling. 3MWY depicted the interaction of ATP and its binding pocket. B, Schematic representing in vitro screen assay for testing Mi-2β chromatin modulatory activity using FRET-based nucleosome repositioning assay. C, The FRET-based nucleosome repositioning assays were performed with different concentrations of Mi-2β and a non-limiting ATP concentration (1 mM) for the indicated incubation time. The curves from top to bottom: 250 nM, 50 nM, 10 nM, 2 nM, 0.4 nM, and 0 nM. D, The ATP titration (concentrations ranging from 0.1 to 300 μM) was performed with the FRET-based nucleosome repositioning assays. The Michaelis-Menten equation was performed to calculate the apparent ATP Km, with the ATP Km of 11.54 μM. Values represent mean±SD.
Figure 10:
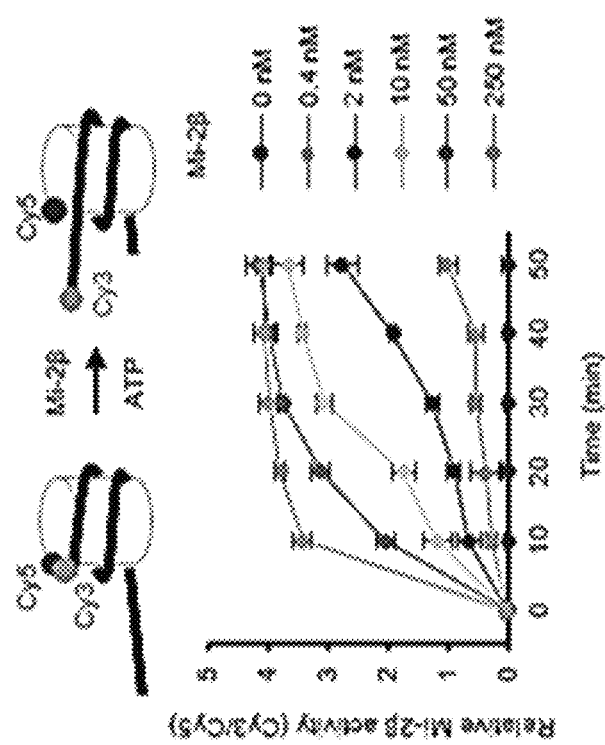
Figure 10:
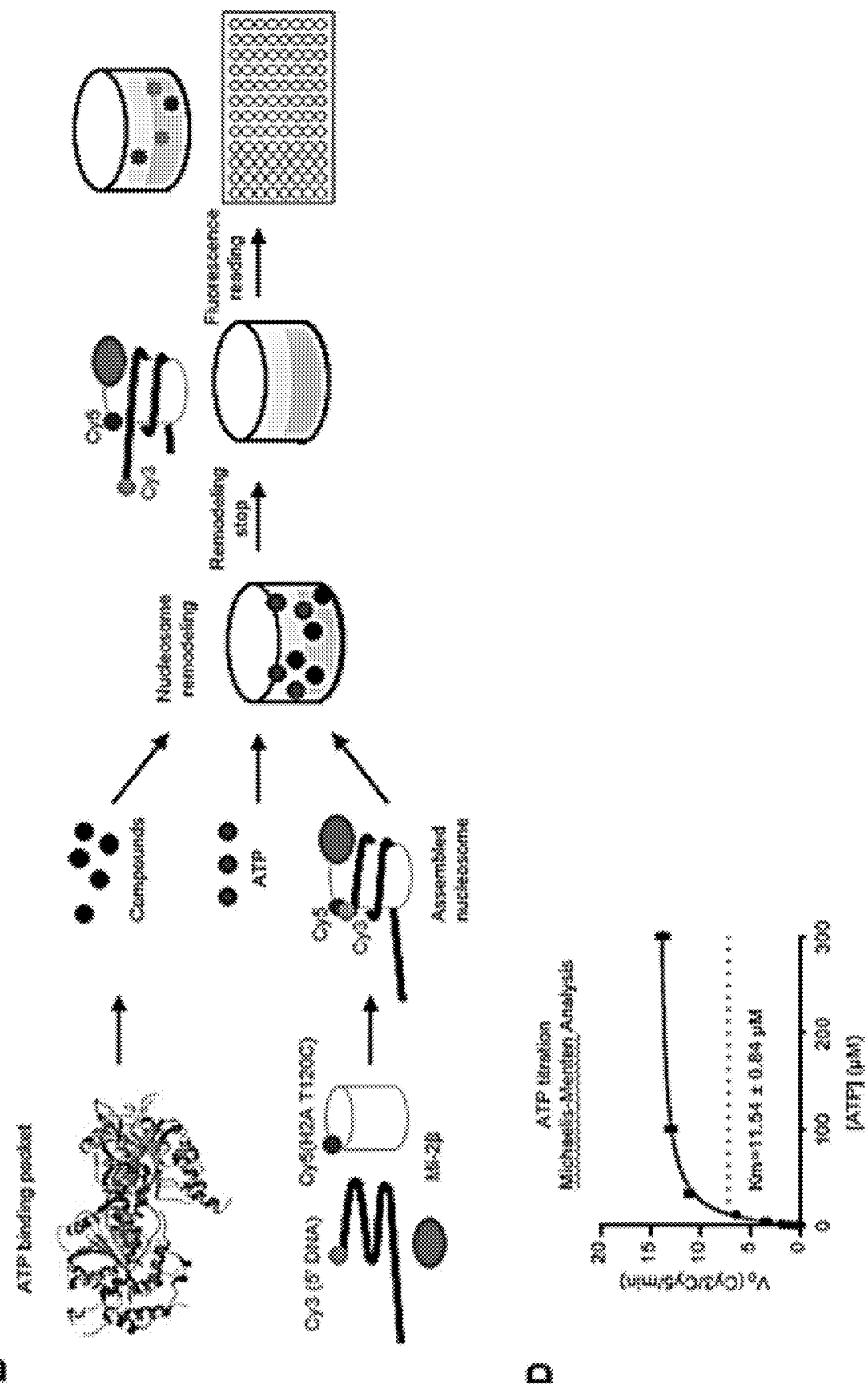
Figure 11:
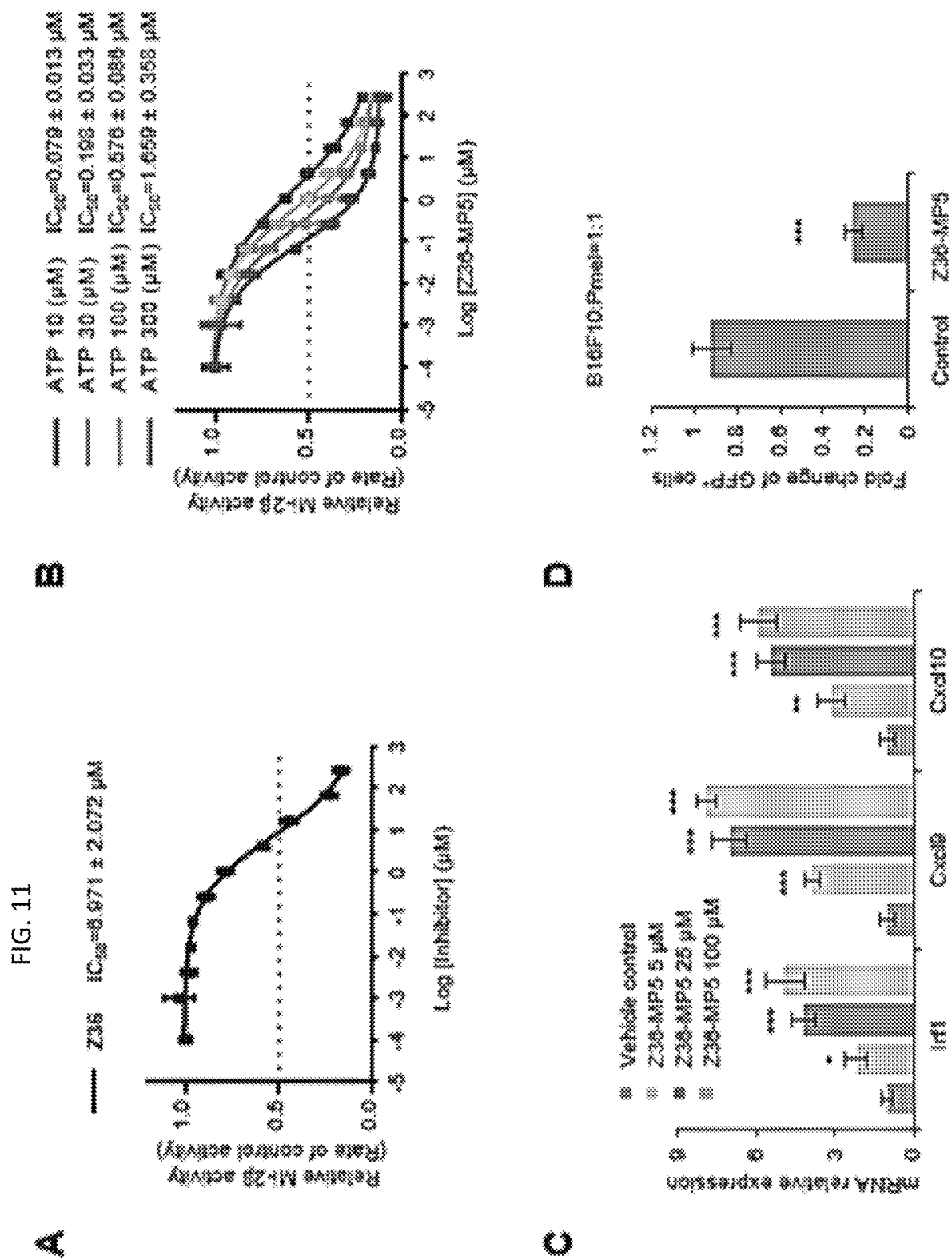
FIG. 11 illustrates In vitro assay for Mi-2β inhibitors. A, The inhibitory activity of Z36 for Mi-2β chromatin modulatory activity, measured as fold changes of Mi-2β activity treated with control vehicle. B, The inhibitory activity of Z36-MP5 with $IC_{50}$ values against Mi-2β at different ATP concentrations. The curves from top to bottom: ATP 300 (μM), ATP 100 (μM), ATP 30 (μM), and ATP 10 (μM). C, The expression of Irf1, Cxc19 and Cxcl10 and Irf1 mRNA in B16F10 cells treated with Z36-MP5 as indicated concentration for 24 hours was determined with RT-qPCR assay. The four bars from left to right: vehicle control, Z36-MP5 5 μM, Z36-MP5 25 μM, and Z36-MP5 100 μM. D, Z36-MP5-treated (25 μM) GFP-labelled B16F10 cells were pretreated with 10 ng/ml of IFN-γ for 24 hours, before co-culture with activated Pmel-1 T cells at a ratio of 1:1 for three days. The fold changes of survival GFP-positive tumor cells were assayed with flow cytometry. Data presents as means±SD E, The body weight changes of C57BL/6J mice treated with Z36-MP5 (30 mg/kg/day) for 2 weeks. Data are mean±SEM (n=5). The top curve: Z36-MP5 (30 mg/kg/day), the bottom curve: control. F, H&E staining of tissues in C57BL/6J mice treated with or without Z36-MP5 (30 mg/kg/day) for 2 weeks. Scale bar=200 μm. G, Blood concentration profiles of Z36-MP5 after a single-dose intraperitoneal injection into 3 male Sprague-Dawley (SD) rats. Values represents the mean±SD. $*p<0.05$, $p<0.01$, $*p<0.001$.
Figure 11:
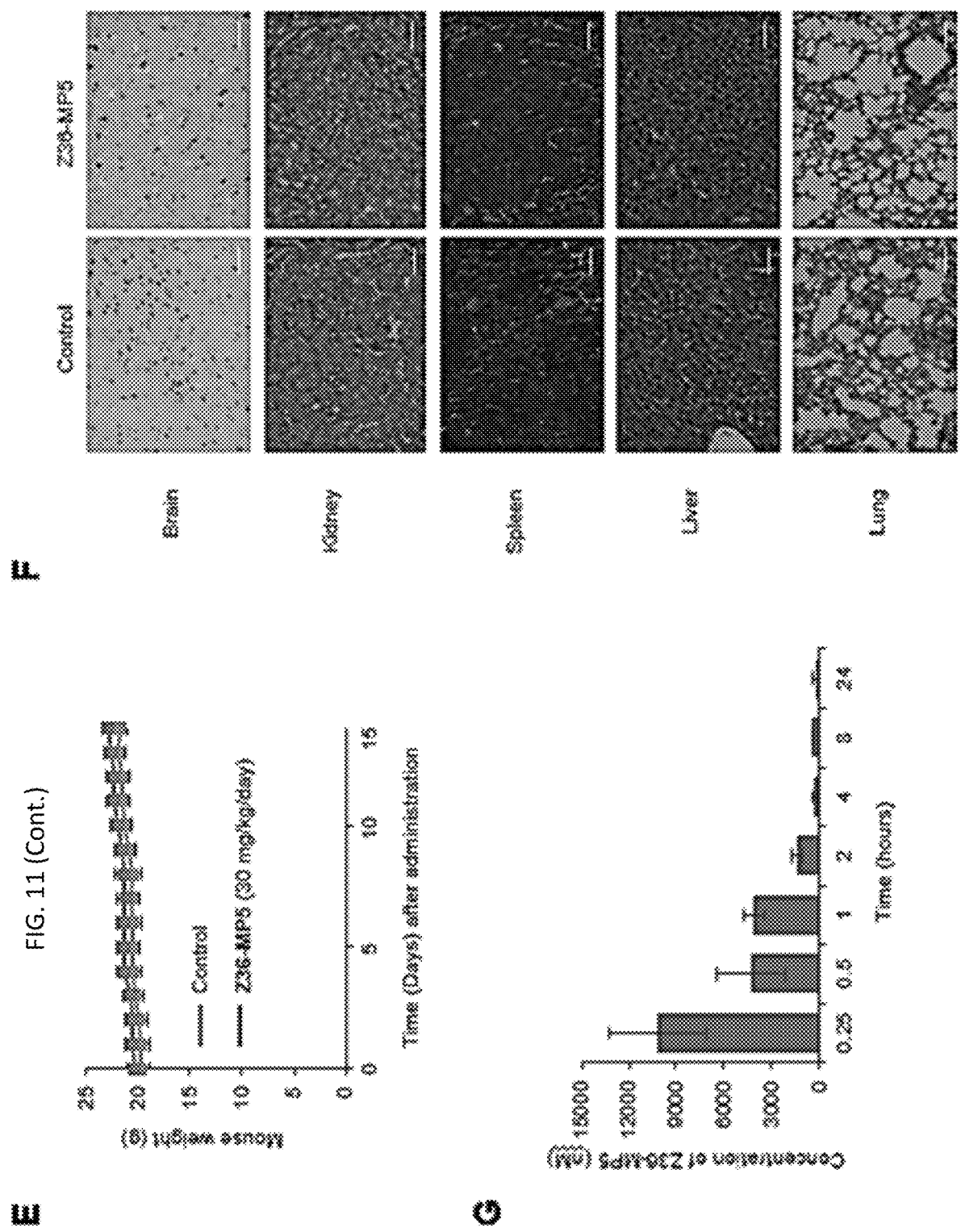

To screen small molecules that inhibit Mi-2β activity, Homology Modeling was carried out using Structure Prediction Wizard in Prime (49, 50). Mi-2β belongs to the CHD family of chromatin remodelers, which share highly conserved ATPase/helicase domains (51, 52). The Homology Model of Mi-2β was generated using the yeast CHD1 structure (PDB code: 3MWY) as template and the sequence was obtained from Uniprot (53), which clearly depicted the interaction of Mi-2β binding pocket and ATP (FIG. 10a). Virtual screening was done with the enzyme hinge region ligands database and nucleoside mimetic database from Enamine. All ligands of ~23,010 compounds were docked to the ATP binding site using SP docking and post-processed with Prime MM-GBSA. Ligands with a methyldihydroimidazopyridinone structure were predicted to bind best to the ATP binding region of Mi-2β. To analyze biochemically the inhibitory activity of those inhibitors, a Fluorescence Resonance Energy Transfer (FRET)-based nucleosome repositioning assay (54, 55) was designed and modified using recombinant purified human Mi-2β protein to screen an in-house library of small molecular compounds with a methyldihydroimidazopyridinone structure (FIG. 10b). Briefly, the recombinant nucleosome substrates consist of a Cy5-labeled human histone octamer (H2A T120C-Cy5) wrapped with 5' Cy3-labeled DNA, which contains a terminal nucleosome 601 positioning sequence. The 601 sequence provides the most thermodynamically preferred locations on DNA for histone octamer (56). FRET signaling was monitored by exciting the nucleosomes at the Cy3 absorption maximum and measuring Cy5 emissions and consequently the FRET signal is at a maximum at the assembled starting point. In the presence of ATP, Mi-2β induces the histone octamer to translocate along the DNA such that the Cy3-labeled DNA 5' end is moved away from the Cy5-labeled octamer and consequently the FRET signal is decreased (FIG. 10b). The reaction conditions for nucleosome repositioning were modified through multiple rounds of optimization and validation (FIG. 10c-d). Z36 was initially identified as the best hit with IC50 values of 6.971±2.072 μM (FIG. 11a). Structure Activity Relationship (SAR) studies were further used to improve the specificity and efficacy of Z36 for Mi-2β inhibition. Through iterative rounds of structure-activity optimization and in vitro assay screens, Z36-MP5 (FIG. 9a) was found to have a high inhibitory activity on Mi-2β function where it was predicted to dock into the ATP binding pocket of Mi-2β (FIG. 9b), with its methyl group extended to a solvent-exposed channel lined with the side chains of Tyr729, Leu755, Met966, and Ile1163. Z36-MP5 could generate H-bonds with Mi-2β via the O atom of its keto group with His727, the O atom of amide group with Gly756, and protonated N atom of imidazole group with Asp873. In vitro assays indicated that Z36-MP5 had IC50 values of 0.082±0.013 μM against Mi-2β (FIG. 9C), ~85 fold more potent than the original compound Z36. Moreover, an ATP acyl phosphate probe assay (57) was performed by ActivX Biosciences inc. to profile of Z36-MP5 inhibition on ATPases in native cell lysates, in which the protein-protein interactions remained intact. Z36-MP5 showed less than 35% inhibition at a concentration of 1 μM against a panel of 233 diverse ATPases (Table 2), These results suggest that Z36-MP5 has a high Mi-2β ATPase selectivity and specificity.

TABLE 2

Profile of Z36-MP5 inhibition on ATPase

| ATPase | Reference | Sequence | Labeling Site | Inhibition (%) by 1 μM Z36-MP5 |
|---|---|---|---|---|
| AARS | UniRef100_P49588 | AGGKHNDLDDVGKDVYHHTFFEMLGS WSFGDYFK (SEQ ID NO: 1) | ATP BS | -29.97 |
| ABCB10 | UniRef100_Q9NRK6 | NVHFAYPARPEVPIFQDFSLSIPSGSVTAL VGPSGSGKSTVLSLLLR (SEQ ID NO: 2) | ATP BS | -6.14 |
| ABCB6 | UniRef100_Q9NP58 | ETLQDVSFTVMPGQTLALVGPSGAGKST ILR (SEQ ID NO: 3) | ATP BS | 8.49 |
| ABCB7 | UniRef100_O75027 | VAIVGGSGSGKSTIVR (SEQ ID NO: 4) | ATP BS | 0.34 |
| ABCC1 | UniRef100_P33527 | TGAGKSSLTLGLFR (SEQ ID NO: 5) | ATP BS | -0.23 |
| ABCC1 | UniRef100_P33527 | SDPPTLNGITFSIPEGALVAVVGQVGCGK SSLLSALLAEMDKVEGHVAIK (SEQ ID NO: 6) | ATP BS | -7.84 |
| ABCC10 | UniRef100_Q5T3U5 | TGSGKSSLLLVLFR (SEQ ID NO: 7) | ATP BS | -3.83 |
| ABCC2 | UniRef100_Q92887 | TGAGKSSLTNCLFR (SEQ ID NO: 8) | ATP BS | 4.09 |
| ABCC3 | UniRef100_O15438 | TGAGKSSMTLCLFR (SEQ ID NO: 9) | ATP BS | 4.57 |
| ABCC3 | UniRef100_O15438 | GALVAVVGPVGCGKSSLVSALLGEMEK (SEQ ID NO: 10) | ATP BS | 9.43 |
| ABCC4 | UniRef100_O15439 | TGAGKSSLISALFR (SEQ ID NO: 11) | ATP BS | 1.76 |
| ABCC4 | UniRef100_O15439 | ASETPTLQGLSFTVRPGELLAVVGPVGA GKSSLLSAVLGELAPSHGLVSVHGR (SEQ ID NO: 12) | ATP BS | 8.93 |
| ABCD3 | UniRef100_P28288 | SGANVLICGPNGCGKSSLFR (SEQ ID NO: 13) | ATP BS | 3.07 |
| ABCD4 | UniRef100_O14678 | ISEGQSLLITGNTGTGKTSLLR (SEQ ID NO: 14) | ATP BS | 11.24 |
| ABCE1 | UniRef100_P61221 | LPIPRPGEVLGLVGTNGIGKSTALK (SEQ ID NO: 15) | ATP BS | -4.76 |
| ABCF1 | UniRef100_Q8NE71 | ICIVGPNGVGKSTLLLLLTGK (SEQ ID NO: 16) | ATP BS | -8.08 |
| ABCF2 | UniRef100_Q9UG63 | VALVGPNGAGKSTLLK (SEQ ID NO: 17) | ATP BS | -7.92 |
| ABCF2 | UniRef100_Q9UG63 | YGLIGLNGIGKSMLLSAIGK (SEQ ID NO: 18) | ATP BS | 26.88 |
| ABCF3 | UniRef100_Q9NUQ8 | ICVVGENGAGKSTMLK (SEQ ID NO: 19) | ATP BS | 5.45 |
| ACACA | UniRef100_Q13085 | DVDDGLQAAEEVGYPVMIKASEGGGGK (SEQ ID NO: 20) | ATP BS | 6.21 |
| ACACB | UniRef100_O00763 | IGFPLMIKASEGGGGK (SEQ ID NO: 21) | ATP BS | -1.87 |
| ACLY | UniRef100_P53396 | GKLGLVGVNLTLDGVK (SEQ ID NO: 22) | ATP BS | -6.87 |
| ACLY | UniRef100_P53396 | LLQDHPWLLSQNLVVKPDQLIKR (SEQ ID NO: 23) | ATP BS | 2.00 |

TABLE 2-continued

Profile of Z36-MP5 inhibition on ATPase

| ATPase | Reference | Sequence | Labeling Site | Inhibition (%) by 1 µM Z36-MP5 |
|---|---|---|---|---|
| ACTA2, ACTB, ACTBL2, ACTC1, ACTG1 | UniRef100_P68032, UniRef100_Q562R1, UniRef100_P63261, UniRef100_P60709, UniRef100_P62736 | KYSVWIGGSILASLSTFQQMWISK (SEQ ID NO: 24) | ATP BS | -15.29 |
| ACTR2 | UniRef100_P61160 | VVVCDNGTGFVKCGYAGSNFPEHIFPAL VGRPIIR (SEQ ID NO: 25) | ATP BS | -16.82 |
| ACTR2 | UniRef100_P61160 | KHMVFLGGAVLADIMK (SEQ ID NO: 26) | ATP BS | -2.20 |
| ACTR3 | UniRef100_P61158 | DREVGIPPEQSLETAKAVK (SEQ ID NO: 27) | ATP BS | 5.36 |
| ACTR3 | UniRef100_P61158 | LPACVVDCGTGYTKLGYAGNTEPQFIIPS CIAIK (SEQ ID NO: 28) | ATP BS | -0.28 |
| AFG3L2 | UniRef100_Q9Y4W6 | GAILTGPPGTGKTLLAK (SEQ ID NO: 29) | ATP BS | -4.85 |
| AHCY | UniRef100_P23526 | SKFDNLYGCR (SEQ ID NO: 30) | ATP BS | -10.85 |
| AK1 | UniRef100_P00568 | TKIIFVVGGPGSGKGTQCEK (SEQ ID NO: 31) | ATP BS | -7.19 |
| AK1 | UniRef100_P00568 | IIFVVGGPGSGKGTQCEK (SEQ ID NO: 32) | ATP BS | -9.87 |
| AK2 | UniRef100_P54819 | AVLLGPPGAGKGTQAPR (SEQ ID NO: 33) | ATP BS | -4.75 |
| AK3 | UniRef100_Q9U117, UniRef100_Q7Z4Y4 | AVIMGAPGSGKGTVSSR (SEQ ID NO: 34) | ATP BS | 19.58 |
| AK4 | UniRef100_P27144 | AVILGPPGSGKGTVCQR (SEQ ID NO: 35) | ATP BS | -9.19 |
| AK5 | UniRef100_Q9Y6K8 | IIFIIGGPGSGKGTQCEK (SEQ ID NO: 36) | ATP BS | 2.21 |
| AK7 | UniRef100_Q96M32 | ICILGPPAVGKSSIAK (SEQ ID NO: 37) | ATP BS | 13.86 |
| ALDH16A1 | UniRef100_Q8IZ83 | DSSGNLHGYVAEGGAKDIR (SEQ ID NO: 38) | ATP BS | -1.13 |
| ALDH18A1 | UniRef100_P54886 | LIDIFYPGDQQSVTFGTKSR (SEQ ID NO: 39) | ATP BS | -6.95 |
| APRT | UniRef100_P07741 | GKLPGPTLWASYSLEYGK (SEQ ID NO: 40) | ATP BS | 0.39 |
| ASNA1 | UniRef100_O43681 | WIFVGGKGGVGK (SEQ ID NO: 41) | ATP BS | -3.04 |
| ASNA1 | UniRef100_O43681 | HKIQAKYLDQMEDLYEDFHIVK (SEQ ID NO: 42) | ATP BS | 0.73 |
| ASS1 | UniRef100_P00966 | QHGIPIPVTPKNPWSMDENLMHISYEAGI LENPK (SEQ ID NO: 43) | ATP BS | 0.53 |
| ATAD1 | UniRef100_Q8NBU5 | HVDLLEVAQETDGFSGSDLKEMCR (SEQ ID NO: 44) | ATP BS | 15.67 |
| ATG7 | UniRef100_O95352 | QPLYEFEDCLGGGKPKALAAADR (SEQ ID NO: 45) | ATP BS | -0.18 |
| ATG7 | UniRef100_O95352 | FLLLTFADLKK (SEQ ID NO: 46) | ATP BS | -6.20 |
| ATIC | UniRef100_P31939 | KKNGNYCVLQMDQSYKPDENEVR (SEQ ID NO: 47) | ATP BS | 4.08 |
| ATP5B | UniRef100_P06576 | IGLFGGAGVGKTVLIMELINNVAK (SEQ ID NO: 48) | ATP BS | -14.96 |
| BAT1 | UniRef100_Q13838 | SGMGKTAVFVLATLQQLEPVTGQVSVL VMCHTR (SEQ ID NO: 49) | ATP BS | -9.58 |
| BAT1, DDX39 | UniRef100_Q13838, UniRef100_O00148 | YQQFKDFQR (SEQ ID NO: 50) | ATP BS | -10.93 |
| CCT2 | UniRef100_P78371 | GMDKILLSSGR (SEQ ID NO: 51) | ATP BS | -6.50 |
| CCT3 | UniRef100_P49368 | ISIPVDISDSDMMLNIINSSITTKAISR (SEQ ID NO: 52) | ATP BS | 10.09 |
| CCT4 | UniRef100_P50991 | DALSDLALHFLNKMK (SEQ ID NO: 53) | ATP BS | 11.95 |
| CCT5 | UniRef100_P48643 | ISDSVLVDIKDTEPLIQTAKTTLGSK (SEQ ID NO: 54) | ATP BS | -2.48 |
| CCT7 | UniRef100_Q99832 | GKATISNDGATILK (SEQ ID NO: 55) | ATP BS | 10.91 |

TABLE 2-continued

Profile of Z36-MP5 inhibition on ATPase

| ATPase | Reference | Sequence | Labeling Site | Inhibition (%) by 1 µM Z36-MP5 |
|---|---|---|---|---|
| CCT8 | UniRef100_P50990 | TSIMSKQYGNEVFLAK (SEQ ID NO: 56) | ATP BS | 9.18 |
| CIID8 | UniRef100_Q9HCK8 | LNTITPVVGKKRK (SEQ ID NO: 57) | ATP BS | −44.26 |
| CLPB | UniRef100_Q9H078 | RKENGWYDEEHPLVFLFLGSSGIGKTEL AK (SEQ ID NO: 58) | ATP BS | −9.00 |
| CLPX | UniRef100_O76031 | SNILLLGPTGSGKTLLAQTLAK (SEQ ID NO: 59) | ATP BS | 0.44 |
| CMPK1 | UniRef100_P30085 | MKPLVVFVLGGPGAGKGTQCAR (SEQ ID NO: 60) | ATP BS | 2.41 |
| CNP | UniRef100_P09543 | AIFTGYYGKGKPVPTQGSR (SEQ ID NO: 61) | ATP BS | −17.28 |
| COASY | UniRef100_Q13057 | SKLLPELLQPYTER (SEQ ID NO: 62) | ATP BS | −3.39 |
| COASY | UniRef100_Q13057 | MLGNLLRPPYERPELPTCLYVIGLTGISGSGKSSIAQR (SEQ ID NO: 63) | ATP BS | 23.55 |
| CPS1 | UniRef100_P31327 | IGSSMKSVGEVMAIGR (SEQ ID NO: 64) | Other | 1.16 |
| DCTPP1 | UniRef100_Q9H773 | KYTELPHGAISEDQAVGPADIPCDSTGQT ST (SEQ ID NO: 65) | ATP BS | 12.74 |
| DDX18 | UniRef100_Q9NVP1 | TGSGKTLAFLIPAVELIVK (SEQ ID NO: 66) | ATP BS | −5.33 |
| DDX21 | UniRef100_Q9NR30 | TGTGKTFSFAIPLIEK (SEQ ID NO: 67) | ATP BS | 3.05 |
| DDX28 | UniRef100_Q9NUL7 | HVVCAAETGSGKTLSYLLPLLQR (SEQ ID NO: 68) | ATP BS | −5.30 |
| DDX39 | UniRef100_O00148 | SGMGKTAVFVLATLQQIEPVNGQVTVL VMCHTR (SEQ ID NO: 69) | ATP BS | −8.90 |
| DDX3X | UniRef100_O00571, UniRef100_F7BMH3 | DLMACAQTGSGKTAAFLLPILSQIYSDGP GEALR (SEQ ID NO: 70) | ATP BS | 11.22 |
| DERA | UniRef100_Q9Y315 | TVKKEWQAAWLLK (SEQ ID NO: 71) | ATP BS | 6.01 |
| DHX15 | UniRef100_O43143 | HQSFVLVGETGSGKTTQIPQWCVEYMR (SEQ ID NO: 72) | ATP BS | −5.22 |
| DHX36 | UniRef100_Q9H2U1 | ELVNLIDNHQVTVISGETGCGKTTQVTQ FILDNYIER (SEQ ID NO: 73) | ATP BS | −20.12 |
| DYNC1H1 | UniRef100_Q14204 | LGGSPFGPAGTGKTESVK (SEQ ID NO: 74) | ATP BS | −1.99 |
| DYNC1H1 | UniRef100_Q14204 | QPQGHLLLIGVSGAGKTTLSR (SEQ ID NO: 75) | ATP BS | 0.38 |
| ENPP1 | UniRef100_P22413 | TFPNHYSIVTGLYPESHGIIDNKMYDPK (SEQ ID NO: 76) | ATP BS | 8.04 |
| EPRS | UniRef100_P07814 | WEFKHPQPFLR (SEQ ID NO: 77) | ATP BS | 0.78 |
| FDPS | UniRef100_P14324 | IGTDIQDNKCSWLVVQCLQR (SEQ ID NO: 78) | ATP BS | 29.13 |
| GARS | UniRef100_P41250 | TSGHVDKFADFMVK (SEQ ID NO: 79) | ATP BS | 16.66 |
| GART | UniRef100_P22102 | ASGLAAGKGVIVAK (SEQ ID NO: 80) | ATP BS | −8.85 |
| GART | UniRef100_P22102 | SAGVQCFGPTAEAAQLESSKR (SEQ ID NO: 81) | ATP BS | −7.56 |
| GART | UniRef100_P22102 | SGCKVDLGGFAGLFDLK (SEQ ID NO: 82) | ATP BS | −2.13 |
| GATB | UniRef100_O75879 | IKQIQLEQDSGK (SEQ ID NO: 83) | ATP BS | −15.35 |
| GATB | UniRef100_O75879 | KHYFYADLPAGYQITQQR (SEQ ID NO: 84) | ATP BS | −4.32 |
| GMPS | UniRef100_P49915 | AELIKTHHNDTELIR (SEQ ID NO: 85) | Other | −13.99 |
| GMPS | UniRef100_P49915 | LGIQVKVINAAHSFYNGTTTLPISDEDRT PR (SEQ ID NO: 86) | Other | 14.54 |
| GSS | UniRef100_P48637 | CPDIATQLAGTKK (SEQ ID NO: 87) | ATP BS | −5.02 |
| GSS | UniRef100_P48637 | TKAIEHADGGVAAGVAVLDNPYPV (SEQ ID NO: 88) | ATP BS | 7.54 |
| HARS | UniRef100_P12081 | TICSSVDKLDKVSWEEVKNEMVGEK (SEQ ID NO: 89) | ATP BS | 4.68 |

TABLE 2-continued

Profile of Z36-MP5 inhibition on ATPase

| ATPase | Reference | Sequence | Labeling Site | Inhibition (%) by 1 µM Z36-MP5 |
|---|---|---|---|---|
| HDDC3 | UniRef100_Q8N4P3 | RKDPEGTPYINHPIGVAR (SEQ ID NO: 90) | ATP BS | 1.23 |
| HDDC3 | UniRef100_Q8N4P3 | LVEEVTDDKTLPKLER (SEQ ID NO: 91) | ATP BS | 17.25 |
| HNRNPU | UniRef100_Q00839 | KDCEVVMMIGLPGAGKTTWVTK (SEQ ID NO: 92) | ATP BS | 6.85 |
| HPRT1 | UniRef100_Q6LET3, UniRef100_P00492 | LKSYCNDQSTGDIK (SEQ ID NO: 93) | ATP BS | 12.92 |
| HSP60 | UniRef100_P10809 | TVIIEQSWGSPKVTK (SEQ ID NO: 94) | ATP BS | 11.39 |
| HSP90AA | UniRef100_P07900 | TLTIVDTGIGMTKADLINNLGTIAKSGTK (SEQ ID NO: 95) | ATP BS | −1.29 |
| HSP90AA, HSP90AA2, HSP90AB1 | UniRef100_Q14568, UniRef100_P08238, UniRef100_P07900 | ADLINNLGTIAKSGTK (SEQ ID NO: 96) | ATP BS | −5.50 |
| HSP90AB1 | UniRef100_P08238 | TLTLVDTGIGMTKADLINNLGTIAKSGTK (SEQ ID NO: 97) | ATP BS | −3.22 |
| HSP90AB1, HSP90AB3P | UniRef100_P08238, UniRef100_Q58FF7 | RAPFDLFENKKK (SEQ ID NO: 98) | ATP BS | −16.94 |
| HSP90B2P, TRA1 | UniRef100_P14625, UniRef100_Q58FF3 | GLFDEYGSKK (SEQ ID NO: 99) | ATP BS | −6.72 |
| HSPA1A | UniRef100_P08107 | LIGDAAKNQVALNPQNTVFDAKR (SEQ ID NO: 100) | ATP BS | −9.44 |
| HSPA1A | UniRef100_P08107 | LIGDAAKNQVALNPQNTVFDAK (SEQ ID NO: 101) | ATP BS | −15.23 |
| HSPA2 | UniRef100_P54652 | LIGDAAKNQVAMNPTNTIFDAKR (SEQ ID NO: 102) | ATP BS | −1.50 |
| HSPA2 | UniRef100_P54652 | LIGDAAKNQVAMNPTNTIFDAK (SEQ ID NO: 103) | ATP BS | −5.18 |
| HSPA5 | UniRef100_P11021 | LIGDAAKNQLTSNPENTVFDAKR (SEQ ID NO: 104) | ATP BS | −16.08 |
| HSPA5 | UniRef100_P11021 | LIGDAAKNQLTSNPENTVFDAK (SEQ ID NO: 105) | ATP BS | −7.84 |
| HSPA8 | UniRef100_P11142 | LIGDAAKNQVAMNPTNTVFDAKR (SEQ ID NO: 106) | ATP BS | 3.27 |
| HSPA8 | UniRef100_P11142 | LIGDAAKNQVAMNPTNTVFDAK (SEQ ID NO: 107) | ATP BS | 4.45 |
| HSPA9 | UniRef100_P38646 | LVGMPAKR (SEQ ID NO: 108) | ATP BS | −4.09 |
| HYOU1 | UniRef100_Q9Y4L1 | RKTPVIVTLKENER (SEQ ID NO: 109) | ATP BS | −13.34 |
| HYOU1 | UniRef100_Q9Y4L1 | KTPVIVTLKENER (SEQ ID NO: 110) | ATP BS | −6.78 |
| IDI1 | UniRef100_Q13907 | QQVQLLAEMCILIDENDNKIGAETKK (SEQ ID NO: 111) | ATP BS | 5.48 |
| KARS | UniRef100_Q15046 | KEICNAYTELNDPMR (SEQ ID NO: 112) | ATP BS | 2.22 |
| KIAA0564 | UniRef100_A3KMH1 | LGHILVVDEADKAPTNVTCILKTLVENG EMILADGRR (SEQ ID NO: 113) | ATP BS | 11.07 |
| LIG1 | UniRef100_P18858 | VREDKQPEQATTSAQVACLYR (SEQ ID NO: 114) | ATP BS | −7.76 |
| LONP1 | UniRef100_P36776 | ILCFYGPPGVGKTSIAR (SEQ ID NO: 115) | Other | 1.81 |
| MCCC1 | UniRef100_Q96RQ3 | HQKIIEEAPAPGIK (SEQ ID NO: 116) | ATP BS | −6.46 |
| MCCC1 | UniRef100_Q96RQ3 | IGYPVMIKAVR (SEQ ID NO: 117) | ATP BS | 4.45 |
| MCM4 | UniRef100_P33991 | SLFSDKQMIK (SEQ ID NO: 118) | ATP BS | 4.98 |
| MCM6 | UniRef100_Q14566 | SQFLKHVEEFSPR (SEQ ID NO: 119) | ATP BS | −5.23 |
| MCM6 | UniRef100_Q14566 | GDINVCIVGDPSTAKSQFLK (SEQ ID NO: 120) | ATP BS | −2.54 |
| MDN1 | UniRef100_Q9NU22 | VVSAGTYPVLIQGETSVGKTSLIQWLAA ATGNHCVR (SEQ ID NO: 121) | ATP BS | 3.28 |
| ME2 | UniRef100_P23368 | SIVDNWPENHVKAVVVTDGER (SEQ ID NO: 122) | ATP BS | −6.47 |

TABLE 2-continued

Profile of Z36-MP5 inhibition on ATPase

| ATPase | Reference | Sequence | Labeling Site | Inhibition (%) by 1 μM Z36-MP5 |
|---|---|---|---|---|
| ME2 | UniRef100_P23368 | AKIDSYQEPFTHSAPESIPDTFEDAVNILK PSTIIGVAGAGR (SEQ ID NO: 123) | ATP BS | −16.71 |
| MMAB | UniRef100_Q96EY8 | RPKDDQVFEAVGTTDELSSAIGFALELVT EK (SEQ ID NO: 124) | ATP BS | −4.08 |
| MTHFD1 | UniRef100_P11586 | YVVVTGITPTPLGEGKSTTTIGLVQALGA HLYQNVFACVR (SEQ ID NO: 125) | ATP BS | −6.16 |
| MTHFD1L | UniRef100_Q6UB35, UniRef100_Q5JYA8 | YVLVAGITPTPLGEGKSTVTIGLVQALTA HLNVNSFACLR (SEQ ID NO: 126) | ATP BS | 1.16 |
| MVK | UniRef100_Q03426 | GLHSKLTGAGGGGCGITLLKPGLEQPEV EATK (SEQ ID NO: 127) | ATP BS | 15.38 |
| MYO1E | UniRef100_Q12965 | NMIIDRENQCVIISGESGAGKTVAAK (SEQ ID NO: 128) | ATP BS | 4.66 |
| NADK2 | UniRef100_Q4G0N4 | VVVVAKTTR (SEQ ID NO: 129) | ATP BS | −11.03 |
| NADSYN1 | UniRef100_Q6IA69 | YDCSSADINPIGGISKTDLR (SEQ ID NO: 130) | ATP BS | −2.19 |
| NARS | UniRef100_O43776 | FPVEIKSFYMQR (SEQ ID NO: 131) | ATP BS | 2.36 |
| NDUFA10 | UniRef100_O95299 | VITVDGNICTGKGK (SEQ ID NO: 132) | ATP BS | 14.09 |
| NME1, NME2 | UniRef100_P15531, UniRef100_P22392 | TFIAIKPDGVQR (SEQ ID NO: 133) | ATP BS | −1.52 |
| NME3 | UniRef100_Q13232 | GDFCIEVGKNLIHGSDSVESAR (SEQ ID NO: 134) | ATP BS | 1.91 |
| NMNAT3 | UniRef100_Q96T66 | DHLHQTGMYQVIQGIISPVNDTYGKK (SEQ ID NO: 135) | ATP BS | 9.62 |
| NOP2 | UniRef100_P46087 | VLLDAPCSGTGVISKDPAVK (SEQ ID NO: 136) | ATP BS | 1.98 |
| NRK1 | UniRef100_Q9NWW6 | TFIIGISGVTNSGKTTLAK (SEQ ID NO: 137) | ATP BS | 0.34 |
| NSF | UniRef100_P46459 | VWIGIKK (SEQ ID NO: 138) | ATP BS | 6.03 |
| NSF | UniRef100_P46459 | GILLYGPPGCGKTLLAR (SEQ ID NO: 139) | ATP BS | −6.18 |
| NT5E | UniRef100_P21589, UniRef100_Q53Z63 | GVDVVVGGHSNTFLYTGNPPSKEVPAG KYPFIVTSDDGR (SEQ ID NO: 140) | ATP BS | −9.95 |
| NTPCR | UniRef100_Q9BSD7 | HVFLTGPPGVGKTTLIHK (SEQ ID NO: 141) | ATP BS | −14.99 |
| NUDT1 | UniRef100_P36639 | VLLGMKK (SEQ ID NO: 142) | ATP BS | 25.70 |
| NUDT1 | UniRef100_P36639 | WNGFGGKVQEGETIEDGAR (SEQ ID NO: 143) | ATP BS | 22.17 |
| NUDT1 | UniRef100_P36639 | LYTLVLVLQPQRVLLGMKK (SEQ ID NO: 144) | ATP BS | 18.32 |
| NUDT2 | UniRef100_P50583 | NKPKTVIYWLAEVKDYDVEIR (SEQ ID NO: 145) | ATP BS | 19.18 |
| NUDT2 | UniRef100_P50583 | VDNNAIEFLLLQASDGIHHWTPPKGHVE PGEDDLETALR (SEQ ID NO: 146) | ATP BS | 11.64 |
| NUDT7 | UniRef100_P0C024 | APGEVCFPGGKRDPTDMDDAATALR (SEQ ID NO: 147) | ATP BS | 19.75 |
| NVL | UniRef100_O15381 | ALGLVTPAGVLLAGPPGCGKTLLAK (SEQ ID NO: 148) | ATP BS | −1.13 |
| NVL | UniRef100_O15381 | GVLLHGPPGCGKTLLAHAIAGELDLPILK (SEQ ID NO: 149) | ATP BS | −8.26 |
| OLA1 | UniRef100_Q9NTK5 | IGIVGLPNVGKSTFFNVLTNSQASAENFP FCTIDPNESR (SEQ ID NO: 150) | ATP BS | −0.68 |
| PAICS | UniRef100_P22234 | TKEVYELLDSPGK (SEQ ID NO: 151) | ATP BS | 19.51 |
| PC | UniRef100_P11498 | HQKVVEIAPAAHLDPQLR (SEQ ID NO: 152) | ATP BS | −15.19 |
| PCCA | UniRef100_P05165 | EIGYPVMIKASAGGGGK (SEQ ID NO: 153) | ATP BS | −5.50 |
| PCCA | UniRef100_P05165 | NQKVVEEAPSIFLDAETRR (SEQ ID NO: 154) | ATP BS | −10.70 |

TABLE 2-continued

Profile of Z36-MP5 inhibition on ATPase

| ATPase | Reference | Sequence | Labeling Site | Inhibition (%) by 1 µM Z36-MP5 |
|---|---|---|---|---|
| PDE12 | UniRef100_Q6L8Q7 | IKQHEGLATFYR (SEQ ID NO: 155) | ATP BS | -5.87 |
| PEX1 | UniRef100_O43933 | NGALLLTGGKGSGK (SEQ ID NO: 156) | ATP BS | -4.27 |
| PFAS | UniRef100_O15067 | HWFFKGQLHVDGQK (SEQ ID NO: 157) | ATP BS | -4.58 |
| PFKFB2 | UniRef100_O60825 | VFFVESVCDDPDVIAANILEVKVSSPDYP ER (SEQ ID NO: 158) | ATP BS | 14.74 |
| PFKM | UniRef100_P08237 | SFMNNWEVYKLLAHVRPPVSK (SEQ ID NO: 159) | ATP BS | -8.93 |
| PGK1 | UniRef100_P00558 | ALESPERPFLAILGGAKVADK (SEQ ID NO: 160) | ATP BS | -4.49 |
| PKM, PKM2 | UniRef100_P14618, UniRef100_Q504U3 | AEGSDVANAVLDGADCIMLSGETAKGD YPLEAVR (SEQ ID NO: 161) | ATP BS | 28.24 |
| PMS2 | UniRef100_P54278 | HHTSKIQEFADLTQVETFGFRGEALSSLC ALSDVTISTCHASAK (SEQ ID NO: 162) | ATP BS | 3.36 |
| PMVK | UniRef100_Q15126 | SGKDFVTEALQSR (SEQ ID NO: 163) | ATP BS | -5.60 |
| POLR3A | UniRef100_O14802 | MAQELKYGDIVER (SEQ ID NO: 164) | ATP BS | 4.31 |
| PPCS | UniRef100_Q9HAB8 | MVPKLLSPLVK (SEQ ID NO: 165) | ATP BS | -7.44 |
| PPCS | UniRef100_Q9HAB8 | AFIISFKLETDPAIVINR (SEQ ID NO: 166) | ATP BS | -9.61 |
| PRKAG1 | UniRef100_P54619 | LPVIDPESGNTLYILTHKR (SEQ ID NO: 167) | ATP BS | -11.56 |
| PRKAG1 | UniRef100_P54619 | GRVVDIYSKFDVINLAAEK (SEQ ID NO: 168) | ATP BS | -7.08 |
| PRKAG1, PRKAG2 | UniRef100_P54619, UniRef100_Q9UGJ0 | VVDIYSKFDVINLAAEK (SEQ ID NO: 169) | ATP BS | -7.97 |
| PRKAG2 | UniRef100_Q9UGJ0 | ISALPVVDESGKVVDIYSKFDVINLAAEK (SEQ ID NO: 170) | ATP BS | -22.54 |
| PRPS1 | UniRef100_P60891, UniRef100_Q53FW2 | NCTIVSPDAGGAKR (SEQ ID NO: 171) | ATP BS | -22.26 |
| PRPS1L1, PRPS2 | UniRef100_P21108, UniRef100_P11908 | NCIIVSPDAGGAKR (SEQ ID NO: 172) | ATP BS | -13.63 |
| PSMC1 | UniRef100_P62191 | GVILYGPPGTGKTLLAK (SEQ ID NO: 173) | ATP BS | -7.42 |
| PSMC2 | UniRef100_P35998 | GVLLFGPPGTGKTLCAR (SEQ ID NO: 174) | ATP BS | -6.44 |
| PSMC3 | UniRef100_P17980 | GVLMYGPPGTGKTLLAR (SEQ ID NO: 175) | ATP BS | 5.71 |
| PSMC4 | UniRef100_P43686 | GVLMYGPPGCGKTMLAK (SEQ ID NO: 176) | ATP BS | 13.36 |
| PSMC5 | UniRef100_P62195 | GVLLYGPPGTGKTLLAR (SEQ ID NO: 177) | ATP BS | -3.98 |
| PSMC6 | UniRef100_P62333 | GCLLYGPPGTGKTLLAR (SEQ ID NO: 178) | ATP BS | -0.83 |
| PSMD9 | UniRef100_O00233 | HNIICLQNDHKAVMK (SEQ ID NO: 179) | ATP BS | 2.13 |
| QARS | UniRef100_P47897 | TGDKWCIYPTYDYTHCLCDSIEHITHSLC TKEFQAR (SEQ ID NO: 180) | ATP BS | -7.77 |
| RAD17 | UniRef100_O75943 | QGGSILLITGPPGCGKTTTLK (SEQ ID NO: 181) | ATP BS | 15.62 |
| RBKS | UniRef100_Q9H477 | FFIGFGGKGANQCVQAAR (SEQ ID NO: 182) | ATP BS | -1.64 |
| RFC1 | UniRef100_P35251 | AALLSGPPGVGKTTTASLVCQELGYSYV ELNASDTR (SEQ ID NO: 183) | ATP BS | -12.52 |
| RFC2 | UniRef100_P35250 | EGNVPNIIIAGPPGTGKTTSILCLAR (SEQ ID NO: 184) | ATP BS | 1.52 |
| RFC4 | UniRef100_P35249 | SLEGADLPNLLFYGPPGTGKTSTILAAAR (SEQ ID NO: 185) | ATP BS | -6.66 |
| RFC5 | UniRef100_P40937 | FINEDRLPHLLLYGPPGTGKTSTILACAK (SEQ ID NO: 186) | ATP BS | 2.11 |

TABLE 2-continued

Profile of Z36-MP5 inhibition on ATPase

| ATPase | Reference | Sequence | Labeling Site | Inhibition (%) by 1 μM Z36-MP5 |
|---|---|---|---|---|
| RFK | UniRef100_Q969G6 | GSKQLGIPTANFPEQVVDNLPADISTGIY YGWASVGSGDVHK (SEQ ID NO: 187) | ATP BS | 10.06 |
| RUVBL1 | UniRef100_Q9Y265 | AVLLAGPPGTGKTALALAIAQELGSK (SEQ ID NO: 188) | ATP BS | -15.57 |
| RUVBL2 | UniRef100_Q9Y230 | AVLIAGQPGTGKTAIAMGMAQALGPDT PFTAIAGSEIFSLEMSK (SEQ ID NO: 189) | ATP BS | -0.97 |
| SARS | UniRef100_P49591, UniRef100_Q53HA4 | KLDLEAWFPGSGAFR (SEQ ID NO: 190) | ATP BS | 3.57 |
| SKIV2L | UniRef100_Q15477 | HDSVFVAAHTSAGKTVVAEYAIALAQK (SEQ ID NO: 191) | ATP BS | -3.49 |
| SLC25A24 | UniRef100_Q6NUK1 | LAVGKTGQYSGIYDCAK (SEQ ID NO: 192) | ATP BS | 11.88 |
| SMC1A | UniRef100_Q14683 | FTAIIGPNGSGKSNLMDAISFVLGEK (SEQ ID NO: 193) | ATP BS | 5.67 |
| SMC3 | UniRef100_Q9UQE7 | NGSGKSNFFYAIQFVLSDEFSHLRPEQR (SEQ ID NO: 194) | ATP BS | -10.19 |
| SMC4 | UniRef100_Q9NTJ3 | LMITHIVNQNFKSYAGEK (SEQ ID NO: 195) | ATP BS | -7.11 |
| SNRNP200 | UniRef100_O75643 | LATYGITVAELTGDHQLCKEEISATQIIVC TPEKWDIITR (SEQ ID NO: 196) | ATP BS | -14.27 |
| SPG7 | UniRef100_Q9UQ90 | GALLLGPPGCGKTLLAK (SEQ ID NO: 197) | ATP BS | 0.12 |
| SUCLA2 | UniRef100_Q9P2R7 | GKGTFESGLK (SEQ ID NO: 198) | ATP BS | -0.65 |
| SUCLA2 | UniRef100_Q9P2R7 | DVVIKAQVLAGGR (SEQ ID NO: 199) | ATP BS | 9.97 |
| TCP1 | UniRef100_P17987 | VLCELADLQDKEVGDGTTSVVIIAAELL K (SEQ ID NO: 200) | ATP BS | 6.76 |
| TK2 | UniRef100_O00142 | TTCLEFFSNATDVEVLTEPVSKWR (SEQ ID NO: 201) | ATP BS | 14.43 |
| TOP2A, TOP2B | UniRef100_Q02880, UniRef100_P11388 | KVTGGRNGYGAK (SEQ ID NO: 202) | ATP BS | 11.93 |
| TOR1A | UniRef100_O14656 | KPLTLSLHGWTGTGKNFVSK (SEQ ID NO: 203) | ATP BS | 4.27 |
| TOR1B | UniRef100_O14657 | KPLTLSLHGWAGTGKNFVSQIVAENLHP K (SEQ ID NO: 204) | ATP BS | 2.00 |
| TOR2A, TOR2X | UniRef100_Q8N2E6, UniRef100_Q5JU69 | AFVRDPAPTKPLVLSLHGWTGTGKSYVS SLLAHYLFQGGLR (SEQ ID NO: 205) | ATP BS | 0.38 |
| TOR3A | UniRef100_Q9H497, UniRef100_Q5W0C6 | ALALSFHGWSGTGKNFVAR (SEQ ID NO: 206) | ATP BS | 6.55 |
| TOR4A | UniRef100_Q9NXH8 | DYLATHVHSRPLLLALHGPSGVGKSHVG R (SEQ ID NO: 207) | ATP BS | 5.38 |
| TRA1 | UniRef100_P14625 | NLGTIAKSGTSEFLNK (SEQ ID NO: 208) | ATP BS | -8.56 |
| TRAP1 | UniRef100_Q12931 | SGSKAFLDALQNQAEASSK (SEQ ID NO: 209) | ATP BS | -10.78 |
| TRAP1 | UniRef100_Q12931 | VLIQTKATDILPK (SEQ ID NO: 210) | ATP BS | -11.57 |
| TRMU | UniRef100_O75648 | TPNPDIVCNKHIK (SEQ ID NO: 211) | ATP BS | -13.98 |
| TRMU | UniRef100_O75648 | LLQAADSFKDQTFFLSQVSQDALRR (SEQ ID NO: 212) | ATP BS | -2.57 |
| TTL | UniRef100_Q8NG68 | KKEDGEGNVWIAKSSAGAK (SEQ ID NO: 213) | ATP BS | 10.59 |
| TTL | UniRef100_Q8NG68 | SSAGAKGEGILISSEASELLDFIDNQGQV HVIQK (SEQ ID NO: 214) | ATP BS | -14.46 |
| TTLL12 | UniRef100_Q14166 | WGEDNHWICKPWNLAR (SEQ ID NO: 215) | ATP BS | -5.29 |
| TTLL12 | UniRef100_Q14166 | LSQERPGVLLNQFPCENLLTVKDCLASIA R (SEQ ID NO: 216) | ATP BS | -17.65 |

TABLE 2-continued

Profile of Z36-MP5 inhibition on ATPase

| ATPase | Reference | Sequence | Labeling Site | Inhibition (%) by 1 μM Z36-MP5 |
|---|---|---|---|---|
| UBA1 | UniRef100_P22314 | GNVQVVIPFLTESYSSSQDPPEKSIPICTL K (SEQ ID NO: 217) | ATP BS | −4.55 |
| UBA2 | UniRef100_Q9UBT2 | VHLAEKGDGAELIWDKDDPSAMDFVTS AANLR (SEQ ID NO: 218) | ATP BS | 0.55 |
| UBA2 | UniRef100_Q9UBT2 | GDGAELIWDKDDPSAMDFVTSAANLR (SEQ ID NO: 219) | ATP BS | 7.64 |
| UBA3 | UniRef100_Q8TBC4 | DIGRPKAEVAAEFLNDRVPNCNVVPHFN K (SEQ ID NO: 220) | ATP BS | −11.62 |
| UBA5 | UniRef100_Q9GZZ9 | LFFQPHQAGLSKVQAAEHTLR (SEQ ID NO: 221) | ATP BS | −12.85 |
| UBA6 | UniRef100_A0AVT1 | GMITVTDPDLIEKSNLNR (SEQ ID NO: 222) | ATP BS | 3.60 |
| UPF1 | UniRef100_Q92900 | TVLQRPLSLIQGPPGTGKTVTSATIVYHL AR (SEQ ID NO: 223) | ATP BS | −1.93 |
| UPF1 | UniRef100_Q92900 | QGNGPVLVCAPSNIAVDQLTEKIHQTGL K (SEQ ID NO: 224) | ATP BS | −3.51 |
| VCP | UniRef100_Q0IIN5, UniRef100_P55072 | GILLYGPPGTGKTLIAR (SEQ ID NO: 225) | ATP BS | −8.02 |
| VCP | UniRef100_Q0IIN5, UniRef100_P55072 | GVLFYGPPGCGKTLLAK (SEQ ID NO: 226) | ATP BS | −2.36 |
| VCP | UniRef100_Q0IIN5, UniRef100_P55072 | TLLAKAIANECQANFISIK (SEQ ID NO: 227) | ATP BS | −7.20 |
| VCP | UniRef100_Q0IIN5, UniRef100_P55072 | IVSQLLTLMDGLKQR (SEQ ID NO: 228) | ATP BS | 7.80 |
| VPS4A, VPS4B | UniRef100_O75351, UniRef100_Q9UN37 | GILLFGPPGTGKSYLAK (SEQ ID NO: 229) | ATP BS | −2.55 |
| XRCC3 | UniRef100_O43542 | SSAGKTQLALQLCLAVQFPR (SEQ ID NO: 230) | ATP BS | −4.81 |
| XRCC5 | UniRef100_P13010 | FFMGNQVLKVFAAR (SEQ ID NO: 231) | ATP BS | 2.24 |
| XRCC6 | UniRef100_P12956 | IQVTPPGFQLVFLPFADDKR (SEQ ID NO: 232) | ATP BS | 10.61 |
| YME1L1 | UniRef100_Q96TA2 | GILLVGPPGTGKTLLAR (SEQ ID NO: 233) | ATP BS | −10.37 |

ATP Binding Site (ATP BS)

Z36-MP5 was chosen for further validation and experimental therapeutics in vivo. The IC$_{50}$ of Z36-MP5 against Mi-2β was increased with increasing concentration of ATP (10 μM to 300 μM) (FIG. 11b), suggesting that Z36-MP5 functions as an ATP-competitive inhibitor. To investigate its cellular inhibitory activity, B16-F10 cells were treated with Z36-MP5 at concentrations ranging from 5 to 100 μM, and the activation of Mi-2β target genes measured by RT-qPCR. Z36-MP5 at 25 μM induced Mi-2β target gene expression including Cxc9, Cxcl10 and Irf1 (FIG. 11c) in B16F10 cells. We also performed the co-culture assays of B16F10 cells with activated Pmel-1 T cells to identify whether Z36-MP5 stimulation can activate T cell mediated cytotoxicity. Z36-MP5 stimulation significantly induced T cell-mediated killing of B16F10 cells (FIG. 1id). Importantly, monitoring mouse weight (FIG. 11e) and organ tissue histological staining (FIG. 11f) showed Z36-MP5 treatment was tolerated without significant toxicity in C57BL/6 mice. In addition, the pharmacokinetic properties of Z36-MP5 in Sprague-Dawley rats with administration of intraperitoneal injection dose of 1.0 mg/kg. The results showed that Z36-MP5 exhibited favorable pharmacokinetic parameters with a half-life T$_{1/2}$ of 0.45 hours and C$_{max}$ of 3.96 g/mL (FIG. 11g). These data suggest that Z36-MP5 is a potent and effective inhibitor for Mi-2β and stimulates T cell mediated cytotoxicity in vitro, which warranted further in vivo studies.

Figure 12:
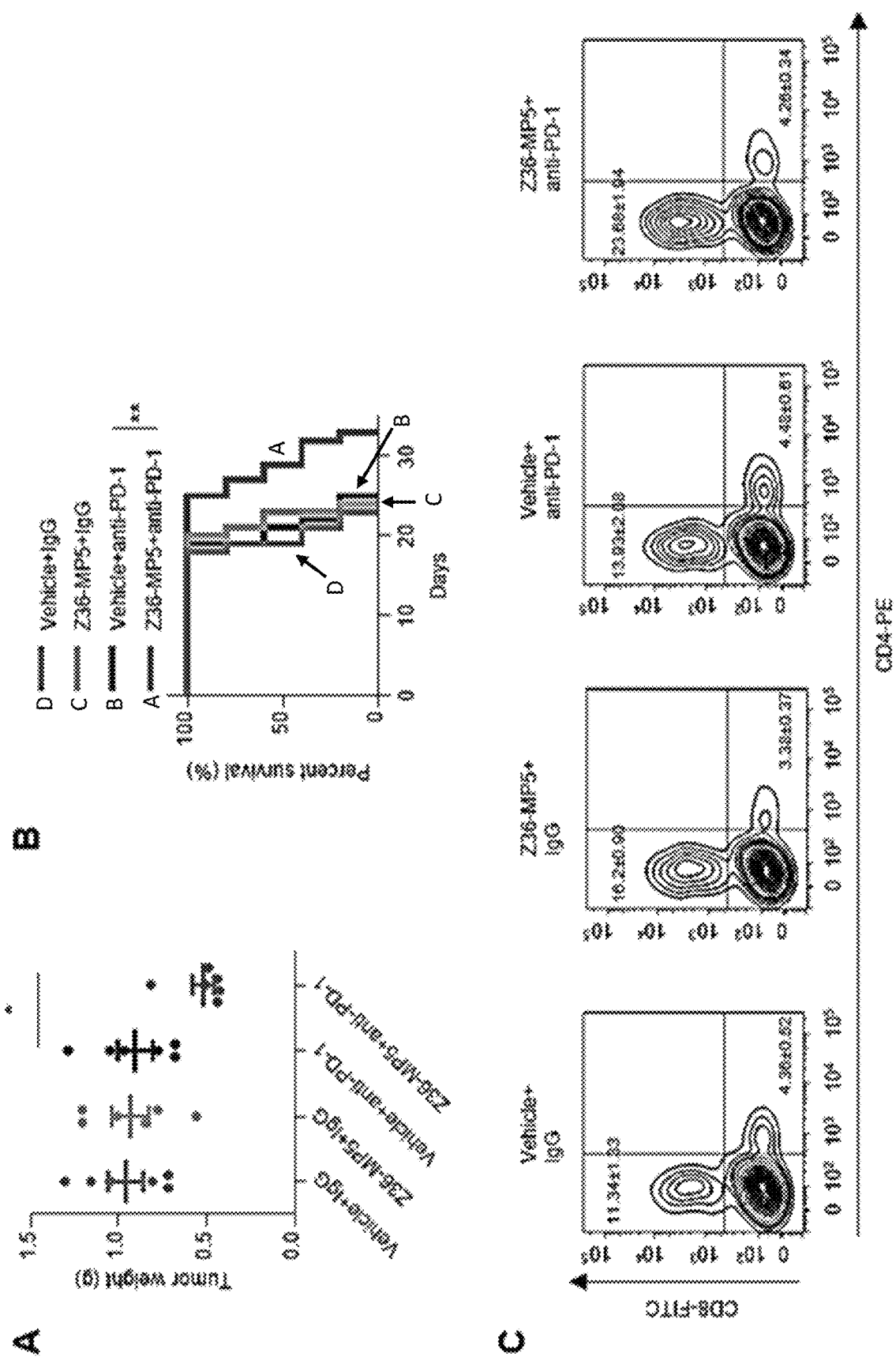
FIG. 12 illustrates combinational treatment of Z36-MP5 and anti-PD-1. Mice bearing B16F10 cells were treated with control IgG or anti-PD-1 antibody, and vehicle control or Z36-MP5, as indicated. For each group n=5. Tumor weight (A) and mouse survival curve (B) were shown, with log-rank test for mouse survival curve P value. As survival rate drops to 0%, curves from left to right: vehicle+IgG, Z36-MP5+IgG, vehicle+anti-PD-1, and Z36-MP5+anti-PD-1. C-F, Tumor-infiltrating lymph cells were assayed and quantified for $CD4^+$ and $CD8^+$ T cell population (C-D), as well as Treg cell population (E) in total $CD45^+$ cells with flow cytometry. F. Expression of activation markers on $CD8^+$ T cells were determined and qualitied with flow cytometry assay. The four bars from left to right: control, Z36-MP5, anti-PD-1, and Z36-MP5+anti-PD-1. G-I, Transgenic mice expressing $BRaf^{V600E}/Pten^{null}$ or $BRaf^{V600E}/Pten^{null}/Mi-2β^{null}$ with measurable tumors were randomly treated with either control IgG antibodies (10 mg/kg) or anti-PD-1 antibodies (10 mg/kg) and Z36-MP5 (30 mg/kg/day) or vehicle control by i.p. administration. For each group n=5. TILs were assayed by flow cytometry assay. The populations of tumor-infiltrating $CD4^+$ T cells (G) and Treg cells (H) gated within $CD45^+$ T cells were assayed and quantified with flow cytometry. i. The activation markers on $CD8^+$ T cells were determined and quantified with flow cytometry assay. MFI, mean fluorescence intensity. Values represent mean±SEM. The four bars from left to right: control, Z36-MP5, anti-PD-1, and Z36-MP5+anti-PD-1.$*p<0.05$, $p<0.01$, $*p<0.001$.
Figure 12:
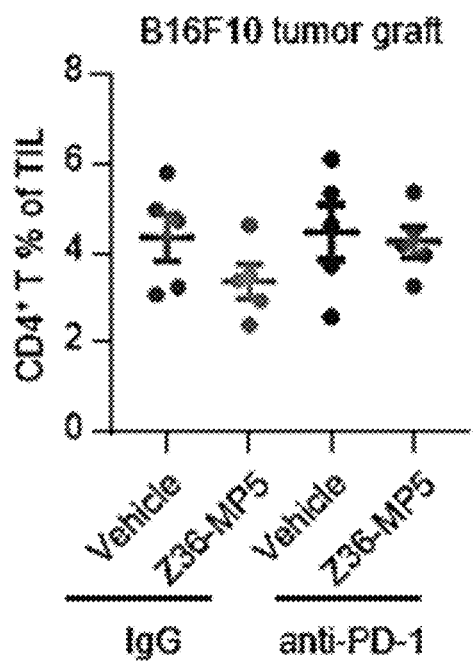
Figure 12:
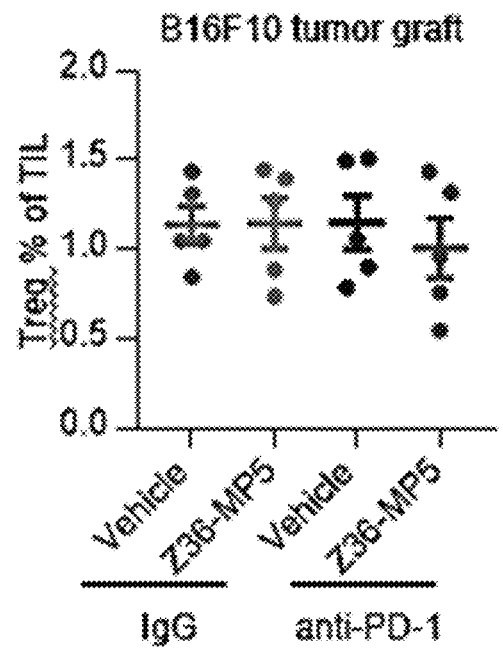
Figure 12:
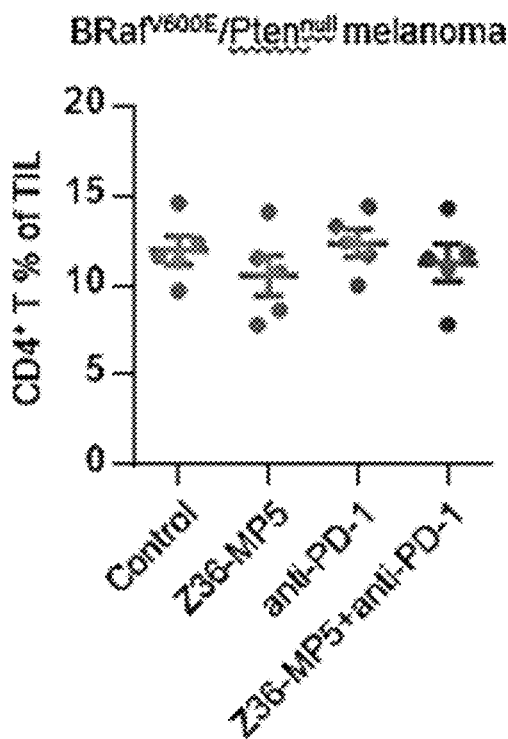
Figure 12:
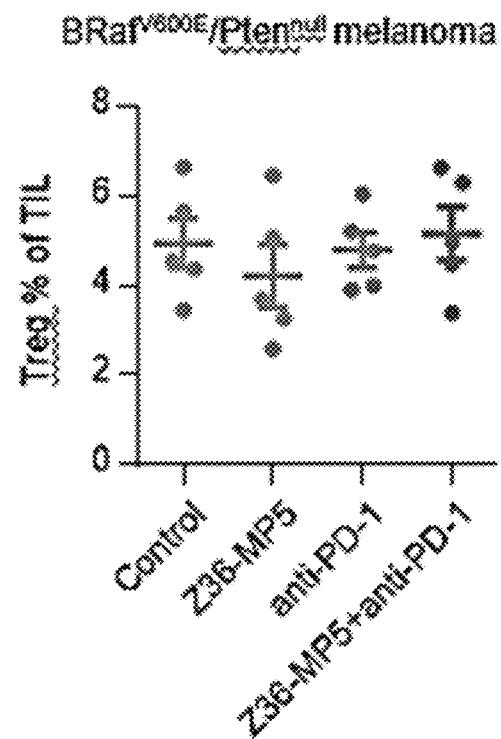
Figure 12:
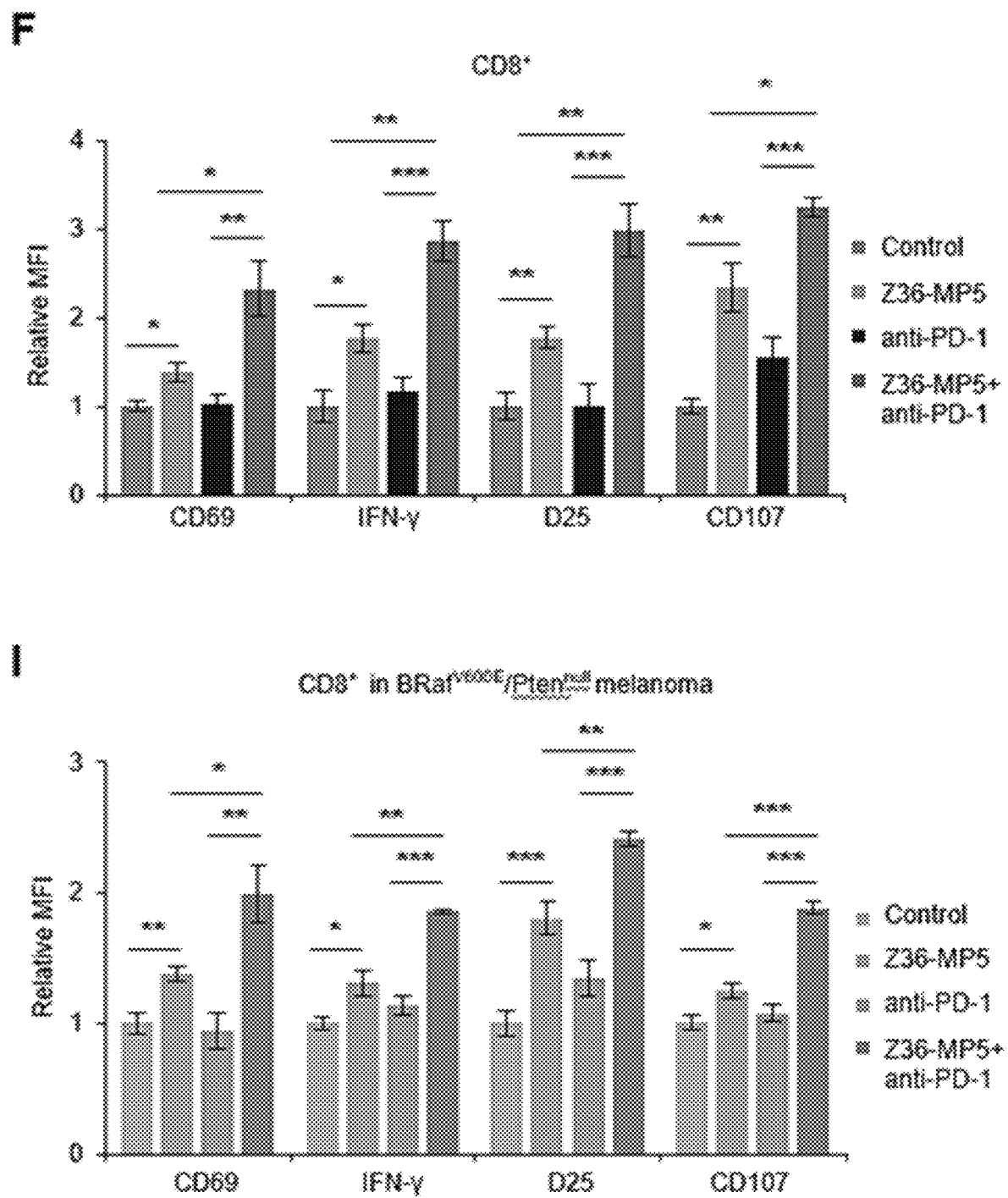
Figure 13:
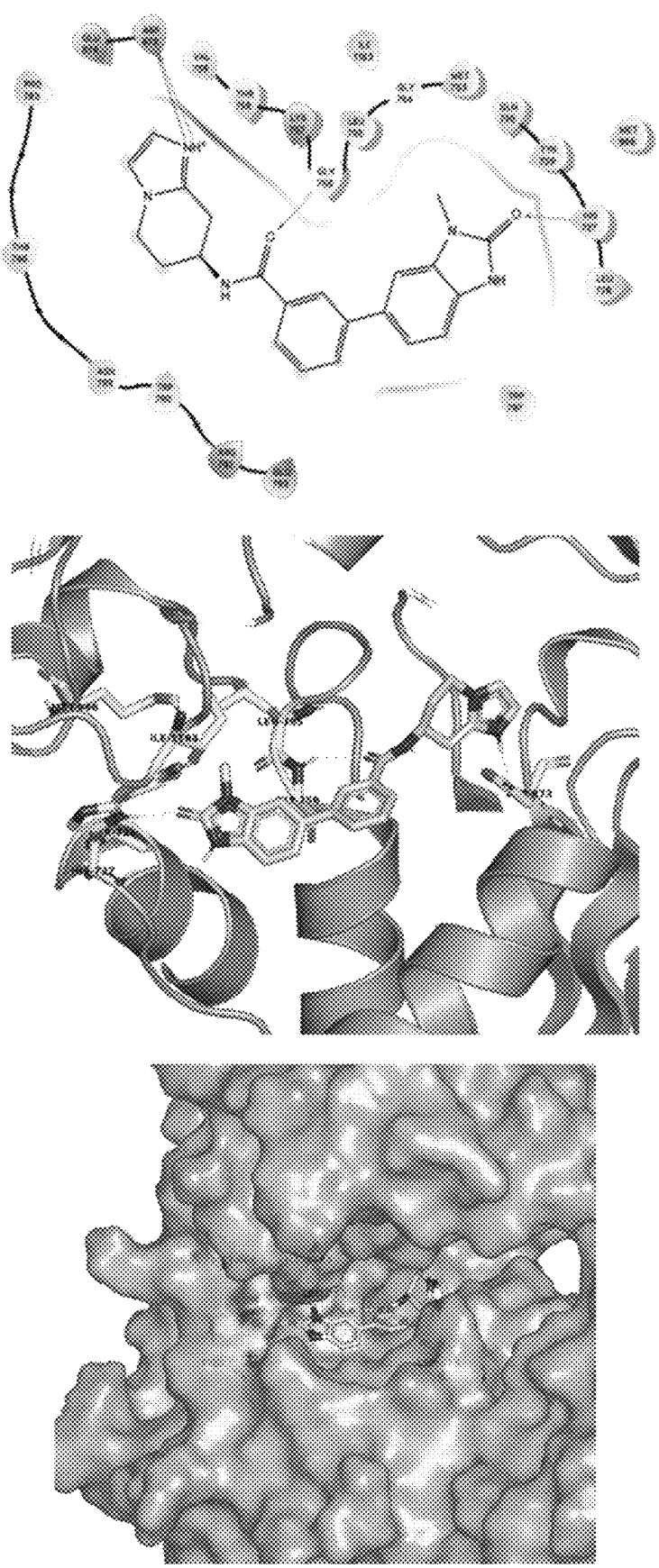
FIG. 13. Orientations of Z36-MP5 to homologized Mi-2β. Z36-MP5 was docked into the ATP binding pocket of homologized Mi-2β. Top: The methyl group of Z36-MP5 extended to a solvent-exposed channel lined with the side chains of Tyr729, Leu755, Met966, and Ile1163, with generating H-bonds via the O atom of keto group with His727, O atom of amide group with Gly756, and protonated N atom of imidazole group with Asp873. Middle & Bottom: 3D view of the binding mode.

To determine whether Z36-MP5 represented a potential therapeutic option for melanoma immunotherapy, especially in combination with anti-PD-1 treatment in vivo, syngeneic mouse melanoma developed by subcutaneously grafted B16F10 in C57BL/6 mice were randomly treated with Z36-MP5 (30 mg/kg) and/or anti-PD-1 (10 mg/kg). The results showed that the combinational treatment of Z36-MP5 and anti-PD-1 conferred a substantial inhibition on tumor growth (FIG. 9d and FIG. 12a) and extended mouse survival (FIG. 12b) compared with control treatment. Treatment with Z36-MP5 or anti-PD-1 alone did not impact tumor growth or mouse survival. Z36-MP5 treatment alone induced a moderate increase in the CD8$^+$ T cell TILs in graft melanomas that was augmented by combining with anti-PD-1 therapy (FIG. 9e and FIG. 12c). However, the population of CD4$^+$ T cell and Treg cells were not changed significantly by either the individual or combinational treatments (FIG. 12c-e). An upregulation of GZMB expression in tumor-infiltrating CD8+ T cells was detected in tumors treated with Z36-MP5, as well as the activation markers CD69, IFN-γ, CD25 and CD107, whose expression was augmented by combinatorial treatment with anti-PD-1 (FIG. 9f and FIG. 12f). These results indicate that Z36-MP5 represents an effective combinational therapeutic option of anti-PD-1 treatment in melanoma.

The potential of Z36-MP5 therapy was further tested in the Tyr::CreER;BRaf$^{CA}$;Pten$^{lox/lox}$ mouse melanoma model. After tamoxifen administration, mice with visible melanomas were randomly treated with Z36-MP5 (30 mg/kg) once a day starting at day 9 and/or anti-PD-1 (10 mg/kg) five times at day 9, 12, 15, 18 and 21 after Cre activation. Z36-MP5 in combination with the anti-PD-1 antibody treatment significantly extended mouse survival in the BRaf$^{V600E}$/Pten$^{null}$ melanoma mice (FIG. 9g). However, Z36-MP5 or anti-PD-1 treatment alone did not extend mouse lifespan in the BRaf$^{V600E}$/Pten$^{null}$ mice, consistent with the previous reports that BRaf$^{V600E}$/Pten$^{null}$ melanoma was insensitive to anti-PD-1 treatment (19) (FIG. 9g). To identify the role of Z36-MP5 treatment in regulating the tumor immune microenvironment, TILs were assayed by flow cytometry. Z36-MP5 treatment alone moderately induced the CD8+ T cell population, which was further augmented by anti-PD-1 treatment (FIG. 9h). However, the CD4+ T cell and Treg populations in BRaf$^{V600E}$/Pten$^{null}$ mouse melanomas were not affected by either Z36-MP5 alone or in combination with anti-PD-1 treatment in BRaf$^{V600E}$/Pten$^{null}$ melanoma (FIG. 12g-h). An increased expression of GZMB, CD69, IFN-γ, CD25 or CD107 in CD8+ T cells was detected in BRaf$^{V600E}$/Pten$^{null}$ melanoma, and their induction was further augmented by the anti-PD-1 treatment (FIG. 9i and FIG. 12i). These data indicate that Z36-MP5 treatment confers a more favorable tumor microenvironment to cytotoxic CD8+ T cells for overcoming the resistance of melanoma to anti-PD-1 treatment.

Comparative Example

Cell-based assay shows ZW-7-015 (Z36-MP5) in the most effective compound with inhibitory activity on Mi-2β function (e.g., enhanced expression of a set of IFN-γ-responsive genes including CXCL9, CXCL10 and IRF1). Besides, compounds ZW-7-023, ZW-7-059, SJW-6-004, and SJW-6-018 also exhibited high inhibitory activity on Mi-2β function (Table 3).

TABLE 3

Inhibitory activity on Mi-2β function

|  | A375 CXCL9 | CXCL9 | CXCL9 | A375 CXCL10 | CXCL10 | CXCL10 | A375 IRF1 | IRF1 | IRF1 |
|---|---|---|---|---|---|---|---|---|---|
| ctl | 0.9386 | 0.9294 | 1.132 | 1.1266 | 0.9771 | 0.8963 | 1.087 | 1.1296 | 0.7834 |
| zw-7-005 | 0.789137 | 0.610537 | 0.918437 | 4.525448 | 4.082748 | 5.659948 | 0.606784 | 0.754284 | 0.559084 |
| zw-7-008 | 1.052178 | 0.986978 | 0.927978 | 0.328229 | 0.544629 | 0.532729 | 0.711532 | 0.647232 | 0.489232 |
| zw-7-015 | 13.01316 | 13.93686 | 15.05076 | 2.171119 | 2.551219 | 2.117419 | 0.165505 | 0.116505 | 0.203205 |
| zw-7-023 | 2.72371 | 2.059321 | 2.96571 | 0.670055 | 0.541855 | 0.729055 | 0.915102 | 0.922802 | 1.108602 |
| zw-7-052 | 1.502167 | 1.144427 | 1.657497 | 1.513653 | 1.387153 | 1.751253 | 0.892932 | 0.965332 | 0.994232 |
| zw-7-053 | 0.993631 | 1.082431 | 1.151131 | 0.365198 | 0.445898 | 0.373798 | 0.758946 | 0.992646 | 0.764546 |
| zw-7-059 | 3.833982 | 4.807788 | 3.178078 | 0.853873 | 0.975447 | 0.798473 | 0.774804 | 0.946904 | 0.958304 |
| zw-7-060 | 4.685192 | 4.173449 | 5.913992 | 0.692773 | 0.756473 | 0.844673 | 1.382292 | 1.042692 | 1.133292 |
| zw-7-061 | 1.677738 | 1.867038 | 1.549438 | 0.823956 | 0.904356 | 0.803656 | 0.990684 | 1.075743 | 0.981543 |
| zw-7-062 | 3.174216 | 3.436016 | 2.709422 | 0.402671 | 0.259771 | 0.493971 | 0.980595 | 0.908295 | 0.831795 |
| zw-6-194 | 2.3878 | 2.2749 | 2.6319 | 0.592 | 0.712714 | 0.5611 | 1.501888 | 1.915488 | 1.728988 |
| ctl | 1.4498 | 1.242 | 0.3082 | 1.0351 | 0.8779 | 1.1221 | 1.1366 | 0.9139 | 0.9495 |
| sjw-6-004 | 7.102888 | 7.034819 | 8.335688 | 0.904746 | 0.819446 | 0.685865 | 0.931075 | 1.067075 | 1.114775 |
| sjw-6-006 | 2.011112 | 2.223612 | 1.692012 | 0.432457 | 0.335974 | 0.208374 | 0.831993 | 0.799493 | 0.938993 |
| sjw-6-015 | 1.110681 | 1.116381 | 1.105681 | 0.201968 | 0.071468 | 0.110668 | 0.838305 | 0.842405 | 1.127005 |
| sjw-6-018 | 8.829091 | 10.09526 | 9.830691 | 3.942814 | 5.088714 | 4.255114 | 0.877709 | 0.890209 | 0.676441 |
| sjw-6-022 | 2.370736 | 2.029804 | 2.500336 | 1.351931 | 1.333231 | 1.300031 | 0.932859 | 0.890016 | 1.110759 |
| sjw-5-200 | 1.36288 | 1.23648 | 1.029038 | 0.743041 | 0.796741 | 0.948741 | 0.739377 | 0.535477 | 0.832877 |

|  | B16 Cxcl9 | Cxcl9 | Cxcl9 | B16 Cxcl10 | Cxcl10 | Cxcl10 | B16 Irf1 | Irf1 | Irf1 |
|---|---|---|---|---|---|---|---|---|---|
| ctl | 0.9285 | 1.0438 | 1.0277 | 0.9265 | 0.8988 | 1.1747 | 1.1118 | 1.0591 | 0.8291 |
| zw-7-005 | 0.23239 | 0.22089 | 0.10579 | 0.424969 | 0.463469 | 0.276669 | 0.950854 | 0.801654 | 1.137754 |
| zw-7-008 | 0.544311 | 0.423611 | 0.685211 | 1.163389 | 1.411989 | 1.321889 | 1.014374 | 0.961874 | 1.159274 |
| zw-7-015 | 3.313923 | 4.377323 | 3.208223 | 1.264891 | 1.526749 | 1.122669 | 0.807162 | 1.013462 | 0.714762 |
| zw-7-023 | 1.719565 | 1.968327 | 1.648665 | 0.894131 | 0.882231 | 0.921231 | 0.75653 | 0.91093 | 0.68643 |
| zw-7-052 | 1.2114 | 1.41666 | 1.074 | 0.747864 | 0.945664 | 0.832964 | 0.674809 | 0.777509 | 0.842109 |
| zw-7-053 | 1.038598 | 1.104598 | 1.31347 | 0.720571 | 0.885771 | 0.678171 | 0.737262 | 0.841862 | 0.698362 |
| zw-7-059 | 2.253495 | 1.853995 | 1.674995 | 0.929789 | 1.080189 | 1.311579 | 0.586949 | 0.761449 | 0.596349 |
| zw-7-060 | 0.823816 | 1.066716 | 0.942816 | 0.913311 | 1.085511 | 1.305021 | 0.67425 | 0.81975 | 0.55205 |
| zw-7-061 | 0.58135 | 0.67315 | 0.61475 | 0.988272 | 0.900072 | 0.860572 | 0.719495 | 0.592595 | 0.746795 |
| zw-7-062 | 0.451986 | 0.503086 | 0.462286 | 0.62407 | 0.84827 | 0.54917 | 0.704506 | 0.600406 | 0.676906 |
| zw-6-194 | 0.426326 | 0.470526 | 0.397226 | 0.718326 | 0.788326 | 0.937426 | 0.752113 | 0.721913 | 0.670313 |
| ctl | 1.1743 | 1.2058 | 0.6199 | 0.9492 | 1.009 | 1.0418 | 1.1349 | 1.2105 | 0.6546 |
| sjw-6-004 | 1.00497 | 1.200077 | 1.08177 | 1.026581 | 1.224381 | 0.975681 | 1.242815 | 1.395315 | 1.490515 |
| sjw-6-006 | 1.789721 | 1.557321 | 1.845521 | 0.964792 | 1.032992 | 1.137292 | 1.292379 | 1.296279 | 1.453579 |
| sjw-6-015 | 1.385278 | 1.520378 | 1.159778 | 1.050787 | 1.219087 | 0.907269 | 1.271287 | 1.403987 | 1.434787 |
| sjw-6-018 | 1.511787 | 1.411587 | 1.705787 | 0.939248 | 1.290048 | 0.944048 | 0.877721 | 1.179421 | 0.926421 |
| sjw-6-022 | 1.135115 | 1.354015 | 1.035215 | 0.918921 | 1.133521 | 0.930521 | 0.900138 | 1.139038 | 1.004338 |
| sjw-5-200 | 1.466001 | 1.182001 | 1.459401 | 0.920683 | 1.058683 | 0.793083 | 0.849649 | 0.563649 | 0.840049 |

TABLE 4

Top 10 GSEA-Hallmark upregulated genes

| Gene Set Name | # Genes in Gene Set (K) | # Genes in Overlap (k) | k/K | p-value | FDR q-value |
|---|---|---|---|---|---|
| HALLMARK_INTERFERON_GAMMA_RESPONSE | 200 | 66 | 0.33 | 4.15E−47 | 2.08E−45 |
| HALLMARK_TNFA_SIGNALING_VIA_NFKB | 200 | 63 | 0.315 | 1.31E−43 | 3.28E−42 |
| HALLMARK_INTERFERON_ALPHA_RESPONSE | 97 | 41 | 0.423 | 7.5E−35 | 1.25E−33 |
| HALLMARK_HYPOXIA | 200 | 46 | 0.23 | 1.29E−25 | 1.61E−24 |
| HALLMARK_INFLAMMATORY_RESPONSE | 200 | 38 | 0.19 | 2.35E−18 | 2.35E−17 |
| HALLMARK_MTORC1_SIGNALING | 200 | 37 | 0.185 | 1.65E−17 | 1.37E−16 |
| HALLMARK_XENOBIOTIC_METABOLISM | 200 | 35 | 0.175 | 7.35E−16 | 5.25E−15 |
| HALLMARK_EPITHELIAL_MESENCHYMAL_TRANSITION | 200 | 33 | 0.165 | 2.85E−14 | 1.78E−13 |
| HALLMARK_HEME_METABOLISM | 200 | 32 | 0.16 | 1.68E−13 | 9.35E−13 |
| HALLMARK_IL2_STAT5_SIGNALING | 200 | 31 | 0.155 | 9.57E−13 | 4.79E−12 |

TABLE 5

Top 10 GSEA-Hallmark downregulated genes

| Gene Set Name | # Genes in Gene Set (K) | # Genes in Overlap (k) | k/K | p-value | FDR q-value |
|---|---|---|---|---|---|
| HALLMARK_G2M_CHECKPOINT | 200 | 50 | 0.25 | 9.96E−30 | 4.98E−28 |
| HALLMARK_E2F_TARGETS | 200 | 48 | 0.24 | 9.97E−28 | 2.49E−26 |
| HALLMARK_MITOTIC_SPINDLE | 199 | 47 | 0.236 | 7.55E−27 | 1.26E−25 |
| HALLMARK_EPITHELIAL_MESENCHYMAL_TRANSITION | 200 | 46 | 0.23 | 8.92E−26 | 1.121E−24 |
| HALLMARK_GLYCOLYSIS | 200 | 37 | 0.185 | 1.24E−17 | 1.24E−16 |
| HALLMARK_APICAL_JUNCTION | 200 | 31 | 0.155 | 1.24E−17 | 5.25E−12 |
| HALLMARK_KRAS_SIGNALING_UP | 200 | 31 | 0.155 | 7.63E−13 | 5.25E−12 |
| HALLMARK_ESTROGEN_RESPONSE_LATE | 200 | 29 | 0.145 | 2.24E−11 | 1.4E−10 |
| HALLMARK_COAGULATION | 138 | 21 | 0.152 | 5.19E−09 | 2.88E−08 |
| HALLMARK_MYOGENESIS | 200 | 25 | 0.125 | 1.19E−08 | 5.94E−08 |

Methods

Plasmids and shRNAs

The plasmid of Flag-Mi-2β was generously provided by Dr. Joel Mackay in University of Sydney. To knockdown Mi-2β in B16F10 melanoma cells, mouse specific short hairpin RNAs of TRC Lentiviral Mouse Mi-2β shRNA (TRCN0000086143: TTTACAACTCAGAAGATGGGC (SEQ ID NO:234) and TRCN0000086146: TAAGTTGTG-GAACCTCTCAGG (SEQ ID NO:235)) (Open Biosystems-Horizon Discovery) targeting Mi-2β were co-transfected with psPAX2 (Addgene, 12260) and pMD2.G (Addgene, 12259) into HEK293FT cells using Lipofectamine 3000. Lentiviruses were harvested 48 h after the transfection, and then used to infected B16F10 cells for 24 h in the presence of 8 μg/mL polybrene. The infected cells were selected by 2 μg/mL puromycin.

LentiCRISPR v2 constructs for knockout mouse Mi-2β were generated following the online guide of CHOPCHOP (chopchop.rc.fas.harvard.edu) (43). Briefly, HEK293FT cells in 6-well plates were transfected with 1.5 μg lentiviral plasmid, 1 μg psPAX2, and 0.5 μg pMD2.G. Lentivirus were collected after 2 days after transfections, and then filtered through a 0.45 m filter. B61F10 Cells were infected with lentivirus for 24 hours, and then refed with fresh medium and selected with 2 μg/mL puromycin.

Cell Culture

B16F10 cells were cultured in complete DMEM media (10% FBS and 100 U/ml of Penicillin-Streptomycin). B16F10-shMi-2β and B16F10-shScramble cells were maintained in complete DMEM media (10% FBS and 100 U/ml of Penicillin-Streptomycin) with 2-5 μg/ml of puromycin. CD8 T cells isolated from mice were cultured in complete RPMI 1640 media (10% FBS, 0.05 mM 2-mercaptoethanol, 20 mM HEPES, 2 mM Lglutamine, 1 mM sodium pyruvateand 100 U/ml streptomycin and penicillin).

Isolation and Activation of Pmel-1 T Cells In Vitro

Pmel-1 TCR transgenic mice were purchased from Jackson Laboratory (stock #005023). The CD8 T cells were isolated from spleen and lymph nodes from Pmel-1 transgenic mice using the CD8a$^+$ T Cell Isolation Kit, mouse (Miltenyi Biotec, Order no: 130-104-075) according to the manufacturer's protocol. Freshly isolated CD8 T cells were stimulated with anti-CD3/CD28 beads (Thermo Fisher Scientific #11452D) for 3 days, and then the recombinant mouse IL-2 (Biolegend, #575406) was added at 20 ng/ml. After 6 days activation, T cells were used for co-culture with B16F10 cells.

Co-Culture Assay of B16F10 Cells with Activated Pmel-1 T Cells

B16F10 cells with shMi-2β or shScrambles were transfected with GFP expression vector pcDNA3-EGFP (Plasmid #13031), and the stable cell line was selection with 800 μg/mL G418. For in vitro validation, Mi-2β-deficient B16F10 cells (GFP positive) were mixed with control B16F10 cells (GFP negative) at a 1:1 ratio. The cells were treated with 10 ng/ml of IFN-γ for 24 hours, and then co-cultured with activated Pmel-1 T cells. After three days, the depletion of Mi-2β knockdown B16F10 cells was determined by FACS, comparing the percentage of knockdown cells (GFP positive) to control B16F10 cells (GFP negative).

Quantitative Real-Time PCR (RT-qPCR)

The total RNA was extracted with QIAGEN RNeasy kit (Invitrogen) for cDNA synthesis with SuperScript II Reverse Transcriptase (Invitrogen). In total, 40 ng cDNA was used for quantitative real-time PCR amplification by TaqMan Gene Expression Master Mix (Thermo Fisher Scientific). The relative transcript levels were normalized with GAPDH expression. The data were calculated with the comparative CT method.

Immunoblot Analysis

The lysis buffer (50 mM Tris pH 7.4, 1% Triton X-100, 0.5 mM EDTA, 0.5 mM EGTA, 150 mM NaCl, 10% glycerol, 1 mM phenylmethylsulfonyl fluoride and complete protease inhibitor cocktail (Roche)) were used to prepare the whole cell lysates, which was followed by homogenization and centrifuge (14,000 rpm for 15 min at 4° C.). Pierce BCA Protein Assay Kit (Thermo Fisher Scientific) was used to detect protein concentration. After SDS-PAGE separation and PVDF membrane (BIO-RAD) transfer of the proteins, the specific primary was probed at 4° C. for overnight, before incubated with corresponding horseradish peroxidase (HRP)-conjugated 2nd antibodies. Pierce ECL Western Blotting Substrate (Thermo Fisher Scientific) was used for protein detection. Antibodies were: anti-Mi-2β (ab70469, Abcam) (1:1000), anti-o-actin-peroxidase antibody (AC15) (1:5000, Sigma-Aldrich) and anti-rabbit secondary antibody (A-4914) (1:10000, Sigma-Aldrich).

Chromatin Immunoprecipitation (ChIP) Assays

ChIP assays were performed and analyzed as previous description (77). Briefly, B16F10 cells ($\sim 1 \times 10^7$) were incubated with 1% formaldehyde for 10 minutes for crosslink, with adding glycine for a final concentration of 0.125 M to stop crosslink. Then the nuclear pellets were prepared, and suspended with ChTP lysis buffer. The DNA was fragmented with sonication. Immunoprecipitation was performed with antibodies anti-Mi-2β (ab70469, Abcam), anti-Stat1 (ab239360, Abcam) and IgG control at 4° C. for overnight. The complex was pulled down with A/G agarose beads (#20422, Thermo Fisher Scientific) and crosslink was reversed with heating at 65° C. for overnight. The DNA was purified and eluted for quantitative PCR assay. Primers were designed based on the binding peak analysis with ChIP-Atlas-Peak Browser. All data were normalized to gene desert regions of the IgH loci. The real time PCR was performed in triplicate. Values of [Δ][Δ] Ct method was used to calculate the relative binding enrichment, with the formula: Ct, template (antibody)−Ct, template (IgG)=[Δ] Ct, and the fold enrichments ([Δ][Δ]Ct) were determined using the formula of 2−[Δ] Ct. (experimental)/2−[Δ] Ct (IgH). Standard error from the mean was calculated from replicate [Δ][Δ] Ct values from independent experiments. Primers for Mi-2β ChTP include Cxcl9 forward: 5'-AGTGCACAG-CATCGGTTGAG-3' (SEQ ID NO:236), Cxcl9 reverse: 5'-TGTAAAGGGGATTCTGGGTGC-3' (SEQ ID NO:237); Cxcl10 forward: 5'-AAAATGACGGCAGCACTTGG-3' (SEQ ID NO:238), Cxcl10 reverse: 5'-AGC-CAATCAGGACTCAGGGA-3' (SEQ ID NO:239); Irf1 forward: 5'-GACCATCATAGGAGCCAGCA-3' (SEQ ID NO:240), Irf1 reverse: 5'-TGTTGTAGAGCTAAGCGGCG-3' (SEQ ID NO:241), and primers for Stat1 ChIP include Cxcl9 forward: 5'-CGTCCTGGGGAAAACCCTAC-3' (SEQ ID NO:242), Cxcl9 reverse: 5'-GGGGTGGTTTCA-CATCCCTT-3' (SEQ ID NO:243); Cxcl10 forward: 5'-CCCTGAGTCCTGATTGGCTG-3' (SEQ ID NO:244), Cxcl10 reverse: 5'-AAGGAGCACAAGAGGGGAGA-3' (SEQ ID NO:245); Irf1 forward: 5'-TTTCCAA-GACAGGCAAGGGG-3' (SEQ ID NO:246), Irf1 reverse: ACTCGGCCTCATCATTTCGG (SEQ ID NO:247); and IgH forward: 5'-GCCGATCAGAACCAGAACACCTGC-3' (SEQ ID NO:248), and IgH reverse: 5'-TGGTGGGGCTGGACAGAGTGTTTC-3' (SEQ ID NO:249).

Microarray Assay

Total RNA was extracted from B16F10 with Mi-2β knockout and the control cells treated with IFN-γ (10 ng/mL) for 24 hours with the RNeasy Mini Kit (74104) (Qiagen, Hilden, Germany). The experimental group cells were cultured in triplicate. The experiment was comprised of 6 Mouse Gene 2.0 ST arrays. The arrays were normalized together using the Robust Multiarray Average algorithm and a CDF (Chip Definition File) that maps the probes on the array to unique Entrez Gene identifiers. The expression values are log 2-transformed by default. The technical quality of the arrays was assessed by two quality metrics: Relative Log Expression (RLE) and Normalized Unscaled Standard Error (NUSE). For each sample, median RLE values >0.1 or NUSE values >1.05 are considered out of the usual limits. All arrays had median RLE and NUSE values well within these limits. Benjamini-Hochberg FDR correction was applied to obtain FDR-corrected p values (q values), which represent the probability that a given result is a false positive based on the distribution of all p values on the array. In addition, the FDR q value was also recomputed after removing genes that were not expressed above the array-wise median value of at least 3 arrays (i.e., the size of each experimental group). The GEO Series ID is GSE151640, with the link of ncbi.nlm.nih.gov and the token: exgreuqmhrcpdkf ELISA Assay B16F10 cells ($1 \times 10^6$) with or without Mi-2β knockdown were seeded in 6-well plates in complete growth medium. Cell medium was changed to serum-free medium, before treatment with IFN-γ at indicated concentration for 24 hours. The secreted chemokines were measured by mouse Cxcl9 ELISA kit (ab203364) and mouse Cxcl10 ELISA Kit (ab214563), according to the manufacturer's protocols. Isolated graft tumors were prepared and minced with blades, then tumor tissue were cultured in PBS (250 mg/500 μl) for 4 hours at 37° C. The secreted amount of the chemokines in the culture were measured by mouse Cxcl9 ELISA kit (ab203364) and mouse Cxcl10 ELISA Kit (ab214563), according to the manufacturer's protocols.

Validation of Genes of the Epigenetic Factors

The gRNA sequences targeting the selected 18 epigenetic factors (3 gRNAs/gene) were cloned into a LentiCRISPRv2GFP vector (Addgene, #82416) following the CHOPCHOP (chopchop.rc.fas.harvard.edu) (43). Briefly, HEK293FT cells in 6-well plates were transfected with 1.5 μg lentiviral plasmid, 1 μg psPAX2, and 0.5 μg pMD2.G with Lipofectamine™ 3000 Transfection Reagent (ThermoFisher, #L3000001). Lentivirus were collected after 2 days of transfections. After filtered through a 0.45 m filter, the lentivirus were stored at −80° C. B61F10 cells were infected with lentivirus for 24 hours individually. Infected cells were sorted based on GFP expression by BD FACS Aria II. For in vitro co-culture assay, gRNA-targeted gene deficient B16F10 cells (GFP positive) were mixed with control B16F10 cells (GFP negative) at a 1:1 ratio. The cells were treated with 10 ng/ml of IFN-γ for 24 hours, and then co-cultured with activated Pmel-1 T cells. After three days, the gene depleted B16F10 cells was determined by FACS, comparing the percentage of knockdown cells (GFP positive) to control B16F10 cells (GFP negative).

Syngeneic Melanoma Graft Mouse Model

Mi-2β knockdown or Scramble B16F10 cells ($1.5 \times 10^5$) were mixed with BD matrigel (Matrix Growth Factor Reduced) (BD, 354230) in 100 μl PBS, and then subcutaneously injected into the right flanks of C57BL/6 mice of 8-10 week old (from the Jackson Laboratory, 000664). Tumor growth was measured with calipers, and size was expressed as one-half of the product of perpendicular length and square width in cubic centimeters every 3 days. For antibody treatment, control IgG antibodies (10 mg/kg) or anti-PD-1 (RMP1-14, BioXCell, 10 mg/kg) was injected intraperitoneally (i.p.) on day 6, 9, 12, 15 and 18 after tumor cell inoculation. For tumor growth curve, grafts were measured with calipers and established (0.5*length×width$^2$) every three days. For survival tests, mice were euthanized when the tumor size exceeded 1 cm$^3$. To test Z36-MP5 function in syngeneic mouse model, B16F10 cells (1.5×105) were mixed with BD matrigel (Matrix Growth Factor Reduced) (BD, 354230) in 100 μl PBS, and then mouse subcutaneous injection and tumor graft monitor were performed as described above. Except that vehicle [5% (w/v) Kolliphor HS 15 (Sigma)] in normal saline or formulated 30 mg/kg Z36-MP5 was administered with i.p. injection once a day starting at day 6, together with i.p. injection of control IgG antibodies (10 mg/kg) or anti-PD-1 (RMP1-14, BioX-Cell, 10 mg/kg) on day 6, 9, 12, 15 and 18. The mice were euthanized after indicated days or when the allowable endpoint size (1 cm$^3$) was reached. All mice were maintained in pathogen-free conditions in the animal facility at Boston University. All animal experiments were performed in accordance with the Guide for the Care and Use of Laboratory Animals of the National Institutes of Health, and the protocol was reviewed and approved by the Animal Science Center (ASC) of Boston University.

Genetically Engineered Mouse Models

Mi-2β$^{lox/lox}$ mice were generated and generously provide by Dr. Georgopoulos lab (Massachusetts General Hospital at Harvard Medical School) (31). Tyr::CreER;BRaf$^{CA}$; Pten$^{lox/lox}$ mice were purchased from Jackson laboratories (Stock No: 013590). All strains of mice were on the background of C57BL/6J background. Gene activation and silencing were induced with intraperitoneal (i.p.) administration of 100 μL/mouse/day tamoxifen (20 mg/mL) for constant 5 days. Mice with measureable tumors were randomly treated with either control IgG antibodies (10 mg/kg) or anti-PD-1 (RMP1-14, BioXCell, 10 mg/kg) by i.p. administration at day 9, 12, 15, 18 and 21 after Cre activation. To test Z36-MP5 function in vivo, vehicle [5% (w/v) Kolliphor HS 15 (Sigma)] in normal saline or formulated 30 mg/kg Z36-MP5 was administered with i.p. injection once a day starting at day 9 after Cre activation, together with i.p. injection of control IgG antibodies (10 mg/kg) or anti-PD-1 (RMP1-14, BioXCell, 10 mg/kg) starting on day 9, 12, 15, 18 and 21 after Cre activation, as indicated. Tumor growth was then monitored each the other day. All mice were bred and maintained in pathogen-free conditions in the animal facility at Boston University. All animal experiments were done according to protocols approved by the Boston University and in accordance with the guidelines set forth by the US National Institutes of Health.

Kaplan-Meier Survival Analysis

TCGA data set was downloaded from website (tcga-browser.ethz.ch). The melanoma patients (n=454) were divided into CD8 High and CD8 Low groups based on the mRNA expression of CD8. The median gene expression of CD8 was set as the cutoff. For each Gene and CD8 High/Low group, we further divide the samples into High and Low subgroups based on the gene's median expression. The Kaplan-Meier survival curves were generated, and their differences were examined using a log-rank test.

Preparation of Tumor-Infiltrating T Cells

Tumors were minced with scissors, and then digested with the digestion buffer (RPMI 1640 medium, 5% FBS, 1% penicillin-streptomycin, 25 mM HEPES, and 300 U collagenase (Sigma C0130)) on a shaker at 37° C. for 2 hours. Single cells were prepared through a 70 m cell strainer. Erythrocytes were removed by incubation in red blood cell lysis buffer (R7757, Sigma) at room temperature for 5 min. The cells were prepared in PBS (with concentration of ~$2 \times 10^7$) for studies.

Flow Cytometry

The single-cell suspension were fixed with 2% paraformaldehyde solution (J19943K2, Thermo Scientific). And then the cells were stained with the follow antibodies: anti-mouse CD45 APC (104, BD pharmingen, 561875), anti-mouse CD3e PE (145-2C11, BD pharmingen, 553063), anti-mouse CD4 FITC (RM4-5, BD pharmingen, 553046), anti-mouse CD4 PE/Cy7 (GK1.5, BioLegend, 100421), anti-mouse CD8 FITC (53-6.7, BD pharmingen, 553031), anti-mouse CD8a APC/Cy7 (53-6.7, BioLegend 100713), anti-mouse IFN-γ PE (XMG1.2, eBioscience, 12731181), anti-mouse CD69 PE (H1.2F3, Biolegend, 104508), anti-mouse CD25 Alexa Fluor 488 (PC61.5, eBioscience, 53025182), anti-mouse CD107a-V450 (1D4B, BD, 560648), anti-human/mouse granzyme B FITC (GB 11, BioLegend, 515403). The regulatory T cells in TILs were stained with the Mouse Regulatory T Cell Staining kit #1 (88-8111, ThermoFisher Scienctific), with antibodies of anti-mouse CD4 FITC (RM4-5), anti-mouse CD25 APC (PC61.5) anti-mouse Foxp3 PE (FJK-16s). BD LSRII was used for data acquisition and FlowJo was used for data analysis.

Protein Expression and Purification

Flag-Mi-2β was expressed and purified from HEK293 cells, which were cultured in DMEM supplemented with 10% Fetal Bovine Serum 100 unites/ml penicillin and 100 μg/ml streptomycin. Flag-Mi-2β in pcDNA3.1 expression vector were transfected into HEK293 cells with Lipofectamine™ 3000 Transfection Reagent (ThermoFisher) for 3 days. The resulted cells were harvested for the nuclear pellet extraction with cytoplasmic lysis buffer (50 mM HEPES, 10 mM KCl, 1.5 mM MgCl2, 1 mM DTT, 1 mM PMSF and 1× protease inhibitor, pH7.5) on ice for 30 minutes. The nuclear pellet was collected by spun down. The nuclear lysis buffer (50 mM HEPES, 0.5 M NaCl, 1 mM EDTA, 1% Triton X-100, 1.5 mM MgCl2, 1 mM DTT, 1 mM PMSF, and 1×protease inhibitor, pH 8) was used to resuspend nuclear pellet for homogenization by sonication. Nuclear extract was incubated with Flag M2 affinity gel beads (Sigma-Aldrich) at 4° C. for overnight. The Flag M2 beads were washed, and Flag-Mi-2β protein was eluted with 300 μg/ml 3×Flag peptide (Sigma-Aldrich), in 20 mM HEPES, 150 mM NaCl, 1 mM DTT, and 10% glycerol, pH 7.5. Protein was confirmed by SDS-PAGE and coomassie stains. All the purified protein samples were concentrated, aliquoted and flash-frozen in liquid nitrogen, and then stored in −80° C. for later use.

TCGA Data Analysis

To analysis the hazard ratio of epigenetic factor in human melanoma samples, we downloaded the ATGC data set of melanoma from http://tcgabrowser.ethz.ch:3839/TEST/on 2018-09-03. Data of 454 melanoma patient samples were available for analysis. The patients were divided into CD8A high and CD8A low groups based on the gene expression of CD8A. The median CD8A expression was chosen as the cutoff.

ATP-Driven Nucleosome Remodeling Reactions

The function of chromatin remodeling enzyme was studied with EpiDyne-FRET (EpiCypher, SKU: 16-4201) according to the protocol. Briefly, Nucleosomes were assembled with the recombinant nucleosome substrates Cy5-labeled human histone octamer (H2A T120C-Cy5) wrapped with 5' Cy3-labeled DNA (207 bp), in which contains a terminally nucleosome positioning Widom 601 element. Cy3-Cy5 FRET is at a maximum level at the assembled starting state. When the histone octamer is relocated towards the DNA 3' by chromatin remodeler enzymes, Cy3-labeled DNA 5' end is moved away from the Cy5-labeled octamer, leading to a reduction in FRET signal. The optimal conditions of the Mi-2β enzyme and the ATP concentrations in the 96-well were determined using FRET signal which was read by QuantStudio 12K Flex Real-Time PCR System with capable of Cy3 (Excitation-531 nm/Emission-579 nm)/Cy5 (emission-685 nm) detection. Data is expressed as the ratio of the raw Cy3 and Cy5 emission signals at each time point. For the Mi-2β concentration and reaction time optimization, Flag-tagged Mi-2β at series of concentrations (ranging from 0.4 to 250 nM), ATP at a non-limiting concentration (1 mM) were added to 96-well white solid plates and incubated for different times (0 to 50 minutes) with the substrate EpiDyne-FRET nucleosome at a saturated concentration (20 nM), in the 50 μL reaction buffer containing 50 mM Tris, pH 7.5, 50 mM KCl and 3 mM MgCl2. The nucleosome remodeling reaction was stopped by adding 10 mM EDTA and 0.25 mg/ml Salmon Sperm DNA. The assay had a sufficiently high assay signal, and a minimal substrate conversion for a sufficient assay window was taken. We finally chose 12.5 nM Mi-2β and a reaction time of 15 minutes as the optimal condition for the nucleosome remodeling assay. The ATP titration was performed with Mi-2β using the enzyme concentration and reaction time previously determined, with at ATP concentrations ranging from 0.1 to 300 μM. The Michaelis-Menten equation was performed to calculate the apparent ATP Km. At the ATP concentration of 11.54 μM, Mi-2β showed a 50% change between the maximum and minimum reaction signal levels.

Z-factor was used to determine the assay quality (Z-factors above 0.5 represent an assay with an excellent quality). In the optimization assay procedure, the wells without Mi-2β was defined as 100% inhibition controls, and that containing Mi-2β was regarded as the 0% inhibition controls. The FRET signaling in each well was detected and Cy3/Cy5 ratio was calculated. Then the average (represented as μ) and standard deviations (represented as G) of the ratios were calculated too. The Z-factor equation is Z-factor=1−3×($\sigma_{0\% \ Inhibition}$+$\sigma_{100\% \ Inhibition}$)/($\mu_{0\% \ Inhibition}$−$\mu_{100\% \ Inhibition}$). The Z-factor was 0.729 for Mi-2β, which confirmed the optimization of assay conditions including enzyme concentration, ATP concentration and the reaction time.

Homology Modeling and Virtual Screening

Homology Modeling was carried out using Structure Prediction Wizard in Prime. The Homology Model of Mi-2β (CHD4) was generated using the yeast CHD1 structure (PDB code:3MWY) as template and the receptor sequence was obtained from Uniprot. Standard options were used when running the program and one homology model was gotten. For the output structure, the receptor was properly prepared using Protein Preparation Guide. Virtual screening was done in the default workflow process. First, enzyme hinge region ligands database and nucleoside mimetics database from Enamine are was prepared using a LigPrep and 3 low energy conformations are generated for each ligand. Then all ligands are docked to the ATP binding site for Mi-2β using SP docking and postprocessed with Prime MM-GBSA. After minimization, we kept top 1000 ligands from MM-GBSA score for each database. We have identified ligands with methyldihydroimidazopyridinone structure can interact well with the ATP warhead binding region of Mi-2β.

Profile of Z36-MP5 Inhibition on ATPases

The Profile of Z36-MP5 inhibition on ATPases was measured by ActivX Biosciences inc. (La Jolla, CA). In briefly, Z36-MP5 was directly added to A375 cell lysates generated with a tip sonicator, and the resulting lysate was clarified by centrifugation at 16100 g for 15 minutes to get the native cell lysate. For the ATP acyl phosphate probe-based chemoproteomics, lysine residues in ATP-binding sites were acylated with a desthiobiotin tag, and labeled peptides were isolated by affinity capture. The probe labeling reaction could be blocked by ATPase inhibitors. Labeled peptides were identified on the basis of their MS spectra generated by data-dependent LC-MS/MS. Duplicated treated samples and control samples were performed and the inhibition results were analyzed as % changes with statistically significance (Student t-test score <0.05).

Pharmacokinetics of Z36-MP5 in Rats

Compound Z36-MP5 was evaluated in a pharmacokinetic study in male Sprague-Dawley (SD) rats following intraperitoneal injection of Z36-MP5 at 1.0 mg/kg as a solution in 5% DMSO, 30% PEG400, and 65% corn oil. Blood was collected at 0.25 h, 0.5 h, 1 h, 2 h, 4 h, 8 h, and 24 h following intraperitoneal injection. The blood samples were placed in wet ice, and serum was collected after centrifugation. Serum samples were frozen and stored at −80° C. The serum samples were analyzed utilizing HPLC-coupled tandem mass spectrometry (LC-MS/MS). Values are calculated from arithmetic mean plasma concentrations (n=3 rats per condition).

Statistical Analysis and Study Design

Animals were grouped randomized. The qualification experiments were blinded by investigators. All samples or animals were included in analysis. The unpaired, two tailed t-test Comparisons were performed between two groups. Statistical tests were done with biological replicates. P<0.05 was considered statistically significant. *P<0.05,  P<0.01, * P<0.001.

The invention claimed is:

1. A method for treating a cancer in a subject comprising administering an effective amount of a Mi-2β inhibitor to the subject, wherein the effective amount of the Mi-2β inhibitor is co-administered with an immunotherapy, and wherein the cancer is resistant to the immunotherapy in the absence of the effective amount of the Mi-2β inhibitor, and wherein the Mi-2β inhibitor is a compound of formula

wherein—
Ring 1 is

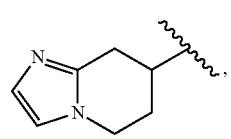 [SMILES: *C1CCn2ccnc2C1]

Ring 2 is

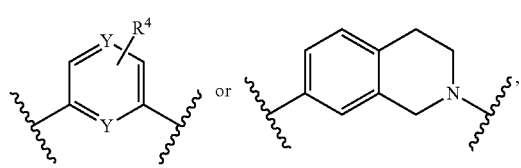

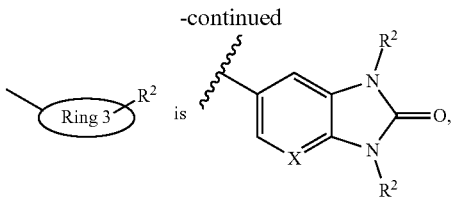

$R^4$ is hydrogen, a halo, or an unsubstituted or substituted, unbranched or branched, saturated or unsaturated $C_1$-$C_6$ alkyl;

each X and Y are independently selected from N or CH;

$R^1$ is hydrogen;

each $R^2$ is independently selected from hydrogen, an unsubstituted or substituted, unbranched or branched, saturated or unsaturated $C_1$-$C_6$ alkyl, an unsubstituted or substituted, unbranched or branched, saturated or unsaturated $C_1$-$C_6$ alkylaryl, an aryl, or -$L^2$-A;

$L^1$ and $L^2$ are independently selected from the group consisting of alkylenyl, heteroalkylenyl, and —(($CH_2$)$_m$—W—($CH_2$)$_n$)p—;

W is selected from the group consisting of —O—, —N($R^2$)—, —C(=O) N($R^2$—N($R^2$)C(=O)—, —C=C—, and —C≡C— or W is absent;

m is 0, 1, 2, 3, 4, 5, 6, 7, or 8;

n is 0, 1, 2, 3, 4, 5, 6, 7, or 8;

p is 0, 1, 2, or 3;

A is selected from the group consisting of:

$A^{1a}$
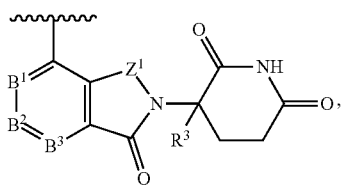

$A^{1b}$
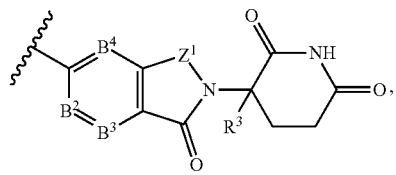

$A^{1c}$
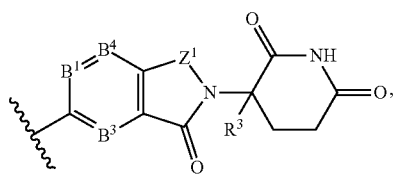

$A^{1d}$
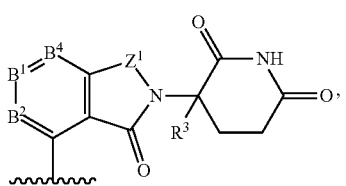

$A^{2a}$
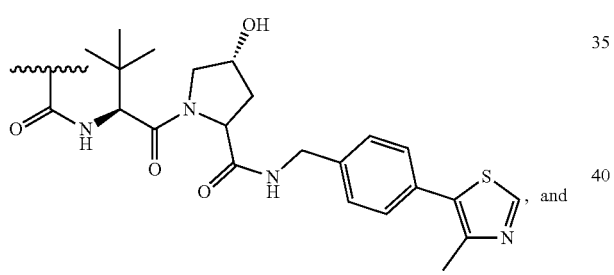, and $A^{2b}$
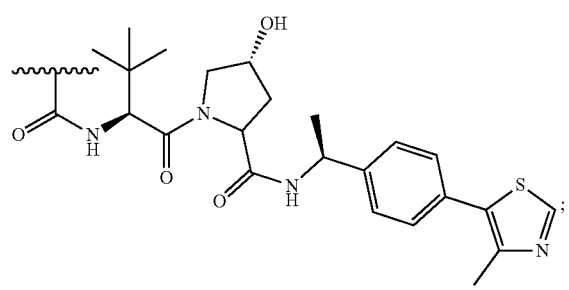;

$B^1$, $B^2$, $B^3$, and $B^4$ are independently selected from the group consisting of —C($R^3$)= and —N=;

$R^3$ is selected from the group consisting of hydrogen, deuterium, methyl, and fluoro; and $Z^1$ is selected from the group consisting of —CH$_2$—, —C(=O)—, and —N=C(CH$_3$)— wherein the nitrogen atom of —N=C(CH$_3$)— is attached to the hex-atomic ring.

2. The method of claim 1, wherein the immunotherapy is a checkpoint inhibitor.

3. The method of claim 2, wherein the checkpoint inhibitor is a PD-1 checkpoint inhibitor.

4. The method of claim 1, wherein the cancer is a melanoma.

5. The method of claim 1, wherein the Mi-2β inhibitor inhibits Mi-2β or degrades Mi-2β.

6. The method of claim 5, wherein the Mi-2β inhibitor binds an ATP binding pocket of the Mi-2β.

7. The method of claim 1, wherein the Mi-2β inhibitor is a compound of formula

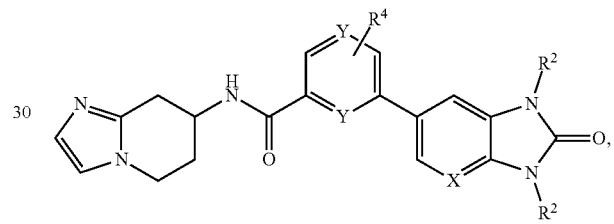

wherein— each $R^2$ is independently selected from hydrogen, an unsubstituted or substituted, unbranched or branched, saturated or unsaturated $C_1$-$C_6$ alkyl, an unsubstituted or substituted, unbranched or branched, saturated or unsaturated $C_1$-$C_6$ alkylaryl, or an aryl.

8. The method of claim 7, wherein the Mi-2β inhibitor is

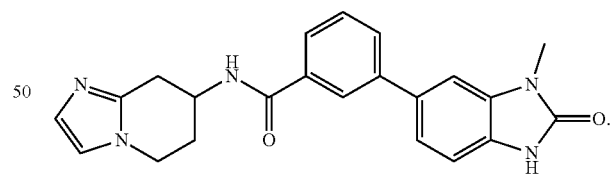

9. The method of claim 1, wherein the Mi-2β inhibitor comprises a member selected from the group consisting of

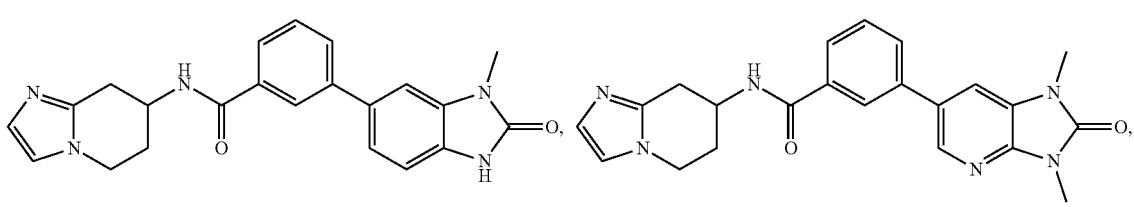

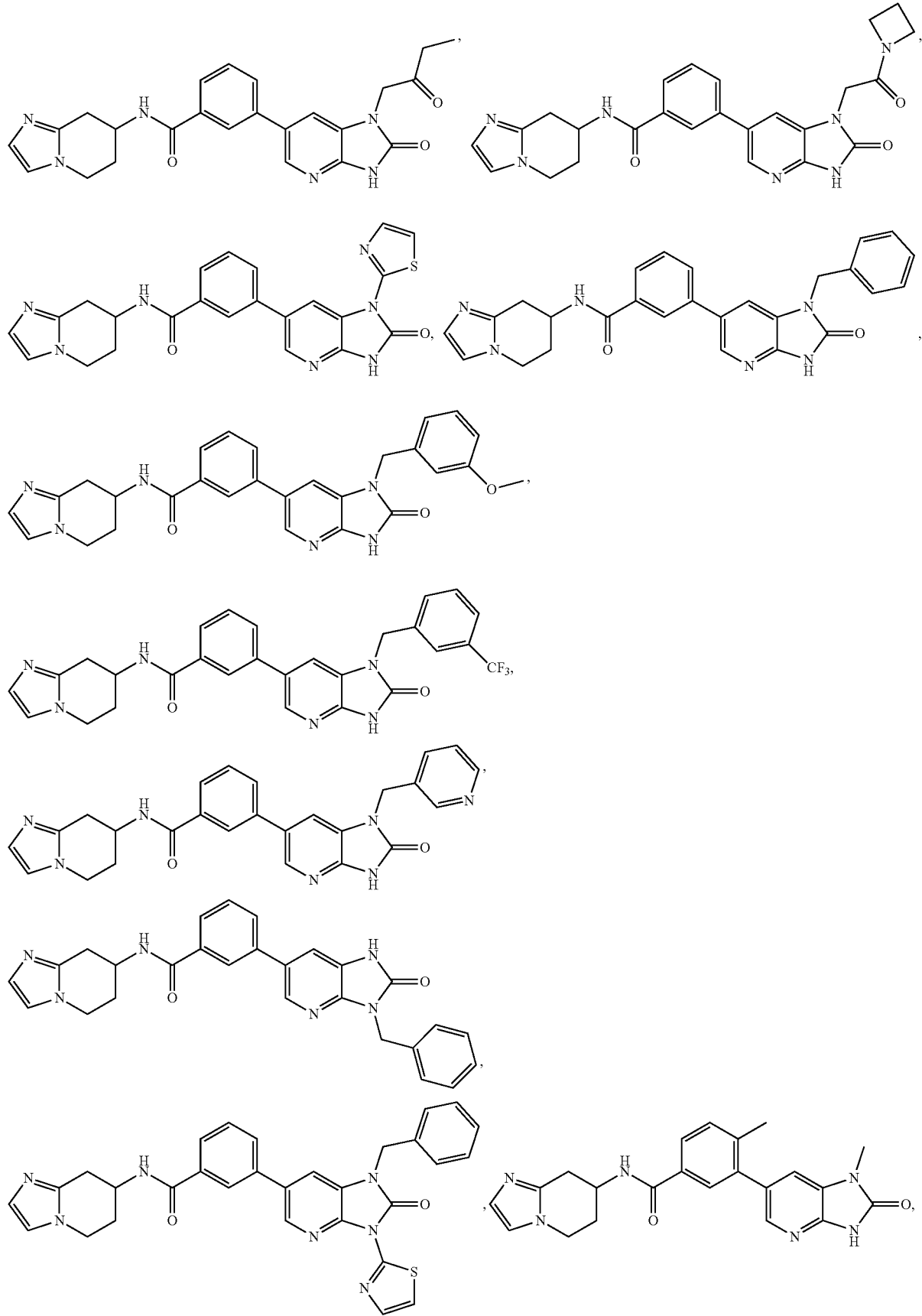

185 186
-continued
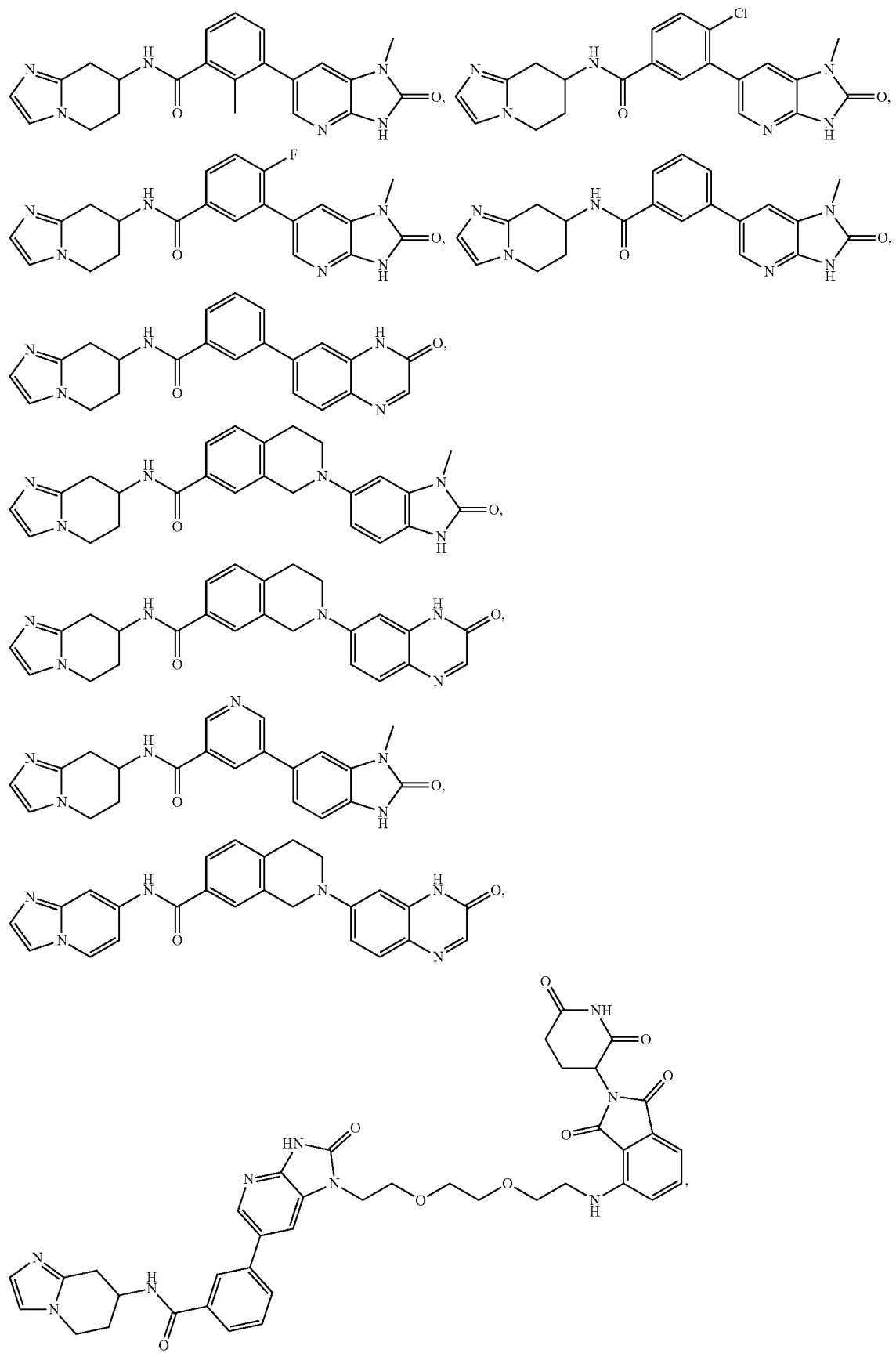

-continued

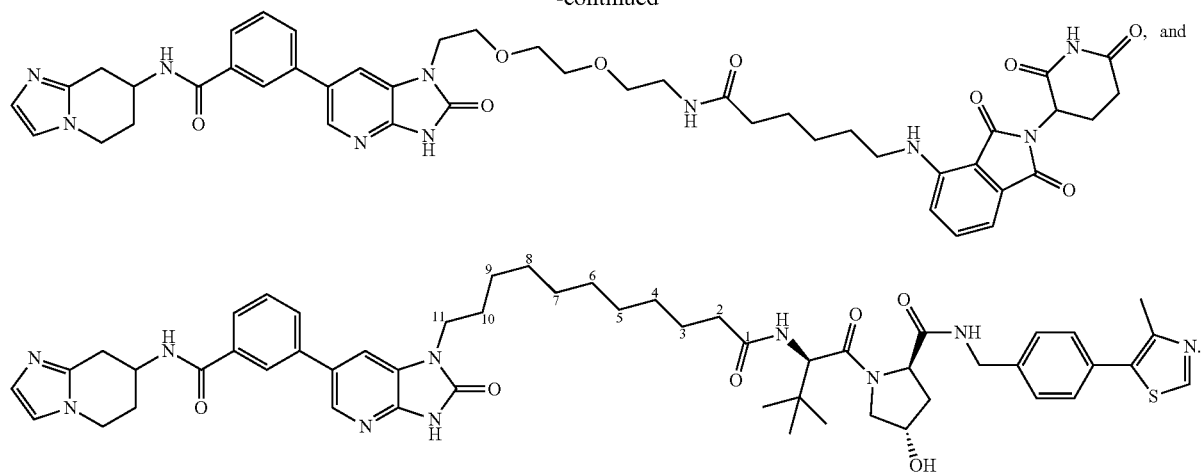

10. The method of claim 1, wherein the Mi-2β inhibitor inhibits expression of Mi-2β.

11. A method for treating a cancer in a subject comprising administering an effective amount of a Mi-2β inhibitor to the subject, wherein the Mi-2β inhibitor is a compound of formula

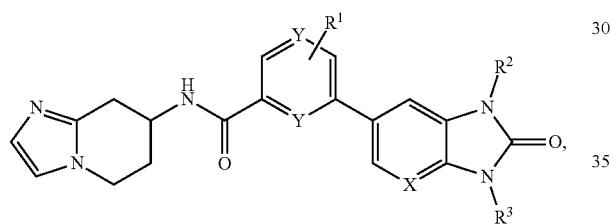

wherein—
each X and Y are independently selected from is N or CH;
$R^1$ is hydrogen, a halo, or an unsubstituted or substituted, unbranched or branched, saturated or unsaturated $C_1$-$C_6$ alkyl; and
$R^2$ and $R^3$ are independently selected from hydrogen, an unsubstituted or substituted, unbranched or branched, saturated or unsaturated $C_1$-$C_6$ alkyl, an unsubstituted or substituted, unbranched or branched, saturated or unsaturated $C_1$-$C_6$ alkylaryl, or an aryl.

12. The method of claim 11, wherein the Mi-2β inhibitor is

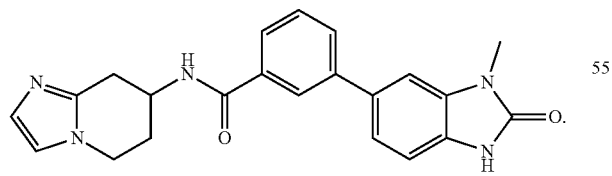

13. The method of claim 11, wherein the effective amount of the Mi-2β inhibitor is co-administered with an immunotherapy.

14. The method of claim 11, wherein the cancer is a melanoma.

15. A method for treating a cancer in a subject comprising administering an effective amount of a Mi-2β inhibitor to the subject, wherein the Mi-2β inhibitor is a compound of formula, wherein the Mi-2β inhibitor is a compound of formula

wherein—
Ring 1 is

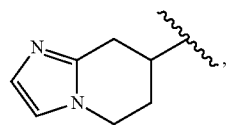 [SMILES: *C1CCn2ccnc2C1]

Ring 2 is

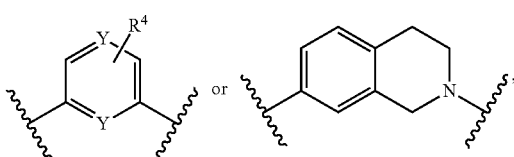

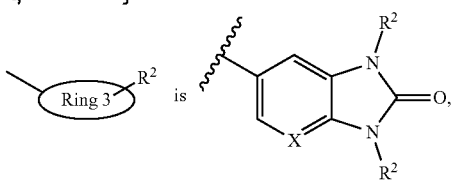

$R^4$ is hydrogen, a halo, or an unsubstituted or substituted, unbranched or branched, saturated or unsaturated $C_1$-$C_6$ alkyl;
each X and Y are independently selected from N or CH;
$R^1$ is hydrogen;
each $R^2$ is independently selected from hydrogen, an unsubstituted or substituted, unbranched or branched, saturated or unsaturated $C_1$-$C_6$ alkyl, an unsubstituted or substituted, unbranched or branched, saturated or unsaturated $C_1$-$C_6$ alkylaryl, an aryl, or -$L^2$-A;

$L^1$ and $L^2$ are independently selected from the group consisting of alkylenyl, heteroalkylenyl, and —$((CH_2)_m$—W—$(CH_2)_n)_p$—;

W is selected from the group consisting of —O—, —N($R^2$)—, —C(=O) N($R^2$)—, —N($R^2$)C(=O)—, —C=C—, and —C≡C— or W is absent;

m is 0, 1, 2, 3, 4, 5, 6, 7, or 8;
n is 0, 1, 2, 3, 4, 5, 6, 7, or 8;
p is 0, 1, 2, or 3;
A is selected from the group consisting of:

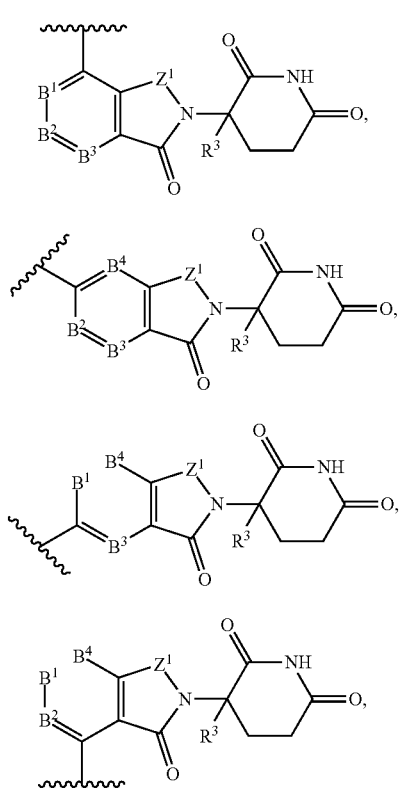

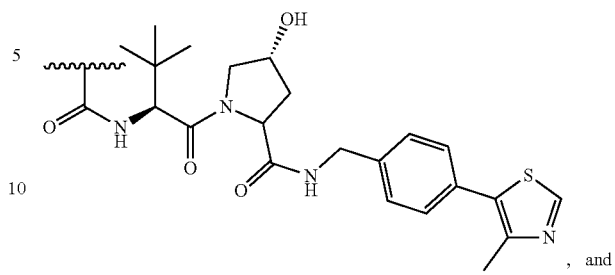

$B^1$, $B^2$, $B^3$, and $B^4$ are independently selected from the group consisting of —C($R^3$)= and —N=;

$R^3$ is selected from the group consisting of hydrogen, deuterium, methyl, and fluoro; and $Z^1$ is selected from the group consisting of —$CH_2$, —C(=O)—, and —N=C($CH_3$)— wherein the nitrogen atom of —N=C($CH_3$)— is attached to the hexatomic ring.

16. The method of claim 15, wherein the Mi-2β inhibitor comprises a member selected from the group consisting of

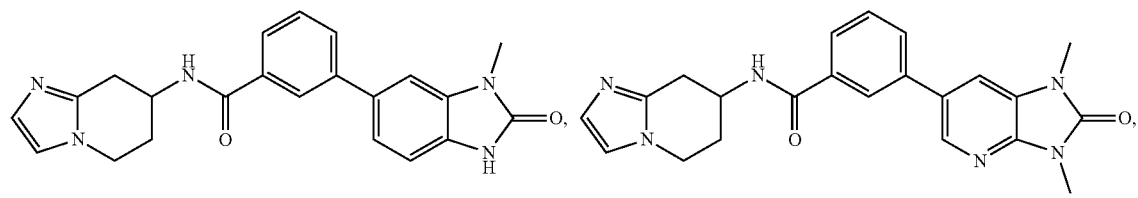

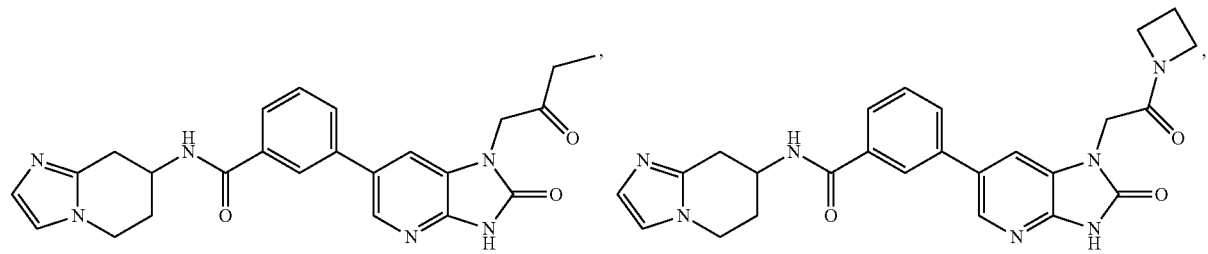

191                    192
-continued
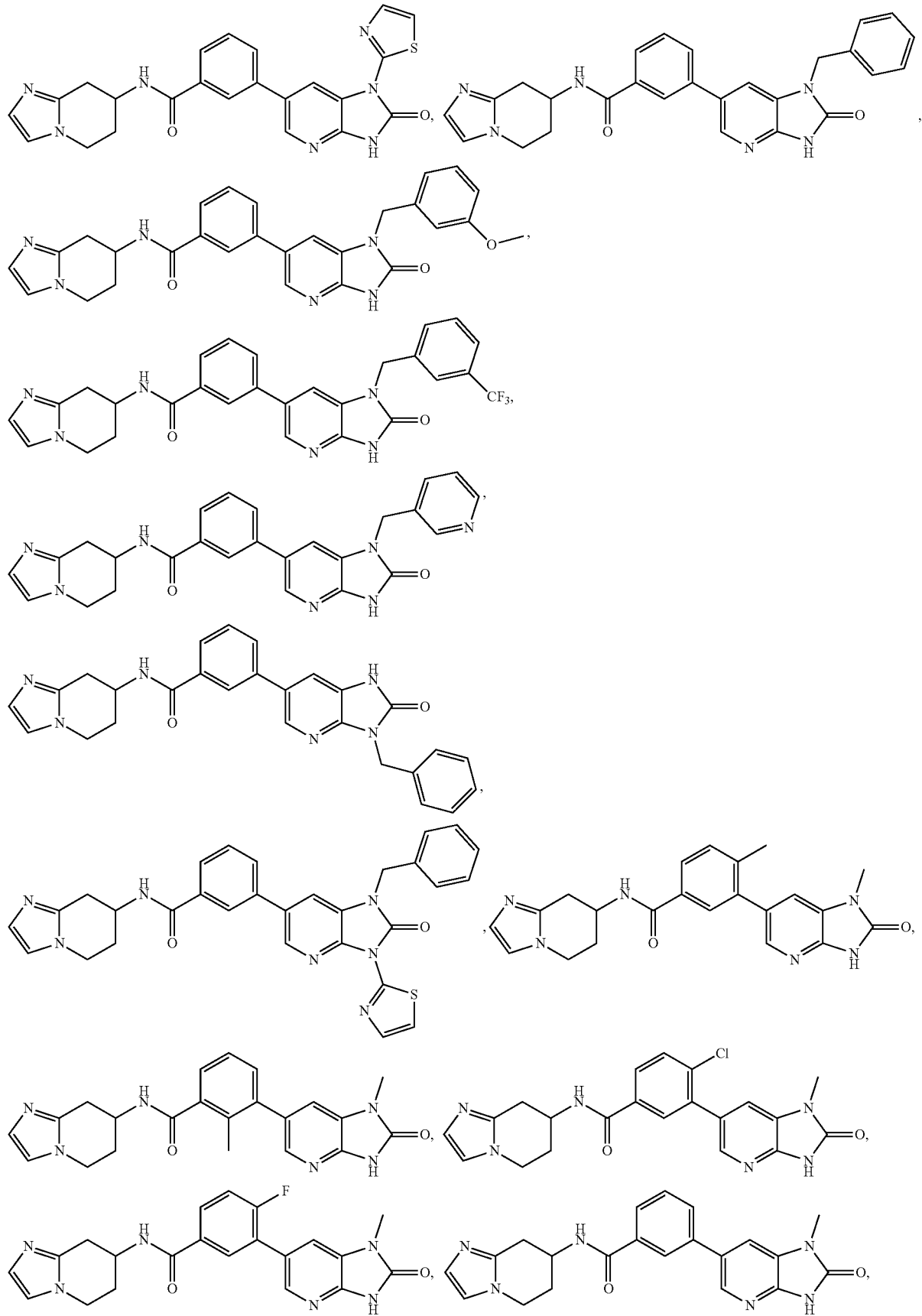

-continued
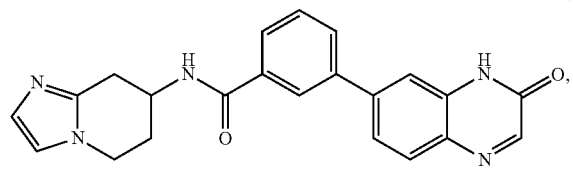
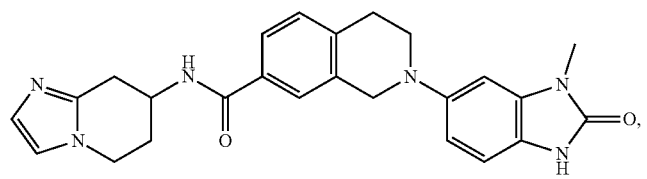
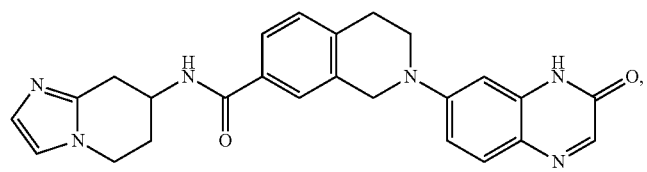
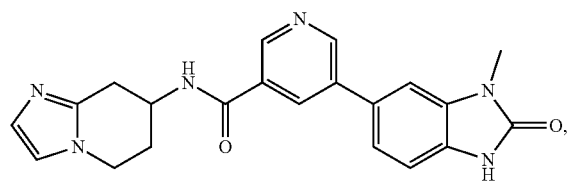
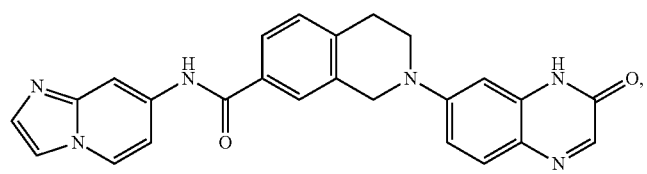
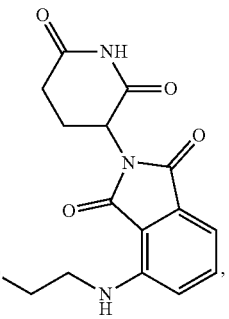
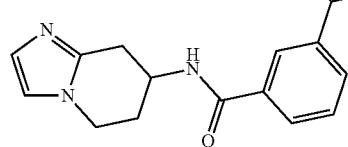
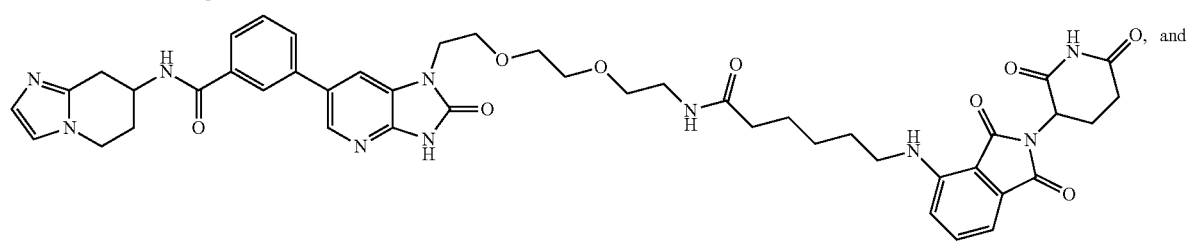

-continued
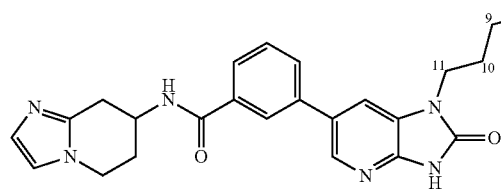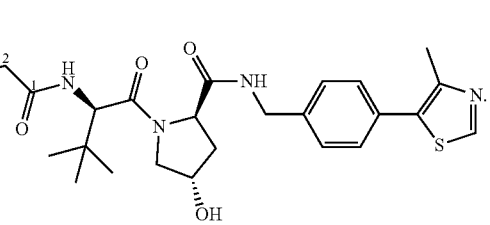
17. The method of claim 15, wherein the effective amount of the Mi-2β inhibitor is co-administered with an immunotherapy.
18. The method of claim 15, wherein the cancer is a melanoma.
* * * * *

SEQUENCE LISTING

<160> NUMBER OF SEQ ID NOS: 249

<210> SEQ ID NO 1
<211> LENGTH: 34
<212> TYPE: PRT
<213> ORGANISM: Homo sapiens

<400> SEQUENCE: 1

-continued

Ala Gly Gly Lys His Asn Asp Leu Asp Asp Val Gly Lys Asp Val Tyr
1               5                   10                  15

His His Thr Phe Phe Glu Met Leu Gly Ser Trp Ser Phe Gly Asp Tyr
            20                  25                  30

Phe Lys

<210> SEQ ID NO 2
<211> LENGTH: 47
<212> TYPE: PRT
<213> ORGANISM: Homo sapiens

<400> SEQUENCE: 2

Asn Val His Phe Ala Tyr Pro Ala Arg Pro Glu Val Pro Ile Phe Gln
1               5                   10                  15

Asp Phe Ser Leu Ser Ile Pro Ser Gly Ser Val Thr Ala Leu Val Gly
            20                  25                  30

Pro Ser Gly Ser Gly Lys Ser Thr Val Leu Ser Leu Leu Leu Arg
        35                  40                  45

<210> SEQ ID NO 3
<211> LENGTH: 31
<212> TYPE: PRT
<213> ORGANISM: Homo sapiens

<400> SEQUENCE: 3

Glu Thr Leu Gln Asp Val Ser Phe Thr Val Met Pro Gly Gln Thr Leu
1               5                   10                  15

Ala Leu Val Gly Pro Ser Gly Ala Gly Lys Ser Thr Ile Leu Arg
            20                  25                  30

<210> SEQ ID NO 4
<211> LENGTH: 16
<212> TYPE: PRT
<213> ORGANISM: Homo sapiens

<400> SEQUENCE: 4

Val Ala Ile Val Gly Gly Ser Gly Ser Gly Lys Ser Thr Ile Val Arg
1               5                   10                  15

<210> SEQ ID NO 5
<211> LENGTH: 14
<212> TYPE: PRT
<213> ORGANISM: Homo sapiens

<400> SEQUENCE: 5

Thr Gly Ala Gly Lys Ser Ser Leu Thr Leu Gly Leu Phe Arg
1               5                   10

<210> SEQ ID NO 6
<211> LENGTH: 50
<212> TYPE: PRT
<213> ORGANISM: Homo sapiens

<400> SEQUENCE: 6

Ser Asp Pro Pro Thr Leu Asn Gly Ile Thr Phe Ser Ile Pro Glu Gly
1               5                   10                  15

Ala Leu Val Ala Val Val Gly Gln Val Gly Cys Gly Lys Ser Ser Leu
            20                  25                  30

Leu Ser Ala Leu Leu Ala Glu Met Asp Lys Val Glu Gly His Val Ala
        35                  40                  45

```
Ile Lys
    50

<210> SEQ ID NO 7
<211> LENGTH: 14
<212> TYPE: PRT
<213> ORGANISM: Homo sapiens

<400> SEQUENCE: 7

Thr Gly Ser Gly Lys Ser Ser Leu Leu Val Leu Phe Arg
1               5                   10

<210> SEQ ID NO 8
<211> LENGTH: 14
<212> TYPE: PRT
<213> ORGANISM: Homo sapiens

<400> SEQUENCE: 8

Thr Gly Ala Gly Lys Ser Ser Leu Thr Asn Cys Leu Phe Arg
1               5                   10

<210> SEQ ID NO 9
<211> LENGTH: 14
<212> TYPE: PRT
<213> ORGANISM: Homo sapiens

<400> SEQUENCE: 9

Thr Gly Ala Gly Lys Ser Ser Met Thr Leu Cys Leu Phe Arg
1               5                   10

<210> SEQ ID NO 10
<211> LENGTH: 27
<212> TYPE: PRT
<213> ORGANISM: Homo sapiens

<400> SEQUENCE: 10

Gly Ala Leu Val Ala Val Val Gly Pro Val Gly Cys Gly Lys Ser Ser
1               5                   10                  15

Leu Val Ser Ala Leu Leu Gly Glu Met Glu Lys
            20                  25

<210> SEQ ID NO 11
<211> LENGTH: 14
<212> TYPE: PRT
<213> ORGANISM: Homo sapiens

<400> SEQUENCE: 11

Thr Gly Ala Gly Lys Ser Ser Leu Ile Ser Ala Leu Phe Arg
1               5                   10

<210> SEQ ID NO 12
<211> LENGTH: 53
<212> TYPE: PRT
<213> ORGANISM: Homo sapiens

<400> SEQUENCE: 12

Ala Ser Glu Thr Pro Thr Leu Gln Gly Leu Ser Phe Thr Val Arg Pro
1               5                   10                  15

Gly Glu Leu Leu Ala Val Val Gly Pro Val Gly Ala Gly Lys Ser Ser
            20                  25                  30

Leu Leu Ser Ala Val Leu Gly Glu Leu Ala Pro Ser His Gly Leu Val
        35                  40                  45

Ser Val His Gly Arg
    50
```

-continued

<210> SEQ ID NO 13
<211> LENGTH: 20
<212> TYPE: PRT
<213> ORGANISM: Homo sapiens

<400> SEQUENCE: 13

Ser Gly Ala Asn Val Leu Ile Cys Gly Pro Asn Gly Cys Gly Lys Ser
1               5                   10                  15

Ser Leu Phe Arg
            20

<210> SEQ ID NO 14
<211> LENGTH: 22
<212> TYPE: PRT
<213> ORGANISM: Homo sapiens

<400> SEQUENCE: 14

Ile Ser Glu Gly Gln Ser Leu Leu Ile Thr Gly Asn Thr Gly Thr Gly
1               5                   10                  15

Lys Thr Ser Leu Leu Arg
            20

<210> SEQ ID NO 15
<211> LENGTH: 25
<212> TYPE: PRT
<213> ORGANISM: Homo sapiens

<400> SEQUENCE: 15

Leu Pro Ile Pro Arg Pro Gly Glu Val Leu Gly Leu Val Gly Thr Asn
1               5                   10                  15

Gly Ile Gly Lys Ser Thr Ala Leu Lys
            20                  25

<210> SEQ ID NO 16
<211> LENGTH: 21
<212> TYPE: PRT
<213> ORGANISM: Homo sapiens

<400> SEQUENCE: 16

Ile Cys Ile Val Gly Pro Asn Gly Val Gly Lys Ser Thr Leu Leu Leu
1               5                   10                  15

Leu Leu Thr Gly Lys
            20

<210> SEQ ID NO 17
<211> LENGTH: 16
<212> TYPE: PRT
<213> ORGANISM: Homo sapiens

<400> SEQUENCE: 17

Val Ala Leu Val Gly Pro Asn Gly Ala Gly Lys Ser Thr Leu Leu Lys
1               5                   10                  15

<210> SEQ ID NO 18
<211> LENGTH: 20
<212> TYPE: PRT
<213> ORGANISM: Homo sapiens

<400> SEQUENCE: 18

Tyr Gly Leu Ile Gly Leu Asn Gly Ile Gly Lys Ser Met Leu Leu Ser
1               5                   10                  15

```
Ala Ile Gly Lys
        20

<210> SEQ ID NO 19
<211> LENGTH: 16
<212> TYPE: PRT
<213> ORGANISM: Homo sapiens

<400> SEQUENCE: 19

Ile Cys Val Val Gly Glu Asn Gly Ala Gly Lys Ser Thr Met Leu Lys
1               5                   10                  15

<210> SEQ ID NO 20
<211> LENGTH: 27
<212> TYPE: PRT
<213> ORGANISM: Homo sapiens

<400> SEQUENCE: 20

Asp Val Asp Asp Gly Leu Gln Ala Ala Glu Glu Val Gly Tyr Pro Val
1               5                   10                  15

Met Ile Lys Ala Ser Glu Gly Gly Gly Lys
            20                  25

<210> SEQ ID NO 21
<211> LENGTH: 16
<212> TYPE: PRT
<213> ORGANISM: Homo sapiens

<400> SEQUENCE: 21

Ile Gly Phe Pro Leu Met Ile Lys Ala Ser Glu Gly Gly Gly Gly Lys
1               5                   10                  15

<210> SEQ ID NO 22
<211> LENGTH: 16
<212> TYPE: PRT
<213> ORGANISM: Homo sapiens

<400> SEQUENCE: 22

Gly Lys Leu Gly Leu Val Gly Val Asn Leu Thr Leu Asp Gly Val Lys
1               5                   10                  15

<210> SEQ ID NO 23
<211> LENGTH: 23
<212> TYPE: PRT
<213> ORGANISM: Homo sapiens

<400> SEQUENCE: 23

Leu Leu Gln Asp His Pro Trp Leu Leu Ser Gln Asn Leu Val Val Lys
1               5                   10                  15

Pro Asp Gln Leu Ile Lys Arg
            20

<210> SEQ ID NO 24
<211> LENGTH: 24
<212> TYPE: PRT
<213> ORGANISM: Homo sapiens

<400> SEQUENCE: 24

Lys Tyr Ser Val Trp Ile Gly Gly Ser Ile Leu Ala Ser Leu Ser Thr
1               5                   10                  15

Phe Gln Gln Met Trp Ile Ser Lys
            20
```

```
<210> SEQ ID NO 25
<211> LENGTH: 35
<212> TYPE: PRT
<213> ORGANISM: Homo sapiens

<400> SEQUENCE: 25

Val Val Val Cys Asp Asn Gly Thr Gly Phe Val Lys Cys Gly Tyr Ala
1               5                   10                  15

Gly Ser Asn Phe Pro Glu His Ile Phe Pro Ala Leu Val Gly Arg Pro
            20                  25                  30

Ile Ile Arg
        35

<210> SEQ ID NO 26
<211> LENGTH: 16
<212> TYPE: PRT
<213> ORGANISM: Homo sapiens

<400> SEQUENCE: 26

Lys His Met Val Phe Leu Gly Gly Ala Val Leu Ala Asp Ile Met Lys
1               5                   10                  15

<210> SEQ ID NO 27
<211> LENGTH: 19
<212> TYPE: PRT
<213> ORGANISM: Homo sapiens

<400> SEQUENCE: 27

Asp Arg Glu Val Gly Ile Pro Pro Glu Gln Ser Leu Glu Thr Ala Lys
1               5                   10                  15

Ala Val Lys

<210> SEQ ID NO 28
<211> LENGTH: 34
<212> TYPE: PRT
<213> ORGANISM: Homo sapiens

<400> SEQUENCE: 28

Leu Pro Ala Cys Val Val Asp Cys Gly Thr Gly Tyr Thr Lys Leu Gly
1               5                   10                  15

Tyr Ala Gly Asn Thr Glu Pro Gln Phe Ile Ile Pro Ser Cys Ile Ala
            20                  25                  30

Ile Lys

<210> SEQ ID NO 29
<211> LENGTH: 17
<212> TYPE: PRT
<213> ORGANISM: Homo sapiens

<400> SEQUENCE: 29

Gly Ala Ile Leu Thr Gly Pro Pro Gly Thr Gly Lys Thr Leu Leu Ala
1               5                   10                  15

Lys

<210> SEQ ID NO 30
<211> LENGTH: 10
<212> TYPE: PRT
<213> ORGANISM: Homo sapiens

<400> SEQUENCE: 30

Ser Lys Phe Asp Asn Leu Tyr Gly Cys Arg
```

-continued

```
<210> SEQ ID NO 31
<211> LENGTH: 20
<212> TYPE: PRT
<213> ORGANISM: Homo sapiens

<400> SEQUENCE: 31

Thr Lys Ile Ile Phe Val Val Gly Gly Pro Gly Ser Gly Lys Gly Thr
1               5                   10                  15

Gln Cys Glu Lys
            20

<210> SEQ ID NO 32
<211> LENGTH: 18
<212> TYPE: PRT
<213> ORGANISM: Homo sapiens

<400> SEQUENCE: 32

Ile Ile Phe Val Val Gly Gly Pro Gly Ser Gly Lys Gly Thr Gln Cys
1               5                   10                  15

Glu Lys

<210> SEQ ID NO 33
<211> LENGTH: 17
<212> TYPE: PRT
<213> ORGANISM: Homo sapiens

<400> SEQUENCE: 33

Ala Val Leu Leu Gly Pro Pro Gly Ala Gly Lys Gly Thr Gln Ala Pro
1               5                   10                  15

Arg

<210> SEQ ID NO 34
<211> LENGTH: 17
<212> TYPE: PRT
<213> ORGANISM: Homo sapiens

<400> SEQUENCE: 34

Ala Val Ile Met Gly Ala Pro Gly Ser Gly Lys Gly Thr Val Ser Ser
1               5                   10                  15

Arg

<210> SEQ ID NO 35
<211> LENGTH: 17
<212> TYPE: PRT
<213> ORGANISM: Homo sapiens

<400> SEQUENCE: 35

Ala Val Ile Leu Gly Pro Pro Gly Ser Gly Lys Gly Thr Val Cys Gln
1               5                   10                  15

Arg

<210> SEQ ID NO 36
<211> LENGTH: 18
<212> TYPE: PRT
<213> ORGANISM: Homo sapiens

<400> SEQUENCE: 36

Ile Ile Phe Ile Ile Gly Gly Pro Gly Ser Gly Lys Gly Thr Gln Cys
1               5                   10                  15
```

Glu Lys

<210> SEQ ID NO 37
<211> LENGTH: 16
<212> TYPE: PRT
<213> ORGANISM: Homo sapiens

<400> SEQUENCE: 37

Ile Cys Ile Leu Gly Pro Pro Ala Val Gly Lys Ser Ser Ile Ala Lys
1               5                   10                  15

<210> SEQ ID NO 38
<211> LENGTH: 19
<212> TYPE: PRT
<213> ORGANISM: Homo sapiens

<400> SEQUENCE: 38

Asp Ser Ser Gly Asn Leu His Gly Tyr Val Ala Glu Gly Gly Ala Lys
1               5                   10                  15

Asp Ile Arg

<210> SEQ ID NO 39
<211> LENGTH: 20
<212> TYPE: PRT
<213> ORGANISM: Homo sapiens

<400> SEQUENCE: 39

Leu Ile Asp Ile Phe Tyr Pro Gly Asp Gln Gln Ser Val Thr Phe Gly
1               5                   10                  15

Thr Lys Ser Arg
            20

<210> SEQ ID NO 40
<211> LENGTH: 18
<212> TYPE: PRT
<213> ORGANISM: Homo sapiens

<400> SEQUENCE: 40

Gly Lys Leu Pro Gly Pro Thr Leu Trp Ala Ser Tyr Ser Leu Glu Tyr
1               5                   10                  15

Gly Lys

<210> SEQ ID NO 41
<211> LENGTH: 12
<212> TYPE: PRT
<213> ORGANISM: Homo sapiens

<400> SEQUENCE: 41

Trp Ile Phe Val Gly Gly Lys Gly Gly Val Gly Lys
1               5                   10

<210> SEQ ID NO 42
<211> LENGTH: 22
<212> TYPE: PRT
<213> ORGANISM: Homo sapiens

<400> SEQUENCE: 42

His Lys Ile Gln Ala Lys Tyr Leu Asp Gln Met Glu Asp Leu Tyr Glu
1               5                   10                  15

Asp Phe His Ile Val Lys
            20

```
<210> SEQ ID NO 43
<211> LENGTH: 34
<212> TYPE: PRT
<213> ORGANISM: Homo sapiens

<400> SEQUENCE: 43

Gln His Gly Ile Pro Ile Pro Val Thr Pro Lys Asn Pro Trp Ser Met
1               5                   10                  15

Asp Glu Asn Leu Met His Ile Ser Tyr Glu Ala Gly Ile Leu Glu Asn
            20                  25                  30

Pro Lys

<210> SEQ ID NO 44
<211> LENGTH: 24
<212> TYPE: PRT
<213> ORGANISM: Homo sapiens

<400> SEQUENCE: 44

His Val Asp Leu Leu Glu Val Ala Gln Glu Thr Asp Gly Phe Ser Gly
1               5                   10                  15

Ser Asp Leu Lys Glu Met Cys Arg
            20

<210> SEQ ID NO 45
<211> LENGTH: 23
<212> TYPE: PRT
<213> ORGANISM: Homo sapiens

<400> SEQUENCE: 45

Gln Pro Leu Tyr Glu Phe Glu Asp Cys Leu Gly Gly Gly Lys Pro Lys
1               5                   10                  15

Ala Leu Ala Ala Ala Asp Arg
            20

<210> SEQ ID NO 46
<211> LENGTH: 11
<212> TYPE: PRT
<213> ORGANISM: Homo sapiens

<400> SEQUENCE: 46

Phe Leu Leu Leu Thr Phe Ala Asp Leu Lys Lys
1               5                   10

<210> SEQ ID NO 47
<211> LENGTH: 23
<212> TYPE: PRT
<213> ORGANISM: Homo sapiens

<400> SEQUENCE: 47

Lys Lys Asn Gly Asn Tyr Cys Val Leu Gln Met Asp Gln Ser Tyr Lys
1               5                   10                  15

Pro Asp Glu Asn Glu Val Arg
            20

<210> SEQ ID NO 48
<211> LENGTH: 24
<212> TYPE: PRT
<213> ORGANISM: Homo sapiens

<400> SEQUENCE: 48

Ile Gly Leu Phe Gly Gly Ala Gly Val Gly Lys Thr Val Leu Ile Met
1               5                   10                  15
```

Glu Leu Ile Asn Asn Val Ala Lys
            20

<210> SEQ ID NO 49
<211> LENGTH: 33
<212> TYPE: PRT
<213> ORGANISM: Homo sapiens

<400> SEQUENCE: 49

Ser Gly Met Gly Lys Thr Ala Val Phe Val Leu Ala Thr Leu Gln Gln
1               5                   10                  15

Leu Glu Pro Val Thr Gly Gln Val Ser Val Leu Val Met Cys His Thr
            20                  25                  30

Arg

<210> SEQ ID NO 50
<211> LENGTH: 9
<212> TYPE: PRT
<213> ORGANISM: Homo sapiens

<400> SEQUENCE: 50

Tyr Gln Gln Phe Lys Asp Phe Gln Arg
1               5

<210> SEQ ID NO 51
<211> LENGTH: 11
<212> TYPE: PRT
<213> ORGANISM: Homo sapiens

<400> SEQUENCE: 51

Gly Met Asp Lys Ile Leu Leu Ser Ser Gly Arg
1               5                   10

<210> SEQ ID NO 52
<211> LENGTH: 28
<212> TYPE: PRT
<213> ORGANISM: Homo sapiens

<400> SEQUENCE: 52

Ile Ser Ile Pro Val Asp Ile Ser Asp Ser Met Met Leu Asn Ile
1               5                   10                  15

Ile Asn Ser Ser Ile Thr Thr Lys Ala Ile Ser Arg
            20                  25

<210> SEQ ID NO 53
<211> LENGTH: 15
<212> TYPE: PRT
<213> ORGANISM: Homo sapiens

<400> SEQUENCE: 53

Asp Ala Leu Ser Asp Leu Ala Leu His Phe Leu Asn Lys Met Lys
1               5                   10                  15

<210> SEQ ID NO 54
<211> LENGTH: 26
<212> TYPE: PRT
<213> ORGANISM: Homo sapiens

<400> SEQUENCE: 54

Ile Ser Asp Ser Val Leu Val Asp Ile Lys Asp Thr Glu Pro Leu Ile
1               5                   10                  15

Gln Thr Ala Lys Thr Thr Leu Gly Ser Lys
            20                  25

```
<210> SEQ ID NO 55
<211> LENGTH: 14
<212> TYPE: PRT
<213> ORGANISM: Homo sapiens

<400> SEQUENCE: 55

Gly Lys Ala Thr Ile Ser Asn Asp Gly Ala Thr Ile Leu Lys
1               5                   10

<210> SEQ ID NO 56
<211> LENGTH: 16
<212> TYPE: PRT
<213> ORGANISM: Homo sapiens

<400> SEQUENCE: 56

Thr Ser Ile Met Ser Lys Gln Tyr Gly Asn Glu Val Phe Leu Ala Lys
1               5                   10                  15

<210> SEQ ID NO 57
<211> LENGTH: 13
<212> TYPE: PRT
<213> ORGANISM: Homo sapiens

<400> SEQUENCE: 57

Leu Asn Thr Ile Thr Pro Val Val Gly Lys Lys Arg Lys
1               5                   10

<210> SEQ ID NO 58
<211> LENGTH: 30
<212> TYPE: PRT
<213> ORGANISM: Homo sapiens

<400> SEQUENCE: 58

Arg Lys Glu Asn Gly Trp Tyr Asp Glu Glu His Pro Leu Val Phe Leu
1               5                   10                  15

Phe Leu Gly Ser Ser Gly Ile Gly Lys Thr Glu Leu Ala Lys
            20                  25                  30

<210> SEQ ID NO 59
<211> LENGTH: 22
<212> TYPE: PRT
<213> ORGANISM: Homo sapiens

<400> SEQUENCE: 59

Ser Asn Ile Leu Leu Leu Gly Pro Thr Gly Ser Gly Lys Thr Leu Leu
1               5                   10                  15

Ala Gln Thr Leu Ala Lys
            20

<210> SEQ ID NO 60
<211> LENGTH: 22
<212> TYPE: PRT
<213> ORGANISM: Homo sapiens

<400> SEQUENCE: 60

Met Lys Pro Leu Val Val Phe Val Leu Gly Gly Pro Gly Ala Gly Lys
1               5                   10                  15

Gly Thr Gln Cys Ala Arg
            20

<210> SEQ ID NO 61
<211> LENGTH: 19
```

```
<212> TYPE: PRT
<213> ORGANISM: Homo sapiens

<400> SEQUENCE: 61

Ala Ile Phe Thr Gly Tyr Tyr Gly Lys Gly Lys Pro Val Pro Thr Gln
1               5                   10                  15

Gly Ser Arg

<210> SEQ ID NO 62
<211> LENGTH: 14
<212> TYPE: PRT
<213> ORGANISM: Homo sapiens

<400> SEQUENCE: 62

Ser Lys Leu Leu Pro Glu Leu Leu Gln Pro Tyr Thr Glu Arg
1               5                   10

<210> SEQ ID NO 63
<211> LENGTH: 38
<212> TYPE: PRT
<213> ORGANISM: Homo sapiens

<400> SEQUENCE: 63

Met Leu Gly Asn Leu Leu Arg Pro Pro Tyr Glu Arg Pro Glu Leu Pro
1               5                   10                  15

Thr Cys Leu Tyr Val Ile Gly Leu Thr Gly Ile Ser Gly Ser Gly Lys
            20                  25                  30

Ser Ser Ile Ala Gln Arg
        35

<210> SEQ ID NO 64
<211> LENGTH: 16
<212> TYPE: PRT
<213> ORGANISM: Homo sapiens

<400> SEQUENCE: 64

Ile Gly Ser Ser Met Lys Ser Val Gly Glu Val Met Ala Ile Gly Arg
1               5                   10                  15

<210> SEQ ID NO 65
<211> LENGTH: 31
<212> TYPE: PRT
<213> ORGANISM: Homo sapiens

<400> SEQUENCE: 65

Lys Tyr Thr Glu Leu Pro His Gly Ala Ile Ser Glu Asp Gln Ala Val
1               5                   10                  15

Gly Pro Ala Asp Ile Pro Cys Asp Ser Thr Gly Gln Thr Ser Thr
            20                  25                  30

<210> SEQ ID NO 66
<211> LENGTH: 19
<212> TYPE: PRT
<213> ORGANISM: Homo sapiens

<400> SEQUENCE: 66

Thr Gly Ser Gly Lys Thr Leu Ala Phe Leu Ile Pro Ala Val Glu Leu
1               5                   10                  15

Ile Val Lys

<210> SEQ ID NO 67
<211> LENGTH: 16
```

```
<212> TYPE: PRT
<213> ORGANISM: Homo sapiens

<400> SEQUENCE: 67

Thr Gly Thr Gly Lys Thr Phe Ser Phe Ala Ile Pro Leu Ile Glu Lys
1               5                   10                  15

<210> SEQ ID NO 68
<211> LENGTH: 23
<212> TYPE: PRT
<213> ORGANISM: Homo sapiens

<400> SEQUENCE: 68

His Val Val Cys Ala Ala Glu Thr Gly Ser Gly Lys Thr Leu Ser Tyr
1               5                   10                  15

Leu Leu Pro Leu Leu Gln Arg
            20

<210> SEQ ID NO 69
<211> LENGTH: 33
<212> TYPE: PRT
<213> ORGANISM: Homo sapiens

<400> SEQUENCE: 69

Ser Gly Met Gly Lys Thr Ala Val Phe Val Leu Ala Thr Leu Gln Gln
1               5                   10                  15

Ile Glu Pro Val Asn Gly Gln Val Thr Val Leu Val Met Cys His Thr
            20                  25                  30

Arg

<210> SEQ ID NO 70
<211> LENGTH: 34
<212> TYPE: PRT
<213> ORGANISM: Homo sapiens

<400> SEQUENCE: 70

Asp Leu Met Ala Cys Ala Gln Thr Gly Ser Gly Lys Thr Ala Ala Phe
1               5                   10                  15

Leu Leu Pro Ile Leu Ser Gln Ile Tyr Ser Asp Gly Pro Gly Glu Ala
            20                  25                  30

Leu Arg

<210> SEQ ID NO 71
<211> LENGTH: 13
<212> TYPE: PRT
<213> ORGANISM: Homo sapiens

<400> SEQUENCE: 71

Thr Val Lys Lys Glu Trp Gln Ala Ala Trp Leu Leu Lys
1               5                   10

<210> SEQ ID NO 72
<211> LENGTH: 27
<212> TYPE: PRT
<213> ORGANISM: Homo sapiens

<400> SEQUENCE: 72

His Gln Ser Phe Val Leu Val Gly Glu Thr Gly Ser Gly Lys Thr Thr
1               5                   10                  15

Gln Ile Pro Gln Trp Cys Val Glu Tyr Met Arg
            20                  25
```

```
<210> SEQ ID NO 73
<211> LENGTH: 37
<212> TYPE: PRT
<213> ORGANISM: Homo sapiens

<400> SEQUENCE: 73

Glu Leu Val Asn Leu Ile Asp Asn His Gln Val Thr Val Ile Ser Gly
1               5                   10                  15

Glu Thr Gly Cys Gly Lys Thr Thr Gln Val Thr Gln Phe Ile Leu Asp
            20                  25                  30

Asn Tyr Ile Glu Arg
        35

<210> SEQ ID NO 74
<211> LENGTH: 18
<212> TYPE: PRT
<213> ORGANISM: Homo sapiens

<400> SEQUENCE: 74

Leu Gly Gly Ser Pro Phe Gly Pro Ala Gly Thr Gly Lys Thr Glu Ser
1               5                   10                  15

Val Lys

<210> SEQ ID NO 75
<211> LENGTH: 21
<212> TYPE: PRT
<213> ORGANISM: Homo sapiens

<400> SEQUENCE: 75

Gln Pro Gln Gly His Leu Leu Ile Gly Val Ser Gly Ala Gly Lys
1               5                   10                  15

Thr Thr Leu Ser Arg
        20

<210> SEQ ID NO 76
<211> LENGTH: 28
<212> TYPE: PRT
<213> ORGANISM: Homo sapiens

<400> SEQUENCE: 76

Thr Phe Pro Asn His Tyr Ser Ile Val Thr Gly Leu Tyr Pro Glu Ser
1               5                   10                  15

His Gly Ile Ile Asp Asn Lys Met Tyr Asp Pro Lys
            20                  25

<210> SEQ ID NO 77
<211> LENGTH: 11
<212> TYPE: PRT
<213> ORGANISM: Homo sapiens

<400> SEQUENCE: 77

Trp Glu Phe Lys His Pro Gln Pro Phe Leu Arg
1               5                   10

<210> SEQ ID NO 78
<211> LENGTH: 20
<212> TYPE: PRT
<213> ORGANISM: Homo sapiens

<400> SEQUENCE: 78

Ile Gly Thr Asp Ile Gln Asp Asn Lys Cys Ser Trp Leu Val Val Gln
1               5                   10                  15
```

Cys Leu Gln Arg
          20

<210> SEQ ID NO 79
<211> LENGTH: 14
<212> TYPE: PRT
<213> ORGANISM: Homo sapiens

<400> SEQUENCE: 79

Thr Ser Gly His Val Asp Lys Phe Ala Asp Phe Met Val Lys
1               5                   10

<210> SEQ ID NO 80
<211> LENGTH: 14
<212> TYPE: PRT
<213> ORGANISM: Homo sapiens

<400> SEQUENCE: 80

Ala Ser Gly Leu Ala Ala Gly Lys Gly Val Ile Val Ala Lys
1               5                   10

<210> SEQ ID NO 81
<211> LENGTH: 21
<212> TYPE: PRT
<213> ORGANISM: Homo sapiens

<400> SEQUENCE: 81

Ser Ala Gly Val Gln Cys Phe Gly Pro Thr Ala Glu Ala Ala Gln Leu
1               5                   10                  15

Glu Ser Ser Lys Arg
          20

<210> SEQ ID NO 82
<211> LENGTH: 17
<212> TYPE: PRT
<213> ORGANISM: Homo sapiens

<400> SEQUENCE: 82

Ser Gly Cys Lys Val Asp Leu Gly Gly Phe Ala Gly Leu Phe Asp Leu
1               5                   10                  15

Lys

<210> SEQ ID NO 83
<211> LENGTH: 12
<212> TYPE: PRT
<213> ORGANISM: Homo sapiens

<400> SEQUENCE: 83

Ile Lys Gln Ile Gln Leu Glu Gln Asp Ser Gly Lys
1               5                   10

<210> SEQ ID NO 84
<211> LENGTH: 18
<212> TYPE: PRT
<213> ORGANISM: Homo sapiens

<400> SEQUENCE: 84

Lys His Tyr Phe Tyr Ala Asp Leu Pro Ala Gly Tyr Gln Ile Thr Gln
1               5                   10                  15

Gln Arg

<210> SEQ ID NO 85

```
<211> LENGTH: 15
<212> TYPE: PRT
<213> ORGANISM: Homo sapiens

<400> SEQUENCE: 85

Ala Glu Leu Ile Lys Thr His His Asn Asp Thr Glu Leu Ile Arg
1               5                   10                  15

<210> SEQ ID NO 86
<211> LENGTH: 31
<212> TYPE: PRT
<213> ORGANISM: Homo sapiens

<400> SEQUENCE: 86

Leu Gly Ile Gln Val Lys Val Ile Asn Ala Ala His Ser Phe Tyr Asn
1               5                   10                  15

Gly Thr Thr Thr Leu Pro Ile Ser Asp Glu Asp Arg Thr Pro Arg
            20                  25                  30

<210> SEQ ID NO 87
<211> LENGTH: 13
<212> TYPE: PRT
<213> ORGANISM: Homo sapiens

<400> SEQUENCE: 87

Cys Pro Asp Ile Ala Thr Gln Leu Ala Gly Thr Lys Lys
1               5                   10

<210> SEQ ID NO 88
<211> LENGTH: 24
<212> TYPE: PRT
<213> ORGANISM: Homo sapiens

<400> SEQUENCE: 88

Thr Lys Ala Ile Glu His Ala Asp Gly Gly Val Ala Ala Gly Val Ala
1               5                   10                  15

Val Leu Asp Asn Pro Tyr Pro Val
            20

<210> SEQ ID NO 89
<211> LENGTH: 25
<212> TYPE: PRT
<213> ORGANISM: Homo sapiens

<400> SEQUENCE: 89

Thr Ile Cys Ser Ser Val Asp Lys Leu Asp Lys Val Ser Trp Glu Glu
1               5                   10                  15

Val Lys Asn Glu Met Val Gly Glu Lys
            20                  25

<210> SEQ ID NO 90
<211> LENGTH: 18
<212> TYPE: PRT
<213> ORGANISM: Homo sapiens

<400> SEQUENCE: 90

Arg Lys Asp Pro Glu Gly Thr Pro Tyr Ile Asn His Pro Ile Gly Val
1               5                   10                  15

Ala Arg

<210> SEQ ID NO 91
<211> LENGTH: 16
<212> TYPE: PRT
```

<213> ORGANISM: Homo sapiens

<400> SEQUENCE: 91

Leu Val Glu Glu Val Thr Asp Asp Lys Thr Leu Pro Lys Leu Glu Arg
1               5                   10                  15

<210> SEQ ID NO 92
<211> LENGTH: 22
<212> TYPE: PRT
<213> ORGANISM: Homo sapiens

<400> SEQUENCE: 92

Lys Asp Cys Glu Val Val Met Met Ile Gly Leu Pro Gly Ala Gly Lys
1               5                   10                  15

Thr Thr Trp Val Thr Lys
            20

<210> SEQ ID NO 93
<211> LENGTH: 14
<212> TYPE: PRT
<213> ORGANISM: Homo sapiens

<400> SEQUENCE: 93

Leu Lys Ser Tyr Cys Asn Asp Gln Ser Thr Gly Asp Ile Lys
1               5                   10

<210> SEQ ID NO 94
<211> LENGTH: 15
<212> TYPE: PRT
<213> ORGANISM: Homo sapiens

<400> SEQUENCE: 94

Thr Val Ile Ile Glu Gln Ser Trp Gly Ser Pro Lys Val Thr Lys
1               5                   10                  15

<210> SEQ ID NO 95
<211> LENGTH: 29
<212> TYPE: PRT
<213> ORGANISM: Homo sapiens

<400> SEQUENCE: 95

Thr Leu Thr Ile Val Asp Thr Gly Ile Gly Met Thr Lys Ala Asp Leu
1               5                   10                  15

Ile Asn Asn Leu Gly Thr Ile Ala Lys Ser Gly Thr Lys
            20                  25

<210> SEQ ID NO 96
<211> LENGTH: 16
<212> TYPE: PRT
<213> ORGANISM: Homo sapiens

<400> SEQUENCE: 96

Ala Asp Leu Ile Asn Asn Leu Gly Thr Ile Ala Lys Ser Gly Thr Lys
1               5                   10                  15

<210> SEQ ID NO 97
<211> LENGTH: 29
<212> TYPE: PRT
<213> ORGANISM: Homo sapiens

<400> SEQUENCE: 97

Thr Leu Thr Leu Val Asp Thr Gly Ile Gly Met Thr Lys Ala Asp Leu
1               5                   10                  15

```
Ile Asn Asn Leu Gly Thr Ile Ala Lys Ser Gly Thr Lys
            20                  25
```

<210> SEQ ID NO 98
<211> LENGTH: 12
<212> TYPE: PRT
<213> ORGANISM: Homo sapiens

<400> SEQUENCE: 98

```
Arg Ala Pro Phe Asp Leu Phe Glu Asn Lys Lys Lys
1               5                   10
```

<210> SEQ ID NO 99
<211> LENGTH: 10
<212> TYPE: PRT
<213> ORGANISM: Homo sapiens

<400> SEQUENCE: 99

```
Gly Leu Phe Asp Glu Tyr Gly Ser Lys Lys
1               5                   10
```

<210> SEQ ID NO 100
<211> LENGTH: 23
<212> TYPE: PRT
<213> ORGANISM: Homo sapiens

<400> SEQUENCE: 100

```
Leu Ile Gly Asp Ala Ala Lys Asn Gln Val Ala Leu Asn Pro Gln Asn
1               5                   10                  15

Thr Val Phe Asp Ala Lys Arg
            20
```

<210> SEQ ID NO 101
<211> LENGTH: 22
<212> TYPE: PRT
<213> ORGANISM: Homo sapiens

<400> SEQUENCE: 101

```
Leu Ile Gly Asp Ala Ala Lys Asn Gln Val Ala Leu Asn Pro Gln Asn
1               5                   10                  15

Thr Val Phe Asp Ala Lys
            20
```

<210> SEQ ID NO 102
<211> LENGTH: 23
<212> TYPE: PRT
<213> ORGANISM: Homo sapiens

<400> SEQUENCE: 102

```
Leu Ile Gly Asp Ala Ala Lys Asn Gln Val Ala Met Asn Pro Thr Asn
1               5                   10                  15

Thr Ile Phe Asp Ala Lys Arg
            20
```

<210> SEQ ID NO 103
<211> LENGTH: 22
<212> TYPE: PRT
<213> ORGANISM: Homo sapiens

<400> SEQUENCE: 103

```
Leu Ile Gly Asp Ala Ala Lys Asn Gln Val Ala Met Asn Pro Thr Asn
1               5                   10                  15

Thr Ile Phe Asp Ala Lys
```

```
<210> SEQ ID NO 104
<211> LENGTH: 23
<212> TYPE: PRT
<213> ORGANISM: Homo sapiens

<400> SEQUENCE: 104

Leu Ile Gly Asp Ala Ala Lys Asn Gln Leu Thr Ser Asn Pro Glu Asn
1               5                   10                  15

Thr Val Phe Asp Ala Lys Arg
            20

<210> SEQ ID NO 105
<211> LENGTH: 22
<212> TYPE: PRT
<213> ORGANISM: Homo sapiens

<400> SEQUENCE: 105

Leu Ile Gly Asp Ala Ala Lys Asn Gln Leu Thr Ser Asn Pro Glu Asn
1               5                   10                  15

Thr Val Phe Asp Ala Lys
            20

<210> SEQ ID NO 106
<211> LENGTH: 23
<212> TYPE: PRT
<213> ORGANISM: Homo sapiens

<400> SEQUENCE: 106

Leu Ile Gly Asp Ala Ala Lys Asn Gln Val Ala Met Asn Pro Thr Asn
1               5                   10                  15

Thr Val Phe Asp Ala Lys Arg
            20

<210> SEQ ID NO 107
<211> LENGTH: 22
<212> TYPE: PRT
<213> ORGANISM: Homo sapiens

<400> SEQUENCE: 107

Leu Ile Gly Asp Ala Ala Lys Asn Gln Val Ala Met Asn Pro Thr Asn
1               5                   10                  15

Thr Val Phe Asp Ala Lys
            20

<210> SEQ ID NO 108
<211> LENGTH: 8
<212> TYPE: PRT
<213> ORGANISM: Homo sapiens

<400> SEQUENCE: 108

Leu Val Gly Met Pro Ala Lys Arg
1               5

<210> SEQ ID NO 109
<211> LENGTH: 14
<212> TYPE: PRT
<213> ORGANISM: Homo sapiens

<400> SEQUENCE: 109

Arg Lys Thr Pro Val Ile Val Thr Leu Lys Glu Asn Glu Arg
1               5                   10
```

```
<210> SEQ ID NO 110
<211> LENGTH: 13
<212> TYPE: PRT
<213> ORGANISM: Homo sapiens

<400> SEQUENCE: 110

Lys Thr Pro Val Ile Val Thr Leu Lys Glu Asn Glu Arg
1               5                   10

<210> SEQ ID NO 111
<211> LENGTH: 26
<212> TYPE: PRT
<213> ORGANISM: Homo sapiens

<400> SEQUENCE: 111

Gln Gln Val Gln Leu Leu Ala Glu Met Cys Ile Leu Ile Asp Glu Asn
1               5                   10                  15

Asp Asn Lys Ile Gly Ala Glu Thr Lys Lys
            20                  25

<210> SEQ ID NO 112
<211> LENGTH: 15
<212> TYPE: PRT
<213> ORGANISM: Homo sapiens

<400> SEQUENCE: 112

Lys Glu Ile Cys Asn Ala Tyr Thr Glu Leu Asn Asp Pro Met Arg
1               5                   10                  15

<210> SEQ ID NO 113
<211> LENGTH: 37
<212> TYPE: PRT
<213> ORGANISM: Homo sapiens

<400> SEQUENCE: 113

Leu Gly His Ile Leu Val Val Asp Glu Ala Asp Lys Ala Pro Thr Asn
1               5                   10                  15

Val Thr Cys Ile Leu Lys Thr Leu Val Glu Asn Gly Glu Met Ile Leu
            20                  25                  30

Ala Asp Gly Arg Arg
            35

<210> SEQ ID NO 114
<211> LENGTH: 21
<212> TYPE: PRT
<213> ORGANISM: Homo sapiens

<400> SEQUENCE: 114

Val Arg Glu Asp Lys Gln Pro Glu Gln Ala Thr Thr Ser Ala Gln Val
1               5                   10                  15

Ala Cys Leu Tyr Arg
            20

<210> SEQ ID NO 115
<211> LENGTH: 17
<212> TYPE: PRT
<213> ORGANISM: Homo sapiens

<400> SEQUENCE: 115

Ile Leu Cys Phe Tyr Gly Pro Pro Gly Val Gly Lys Thr Ser Ile Ala
1               5                   10                  15
```

Arg

<210> SEQ ID NO 116
<211> LENGTH: 14
<212> TYPE: PRT
<213> ORGANISM: Homo sapiens

<400> SEQUENCE: 116

His Gln Lys Ile Ile Glu Glu Ala Pro Ala Pro Gly Ile Lys
1               5                   10

<210> SEQ ID NO 117
<211> LENGTH: 11
<212> TYPE: PRT
<213> ORGANISM: Homo sapiens

<400> SEQUENCE: 117

Ile Gly Tyr Pro Val Met Ile Lys Ala Val Arg
1               5                   10

<210> SEQ ID NO 118
<211> LENGTH: 10
<212> TYPE: PRT
<213> ORGANISM: Homo sapiens

<400> SEQUENCE: 118

Ser Leu Phe Ser Asp Lys Gln Met Ile Lys
1               5                   10

<210> SEQ ID NO 119
<211> LENGTH: 13
<212> TYPE: PRT
<213> ORGANISM: Homo sapiens

<400> SEQUENCE: 119

Ser Gln Phe Leu Lys His Val Glu Glu Phe Ser Pro Arg
1               5                   10

<210> SEQ ID NO 120
<211> LENGTH: 20
<212> TYPE: PRT
<213> ORGANISM: Homo sapiens

<400> SEQUENCE: 120

Gly Asp Ile Asn Val Cys Ile Val Gly Asp Pro Ser Thr Ala Lys Ser
1               5                   10                  15

Gln Phe Leu Lys
            20

<210> SEQ ID NO 121
<211> LENGTH: 36
<212> TYPE: PRT
<213> ORGANISM: Homo sapiens

<400> SEQUENCE: 121

Val Val Ser Ala Gly Thr Tyr Pro Val Leu Ile Gln Gly Glu Thr Ser
1               5                   10                  15

Val Gly Lys Thr Ser Leu Ile Gln Trp Leu Ala Ala Ala Thr Gly Asn
            20                  25                  30

His Cys Val Arg
            35

<210> SEQ ID NO 122

```
<211> LENGTH: 21
<212> TYPE: PRT
<213> ORGANISM: Homo sapiens

<400> SEQUENCE: 122

Ser Ile Val Asp Asn Trp Pro Glu Asn His Val Lys Ala Val Val
1               5                   10                  15

Thr Asp Gly Glu Arg
            20

<210> SEQ ID NO 123
<211> LENGTH: 42
<212> TYPE: PRT
<213> ORGANISM: Homo sapiens

<400> SEQUENCE: 123

Ala Lys Ile Asp Ser Tyr Gln Glu Pro Phe Thr His Ser Ala Pro Glu
1               5                   10                  15

Ser Ile Pro Asp Thr Phe Glu Asp Ala Val Asn Ile Leu Lys Pro Ser
            20                  25                  30

Thr Ile Ile Gly Val Ala Gly Ala Gly Arg
        35                  40

<210> SEQ ID NO 124
<211> LENGTH: 31
<212> TYPE: PRT
<213> ORGANISM: Homo sapiens

<400> SEQUENCE: 124

Arg Pro Lys Asp Asp Gln Val Phe Glu Ala Val Gly Thr Thr Asp Glu
1               5                   10                  15

Leu Ser Ser Ala Ile Gly Phe Ala Leu Glu Leu Val Thr Glu Lys
            20                  25                  30

<210> SEQ ID NO 125
<211> LENGTH: 40
<212> TYPE: PRT
<213> ORGANISM: Homo sapiens

<400> SEQUENCE: 125

Tyr Val Val Val Thr Gly Ile Thr Pro Thr Pro Leu Gly Glu Gly Lys
1               5                   10                  15

Ser Thr Thr Thr Ile Gly Leu Val Gln Ala Leu Gly Ala His Leu Tyr
            20                  25                  30

Gln Asn Val Phe Ala Cys Val Arg
        35                  40

<210> SEQ ID NO 126
<211> LENGTH: 40
<212> TYPE: PRT
<213> ORGANISM: Homo sapiens

<400> SEQUENCE: 126

Tyr Val Leu Val Ala Gly Ile Thr Pro Thr Pro Leu Gly Glu Gly Lys
1               5                   10                  15

Ser Thr Val Thr Ile Gly Leu Val Gln Ala Leu Thr Ala His Leu Asn
            20                  25                  30

Val Asn Ser Phe Ala Cys Leu Arg
        35                  40

<210> SEQ ID NO 127
```

<211> LENGTH: 32
<212> TYPE: PRT
<213> ORGANISM: Homo sapiens

<400> SEQUENCE: 127

Gly Leu His Ser Lys Leu Thr Gly Ala Gly Gly Gly Cys Gly Ile
1               5                   10                  15

Thr Leu Leu Lys Pro Gly Leu Glu Gln Pro Glu Val Glu Ala Thr Lys
            20                  25                  30

<210> SEQ ID NO 128
<211> LENGTH: 26
<212> TYPE: PRT
<213> ORGANISM: Homo sapiens

<400> SEQUENCE: 128

Asn Met Ile Ile Asp Arg Glu Asn Gln Cys Val Ile Ile Ser Gly Glu
1               5                   10                  15

Ser Gly Ala Gly Lys Thr Val Ala Ala Lys
            20                  25

<210> SEQ ID NO 129
<211> LENGTH: 9
<212> TYPE: PRT
<213> ORGANISM: Homo sapiens

<400> SEQUENCE: 129

Val Val Val Val Ala Lys Thr Thr Arg
1               5

<210> SEQ ID NO 130
<211> LENGTH: 20
<212> TYPE: PRT
<213> ORGANISM: Homo sapiens

<400> SEQUENCE: 130

Tyr Asp Cys Ser Ser Ala Asp Ile Asn Pro Ile Gly Gly Ile Ser Lys
1               5                   10                  15

Thr Asp Leu Arg
            20

<210> SEQ ID NO 131
<211> LENGTH: 12
<212> TYPE: PRT
<213> ORGANISM: Homo sapiens

<400> SEQUENCE: 131

Phe Pro Val Glu Ile Lys Ser Phe Tyr Met Gln Arg
1               5                   10

<210> SEQ ID NO 132
<211> LENGTH: 14
<212> TYPE: PRT
<213> ORGANISM: Homo sapiens

<400> SEQUENCE: 132

Val Ile Thr Val Asp Gly Asn Ile Cys Thr Gly Lys Gly Lys
1               5                   10

<210> SEQ ID NO 133
<211> LENGTH: 12
<212> TYPE: PRT
<213> ORGANISM: Homo sapiens

```
<400> SEQUENCE: 133

Thr Phe Ile Ala Ile Lys Pro Asp Gly Val Gln Arg
1               5                   10

<210> SEQ ID NO 134
<211> LENGTH: 22
<212> TYPE: PRT
<213> ORGANISM: Homo sapiens

<400> SEQUENCE: 134

Gly Asp Phe Cys Ile Glu Val Gly Lys Asn Leu Ile His Gly Ser Asp
1               5                   10                  15

Ser Val Glu Ser Ala Arg
            20

<210> SEQ ID NO 135
<211> LENGTH: 26
<212> TYPE: PRT
<213> ORGANISM: Homo sapiens

<400> SEQUENCE: 135

Asp His Leu His Gln Thr Gly Met Tyr Gln Val Ile Gln Gly Ile Ile
1               5                   10                  15

Ser Pro Val Asn Asp Thr Tyr Gly Lys Lys
            20                  25

<210> SEQ ID NO 136
<211> LENGTH: 20
<212> TYPE: PRT
<213> ORGANISM: Homo sapiens

<400> SEQUENCE: 136

Val Leu Leu Asp Ala Pro Cys Ser Gly Thr Gly Val Ile Ser Lys Asp
1               5                   10                  15

Pro Ala Val Lys
            20

<210> SEQ ID NO 137
<211> LENGTH: 19
<212> TYPE: PRT
<213> ORGANISM: Homo sapiens

<400> SEQUENCE: 137

Thr Phe Ile Ile Gly Ile Ser Gly Val Thr Asn Ser Gly Lys Thr Thr
1               5                   10                  15

Leu Ala Lys

<210> SEQ ID NO 138
<211> LENGTH: 7
<212> TYPE: PRT
<213> ORGANISM: Homo sapiens

<400> SEQUENCE: 138

Val Trp Ile Gly Ile Lys Lys
1               5

<210> SEQ ID NO 139
<211> LENGTH: 17
<212> TYPE: PRT
<213> ORGANISM: Homo sapiens

<400> SEQUENCE: 139
```

-continued

Gly Ile Leu Leu Tyr Gly Pro Pro Gly Cys Gly Lys Thr Leu Leu Ala
1               5                   10                  15
Arg

<210> SEQ ID NO 140
<211> LENGTH: 39
<212> TYPE: PRT
<213> ORGANISM: Homo sapiens

<400> SEQUENCE: 140

Gly Val Asp Val Val Gly Gly His Ser Asn Thr Phe Leu Tyr Thr
1               5                   10                  15

Gly Asn Pro Pro Ser Lys Glu Val Pro Ala Gly Lys Tyr Pro Phe Ile
            20                  25                  30

Val Thr Ser Asp Asp Gly Arg
        35

<210> SEQ ID NO 141
<211> LENGTH: 18
<212> TYPE: PRT
<213> ORGANISM: Homo sapiens

<400> SEQUENCE: 141

His Val Phe Leu Thr Gly Pro Pro Gly Val Gly Lys Thr Thr Leu Ile
1               5                   10                  15
His Lys

<210> SEQ ID NO 142
<211> LENGTH: 7
<212> TYPE: PRT
<213> ORGANISM: Homo sapiens

<400> SEQUENCE: 142

Val Leu Leu Gly Met Lys Lys
1               5

<210> SEQ ID NO 143
<211> LENGTH: 19
<212> TYPE: PRT
<213> ORGANISM: Homo sapiens

<400> SEQUENCE: 143

Trp Asn Gly Phe Gly Gly Lys Val Gln Glu Gly Glu Thr Ile Glu Asp
1               5                   10                  15
Gly Ala Arg

<210> SEQ ID NO 144
<211> LENGTH: 19
<212> TYPE: PRT
<213> ORGANISM: Homo sapiens

<400> SEQUENCE: 144

Leu Tyr Thr Leu Val Leu Val Leu Gln Pro Gln Arg Val Leu Leu Gly
1               5                   10                  15
Met Lys Lys

<210> SEQ ID NO 145
<211> LENGTH: 21
<212> TYPE: PRT
<213> ORGANISM: Homo sapiens

<400> SEQUENCE: 145

Asn Lys Pro Lys Thr Val Ile Tyr Trp Leu Ala Glu Val Lys Asp Tyr
1               5                   10                  15

Asp Val Glu Ile Arg
            20

<210> SEQ ID NO 146
<211> LENGTH: 39
<212> TYPE: PRT
<213> ORGANISM: Homo sapiens

<400> SEQUENCE: 146

Val Asp Asn Asn Ala Ile Glu Phe Leu Leu Gln Ala Ser Asp Gly
1               5                   10                  15

Ile His His Trp Thr Pro Pro Lys Gly His Val Glu Pro Gly Glu Asp
            20                  25                  30

Asp Leu Glu Thr Ala Leu Arg
            35

<210> SEQ ID NO 147
<211> LENGTH: 25
<212> TYPE: PRT
<213> ORGANISM: Homo sapiens

<400> SEQUENCE: 147

Ala Pro Gly Glu Val Cys Phe Pro Gly Gly Lys Arg Asp Pro Thr Asp
1               5                   10                  15

Met Asp Asp Ala Ala Thr Ala Leu Arg
            20                  25

<210> SEQ ID NO 148
<211> LENGTH: 25
<212> TYPE: PRT
<213> ORGANISM: Homo sapiens

<400> SEQUENCE: 148

Ala Leu Gly Leu Val Thr Pro Ala Gly Val Leu Leu Ala Gly Pro Pro
1               5                   10                  15

Gly Cys Gly Lys Thr Leu Leu Ala Lys
            20                  25

<210> SEQ ID NO 149
<211> LENGTH: 29
<212> TYPE: PRT
<213> ORGANISM: Homo sapiens

<400> SEQUENCE: 149

Gly Val Leu Leu His Gly Pro Pro Gly Cys Gly Lys Thr Leu Leu Ala
1               5                   10                  15

His Ala Ile Ala Gly Glu Leu Asp Leu Pro Ile Leu Lys
            20                  25

<210> SEQ ID NO 150
<211> LENGTH: 39
<212> TYPE: PRT
<213> ORGANISM: Homo sapiens

<400> SEQUENCE: 150

Ile Gly Ile Val Gly Leu Pro Asn Val Gly Lys Ser Thr Phe Phe Asn
1               5                   10                  15

Val Leu Thr Asn Ser Gln Ala Ser Ala Glu Asn Phe Pro Phe Cys Thr
            20                  25                  30

Ile Asp Pro Asn Glu Ser Arg
            35

<210> SEQ ID NO 151
<211> LENGTH: 13
<212> TYPE: PRT
<213> ORGANISM: Homo sapiens

<400> SEQUENCE: 151

Thr Lys Glu Val Tyr Glu Leu Leu Asp Ser Pro Gly Lys
1               5                   10

<210> SEQ ID NO 152
<211> LENGTH: 18
<212> TYPE: PRT
<213> ORGANISM: Homo sapiens

<400> SEQUENCE: 152

His Gln Lys Val Val Glu Ile Ala Pro Ala Ala His Leu Asp Pro Gln
1               5                   10                  15

Leu Arg

<210> SEQ ID NO 153
<211> LENGTH: 17
<212> TYPE: PRT
<213> ORGANISM: Homo sapiens

<400> SEQUENCE: 153

Glu Ile Gly Tyr Pro Val Met Ile Lys Ala Ser Ala Gly Gly Gly Gly
1               5                   10                  15

Lys

<210> SEQ ID NO 154
<211> LENGTH: 19
<212> TYPE: PRT
<213> ORGANISM: Homo sapiens

<400> SEQUENCE: 154

Asn Gln Lys Val Val Glu Glu Ala Pro Ser Ile Phe Leu Asp Ala Glu
1               5                   10                  15

Thr Arg Arg

<210> SEQ ID NO 155
<211> LENGTH: 12
<212> TYPE: PRT
<213> ORGANISM: Homo sapiens

<400> SEQUENCE: 155

Ile Lys Gln His Glu Gly Leu Ala Thr Phe Tyr Arg
1               5                   10

<210> SEQ ID NO 156
<211> LENGTH: 14
<212> TYPE: PRT
<213> ORGANISM: Homo sapiens

<400> SEQUENCE: 156

Asn Gly Ala Leu Leu Leu Thr Gly Gly Lys Gly Ser Gly Lys
1               5                   10

<210> SEQ ID NO 157
<211> LENGTH: 14

```
<212> TYPE: PRT
<213> ORGANISM: Homo sapiens

<400> SEQUENCE: 157

His Trp Phe Phe Lys Gly Gln Leu His Val Asp Gly Gln Lys
1               5                   10

<210> SEQ ID NO 158
<211> LENGTH: 31
<212> TYPE: PRT
<213> ORGANISM: Homo sapiens

<400> SEQUENCE: 158

Val Phe Phe Val Glu Ser Val Cys Asp Asp Pro Asp Val Ile Ala Ala
1               5                   10                  15

Asn Ile Leu Glu Val Lys Val Ser Ser Pro Asp Tyr Pro Glu Arg
            20                  25                  30

<210> SEQ ID NO 159
<211> LENGTH: 21
<212> TYPE: PRT
<213> ORGANISM: Homo sapiens

<400> SEQUENCE: 159

Ser Phe Met Asn Asn Trp Glu Val Tyr Lys Leu Leu Ala His Val Arg
1               5                   10                  15

Pro Pro Val Ser Lys
            20

<210> SEQ ID NO 160
<211> LENGTH: 21
<212> TYPE: PRT
<213> ORGANISM: Homo sapiens

<400> SEQUENCE: 160

Ala Leu Glu Ser Pro Glu Arg Pro Phe Leu Ala Ile Leu Gly Gly Ala
1               5                   10                  15

Lys Val Ala Asp Lys
            20

<210> SEQ ID NO 161
<211> LENGTH: 34
<212> TYPE: PRT
<213> ORGANISM: Homo sapiens

<400> SEQUENCE: 161

Ala Glu Gly Ser Asp Val Ala Asn Ala Val Leu Asp Gly Ala Asp Cys
1               5                   10                  15

Ile Met Leu Ser Gly Glu Thr Ala Lys Gly Asp Tyr Pro Leu Glu Ala
            20                  25                  30

Val Arg

<210> SEQ ID NO 162
<211> LENGTH: 44
<212> TYPE: PRT
<213> ORGANISM: Homo sapiens

<400> SEQUENCE: 162

His His Thr Ser Lys Ile Gln Glu Phe Ala Asp Leu Thr Gln Val Glu
1               5                   10                  15

Thr Phe Gly Phe Arg Gly Glu Ala Leu Ser Ser Leu Cys Ala Leu Ser
            20                  25                  30
```

Asp Val Thr Ile Ser Thr Cys His Ala Ser Ala Lys
        35                  40

<210> SEQ ID NO 163
<211> LENGTH: 13
<212> TYPE: PRT
<213> ORGANISM: Homo sapiens

<400> SEQUENCE: 163

Ser Gly Lys Asp Phe Val Thr Glu Ala Leu Gln Ser Arg
1               5                   10

<210> SEQ ID NO 164
<211> LENGTH: 13
<212> TYPE: PRT
<213> ORGANISM: Homo sapiens

<400> SEQUENCE: 164

Met Ala Gln Glu Leu Lys Tyr Gly Asp Ile Val Glu Arg
1               5                   10

<210> SEQ ID NO 165
<211> LENGTH: 11
<212> TYPE: PRT
<213> ORGANISM: Homo sapiens

<400> SEQUENCE: 165

Met Val Pro Lys Leu Leu Ser Pro Leu Val Lys
1               5                   10

<210> SEQ ID NO 166
<211> LENGTH: 18
<212> TYPE: PRT
<213> ORGANISM: Homo sapiens

<400> SEQUENCE: 166

Ala Phe Ile Ile Ser Phe Lys Leu Glu Thr Asp Pro Ala Ile Val Ile
1               5                   10                  15

Asn Arg

<210> SEQ ID NO 167
<211> LENGTH: 19
<212> TYPE: PRT
<213> ORGANISM: Homo sapiens

<400> SEQUENCE: 167

Leu Pro Val Ile Asp Pro Glu Ser Gly Asn Thr Leu Tyr Ile Leu Thr
1               5                   10                  15

His Lys Arg

<210> SEQ ID NO 168
<211> LENGTH: 19
<212> TYPE: PRT
<213> ORGANISM: Homo sapiens

<400> SEQUENCE: 168

Gly Arg Val Val Asp Ile Tyr Ser Lys Phe Asp Val Ile Asn Leu Ala
1               5                   10                  15

Ala Glu Lys

<210> SEQ ID NO 169
<211> LENGTH: 17

```
<212> TYPE: PRT
<213> ORGANISM: Homo sapiens

<400> SEQUENCE: 169

Val Val Asp Ile Tyr Ser Lys Phe Asp Val Ile Asn Leu Ala Ala Glu
1               5                   10                  15

Lys

<210> SEQ ID NO 170
<211> LENGTH: 29
<212> TYPE: PRT
<213> ORGANISM: Homo sapiens

<400> SEQUENCE: 170

Ile Ser Ala Leu Pro Val Val Asp Glu Ser Gly Lys Val Val Asp Ile
1               5                   10                  15

Tyr Ser Lys Phe Asp Val Ile Asn Leu Ala Ala Glu Lys
            20                  25

<210> SEQ ID NO 171
<211> LENGTH: 14
<212> TYPE: PRT
<213> ORGANISM: Homo sapiens

<400> SEQUENCE: 171

Asn Cys Thr Ile Val Ser Pro Asp Ala Gly Gly Ala Lys Arg
1               5                   10

<210> SEQ ID NO 172
<211> LENGTH: 14
<212> TYPE: PRT
<213> ORGANISM: Homo sapiens

<400> SEQUENCE: 172

Asn Cys Ile Ile Val Ser Pro Asp Ala Gly Gly Ala Lys Arg
1               5                   10

<210> SEQ ID NO 173
<211> LENGTH: 17
<212> TYPE: PRT
<213> ORGANISM: Homo sapiens

<400> SEQUENCE: 173

Gly Val Ile Leu Tyr Gly Pro Pro Gly Thr Gly Lys Thr Leu Leu Ala
1               5                   10                  15

Lys

<210> SEQ ID NO 174
<211> LENGTH: 17
<212> TYPE: PRT
<213> ORGANISM: Homo sapiens

<400> SEQUENCE: 174

Gly Val Leu Leu Phe Gly Pro Pro Gly Thr Gly Lys Thr Leu Cys Ala
1               5                   10                  15

Arg

<210> SEQ ID NO 175
<211> LENGTH: 17
<212> TYPE: PRT
<213> ORGANISM: Homo sapiens

<400> SEQUENCE: 175
```

Gly Val Leu Met Tyr Gly Pro Pro Gly Thr Gly Lys Thr Leu Leu Ala
1               5                   10                  15

Arg

<210> SEQ ID NO 176
<211> LENGTH: 17
<212> TYPE: PRT
<213> ORGANISM: Homo sapiens

<400> SEQUENCE: 176

Gly Val Leu Met Tyr Gly Pro Pro Gly Cys Gly Lys Thr Met Leu Ala
1               5                   10                  15

Lys

<210> SEQ ID NO 177
<211> LENGTH: 17
<212> TYPE: PRT
<213> ORGANISM: Homo sapiens

<400> SEQUENCE: 177

Gly Val Leu Leu Tyr Gly Pro Pro Gly Thr Gly Lys Thr Leu Leu Ala
1               5                   10                  15

Arg

<210> SEQ ID NO 178
<211> LENGTH: 17
<212> TYPE: PRT
<213> ORGANISM: Homo sapiens

<400> SEQUENCE: 178

Gly Cys Leu Leu Tyr Gly Pro Pro Gly Thr Gly Lys Thr Leu Leu Ala
1               5                   10                  15

Arg

<210> SEQ ID NO 179
<211> LENGTH: 15
<212> TYPE: PRT
<213> ORGANISM: Homo sapiens

<400> SEQUENCE: 179

His Asn Ile Ile Cys Leu Gln Asn Asp His Lys Ala Val Met Lys
1               5                   10                  15

<210> SEQ ID NO 180
<211> LENGTH: 36
<212> TYPE: PRT
<213> ORGANISM: Homo sapiens

<400> SEQUENCE: 180

Thr Gly Asp Lys Trp Cys Ile Tyr Pro Thr Tyr Asp Tyr Thr His Cys
1               5                   10                  15

Leu Cys Asp Ser Ile Glu His Ile Thr His Ser Leu Cys Thr Lys Glu
                20                  25                  30

Phe Gln Ala Arg
            35

<210> SEQ ID NO 181
<211> LENGTH: 21
<212> TYPE: PRT
<213> ORGANISM: Homo sapiens

```
<400> SEQUENCE: 181

Gln Gly Gly Ser Ile Leu Leu Ile Thr Gly Pro Pro Gly Cys Gly Lys
1               5                   10                  15

Thr Thr Thr Leu Lys
            20

<210> SEQ ID NO 182
<211> LENGTH: 18
<212> TYPE: PRT
<213> ORGANISM: Homo sapiens

<400> SEQUENCE: 182

Phe Phe Ile Gly Phe Gly Gly Lys Gly Ala Asn Gln Cys Val Gln Ala
1               5                   10                  15

Ala Arg

<210> SEQ ID NO 183
<211> LENGTH: 36
<212> TYPE: PRT
<213> ORGANISM: Homo sapiens

<400> SEQUENCE: 183

Ala Ala Leu Leu Ser Gly Pro Pro Gly Val Gly Lys Thr Thr Thr Ala
1               5                   10                  15

Ser Leu Val Cys Gln Glu Leu Gly Tyr Ser Tyr Val Glu Leu Asn Ala
            20                  25                  30

Ser Asp Thr Arg
        35

<210> SEQ ID NO 184
<211> LENGTH: 26
<212> TYPE: PRT
<213> ORGANISM: Homo sapiens

<400> SEQUENCE: 184

Glu Gly Asn Val Pro Asn Ile Ile Ala Gly Pro Pro Gly Thr Gly
1               5                   10                  15

Lys Thr Thr Ser Ile Leu Cys Leu Ala Arg
            20                  25

<210> SEQ ID NO 185
<211> LENGTH: 29
<212> TYPE: PRT
<213> ORGANISM: Homo sapiens

<400> SEQUENCE: 185

Ser Leu Glu Gly Ala Asp Leu Pro Asn Leu Leu Phe Tyr Gly Pro Pro
1               5                   10                  15

Gly Thr Gly Lys Thr Ser Thr Ile Leu Ala Ala Ala Arg
            20                  25

<210> SEQ ID NO 186
<211> LENGTH: 29
<212> TYPE: PRT
<213> ORGANISM: Homo sapiens

<400> SEQUENCE: 186

Phe Ile Asn Glu Asp Arg Leu Pro His Leu Leu Tyr Gly Pro Pro
1               5                   10                  15

Gly Thr Gly Lys Thr Ser Thr Ile Leu Ala Cys Ala Lys
            20                  25
```

<210> SEQ ID NO 187
<211> LENGTH: 42
<212> TYPE: PRT
<213> ORGANISM: Homo sapiens

<400> SEQUENCE: 187

Gly Ser Lys Gln Leu Gly Ile Pro Thr Ala Asn Phe Pro Glu Gln Val
1               5                   10                  15

Val Asp Asn Leu Pro Ala Asp Ile Ser Thr Gly Ile Tyr Tyr Gly Trp
            20                  25                  30

Ala Ser Val Gly Ser Gly Asp Val His Lys
        35                  40

<210> SEQ ID NO 188
<211> LENGTH: 26
<212> TYPE: PRT
<213> ORGANISM: Homo sapiens

<400> SEQUENCE: 188

Ala Val Leu Leu Ala Gly Pro Pro Gly Thr Gly Lys Thr Ala Leu Ala
1               5                   10                  15

Leu Ala Ile Ala Gln Glu Leu Gly Ser Lys
            20                  25

<210> SEQ ID NO 189
<211> LENGTH: 44
<212> TYPE: PRT
<213> ORGANISM: Homo sapiens

<400> SEQUENCE: 189

Ala Val Leu Ile Ala Gly Gln Pro Gly Thr Gly Lys Thr Ala Ile Ala
1               5                   10                  15

Met Gly Met Ala Gln Ala Leu Gly Pro Asp Thr Pro Phe Thr Ala Ile
            20                  25                  30

Ala Gly Ser Glu Ile Phe Ser Leu Glu Met Ser Lys
        35                  40

<210> SEQ ID NO 190
<211> LENGTH: 15
<212> TYPE: PRT
<213> ORGANISM: Homo sapiens

<400> SEQUENCE: 190

Lys Leu Asp Leu Glu Ala Trp Phe Pro Gly Ser Gly Ala Phe Arg
1               5                   10                  15

<210> SEQ ID NO 191
<211> LENGTH: 27
<212> TYPE: PRT
<213> ORGANISM: Homo sapiens

<400> SEQUENCE: 191

His Asp Ser Val Phe Val Ala Ala His Thr Ser Ala Gly Lys Thr Val
1               5                   10                  15

Val Ala Glu Tyr Ala Ile Ala Leu Ala Gln Lys
            20                  25

<210> SEQ ID NO 192
<211> LENGTH: 17
<212> TYPE: PRT
<213> ORGANISM: Homo sapiens -continued

```
<400> SEQUENCE: 192

Leu Ala Val Gly Lys Thr Gly Gln Tyr Ser Gly Ile Tyr Asp Cys Ala
1               5                   10                  15

Lys

<210> SEQ ID NO 193
<211> LENGTH: 26
<212> TYPE: PRT
<213> ORGANISM: Homo sapiens

<400> SEQUENCE: 193

Phe Thr Ala Ile Ile Gly Pro Asn Gly Ser Gly Lys Ser Asn Leu Met
1               5                   10                  15

Asp Ala Ile Ser Phe Val Leu Gly Glu Lys
            20                  25

<210> SEQ ID NO 194
<211> LENGTH: 28
<212> TYPE: PRT
<213> ORGANISM: Homo sapiens

<400> SEQUENCE: 194

Asn Gly Ser Gly Lys Ser Asn Phe Phe Tyr Ala Ile Gln Phe Val Leu
1               5                   10                  15

Ser Asp Glu Phe Ser His Leu Arg Pro Glu Gln Arg
            20                  25

<210> SEQ ID NO 195
<211> LENGTH: 18
<212> TYPE: PRT
<213> ORGANISM: Homo sapiens

<400> SEQUENCE: 195

Leu Met Ile Thr His Ile Val Asn Gln Asn Phe Lys Ser Tyr Ala Gly
1               5                   10                  15

Glu Lys

<210> SEQ ID NO 196
<211> LENGTH: 40
<212> TYPE: PRT
<213> ORGANISM: Homo sapiens

<400> SEQUENCE: 196

Leu Ala Thr Tyr Gly Ile Thr Val Ala Glu Leu Thr Gly Asp His Gln
1               5                   10                  15

Leu Cys Lys Glu Glu Ile Ser Ala Thr Gln Ile Ile Val Cys Thr Pro
            20                  25                  30

Glu Lys Trp Asp Ile Ile Thr Arg
        35                  40

<210> SEQ ID NO 197
<211> LENGTH: 17
<212> TYPE: PRT
<213> ORGANISM: Homo sapiens

<400> SEQUENCE: 197

Gly Ala Leu Leu Leu Gly Pro Pro Gly Cys Gly Lys Thr Leu Leu Ala
1               5                   10                  15

Lys
```

```
<210> SEQ ID NO 198
<211> LENGTH: 10
<212> TYPE: PRT
<213> ORGANISM: Homo sapiens

<400> SEQUENCE: 198

Gly Lys Gly Thr Phe Glu Ser Gly Leu Lys
1               5                   10

<210> SEQ ID NO 199
<211> LENGTH: 13
<212> TYPE: PRT
<213> ORGANISM: Homo sapiens

<400> SEQUENCE: 199

Asp Val Val Ile Lys Ala Gln Val Leu Ala Gly Gly Arg
1               5                   10

<210> SEQ ID NO 200
<211> LENGTH: 29
<212> TYPE: PRT
<213> ORGANISM: Homo sapiens

<400> SEQUENCE: 200

Val Leu Cys Glu Leu Ala Asp Leu Gln Asp Lys Glu Val Gly Asp Gly
1               5                   10                  15

Thr Thr Ser Val Val Ile Ile Ala Ala Glu Leu Leu Lys
            20                  25

<210> SEQ ID NO 201
<211> LENGTH: 24
<212> TYPE: PRT
<213> ORGANISM: Homo sapiens

<400> SEQUENCE: 201

Thr Thr Cys Leu Glu Phe Phe Ser Asn Ala Thr Asp Val Glu Val Leu
1               5                   10                  15

Thr Glu Pro Val Ser Lys Trp Arg
            20

<210> SEQ ID NO 202
<211> LENGTH: 12
<212> TYPE: PRT
<213> ORGANISM: Homo sapiens

<400> SEQUENCE: 202

Lys Val Thr Gly Gly Arg Asn Gly Tyr Gly Ala Lys
1               5                   10

<210> SEQ ID NO 203
<211> LENGTH: 20
<212> TYPE: PRT
<213> ORGANISM: Homo sapiens

<400> SEQUENCE: 203

Lys Pro Leu Thr Leu Ser Leu His Gly Trp Thr Gly Thr Gly Lys Asn
1               5                   10                  15

Phe Val Ser Lys
            20

<210> SEQ ID NO 204
<211> LENGTH: 29
<212> TYPE: PRT
```

-continued

<213> ORGANISM: Homo sapiens

<400> SEQUENCE: 204

Lys Pro Leu Thr Leu Ser Leu His Gly Trp Ala Gly Thr Gly Lys Asn
1               5                   10                  15
Phe Val Ser Gln Ile Val Ala Glu Asn Leu His Pro Lys
            20                  25

<210> SEQ ID NO 205
<211> LENGTH: 41
<212> TYPE: PRT
<213> ORGANISM: Homo sapiens

<400> SEQUENCE: 205

Ala Phe Val Arg Asp Pro Ala Pro Thr Lys Pro Leu Val Leu Ser Leu
1               5                   10                  15
His Gly Trp Thr Gly Thr Gly Lys Ser Tyr Val Ser Ser Leu Leu Ala
            20                  25                  30
His Tyr Leu Phe Gln Gly Gly Leu Arg
        35                  40

<210> SEQ ID NO 206
<211> LENGTH: 19
<212> TYPE: PRT
<213> ORGANISM: Homo sapiens

<400> SEQUENCE: 206

Ala Leu Ala Leu Ser Phe His Gly Trp Ser Gly Thr Gly Lys Asn Phe
1               5                   10                  15
Val Ala Arg

<210> SEQ ID NO 207
<211> LENGTH: 29
<212> TYPE: PRT
<213> ORGANISM: Homo sapiens

<400> SEQUENCE: 207

Asp Tyr Leu Ala Thr His Val His Ser Arg Pro Leu Leu Ala Leu
1               5                   10                  15
His Gly Pro Ser Gly Val Gly Lys Ser His Val Gly Arg
            20                  25

<210> SEQ ID NO 208
<211> LENGTH: 16
<212> TYPE: PRT
<213> ORGANISM: Homo sapiens

<400> SEQUENCE: 208

Asn Leu Gly Thr Ile Ala Lys Ser Gly Thr Ser Glu Phe Leu Asn Lys
1               5                   10                  15

<210> SEQ ID NO 209
<211> LENGTH: 19
<212> TYPE: PRT
<213> ORGANISM: Homo sapiens

<400> SEQUENCE: 209

Ser Gly Ser Lys Ala Phe Leu Asp Ala Leu Gln Asn Gln Ala Glu Ala
1               5                   10                  15
Ser Ser Lys

```
<210> SEQ ID NO 210
<211> LENGTH: 13
<212> TYPE: PRT
<213> ORGANISM: Homo sapiens

<400> SEQUENCE: 210

Val Leu Ile Gln Thr Lys Ala Thr Asp Ile Leu Pro Lys
1               5                   10

<210> SEQ ID NO 211
<211> LENGTH: 13
<212> TYPE: PRT
<213> ORGANISM: Homo sapiens

<400> SEQUENCE: 211

Thr Pro Asn Pro Asp Ile Val Cys Asn Lys His Ile Lys
1               5                   10

<210> SEQ ID NO 212
<211> LENGTH: 25
<212> TYPE: PRT
<213> ORGANISM: Homo sapiens

<400> SEQUENCE: 212

Leu Leu Gln Ala Ala Asp Ser Phe Lys Asp Gln Thr Phe Phe Leu Ser
1               5                   10                  15

Gln Val Ser Gln Asp Ala Leu Arg Arg
            20                  25

<210> SEQ ID NO 213
<211> LENGTH: 19
<212> TYPE: PRT
<213> ORGANISM: Homo sapiens

<400> SEQUENCE: 213

Lys Lys Glu Asp Gly Glu Gly Asn Val Trp Ile Ala Lys Ser Ser Ala
1               5                   10                  15

Gly Ala Lys

<210> SEQ ID NO 214
<211> LENGTH: 34
<212> TYPE: PRT
<213> ORGANISM: Homo sapiens

<400> SEQUENCE: 214

Ser Ser Ala Gly Ala Lys Gly Glu Gly Ile Leu Ile Ser Ser Glu Ala
1               5                   10                  15

Ser Glu Leu Leu Asp Phe Ile Asp Asn Gln Gly Gln Val His Val Ile
            20                  25                  30

Gln Lys

<210> SEQ ID NO 215
<211> LENGTH: 16
<212> TYPE: PRT
<213> ORGANISM: Homo sapiens

<400> SEQUENCE: 215

Trp Gly Glu Asp Asn His Trp Ile Cys Lys Pro Trp Asn Leu Ala Arg
1               5                   10                  15

<210> SEQ ID NO 216
<211> LENGTH: 30
<212> TYPE: PRT
```

<213> ORGANISM: Homo sapiens

<400> SEQUENCE: 216

Leu Ser Gln Glu Arg Pro Gly Val Leu Leu Asn Gln Phe Pro Cys Glu
1               5                   10                  15
Asn Leu Leu Thr Val Lys Asp Cys Leu Ala Ser Ile Ala Arg
            20                  25                  30

<210> SEQ ID NO 217
<211> LENGTH: 31
<212> TYPE: PRT
<213> ORGANISM: Homo sapiens

<400> SEQUENCE: 217

Gly Asn Val Gln Val Val Ile Pro Phe Leu Thr Glu Ser Tyr Ser Ser
1               5                   10                  15
Ser Gln Asp Pro Pro Glu Lys Ser Ile Pro Ile Cys Thr Leu Lys
            20                  25                  30

<210> SEQ ID NO 218
<211> LENGTH: 32
<212> TYPE: PRT
<213> ORGANISM: Homo sapiens

<400> SEQUENCE: 218

Val His Leu Ala Glu Lys Gly Asp Gly Ala Glu Leu Ile Trp Asp Lys
1               5                   10                  15
Asp Asp Pro Ser Ala Met Asp Phe Val Thr Ser Ala Ala Asn Leu Arg
            20                  25                  30

<210> SEQ ID NO 219
<211> LENGTH: 26
<212> TYPE: PRT
<213> ORGANISM: Homo sapiens

<400> SEQUENCE: 219

Gly Asp Gly Ala Glu Leu Ile Trp Asp Lys Asp Asp Pro Ser Ala Met
1               5                   10                  15
Asp Phe Val Thr Ser Ala Ala Asn Leu Arg
            20                  25

<210> SEQ ID NO 220
<211> LENGTH: 29
<212> TYPE: PRT
<213> ORGANISM: Homo sapiens

<400> SEQUENCE: 220

Asp Ile Gly Arg Pro Lys Ala Glu Val Ala Ala Glu Phe Leu Asn Asp
1               5                   10                  15
Arg Val Pro Asn Cys Asn Val Val Pro His Phe Asn Lys
            20                  25

<210> SEQ ID NO 221
<211> LENGTH: 21
<212> TYPE: PRT
<213> ORGANISM: Homo sapiens

<400> SEQUENCE: 221

Leu Phe Phe Gln Pro His Gln Ala Gly Leu Ser Lys Val Gln Ala Ala
1               5                   10                  15
Glu His Thr Leu Arg
            20

<210> SEQ ID NO 222
<211> LENGTH: 18
<212> TYPE: PRT
<213> ORGANISM: Homo sapiens

<400> SEQUENCE: 222

Gly Met Ile Thr Val Thr Asp Pro Asp Leu Ile Glu Lys Ser Asn Leu
1               5                   10                  15

Asn Arg

<210> SEQ ID NO 223
<211> LENGTH: 31
<212> TYPE: PRT
<213> ORGANISM: Homo sapiens

<400> SEQUENCE: 223

Thr Val Leu Gln Arg Pro Leu Ser Leu Ile Gln Gly Pro Pro Gly Thr
1               5                   10                  15

Gly Lys Thr Val Thr Ser Ala Thr Ile Val Tyr His Leu Ala Arg
            20                  25                  30

<210> SEQ ID NO 224
<211> LENGTH: 29
<212> TYPE: PRT
<213> ORGANISM: Homo sapiens

<400> SEQUENCE: 224

Gln Gly Asn Gly Pro Val Leu Val Cys Ala Pro Ser Asn Ile Ala Val
1               5                   10                  15

Asp Gln Leu Thr Glu Lys Ile His Gln Thr Gly Leu Lys
            20                  25

<210> SEQ ID NO 225
<211> LENGTH: 17
<212> TYPE: PRT
<213> ORGANISM: Homo sapiens

<400> SEQUENCE: 225

Gly Ile Leu Leu Tyr Gly Pro Pro Gly Thr Gly Lys Thr Leu Ile Ala
1               5                   10                  15

Arg

<210> SEQ ID NO 226
<211> LENGTH: 17
<212> TYPE: PRT
<213> ORGANISM: Homo sapiens

<400> SEQUENCE: 226

Gly Val Leu Phe Tyr Gly Pro Pro Gly Cys Gly Lys Thr Leu Leu Ala
1               5                   10                  15

Lys

<210> SEQ ID NO 227
<211> LENGTH: 19
<212> TYPE: PRT
<213> ORGANISM: Homo sapiens

<400> SEQUENCE: 227

Thr Leu Leu Ala Lys Ala Ile Ala Asn Glu Cys Gln Ala Asn Phe Ile
1               5                   10                  15

Ser Ile Lys

<210> SEQ ID NO 228
<211> LENGTH: 15
<212> TYPE: PRT
<213> ORGANISM: Homo sapiens

<400> SEQUENCE: 228

Ile Val Ser Gln Leu Leu Thr Leu Met Asp Gly Leu Lys Gln Arg
1               5                   10                  15

<210> SEQ ID NO 229
<211> LENGTH: 17
<212> TYPE: PRT
<213> ORGANISM: Homo sapiens

<400> SEQUENCE: 229

Gly Ile Leu Leu Phe Gly Pro Pro Gly Thr Gly Lys Ser Tyr Leu Ala
1               5                   10                  15

Lys

<210> SEQ ID NO 230
<211> LENGTH: 20
<212> TYPE: PRT
<213> ORGANISM: Homo sapiens

<400> SEQUENCE: 230

Ser Ser Ala Gly Lys Thr Gln Leu Ala Leu Gln Leu Cys Leu Ala Val
1               5                   10                  15

Gln Phe Pro Arg
            20

<210> SEQ ID NO 231
<211> LENGTH: 14
<212> TYPE: PRT
<213> ORGANISM: Homo sapiens

<400> SEQUENCE: 231

Phe Phe Met Gly Asn Gln Val Leu Lys Val Phe Ala Ala Arg
1               5                   10

<210> SEQ ID NO 232
<211> LENGTH: 20
<212> TYPE: PRT
<213> ORGANISM: Homo sapiens

<400> SEQUENCE: 232

Ile Gln Val Thr Pro Pro Gly Phe Gln Leu Val Phe Leu Pro Phe Ala
1               5                   10                  15

Asp Asp Lys Arg
            20

<210> SEQ ID NO 233
<211> LENGTH: 17
<212> TYPE: PRT
<213> ORGANISM: Homo sapiens

<400> SEQUENCE: 233

Gly Ile Leu Leu Val Gly Pro Pro Gly Thr Gly Lys Thr Leu Leu Ala
1               5                   10                  15

Arg

```
<210> SEQ ID NO 234
<211> LENGTH: 21
<212> TYPE: DNA
<213> ORGANISM: Artificial Sequence
<220> FEATURE:
<223> OTHER INFORMATION: Synthetic - TRC Lentiviral Mouse Mi-2beta shRNA

<400> SEQUENCE: 234
tttacaactc agaagatggg c                                              21

<210> SEQ ID NO 235
<211> LENGTH: 21
<212> TYPE: DNA
<213> ORGANISM: Artificial Sequence
<220> FEATURE:
<223> OTHER INFORMATION: Synthetic - TRC Lentiviral Mouse Mi-2beta shRNA

<400> SEQUENCE: 235
taagttgtgg aacctctcag g                                              21

<210> SEQ ID NO 236
<211> LENGTH: 20
<212> TYPE: DNA
<213> ORGANISM: Artificial Sequence
<220> FEATURE:
<223> OTHER INFORMATION: Synthetic - Primer for Mi-2beta ChIP

<400> SEQUENCE: 236
agtgcacagc atcggttgag                                                20

<210> SEQ ID NO 237
<211> LENGTH: 21
<212> TYPE: DNA
<213> ORGANISM: Artificial Sequence
<220> FEATURE:
<223> OTHER INFORMATION: Synthetic - Primer for Mi-2beta ChIP

<400> SEQUENCE: 237
tgtaaagggg attctgggtg c                                              21

<210> SEQ ID NO 238
<211> LENGTH: 20
<212> TYPE: DNA
<213> ORGANISM: Artificial Sequence
<220> FEATURE:
<223> OTHER INFORMATION: Synthetic - Primer for Mi-2beta ChIP

<400> SEQUENCE: 238
aaaatgacgg cagcacttgg                                                20

<210> SEQ ID NO 239
<211> LENGTH: 20
<212> TYPE: DNA
<213> ORGANISM: Artificial Sequence
<220> FEATURE:
<223> OTHER INFORMATION: Synthetic - Primer for Mi-2beta ChIP

<400> SEQUENCE: 239
agccaatcag gactcaggga                                                20

<210> SEQ ID NO 240
<211> LENGTH: 20
<212> TYPE: DNA
<213> ORGANISM: Artificial Sequence
<220> FEATURE:
<223> OTHER INFORMATION: Synthetic - Primer for Mi-2beta ChIP
```

```
<400> SEQUENCE: 240
gaccatcata ggagccagca                                               20

<210> SEQ ID NO 241
<211> LENGTH: 20
<212> TYPE: DNA
<213> ORGANISM: Artificial Sequence
<220> FEATURE:
<223> OTHER INFORMATION: Synthetic - Primer for Mi-2beta ChIP

<400> SEQUENCE: 241
tgttgtagag ctaagcggcg                                               20

<210> SEQ ID NO 242
<211> LENGTH: 20
<212> TYPE: DNA
<213> ORGANISM: Artificial Sequence
<220> FEATURE:
<223> OTHER INFORMATION: Synthetic - Primer for Stat1 ChIP

<400> SEQUENCE: 242
cgtcctgggg aaaaccctac                                               20

<210> SEQ ID NO 243
<211> LENGTH: 20
<212> TYPE: DNA
<213> ORGANISM: Artificial Sequence
<220> FEATURE:
<223> OTHER INFORMATION: Synthetic - Primer for Stat1 ChIP

<400> SEQUENCE: 243
ggggtggttt cacatccctt                                               20

<210> SEQ ID NO 244
<211> LENGTH: 20
<212> TYPE: DNA
<213> ORGANISM: Artificial Sequence
<220> FEATURE:
<223> OTHER INFORMATION: Synthetic - Primer for Stat1 ChIP

<400> SEQUENCE: 244
ccctgagtcc tgattggctg                                               20

<210> SEQ ID NO 245
<211> LENGTH: 20
<212> TYPE: DNA
<213> ORGANISM: Artificial Sequence
<220> FEATURE:
<223> OTHER INFORMATION: Synthetic - Primer for Stat1 ChIP

<400> SEQUENCE: 245
aaggagcaca agaggggaga                                               20

<210> SEQ ID NO 246
<211> LENGTH: 20
<212> TYPE: DNA
<213> ORGANISM: Artificial Sequence
<220> FEATURE:
<223> OTHER INFORMATION: Synthetic - Primer for Stat1 ChIP

<400> SEQUENCE: 246
tttccaagac aggcaagggg                                               20

<210> SEQ ID NO 247
<211> LENGTH: 20
```